(12) United States Patent
Zhao et al.

(10) Patent No.: US 12,421,292 B2
(45) Date of Patent: Sep. 23, 2025

(54) ANTI-DLL3 CHIMERIC ANTIGEN RECEPTORS AND USES THEREOF

(71) Applicant: Legend Biotech Ireland Limited, Dublin (IE)

(72) Inventors: Tao Zhao, Nanjing (CN); Yuanyuan Peng, Nanjing (CN); An Tang, Nanjing (CN); Sujuan Wang, Nanjing (CN); Shuai Yang, Nanjing (CN); Wang Zhang, Nanjing (CN); Shu Wu, Nanjing (CN); Ruidong Hao, Shanghai (CN)

(73) Assignee: Legend Biotech Ireland Limited, Dublin (IE)

( * ) Notice: Subject to any disclaimer, the term of this patent is extended or adjusted under 35 U.S.C. 154(b) by 954 days.

(21) Appl. No.: 17/618,642

(22) PCT Filed: Jul. 17, 2020

(86) PCT No.: PCT/CN2020/102717
§ 371 (c)(1),
(2) Date: Dec. 13, 2021

(87) PCT Pub. No.: WO2021/008610
PCT Pub. Date: Jan. 21, 2021

(65) Prior Publication Data
US 2022/0249563 A1 Aug. 11, 2022

(30) Foreign Application Priority Data

Jul. 17, 2019 (WO) ................ PCT/CN2019/096360
May 15, 2020 (WO) ................ PCT/CN2020/090587

(51) Int. Cl.
| | | |
|---|---|---|
| *A61K 40/31* | (2025.01) | |
| *A61K 39/395* | (2006.01) | |
| *A61K 40/11* | (2025.01) | |
| *A61K 40/42* | (2025.01) | |
| *A61P 35/00* | (2006.01) | |
| *C07K 14/705* | (2006.01) | |
| *C07K 14/71* | (2006.01) | |
| *C07K 14/725* | (2006.01) | |
| *C07K 16/18* | (2006.01) | |
| *C12N 5/0783* | (2010.01) | |
| *A61K 38/00* | (2006.01) | |
| *A61K 39/00* | (2006.01) | |

(52) U.S. Cl.
CPC ........ *C07K 14/70521* (2013.01); *A61K 40/11* (2025.01); *A61K 40/31* (2025.01); *A61K 40/4202* (2025.01); *A61K 40/4229* (2025.01); *A61P 35/00* (2018.01); *C07K 14/7051* (2013.01); *C07K 14/70596* (2013.01); *C07K 14/71* (2013.01); *C07K 16/18* (2013.01); *C12N 5/0636* (2013.01); *C12N 5/0638* (2013.01); *C12N 5/0646* (2013.01); *A61K 38/00* (2013.01); *A61K 2039/505* (2013.01); *A61K 2239/31* (2023.05); *A61K 2239/38* (2023.05); *C07K 2317/22* (2013.01); *C07K 2317/569* (2013.01); *C07K 2317/622* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,530,101 A | 6/1996 | Queen et al. |
| 5,565,332 A | 10/1996 | Hoogenboom et al. |
| 5,585,089 A | 12/1996 | Queen et al. |
| 6,982,321 B2 | 1/2006 | Winter |
| 7,087,409 B2 | 8/2006 | Barbas, III et al. |

FOREIGN PATENT DOCUMENTS

| | | | |
|---|---|---|---|
| CN | 105153315 | 4/2019 | |
| EP | 519596 | 12/1992 | |
| EP | 592106 | 4/1994 | |
| JP | 2018-506981 A | 3/2018 | |
| WO | WO 2016138038 | 9/2016 | |
| WO | WO-2016138038 A1 * | 9/2016 | ............. A61K 35/17 |
| WO | WO 2018044866 | 3/2018 | |
| WO | WO 2018121712 | 7/2018 | |
| WO | WO 2019067805 | 4/2019 | |
| WO | WO 2018195348 | 10/2019 | |
| WO | WO 2019195408 | 10/2019 | |
| WO | WO 2019200007 | 10/2019 | |

OTHER PUBLICATIONS

Alvarado-Luna et al., "Treatment for small cell lung cancer, where are we now ?—a review," Feb. 2016, Translational Lung Cancer Research 5(1):26-38.
Chothia et al., "Domain association in immunoglobulin molecules. The packing of variable domains," Journal of Molecular Biology, Dec. 1985, 186(3):651-653.
Foote et al., "Antibody framework residues affecting the conformation of the hypervariable loops," Journal of Molecular Biology, Mar. 1992, 224:487-499.
Harris, "Production of humanized monoclonal antibodies for in vivo imaging and therapy," Biochemical Society Transactions, Nov. 1995, 23(4):1035-1038.
Hurle et al., "Protein engineering techniques for antibody humanization," Current Opinion in Biotechnology, Aug. 1994, 5(4):428-433.
International Search Report and Written Opinion in International Appln. No. PCT/CN2020/102717, dated Oct. 22, 2020, 12 pages.
Jones et al., "Replacing the complementarity-determining regions in a human antibody with those from a mouse," Nature, May 1986, 321:522-525.

(Continued)

*Primary Examiner* — Laura B Goddard
(74) *Attorney, Agent, or Firm* — Fish & Richardson P.C.

(57) ABSTRACT

Provided herein are anti-DLL3 chimeric antigen receptors (CARs), DLL3 binding proteins and uses of such CARs or DLL3 binding proteins in the treatment of DLL3 associated disorders, such as small cell lung cancer.

6 Claims, 34 Drawing Sheets

Specification includes a Sequence Listing.

(56) References Cited

OTHER PUBLICATIONS

Morea et al., "Antibody modeling: implications for engineering and design," Methods, Mar. 2000, 20(3):267-279.
Owen et al., "DLL3: an emerging target in small cell lung cancer," Journal of Hematology & Oncology, Jun. 2019, 12:8 pages.
Presta, "Antibody engineering," Current Opinion in Structural Biology, Aug. 1992, 2(4):593-596.
Rebay et al., "Specific EGF repeats of Notch mediate interactions with Delta and Serrate: implications for notch as a multifunctional receptor," Cell, Nov. 1991, 67(4):687-699.
Riechmann et al., "Reshaping human antibodies for therapy," Nature, Mar. 1988, 332:323-329.
Siegel et al., "Cancer Statistics," CA: A Cancer Journal for Clinicians, Jan. 2017, 67(1):7-30.
Vaswani et al., "Humanized antibodies as potential therapeutic drugs," Annals of Allergy, Asthma & Immunology, Aug. 1998, 81(2):105-115.
Wharton et al., "Nucleotide sequence from the neurogenic locus Notch implies a gene product that shares homology with proteins containing EGF-like repeats," Cell, Dec. 1985, 43(3):567-581.
Yoon et al., "Incorporation of Immune Checkpoint Blockade into Chimeric Antigen Receptor T Cells (CAR-Ts): Combination or Built-In CAR-T," Int J Mol Sci, Jan. 24, 2018, 19(2), 340, 16 pages.
Extended European Search Report in European Appln. No. 20840073.9, 9 pages.
Furuta et al., "DLL3 regulates the migration and invasion of small cell lung cancer by modulating Snail," Cancer Science, May 21, 2019, 110(5):1599-1608.
Owonikoko et al., "Two novel immunotherapy agents targeting DLL3 in SCLC: Trials in progress of AMG 757 and AMG 119," Journal of Thoracic Oncology, Sep. 26, 2018, 13(1) 10S: S351.
Rudin et al., "Emerging therapies targeting the delta-like ligand 3 (DLL3) in small cell lung cancer," Journal of Hematology & Oncology, Jun. 24, 2023, vol. 16, No. 1, 21 pages.

* cited by examiner

FIG. 4

DLL3 Total CAR-T+ cell Expanded
(Co-culture with SHP-77)

CAR-T+:SHP-77=2:1

- CAS63997
- CAS64380
- CAS64511
- CAS63931
- CAS69443
- CAR3

FIG. 5

- G1: Vehicle, i.v.
- G2: unT-1, i.v.
- G3: CAR3, 1M, i.v.
- G4: CAS64380, 1M, i.v.
- G5: CAS64511, 1M, i.v.
- G6: CAS63931, 1M, i.v.
- G7: CAS63997, 1M, i.v.

```
                        SEQUENCE LISTING

<160> NUMBER OF SEQ ID NOS: 529

<210> SEQ ID NO 1
<211> LENGTH: 10
<212> TYPE: PRT
<213> ORGANISM: Artificial
<220> FEATURE:
<223> OTHER INFORMATION: AS63930 CDR1

<400> SEQUENCE: 1

Gly Tyr Thr Tyr Ser Gly Asn Tyr Met Ala
1               5                   10

<210> SEQ ID NO 2
<211> LENGTH: 10
<212> TYPE: PRT
<213> ORGANISM: Artificial
<220> FEATURE:
<223> OTHER INFORMATION: AS63932 CDR1

<400> SEQUENCE: 2

Gly Tyr Thr Tyr Gly Ser Thr Phe Met Gly
1               5                   10

<210> SEQ ID NO 3
<211> LENGTH: 10
<212> TYPE: PRT
<213> ORGANISM: Artificial
<220> FEATURE:
<223> OTHER INFORMATION: AS63951 CDR1

<400> SEQUENCE: 3

Arg Asp Ile Tyr Gly Asn Asn Cys Met Ala
1               5                   10

<210> SEQ ID NO 4
<211> LENGTH: 10
<212> TYPE: PRT
<213> ORGANISM: Artificial
<220> FEATURE:
<223> OTHER INFORMATION: AS63984 CDR1

<400> SEQUENCE: 4

Gly Tyr Thr Tyr Ser Ser Asn Phe Met Gly
1               5                   10

<210> SEQ ID NO 5
<211> LENGTH: 7
<212> TYPE: PRT
<213> ORGANISM: Artificial
<220> FEATURE:
<223> OTHER INFORMATION: AS63987 CDR1

<400> SEQUENCE: 5

Gly Tyr Arg Asn Cys Met Ala
1               5

<210> SEQ ID NO 6
<211> LENGTH: 10
<212> TYPE: PRT
<213> ORGANISM: Artificial
<220> FEATURE:
<223> OTHER INFORMATION: AS63997 CDR1
```

```
<400> SEQUENCE: 6

Phe Ser Gly Tyr Gly Val Ser Thr Met Ala
1               5                   10

<210> SEQ ID NO 7
<211> LENGTH: 10
<212> TYPE: PRT
<213> ORGANISM: Artificial
<220> FEATURE:
<223> OTHER INFORMATION: AS64047 CDR1

<400> SEQUENCE: 7

Gln Tyr Val Tyr Arg Trp Asp Leu Met Gly
1               5                   10

<210> SEQ ID NO 8
<211> LENGTH: 10
<212> TYPE: PRT
<213> ORGANISM: Artificial
<220> FEATURE:
<223> OTHER INFORMATION: AS64052 CDR1

<400> SEQUENCE: 8

Gly Tyr Thr Tyr Arg Ser Asn Phe Met Gly
1               5                   10

<210> SEQ ID NO 9
<211> LENGTH: 11
<212> TYPE: PRT
<213> ORGANISM: Artificial
<220> FEATURE:
<223> OTHER INFORMATION: AS64062 CDR1

<400> SEQUENCE: 9

Arg Ser Pro Tyr Ser Ser Ser Arg Cys Met Gly
1               5                   10

<210> SEQ ID NO 10
<211> LENGTH: 10
<212> TYPE: PRT
<213> ORGANISM: Artificial
<220> FEATURE:
<223> OTHER INFORMATION: AS64072 CDR1

<400> SEQUENCE: 10

Gly Tyr Ser Tyr Tyr Ile Asn Leu Met Ala
1               5                   10

<210> SEQ ID NO 11
<211> LENGTH: 10
<212> TYPE: PRT
<213> ORGANISM: Artificial
<220> FEATURE:
<223> OTHER INFORMATION: AS64097 CDR1

<400> SEQUENCE: 11

Gly Tyr Thr Tyr Ser Arg Asn Cys Met Gly
1               5                   10

<210> SEQ ID NO 12
<211> LENGTH: 10
<212> TYPE: PRT
<213> ORGANISM: Artificial
<220> FEATURE:
<223> OTHER INFORMATION: AS64114 CDR1
```

```
<400> SEQUENCE: 12

Gly Asn Thr Tyr Ser Thr Asn Tyr Met Gly
1               5                   10

<210> SEQ ID NO 13
<211> LENGTH: 10
<212> TYPE: PRT
<213> ORGANISM: Artificial
<220> FEATURE:
<223> OTHER INFORMATION: AS64123 CDR1

<400> SEQUENCE: 13

Gly Tyr Thr Tyr Thr Ser Asn Trp Leu Gly
1               5                   10

<210> SEQ ID NO 14
<211> LENGTH: 10
<212> TYPE: PRT
<213> ORGANISM: Artificial
<220> FEATURE:
<223> OTHER INFORMATION: AS64130 CDR1

<400> SEQUENCE: 14

Gly Tyr Thr Tyr Arg Ser Asn Phe Met Gly
1               5                   10

<210> SEQ ID NO 15
<211> LENGTH: 10
<212> TYPE: PRT
<213> ORGANISM: Artificial
<220> FEATURE:
<223> OTHER INFORMATION: AS64137 CDR1

<400> SEQUENCE: 15

Gly Ser Thr Tyr Ser Thr Asn Phe Met Gly
1               5                   10

<210> SEQ ID NO 16
<211> LENGTH: 10
<212> TYPE: PRT
<213> ORGANISM: Artificial
<220> FEATURE:
<223> OTHER INFORMATION: AS64142 CDR1

<400> SEQUENCE: 16

Gly Phe Thr Phe Asp Arg Asn Ala Met Arg
1               5                   10

<210> SEQ ID NO 17
<211> LENGTH: 10
<212> TYPE: PRT
<213> ORGANISM: Artificial
<220> FEATURE:
<223> OTHER INFORMATION: AS64154 CDR1

<400> SEQUENCE: 17

Gly Tyr Thr Tyr Arg Tyr Leu Tyr Met Gly
1               5                   10

<210> SEQ ID NO 18
<211> LENGTH: 10
<212> TYPE: PRT
<213> ORGANISM: Artificial
<220> FEATURE:
<223> OTHER INFORMATION: AS64160 CDR1

<400> SEQUENCE: 18
```

```
Val Tyr Thr Ser Ser Ser Tyr Cys Met Gly
1               5                   10

<210> SEQ ID NO 19
<211> LENGTH: 10
<212> TYPE: PRT
<213> ORGANISM: Artificial
<220> FEATURE:
<223> OTHER INFORMATION: AS64228 CDR1

<400> SEQUENCE: 19

Gly Val Ser Tyr Asn Arg Cys Ser Met Gly
1               5                   10

<210> SEQ ID NO 20
<211> LENGTH: 10
<212> TYPE: PRT
<213> ORGANISM: Artificial
<220> FEATURE:
<223> OTHER INFORMATION: AS64300 CDR1

<400> SEQUENCE: 20

Gly Asp Ile Tyr Asn Leu Met Ser Met Ala
1               5                   10

<210> SEQ ID NO 21
<211> LENGTH: 10
<212> TYPE: PRT
<213> ORGANISM: Artificial
<220> FEATURE:
<223> OTHER INFORMATION: AS64380 CDR1

<400> SEQUENCE: 21

Gly Asn Thr Tyr Ser Ser Asn Tyr Met Gly
1               5                   10

<210> SEQ ID NO 22
<211> LENGTH: 10
<212> TYPE: PRT
<213> ORGANISM: Artificial
<220> FEATURE:
<223> OTHER INFORMATION: AS64395 CDR1

<400> SEQUENCE: 22

Gly Ser Thr Tyr Ser Thr Asn Phe Met Gly
1               5                   10

<210> SEQ ID NO 23
<211> LENGTH: 10
<212> TYPE: PRT
<213> ORGANISM: Artificial
<220> FEATURE:
<223> OTHER INFORMATION: AS64443 CDR1

<400> SEQUENCE: 23

Gly Tyr Thr Asp Ser Ser Val Tyr Ile Gly
1               5                   10

<210> SEQ ID NO 24
<211> LENGTH: 10
<212> TYPE: PRT
<213> ORGANISM: Artificial
<220> FEATURE:
<223> OTHER INFORMATION: AS64511 CDR1

<400> SEQUENCE: 24
```

Arg Ala Thr Tyr Ser Thr Asn Tyr Ile Ser
1               5                   10

<210> SEQ ID NO 25
<211> LENGTH: 10
<212> TYPE: PRT
<213> ORGANISM: Artificial
<220> FEATURE:
<223> OTHER INFORMATION: AS64536 CDR1

<400> SEQUENCE: 25

Arg Tyr Thr Asp Asn Phe Val Tyr Met Gly
1               5                   10

<210> SEQ ID NO 26
<211> LENGTH: 10
<212> TYPE: PRT
<213> ORGANISM: Artificial
<220> FEATURE:
<223> OTHER INFORMATION: AS64597 CDR1

<400> SEQUENCE: 26

Gly Tyr Thr Tyr Arg Val Asn Phe Met Gly
1               5                   10

<210> SEQ ID NO 27
<211> LENGTH: 9
<212> TYPE: PRT
<213> ORGANISM: Artificial
<220> FEATURE:
<223> OTHER INFORMATION: AS64617 CDR1

<400> SEQUENCE: 27

Gly Tyr Thr Asp Arg Cys Ser Met Ala
1               5

<210> SEQ ID NO 28
<211> LENGTH: 12
<212> TYPE: PRT
<213> ORGANISM: Artificial
<220> FEATURE:
<223> OTHER INFORMATION: AS64634 CDR1

<400> SEQUENCE: 28

Gly Tyr Ser Phe Arg Gly Asp Phe Met Cys Met Gly
1               5                   10

<210> SEQ ID NO 29
<211> LENGTH: 10
<212> TYPE: PRT
<213> ORGANISM: Artificial
<220> FEATURE:
<223> OTHER INFORMATION: AS69498 CDR1

<400> SEQUENCE: 29

Gly Asn Thr Tyr Ser Ser Asn Tyr Met Ala
1               5                   10

<210> SEQ ID NO 30
<211> LENGTH: 10
<212> TYPE: PRT
<213> ORGANISM: Artificial
<220> FEATURE:
<223> OTHER INFORMATION: AS69500 CDR1

<400> SEQUENCE: 30

Arg Tyr Thr Tyr Ser Ser Ala Cys Met Gly

```
<210> SEQ ID NO 31
<211> LENGTH: 10
<212> TYPE: PRT
<213> ORGANISM: Artificial
<220> FEATURE:
<223> OTHER INFORMATION: AS69527 CDR1

<400> SEQUENCE: 31

Arg Tyr Thr Phe Ser Ser Thr Cys Met Ala
1               5                   10

<210> SEQ ID NO 32
<211> LENGTH: 10
<212> TYPE: PRT
<213> ORGANISM: Artificial
<220> FEATURE:
<223> OTHER INFORMATION: AS68280 CDR1

<400> SEQUENCE: 32

Gly Ser Thr Tyr Ser Ser Asn Tyr Leu Gly
1               5                   10

<210> SEQ ID NO 33
<211> LENGTH: 10
<212> TYPE: PRT
<213> ORGANISM: Artificial
<220> FEATURE:
<223> OTHER INFORMATION: AS68355 CDR1

<400> SEQUENCE: 33

Gly Tyr Thr Tyr Ser Gly Val Cys Met Gly
1               5                   10

<210> SEQ ID NO 34
<211> LENGTH: 10
<212> TYPE: PRT
<213> ORGANISM: Artificial
<220> FEATURE:
<223> OTHER INFORMATION: AS69443 CDR1

<400> SEQUENCE: 34

Gly Phe Thr Phe Asp Asp Ser Asp Met Ala
1               5                   10

<210> SEQ ID NO 35
<211> LENGTH: 10
<212> TYPE: PRT
<213> ORGANISM: Artificial
<220> FEATURE:
<223> OTHER INFORMATION: AS75376 CDR1

<400> SEQUENCE: 35

Gly Tyr Thr Tyr Ser Ser His Ser Met Gly
1               5                   10

<210> SEQ ID NO 36
<211> LENGTH: 10
<212> TYPE: PRT
<213> ORGANISM: Artificial
<220> FEATURE:
<223> OTHER INFORMATION: AS75387 CDR1

<400> SEQUENCE: 36

Gly Tyr Pro Tyr Ser Ser Pro Cys Met Ala
1               5                   10
```

<210> SEQ ID NO 37
<211> LENGTH: 10
<212> TYPE: PRT
<213> ORGANISM: Artificial
<220> FEATURE:
<223> OTHER INFORMATION: AS75695 CDR1

<400> SEQUENCE: 37

Gly Tyr Thr Val Ser Ala Tyr Cys Met Gly
1               5                   10

<210> SEQ ID NO 38
<211> LENGTH: 10
<212> TYPE: PRT
<213> ORGANISM: Artificial
<220> FEATURE:
<223> OTHER INFORMATION: AS76169 CDR1

<400> SEQUENCE: 38

Gly Tyr Ile Tyr Ser Ser Phe Cys Met Gly
1               5                   10

<210> SEQ ID NO 39
<211> LENGTH: 10
<212> TYPE: PRT
<213> ORGANISM: Artificial
<220> FEATURE:
<223> OTHER INFORMATION: AS63931 CDR1

<400> SEQUENCE: 39

Phe Ser Gly Tyr Gly Val Ser Thr Met Ala
1               5                   10

<210> SEQ ID NO 40
<211> LENGTH: 10
<212> TYPE: PRT
<213> ORGANISM: Artificial
<220> FEATURE:
<223> OTHER INFORMATION: AS63937 CDR1

<400> SEQUENCE: 40

Gly Ser Thr Ile Ser Ser Arg Pro Met Ala
1               5                   10

<210> SEQ ID NO 41
<211> LENGTH: 10
<212> TYPE: PRT
<213> ORGANISM: Artificial
<220> FEATURE:
<223> OTHER INFORMATION: AS63948 CDR1

<400> SEQUENCE: 41

Gly Tyr Thr Tyr Arg Tyr Leu Tyr Met Gly
1               5                   10

<210> SEQ ID NO 42
<211> LENGTH: 10
<212> TYPE: PRT
<213> ORGANISM: Artificial
<220> FEATURE:
<223> OTHER INFORMATION: AS63956 CDR1

<400> SEQUENCE: 42

Gly Phe Thr Tyr Ser Asn Cys Cys Met Arg
1               5                   10

<210> SEQ ID NO 43
<211> LENGTH: 10
<212> TYPE: PRT
<213> ORGANISM: Artificial
<220> FEATURE:
<223> OTHER INFORMATION: AS63965 CDR1

<400> SEQUENCE: 43

Gly Tyr Ser Ser Gly Ser Cys Arg Met Gly
1               5                   10

<210> SEQ ID NO 44
<211> LENGTH: 10
<212> TYPE: PRT
<213> ORGANISM: Artificial
<220> FEATURE:
<223> OTHER INFORMATION: AS63993 CDR1

<400> SEQUENCE: 44

Gly Phe Thr Phe Asp Asp Leu Val Met Ala
1               5                   10

<210> SEQ ID NO 45
<211> LENGTH: 10
<212> TYPE: PRT
<213> ORGANISM: Artificial
<220> FEATURE:
<223> OTHER INFORMATION: AS63999 CDR1

<400> SEQUENCE: 45

Gly Tyr Thr Tyr Ser Ser Asn Trp Met Gly
1               5                   10

<210> SEQ ID NO 46
<211> LENGTH: 10
<212> TYPE: PRT
<213> ORGANISM: Artificial
<220> FEATURE:
<223> OTHER INFORMATION: AS64006 CDR1

<400> SEQUENCE: 46

Gly Tyr Thr Gly Asp Thr Thr Tyr Ile Gly
1               5                   10

<210> SEQ ID NO 47
<211> LENGTH: 10
<212> TYPE: PRT
<213> ORGANISM: Artificial
<220> FEATURE:
<223> OTHER INFORMATION: AS64057 CDR1

<400> SEQUENCE: 47

Gly Phe Thr Phe Asp Arg Asn Ala Met Arg
1               5                   10

<210> SEQ ID NO 48
<211> LENGTH: 10
<212> TYPE: PRT
<213> ORGANISM: Artificial
<220> FEATURE:
<223> OTHER INFORMATION: AS64060 CDR1

<400> SEQUENCE: 48

Gly Ser Thr Tyr Cys Thr Tyr Arg Met Ser
1               5                   10

```
<210> SEQ ID NO 49
<211> LENGTH: 10
<212> TYPE: PRT
<213> ORGANISM: Artificial
<220> FEATURE:
<223> OTHER INFORMATION: AS64071 CDR1

<400> SEQUENCE: 49

Gly Asn Thr Tyr Arg Leu Asn Ser Met Gly
1               5                   10

<210> SEQ ID NO 50
<211> LENGTH: 10
<212> TYPE: PRT
<213> ORGANISM: Artificial
<220> FEATURE:
<223> OTHER INFORMATION: AS64093 CDR1

<400> SEQUENCE: 50

Arg Tyr Ile Tyr Gly Asn Asn Cys Met Ala
1               5                   10

<210> SEQ ID NO 51
<211> LENGTH: 10
<212> TYPE: PRT
<213> ORGANISM: Artificial
<220> FEATURE:
<223> OTHER INFORMATION: AS64118 CDR1

<400> SEQUENCE: 51

Gly Tyr Thr Tyr Ser Ala Cys Arg Met Ala
1               5                   10

<210> SEQ ID NO 52
<211> LENGTH: 10
<212> TYPE: PRT
<213> ORGANISM: Artificial
<220> FEATURE:
<223> OTHER INFORMATION: AS64120 CDR1

<400> SEQUENCE: 52

Arg Tyr Ile Tyr Gly Asn Asn Cys Met Ala
1               5                   10

<210> SEQ ID NO 53
<211> LENGTH: 10
<212> TYPE: PRT
<213> ORGANISM: Artificial
<220> FEATURE:
<223> OTHER INFORMATION: AS64124 CDR1

<400> SEQUENCE: 53

Thr Tyr Thr Pro Ser Asn Asn Tyr Met Gly
1               5                   10

<210> SEQ ID NO 54
<211> LENGTH: 10
<212> TYPE: PRT
<213> ORGANISM: Artificial
<220> FEATURE:
<223> OTHER INFORMATION: AS64135 CDR1

<400> SEQUENCE: 54

Thr Ser Thr Tyr Cys Arg Tyr Tyr Met Arg
1               5                   10

<210> SEQ ID NO 55
```

```
<211> LENGTH: 10
<212> TYPE: PRT
<213> ORGANISM: Artificial
<220> FEATURE:
<223> OTHER INFORMATION: AS64163 CDR1

<400> SEQUENCE: 55

Gly Tyr Arg Tyr Arg Trp Asn Cys Met Ala
1               5                   10

<210> SEQ ID NO 56
<211> LENGTH: 10
<212> TYPE: PRT
<213> ORGANISM: Artificial
<220> FEATURE:
<223> OTHER INFORMATION: AS64182 CDR1

<400> SEQUENCE: 56

Gly Gln Thr Ser Arg Tyr Leu Tyr Met Gly
1               5                   10

<210> SEQ ID NO 57
<211> LENGTH: 10
<212> TYPE: PRT
<213> ORGANISM: Artificial
<220> FEATURE:
<223> OTHER INFORMATION: AS64183 CDR1

<400> SEQUENCE: 57

Gly His Thr Tyr Ser Ala Asn Cys Met Ala
1               5                   10

<210> SEQ ID NO 58
<211> LENGTH: 10
<212> TYPE: PRT
<213> ORGANISM: Artificial
<220> FEATURE:
<223> OTHER INFORMATION: AS64207 CDR1

<400> SEQUENCE: 58

Gly Tyr Thr Tyr Ser Ser Asn Phe Met Gly
1               5                   10

<210> SEQ ID NO 59
<211> LENGTH: 10
<212> TYPE: PRT
<213> ORGANISM: Artificial
<220> FEATURE:
<223> OTHER INFORMATION: AS64276 CDR1

<400> SEQUENCE: 59

Gly Tyr Thr Gly Ser Ser Arg Cys Met Ala
1               5                   10

<210> SEQ ID NO 60
<211> LENGTH: 10
<212> TYPE: PRT
<213> ORGANISM: Artificial
<220> FEATURE:
<223> OTHER INFORMATION: AS64336 CDR1

<400> SEQUENCE: 60

Gly Arg Thr Tyr Ser Ser Cys Ser Met Gly
1               5                   10

<210> SEQ ID NO 61
<211> LENGTH: 7
```

```
<212> TYPE: PRT
<213> ORGANISM: Artificial
<220> FEATURE:
<223> OTHER INFORMATION: AS64346 CDR1

<400> SEQUENCE: 61

Gly Tyr Thr Tyr Phe Met Gly
1               5

<210> SEQ ID NO 62
<211> LENGTH: 10
<212> TYPE: PRT
<213> ORGANISM: Artificial
<220> FEATURE:
<223> OTHER INFORMATION: AS64420 CDR1

<400> SEQUENCE: 62

Gly Asp Thr Ser Arg Ser Val Trp Met Gly
1               5                   10

<210> SEQ ID NO 63
<211> LENGTH: 10
<212> TYPE: PRT
<213> ORGANISM: Artificial
<220> FEATURE:
<223> OTHER INFORMATION: AS64473 CDR1

<400> SEQUENCE: 63

Gly Tyr Thr Tyr Arg Tyr Leu Tyr Met Ala
1               5                   10

<210> SEQ ID NO 64
<211> LENGTH: 10
<212> TYPE: PRT
<213> ORGANISM: Artificial
<220> FEATURE:
<223> OTHER INFORMATION: AS64475 CDR1

<400> SEQUENCE: 64

Gly Tyr Thr Trp Ser Arg Asn Trp Met Gly
1               5                   10

<210> SEQ ID NO 65
<211> LENGTH: 10
<212> TYPE: PRT
<213> ORGANISM: Artificial
<220> FEATURE:
<223> OTHER INFORMATION: AS64513 CDR1

<400> SEQUENCE: 65

Asp Tyr Pro Tyr Ile Asp Asn Cys Met Gly
1               5                   10

<210> SEQ ID NO 66
<211> LENGTH: 10
<212> TYPE: PRT
<213> ORGANISM: Artificial
<220> FEATURE:
<223> OTHER INFORMATION: AS64562 CDR1

<400> SEQUENCE: 66

Gly Tyr Thr Ala Arg Arg Asp Phe Met Ala
1               5                   10

<210> SEQ ID NO 67
<211> LENGTH: 10
<212> TYPE: PRT
```

```
<213> ORGANISM: Artificial
<220> FEATURE:
<223> OTHER INFORMATION: AS64583 CDR1

<400> SEQUENCE: 67

Gly Phe Thr Ile Ala Val Tyr Thr Met Gly
1               5                   10

<210> SEQ ID NO 68
<211> LENGTH: 10
<212> TYPE: PRT
<213> ORGANISM: Artificial
<220> FEATURE:
<223> OTHER INFORMATION: AS64594 CDR1

<400> SEQUENCE: 68

Gly Tyr Thr Tyr Asn Ser Asn Tyr Met Gly
1               5                   10

<210> SEQ ID NO 69
<211> LENGTH: 10
<212> TYPE: PRT
<213> ORGANISM: Artificial
<220> FEATURE:
<223> OTHER INFORMATION: AS64605 CDR1

<400> SEQUENCE: 69

Arg Tyr Pro Tyr Ser Ser Ile Cys Met Gly
1               5                   10

<210> SEQ ID NO 70
<211> LENGTH: 10
<212> TYPE: PRT
<213> ORGANISM: Artificial
<220> FEATURE:
<223> OTHER INFORMATION: AS64606 CDR1

<400> SEQUENCE: 70

Gly Tyr Thr Ser Arg Ser Asn Tyr Met Gly
1               5                   10

<210> SEQ ID NO 71
<211> LENGTH: 10
<212> TYPE: PRT
<213> ORGANISM: Artificial
<220> FEATURE:
<223> OTHER INFORMATION: AS68121 CDR1

<400> SEQUENCE: 71

Gly Tyr Thr Tyr Ser Arg Asn Cys Met Gly
1               5                   10

<210> SEQ ID NO 72
<211> LENGTH: 10
<212> TYPE: PRT
<213> ORGANISM: Artificial
<220> FEATURE:
<223> OTHER INFORMATION: AS68170 CDR1

<400> SEQUENCE: 72

Gly Tyr Thr Tyr Arg Ser Asn Cys Met Gly
1               5                   10

<210> SEQ ID NO 73
<211> LENGTH: 10
<212> TYPE: PRT
<213> ORGANISM: Artificial
```

```
<220> FEATURE:
<223> OTHER INFORMATION: AS63964 CDR1

<400> SEQUENCE: 73

Gly Tyr Thr Tyr Ser Tyr Asn Asn Met Gly
1               5                   10

<210> SEQ ID NO 74
<211> LENGTH: 8
<212> TYPE: PRT
<213> ORGANISM: Artificial
<220> FEATURE:
<223> OTHER INFORMATION: AS64116 CDR1

<400> SEQUENCE: 74

Gly Tyr Ile Tyr Ser Cys Val Gly
1               5

<210> SEQ ID NO 75
<211> LENGTH: 13
<212> TYPE: PRT
<213> ORGANISM: Artificial
<220> FEATURE:
<223> OTHER INFORMATION: AS68270 CDR1

<400> SEQUENCE: 75

Gly Tyr Pro Ser Ser Thr Tyr Tyr Met Leu Ser Met Ala
1               5                   10

<210> SEQ ID NO 76
<211> LENGTH: 10
<212> TYPE: PRT
<213> ORGANISM: Artificial
<220> FEATURE:
<223> OTHER INFORMATION: AS68320 CDR1

<400> SEQUENCE: 76

Gly Tyr Thr Tyr Asn Thr Asn Tyr Met Gly
1               5                   10

<210> SEQ ID NO 77
<211> LENGTH: 10
<212> TYPE: PRT
<213> ORGANISM: Artificial
<220> FEATURE:
<223> OTHER INFORMATION: AS68351 CDR1

<400> SEQUENCE: 77

Gly Asp Thr Phe Arg Ala Tyr Tyr Met Asn
1               5                   10

<210> SEQ ID NO 78
<211> LENGTH: 10
<212> TYPE: PRT
<213> ORGANISM: Artificial
<220> FEATURE:
<223> OTHER INFORMATION: AS75378 CDR1

<400> SEQUENCE: 78

Gly Asn Thr Arg Ser Thr Thr Tyr Met Gly
1               5                   10

<210> SEQ ID NO 79
<211> LENGTH: 10
<212> TYPE: PRT
<213> ORGANISM: Artificial
<220> FEATURE:
```

<223> OTHER INFORMATION: AS75383 CDR1

<400> SEQUENCE: 79

Gly Tyr Thr Phe Ser Ser Tyr Cys Leu Gly
1               5                   10

<210> SEQ ID NO 80
<211> LENGTH: 11
<212> TYPE: PRT
<213> ORGANISM: Artificial
<220> FEATURE:
<223> OTHER INFORMATION: AS75751 CDR1

<400> SEQUENCE: 80

Gly Tyr Phe Tyr Asn Thr Tyr Tyr Phe Met Gly
1               5                   10

<210> SEQ ID NO 81
<211> LENGTH: 10
<212> TYPE: PRT
<213> ORGANISM: Artificial
<220> FEATURE:
<223> OTHER INFORMATION: AS76422 CDR1

<400> SEQUENCE: 81

Gly Tyr Thr Phe Ala Gly Asn Cys Leu Gly
1               5                   10

<210> SEQ ID NO 82
<211> LENGTH: 20
<212> TYPE: PRT
<213> ORGANISM: Artificial
<220> FEATURE:
<223> OTHER INFORMATION: AS63930 CDR2

<400> SEQUENCE: 82

Val Val Tyr Asn Ile Asp Gly Gly Arg Phe Thr Thr Tyr Ala Asp
1               5                   10                  15

Ser Val Lys Gly
            20

<210> SEQ ID NO 83
<211> LENGTH: 17
<212> TYPE: PRT
<213> ORGANISM: Artificial
<220> FEATURE:
<223> OTHER INFORMATION: AS63932 CDR2

<400> SEQUENCE: 83

Val Ile Tyr Thr Gly Gly Ser Thr Trp Tyr Ala Ser Ser Val Lys
1               5                   10                  15

Gly

<210> SEQ ID NO 84
<211> LENGTH: 17
<212> TYPE: PRT
<213> ORGANISM: Artificial
<220> FEATURE:
<223> OTHER INFORMATION: AS63951 CDR2

<400> SEQUENCE: 84

Ser Ile Tyr Pro Ala Gly Gly Arg Pro Tyr Tyr Ala Asp Ser Val Lys
1               5                   10                  15

Gly

<210> SEQ ID NO 85
<211> LENGTH: 17
<212> TYPE: PRT
<213> ORGANISM: Artificial
<220> FEATURE:
<223> OTHER INFORMATION: AS63984 CDR2

<400> SEQUENCE: 85

Thr Ile Val Ser Gly Gly Thr Thr Tyr Tyr Ala Asp Ser Val Arg
1               5                   10                  15

Gly

<210> SEQ ID NO 86
<211> LENGTH: 17
<212> TYPE: PRT
<213> ORGANISM: Artificial
<220> FEATURE:
<223> OTHER INFORMATION: AS63987 CDR2

<400> SEQUENCE: 86

Val Ile Tyr Thr Pro Ser Gly Ile Thr Asp Tyr Ala Ser Ser Val Lys
1               5                   10                  15

Gly

<210> SEQ ID NO 87
<211> LENGTH: 17
<212> TYPE: PRT
<213> ORGANISM: Artificial
<220> FEATURE:
<223> OTHER INFORMATION: AS63997 CDR2

<400> SEQUENCE: 87

Ala Ile Thr Val Gly Ser Gly Asn Thr Tyr Tyr Ala Asp Ser Val Lys
1               5                   10                  15

Gly

<210> SEQ ID NO 88
<211> LENGTH: 17
<212> TYPE: PRT
<213> ORGANISM: Artificial
<220> FEATURE:
<223> OTHER INFORMATION: AS64047 CDR2

<400> SEQUENCE: 88

Ala Val Tyr Thr Gly Asp Gly Ile Thr Tyr Tyr Ala Asp Ser Val Lys
1               5                   10                  15

Gly

<210> SEQ ID NO 89
<211> LENGTH: 17
<212> TYPE: PRT
<213> ORGANISM: Artificial
<220> FEATURE:
<223> OTHER INFORMATION: AS64052 CDR2

<400> SEQUENCE: 89

Thr Ile His Ser Gly Val Ala Thr Thr Tyr Tyr Ala Asp Ser Val Lys
1               5                   10                  15

Gly

<210> SEQ ID NO 90
<211> LENGTH: 17
<212> TYPE: PRT

```
<213> ORGANISM: Artificial
<220> FEATURE:
<223> OTHER INFORMATION: AS64062 CDR2

<400> SEQUENCE: 90

Ala Leu Tyr Thr Gly Gly Ser Thr Ser Tyr Ala Asp Ser Val Lys
1               5                   10                  15
Gly

<210> SEQ ID NO 91
<211> LENGTH: 17
<212> TYPE: PRT
<213> ORGANISM: Artificial
<220> FEATURE:
<223> OTHER INFORMATION: AS64072 CDR2

<400> SEQUENCE: 91

Ala His Gly Pro Val Ser Gly Thr Ala Tyr Tyr Thr Asp Ser Val Lys
1               5                   10                  15
Gly

<210> SEQ ID NO 92
<211> LENGTH: 17
<212> TYPE: PRT
<213> ORGANISM: Artificial
<220> FEATURE:
<223> OTHER INFORMATION: AS64097 CDR2

<400> SEQUENCE: 92

Ala Ile Asn Thr Gly Gly Gly Ser Thr Tyr Tyr Ala Asp Ser Leu Glu
1               5                   10                  15
Gly

<210> SEQ ID NO 93
<211> LENGTH: 17
<212> TYPE: PRT
<213> ORGANISM: Artificial
<220> FEATURE:
<223> OTHER INFORMATION: AS64114 CDR2

<400> SEQUENCE: 93

Val Ile Tyr Thr Arg Gly Gly His Thr Tyr Tyr Val Asp Ser Val Arg
1               5                   10                  15
Gly

<210> SEQ ID NO 94
<211> LENGTH: 17
<212> TYPE: PRT
<213> ORGANISM: Artificial
<220> FEATURE:
<223> OTHER INFORMATION: AS64123 CDR2

<400> SEQUENCE: 94

Ile Ile Tyr Thr Gly Ser Gly Ser Thr His Tyr Arg Ser Ser Val Lys
1               5                   10                  15
Gly

<210> SEQ ID NO 95
<211> LENGTH: 17
<212> TYPE: PRT
<213> ORGANISM: Artificial
<220> FEATURE:
<223> OTHER INFORMATION: AS64130 CDR2
```

```
<400> SEQUENCE: 95

Thr Ile Asp Ser Arg Gly Thr Ile Thr Tyr Tyr Ala Asp Ser Val Lys
1               5                   10                  15

Gly

<210> SEQ ID NO 96
<211> LENGTH: 17
<212> TYPE: PRT
<213> ORGANISM: Artificial
<220> FEATURE:
<223> OTHER INFORMATION: AS64137 CDR2

<400> SEQUENCE: 96

Thr Leu Val Thr Trp Val Glu Arg Thr Ala Tyr Ala Asp Ser Val Lys
1               5                   10                  15

Gly

<210> SEQ ID NO 97
<211> LENGTH: 17
<212> TYPE: PRT
<213> ORGANISM: Artificial
<220> FEATURE:
<223> OTHER INFORMATION: AS64142 CDR2

<400> SEQUENCE: 97

Cys Ile Asp Trp Thr Gly Ala Asn Ile Ala Tyr Ala Asp Ser Val Lys
1               5                   10                  15

Gly

<210> SEQ ID NO 98
<211> LENGTH: 17
<212> TYPE: PRT
<213> ORGANISM: Artificial
<220> FEATURE:
<223> OTHER INFORMATION: AS64154 CDR2

<400> SEQUENCE: 98

Cys Ile Tyr Thr Gly Ser Gly Ser Thr Gly Tyr Ala Asp Ser Val Lys
1               5                   10                  15

Gly

<210> SEQ ID NO 99
<211> LENGTH: 17
<212> TYPE: PRT
<213> ORGANISM: Artificial
<220> FEATURE:
<223> OTHER INFORMATION: AS64160 CDR2

<400> SEQUENCE: 99

Ala Met Cys Phe Gly Gly Leu Val Thr His Tyr Ala Asp Ser Val Lys
1               5                   10                  15

Gly

<210> SEQ ID NO 100
<211> LENGTH: 16
<212> TYPE: PRT
<213> ORGANISM: Artificial
<220> FEATURE:
<223> OTHER INFORMATION: AS64228 CDR2

<400> SEQUENCE: 100

Arg Ile Gln Pro Gly Gly Asn Thr Tyr Tyr Ala Asp Ser Val Lys Gly
1               5                   10                  15
```

```
<210> SEQ ID NO 101
<211> LENGTH: 17
<212> TYPE: PRT
<213> ORGANISM: Artificial
<220> FEATURE:
<223> OTHER INFORMATION: AS64300 CDR2

<400> SEQUENCE: 101

Tyr Ile Asn Thr Ile Gly Asn Thr Tyr Tyr Thr Asp Ser Val Lys
1               5                   10                  15

Gly

<210> SEQ ID NO 102
<211> LENGTH: 17
<212> TYPE: PRT
<213> ORGANISM: Artificial
<220> FEATURE:
<223> OTHER INFORMATION: AS64380 CDR2

<400> SEQUENCE: 102

Val Ile Tyr Thr Arg Gly Gly His Thr Tyr Tyr Val Asp Ser Val Arg
1               5                   10                  15

Gly

<210> SEQ ID NO 103
<211> LENGTH: 17
<212> TYPE: PRT
<213> ORGANISM: Artificial
<220> FEATURE:
<223> OTHER INFORMATION: AS64395 CDR2

<400> SEQUENCE: 103

Thr Leu Val Thr Trp Ala Glu Arg Thr Ala Tyr Ala Asp Ser Val Lys
1               5                   10                  15

Gly

<210> SEQ ID NO 104
<211> LENGTH: 17
<212> TYPE: PRT
<213> ORGANISM: Artificial
<220> FEATURE:
<223> OTHER INFORMATION: AS64443 CDR2

<400> SEQUENCE: 104

Ile Ile Tyr Thr Gly Gly Glu Ser Thr His Tyr Arg Ser Ser Val Lys
1               5                   10                  15

Gly

<210> SEQ ID NO 105
<211> LENGTH: 17
<212> TYPE: PRT
<213> ORGANISM: Artificial
<220> FEATURE:
<223> OTHER INFORMATION: AS64511 CDR2

<400> SEQUENCE: 105

Thr Ile Thr Thr Gly Asp Gly Glu Thr Ala Tyr Ala Asp Ser Val Lys
1               5                   10                  15

Gly

<210> SEQ ID NO 106
<211> LENGTH: 17
```

```
<212> TYPE: PRT
<213> ORGANISM: Artificial
<220> FEATURE:
<223> OTHER INFORMATION: AS64536 CDR2

<400> SEQUENCE: 106

Leu Ile Tyr Pro Gly Gly Gly Ser Thr Tyr Tyr Ala Ser Ser Val Lys
1               5                   10                  15

Gly

<210> SEQ ID NO 107
<211> LENGTH: 17
<212> TYPE: PRT
<213> ORGANISM: Artificial
<220> FEATURE:
<223> OTHER INFORMATION: AS64597 CDR2

<400> SEQUENCE: 107

Thr Ile Asp Ser Gly Val Gly Thr Thr Tyr Tyr Ala Asp Ser Val Lys
1               5                   10                  15

Gly

<210> SEQ ID NO 108
<211> LENGTH: 16
<212> TYPE: PRT
<213> ORGANISM: Artificial
<220> FEATURE:
<223> OTHER INFORMATION: AS64617 CDR2

<400> SEQUENCE: 108

Arg Ile Ser Thr Ser Gly Phe Thr Asn Tyr Ala Ala Ser Val Lys Gly
1               5                   10                  15

<210> SEQ ID NO 109
<211> LENGTH: 17
<212> TYPE: PRT
<213> ORGANISM: Artificial
<220> FEATURE:
<223> OTHER INFORMATION: AS64634 CDR2

<400> SEQUENCE: 109

Val Phe Tyr Pro Gly Gly Gly Ser Thr Asn Tyr Ala Asp Ser Ala Lys
1               5                   10                  15

Gly

<210> SEQ ID NO 110
<211> LENGTH: 17
<212> TYPE: PRT
<213> ORGANISM: Artificial
<220> FEATURE:
<223> OTHER INFORMATION: AS69498 CDR2

<400> SEQUENCE: 110

Val Ile Tyr Thr Arg Gly Gly His Thr Tyr Tyr Ile Asp Ser Val Arg
1               5                   10                  15

Gly

<210> SEQ ID NO 111
<211> LENGTH: 18
<212> TYPE: PRT
<213> ORGANISM: Artificial
<220> FEATURE:
<223> OTHER INFORMATION: AS69500 CDR2

<400> SEQUENCE: 111
```

```
Ser Ile Phe Thr Gly Thr Gly Gly Ser Thr Tyr Tyr Ala Asp Ser Val
1               5                   10                  15
Lys Gly

<210> SEQ ID NO 112
<211> LENGTH: 17
<212> TYPE: PRT
<213> ORGANISM: Artificial
<220> FEATURE:
<223> OTHER INFORMATION: AS69527 CDR2

<400> SEQUENCE: 112

Ala Ile Tyr Thr Asp Asp Gly Ser Thr Trp Tyr Ala Asp Ser Val Lys
1               5                   10                  15
Gly

<210> SEQ ID NO 113
<211> LENGTH: 17
<212> TYPE: PRT
<213> ORGANISM: Artificial
<220> FEATURE:
<223> OTHER INFORMATION: AS68280 CDR2

<400> SEQUENCE: 113

Ala Ile Ser Thr Gly Asp Gly Ala Thr Ala Tyr Ala Asp Ser Val Lys
1               5                   10                  15
Gly

<210> SEQ ID NO 114
<211> LENGTH: 16
<212> TYPE: PRT
<213> ORGANISM: Artificial
<220> FEATURE:
<223> OTHER INFORMATION: AS68355 CDR2

<400> SEQUENCE: 114

Ala Ile Asp Ser Asp Gly Ser Thr Ser Tyr Ala Asp Ser Val Lys Gly
1               5                   10                  15

<210> SEQ ID NO 115
<211> LENGTH: 16
<212> TYPE: PRT
<213> ORGANISM: Artificial
<220> FEATURE:
<223> OTHER INFORMATION: AS69443 CDR2

<400> SEQUENCE: 115

Thr Ile Ser Ser Asp Gly Ser Thr Tyr Tyr Ala Asp Ser Val Lys Gly
1               5                   10                  15

<210> SEQ ID NO 116
<211> LENGTH: 17
<212> TYPE: PRT
<213> ORGANISM: Artificial
<220> FEATURE:
<223> OTHER INFORMATION: AS75376 CDR2

<400> SEQUENCE: 116

Val Ile Tyr Thr Gly Asp Gly Ser Thr Tyr Tyr Ala Asp Ser Val Lys
1               5                   10                  15
Gly

<210> SEQ ID NO 117
```

```
<211> LENGTH: 17
<212> TYPE: PRT
<213> ORGANISM: Artificial
<220> FEATURE:
<223> OTHER INFORMATION: AS75387 CDR2

<400> SEQUENCE: 117

Val Ala Tyr Thr Gly Gly Asp Ile Gln Tyr Leu Thr Asp Ser Val Lys
1               5                   10                  15

Gly

<210> SEQ ID NO 118
<211> LENGTH: 16
<212> TYPE: PRT
<213> ORGANISM: Artificial
<220> FEATURE:
<223> OTHER INFORMATION: AS75695 CDR2

<400> SEQUENCE: 118

Phe Ile Asp Ala Gly Gly Ala Thr Ile Tyr Ala Asp Pro Val Lys Gly
1               5                   10                  15

<210> SEQ ID NO 119
<211> LENGTH: 16
<212> TYPE: PRT
<213> ORGANISM: Artificial
<220> FEATURE:
<223> OTHER INFORMATION: AS76169 CDR2

<400> SEQUENCE: 119

Tyr Ile Arg Asp Asn Ile Met Thr Ser Tyr Asp Ser Val Lys Gly
1               5                   10                  15

<210> SEQ ID NO 120
<211> LENGTH: 17
<212> TYPE: PRT
<213> ORGANISM: Artificial
<220> FEATURE:
<223> OTHER INFORMATION: AS63931 CDR2

<400> SEQUENCE: 120

Ala Ile Thr Val Gly Ser Gly Asn Thr Tyr Tyr Ala Asp Ser Val Thr
1               5                   10                  15

Gly

<210> SEQ ID NO 121
<211> LENGTH: 17
<212> TYPE: PRT
<213> ORGANISM: Artificial
<220> FEATURE:
<223> OTHER INFORMATION: AS63937 CDR2

<400> SEQUENCE: 121

Cys Ile His Thr Gly Leu Gly Arg Thr Tyr Tyr Ala Asp Ser Val Lys
1               5                   10                  15

Gly

<210> SEQ ID NO 122
<211> LENGTH: 17
<212> TYPE: PRT
<213> ORGANISM: Artificial
<220> FEATURE:
<223> OTHER INFORMATION: AS63948 CDR2

<400> SEQUENCE: 122
```

```
Cys Ile Tyr Thr Gly Ser Gly Ser Thr Gly Tyr Ala Asp Ser Val Lys
1               5                   10                  15

Gly

<210> SEQ ID NO 123
<211> LENGTH: 16
<212> TYPE: PRT
<213> ORGANISM: Artificial
<220> FEATURE:
<223> OTHER INFORMATION: AS63956 CDR2

<400> SEQUENCE: 123

Leu Ile Asn Ser Ser Gly Gly Thr Tyr Tyr Ala Asp Ser Val Arg Gly
1               5                   10                  15

<210> SEQ ID NO 124
<211> LENGTH: 16
<212> TYPE: PRT
<213> ORGANISM: Artificial
<220> FEATURE:
<223> OTHER INFORMATION: AS63965 CDR2

<400> SEQUENCE: 124

Lys Val Ile Ser Asp Gly Thr Thr Val Tyr Ala Asp Ser Val Lys Gly
1               5                   10                  15

<210> SEQ ID NO 125
<211> LENGTH: 16
<212> TYPE: PRT
<213> ORGANISM: Artificial
<220> FEATURE:
<223> OTHER INFORMATION: AS63993 CDR2

<400> SEQUENCE: 125

Leu Val Ala Thr Ala Gly Asn Ser Val Tyr Ala Asp Ser Val Lys Gly
1               5                   10                  15

<210> SEQ ID NO 126
<211> LENGTH: 17
<212> TYPE: PRT
<213> ORGANISM: Artificial
<220> FEATURE:
<223> OTHER INFORMATION: AS63999 CDR2

<400> SEQUENCE: 126

Ile Ile Tyr Thr Gly Gly Ile Ser Thr His Tyr Arg Ser Ser Val Lys
1               5                   10                  15

Gly

<210> SEQ ID NO 127
<211> LENGTH: 17
<212> TYPE: PRT
<213> ORGANISM: Artificial
<220> FEATURE:
<223> OTHER INFORMATION: AS64006 CDR2

<400> SEQUENCE: 127

Leu Ile Tyr Thr Ser Gly Thr Ser Glu Tyr Tyr Ala Asp Ser Val Lys
1               5                   10                  15

Gly

<210> SEQ ID NO 128
<211> LENGTH: 17
<212> TYPE: PRT
<213> ORGANISM: Artificial
```

```
<220> FEATURE:
<223> OTHER INFORMATION: AS64057 CDR2

<400> SEQUENCE: 128

Cys Ile Ser Trp Thr Gly Ala Asn Ile Ala Tyr Ala Asp Ser Val Lys
1               5                   10                  15
Gly

<210> SEQ ID NO 129
<211> LENGTH: 16
<212> TYPE: PRT
<213> ORGANISM: Artificial
<220> FEATURE:
<223> OTHER INFORMATION: AS64060 CDR2

<400> SEQUENCE: 129

Val Ile Asp Ser Gly Gly Ser Thr Ser Tyr Ala Asp Ser Val Lys Gly
1               5                   10                  15

<210> SEQ ID NO 130
<211> LENGTH: 17
<212> TYPE: PRT
<213> ORGANISM: Artificial
<220> FEATURE:
<223> OTHER INFORMATION: AS64071 CDR2

<400> SEQUENCE: 130

Phe Ile Val Met Ile Arg Gly Thr Thr Tyr Tyr Gly Ala Ser Val Lys
1               5                   10                  15
Gly

<210> SEQ ID NO 131
<211> LENGTH: 17
<212> TYPE: PRT
<213> ORGANISM: Artificial
<220> FEATURE:
<223> OTHER INFORMATION: AS64093 CDR2

<400> SEQUENCE: 131

Ser Ile Tyr Pro Ala Gly Gly Arg Thr Tyr Tyr Ala Asp Ser Val Lys
1               5                   10                  15
Gly

<210> SEQ ID NO 132
<211> LENGTH: 16
<212> TYPE: PRT
<213> ORGANISM: Artificial
<220> FEATURE:
<223> OTHER INFORMATION: AS64118 CDR2

<400> SEQUENCE: 132

Phe Ile Asn Ser Ala Gly Ser Thr Tyr Tyr Ala Asp Ser Val Lys Gly
1               5                   10                  15

<210> SEQ ID NO 133
<211> LENGTH: 17
<212> TYPE: PRT
<213> ORGANISM: Artificial
<220> FEATURE:
<223> OTHER INFORMATION: AS64120 CDR2

<400> SEQUENCE: 133

Ser Ile Tyr Pro Ala Gly Gly Arg Pro Tyr Tyr Ala Asp Ser Val Lys
1               5                   10                  15
```

Gly

```
<210> SEQ ID NO 134
<211> LENGTH: 17
<212> TYPE: PRT
<213> ORGANISM: Artificial
<220> FEATURE:
<223> OTHER INFORMATION: AS64124 CDR2

<400> SEQUENCE: 134

Ala Ile Ala Thr Ile Gly Gly Thr Thr Arg Tyr Ala Asp Ser Val Lys
1               5                   10                  15

Gly

<210> SEQ ID NO 135
<211> LENGTH: 16
<212> TYPE: PRT
<213> ORGANISM: Artificial
<220> FEATURE:
<223> OTHER INFORMATION: AS64135 CDR2

<400> SEQUENCE: 135

Ala Met Gln Pro Asp Gly Thr Thr Ser Tyr Ser Asp Ser Val Lys Gly
1               5                   10                  15

<210> SEQ ID NO 136
<211> LENGTH: 17
<212> TYPE: PRT
<213> ORGANISM: Artificial
<220> FEATURE:
<223> OTHER INFORMATION: AS64163 CDR2

<400> SEQUENCE: 136

Ala Ile Ser Thr Gly Ser Gly Ser Thr Tyr Tyr Ala Gly Ser Val Lys
1               5                   10                  15

Gly

<210> SEQ ID NO 137
<211> LENGTH: 17
<212> TYPE: PRT
<213> ORGANISM: Artificial
<220> FEATURE:
<223> OTHER INFORMATION: AS64182 CDR2

<400> SEQUENCE: 137

Cys Ile Tyr Thr Gly Ser Gly Ser Thr Gly Tyr Ala Asp Ser Val Lys
1               5                   10                  15

Gly

<210> SEQ ID NO 138
<211> LENGTH: 17
<212> TYPE: PRT
<213> ORGANISM: Artificial
<220> FEATURE:
<223> OTHER INFORMATION: AS64183 CDR2

<400> SEQUENCE: 138

Ser Val Tyr Thr Asp Asp Asp Ser Thr Met Tyr Thr Asp Ser Val Lys
1               5                   10                  15

Gly

<210> SEQ ID NO 139
<211> LENGTH: 17
<212> TYPE: PRT
```

```
<213> ORGANISM: Artificial
<220> FEATURE:
<223> OTHER INFORMATION: AS64207 CDR2

<400> SEQUENCE: 139

Thr Ile Val Ser Gly Gly Thr Thr Tyr Tyr Ala Asp Ser Val Arg
1               5                   10                  15
Gly

<210> SEQ ID NO 140
<211> LENGTH: 17
<212> TYPE: PRT
<213> ORGANISM: Artificial
<220> FEATURE:
<223> OTHER INFORMATION: AS64276 CDR2

<400> SEQUENCE: 140

Gln Ile Phe Thr Gly Arg Gly Thr Thr Gly Tyr Ala Asp Ser Val Lys
1               5                   10                  15
Gly

<210> SEQ ID NO 141
<211> LENGTH: 16
<212> TYPE: PRT
<213> ORGANISM: Artificial
<220> FEATURE:
<223> OTHER INFORMATION: AS64336 CDR2

<400> SEQUENCE: 141

His Ile Phe Ser Asp Gly Ser Arg Tyr Tyr Ala Asp Ser Val Lys Gly
1               5                   10                  15

<210> SEQ ID NO 142
<211> LENGTH: 20
<212> TYPE: PRT
<213> ORGANISM: Artificial
<220> FEATURE:
<223> OTHER INFORMATION: AS64346 CDR2

<400> SEQUENCE: 142

Thr Ile Gly Thr Gly Asp Ile Phe Asn Gly Ala Ala Tyr Tyr Val Asp
1               5                   10                  15
Ser Val Lys Gly
            20

<210> SEQ ID NO 143
<211> LENGTH: 17
<212> TYPE: PRT
<213> ORGANISM: Artificial
<220> FEATURE:
<223> OTHER INFORMATION: AS64420 CDR2

<400> SEQUENCE: 143

Thr Ile Ser Thr Ala Gly Gly Ser Thr Trp Tyr Thr Asp Ser Val Lys
1               5                   10                  15
Gly

<210> SEQ ID NO 144
<211> LENGTH: 17
<212> TYPE: PRT
<213> ORGANISM: Artificial
<220> FEATURE:
<223> OTHER INFORMATION: AS64473 CDR2

<400> SEQUENCE: 144
```

```
Cys Ile Tyr Thr Gly Ser Gly Thr Thr Gly Tyr Ala Asp Ser Val Lys
1               5                   10                  15

Gly

<210> SEQ ID NO 145
<211> LENGTH: 17
<212> TYPE: PRT
<213> ORGANISM: Artificial
<220> FEATURE:
<223> OTHER INFORMATION: AS64475 CDR2

<400> SEQUENCE: 145

Thr Ile Thr Ile Ser Gly Gly Ser Thr Trp Tyr Ala Asp Ser Val Lys
1               5                   10                  15

Gly

<210> SEQ ID NO 146
<211> LENGTH: 17
<212> TYPE: PRT
<213> ORGANISM: Artificial
<220> FEATURE:
<223> OTHER INFORMATION: AS64513 CDR2

<400> SEQUENCE: 146

Ala Ala Cys Thr Gly Gly Gly Ser Thr Tyr Tyr Ala Asp Ser Val Lys
1               5                   10                  15

Gly

<210> SEQ ID NO 147
<211> LENGTH: 17
<212> TYPE: PRT
<213> ORGANISM: Artificial
<220> FEATURE:
<223> OTHER INFORMATION: AS64562 CDR2

<400> SEQUENCE: 147

Val Ile His Thr Gly Gly Asp Thr Thr Tyr Tyr Ala Asp Ser Val Lys
1               5                   10                  15

Gly

<210> SEQ ID NO 148
<211> LENGTH: 17
<212> TYPE: PRT
<213> ORGANISM: Artificial
<220> FEATURE:
<223> OTHER INFORMATION: AS64583 CDR2

<400> SEQUENCE: 148

Cys Thr Ser Trp Ala Gly Gly Arg Thr Tyr Thr Ala Asp Ser Val Lys
1               5                   10                  15

Gly

<210> SEQ ID NO 149
<211> LENGTH: 17
<212> TYPE: PRT
<213> ORGANISM: Artificial
<220> FEATURE:
<223> OTHER INFORMATION: AS64594 CDR2

<400> SEQUENCE: 149

Leu Ile Tyr Thr Gly Gly Gly Ser Thr Tyr Tyr Ala Asp Ser Val Lys
1               5                   10                  15
```

Gly

<210> SEQ ID NO 150
<211> LENGTH: 17
<212> TYPE: PRT
<213> ORGANISM: Artificial
<220> FEATURE:
<223> OTHER INFORMATION: AS64605 CDR2

<400> SEQUENCE: 150

Arg Ile Tyr Thr Gly Thr Gly Ser Thr Trp Tyr Thr Asp Ser Val Lys
1               5                   10                  15

Gly

<210> SEQ ID NO 151
<211> LENGTH: 20
<212> TYPE: PRT
<213> ORGANISM: Artificial
<220> FEATURE:
<223> OTHER INFORMATION: AS64606 CDR2

<400> SEQUENCE: 151

Ala Phe Tyr Leu Ile Tyr Thr Arg Gly Gly Ser Thr Tyr Tyr Ala Ser
1               5                   10                  15

Ser Val Lys Gly
            20

<210> SEQ ID NO 152
<211> LENGTH: 17
<212> TYPE: PRT
<213> ORGANISM: Artificial
<220> FEATURE:
<223> OTHER INFORMATION: AS68121 CDR2

<400> SEQUENCE: 152

Thr Asp Tyr Ile Arg Phe Gly Arg Thr Tyr Tyr Ala Asp Ser Val Lys
1               5                   10                  15

Gly

<210> SEQ ID NO 153
<211> LENGTH: 18
<212> TYPE: PRT
<213> ORGANISM: Artificial
<220> FEATURE:
<223> OTHER INFORMATION: AS68170 CDR2

<400> SEQUENCE: 153

Thr Ile Tyr Thr Gly Gly Gly Arg Asn Leu Tyr Tyr Ala Asp Ser Val
1               5                   10                  15

Lys Gly

<210> SEQ ID NO 154
<211> LENGTH: 16
<212> TYPE: PRT
<213> ORGANISM: Artificial
<220> FEATURE:
<223> OTHER INFORMATION: AS63964 CDR2

<400> SEQUENCE: 154

Ala Ile Ser Gly Gly Arg Phe Thr Ala Tyr Ala Asp Ser Val Lys Gly
1               5                   10                  15

<210> SEQ ID NO 155
<211> LENGTH: 17

```
<212> TYPE: PRT
<213> ORGANISM: Artificial
<220> FEATURE:
<223> OTHER INFORMATION: AS64116 CDR2

<400> SEQUENCE: 155

Gly Ile Ser Thr Gly Gly Gly Thr Val Tyr Ala Asp Ser Val Lys
1               5                   10                  15

Gly

<210> SEQ ID NO 156
<211> LENGTH: 17
<212> TYPE: PRT
<213> ORGANISM: Artificial
<220> FEATURE:
<223> OTHER INFORMATION: AS68270 CDR2

<400> SEQUENCE: 156

Ala Ile Thr Ser Gly Thr Gly Ser Thr Ser Tyr Ala Asp Ser Val Lys
1               5                   10                  15

Asp

<210> SEQ ID NO 157
<211> LENGTH: 17
<212> TYPE: PRT
<213> ORGANISM: Artificial
<220> FEATURE:
<223> OTHER INFORMATION: AS68320 CDR2

<400> SEQUENCE: 157

Ala Ile Tyr Arg His Ser Gly Asn Thr Ala Tyr Ala Asp Ser Val Lys
1               5                   10                  15

Gly

<210> SEQ ID NO 158
<211> LENGTH: 17
<212> TYPE: PRT
<213> ORGANISM: Artificial
<220> FEATURE:
<223> OTHER INFORMATION: AS68351 CDR2

<400> SEQUENCE: 158

Gly Ile Ser Ala Ser Gly Gly Arg Thr Ser Tyr Ala Asp Ser Val Lys
1               5                   10                  15

Gly

<210> SEQ ID NO 159
<211> LENGTH: 17
<212> TYPE: PRT
<213> ORGANISM: Artificial
<220> FEATURE:
<223> OTHER INFORMATION: AS75378 CDR2

<400> SEQUENCE: 159

Ile Val Tyr Thr Gly Gly Arg Asp Thr Tyr Tyr Ala Ala Ser Val Lys
1               5                   10                  15

Gly

<210> SEQ ID NO 160
<211> LENGTH: 16
<212> TYPE: PRT
<213> ORGANISM: Artificial
<220> FEATURE:
<223> OTHER INFORMATION: AS75383 CDR2
```

<400> SEQUENCE: 160

Thr Phe Asn Asn Arg Gly Val Ala Asn Tyr His Asp Ser Val Lys Gly
1               5                   10                  15

<210> SEQ ID NO 161
<211> LENGTH: 16
<212> TYPE: PRT
<213> ORGANISM: Artificial
<220> FEATURE:
<223> OTHER INFORMATION: AS75751 CDR2

<400> SEQUENCE: 161

Ala Ile Asp Thr Asp Gly Arg Thr Ser Tyr Ala Asp Ser Val Lys Gly
1               5                   10                  15

<210> SEQ ID NO 162
<211> LENGTH: 16
<212> TYPE: PRT
<213> ORGANISM: Artificial
<220> FEATURE:
<223> OTHER INFORMATION: AS76422 CDR2

<400> SEQUENCE: 162

Thr Tyr Asn Asn Phe Gly Val Ala Asn Tyr Ala Asp Ser Val Lys Gly
1               5                   10                  15

<210> SEQ ID NO 163
<211> LENGTH: 17
<212> TYPE: PRT
<213> ORGANISM: Artificial
<220> FEATURE:
<223> OTHER INFORMATION: AS63930 CDR3

<400> SEQUENCE: 163

Glu Val Ala Asp Pro Thr Trp Gly Ser Arg Asp Gln Arg Arg Tyr Lys
1               5                   10                  15
Tyr

<210> SEQ ID NO 164
<211> LENGTH: 9
<212> TYPE: PRT
<213> ORGANISM: Artificial
<220> FEATURE:
<223> OTHER INFORMATION: AS63932 CDR3

<400> SEQUENCE: 164

Arg Tyr Gly Ser Gly Asn Val Asn Tyr
1               5

<210> SEQ ID NO 165
<211> LENGTH: 21
<212> TYPE: PRT
<213> ORGANISM: Artificial
<220> FEATURE:
<223> OTHER INFORMATION: AS63951 CDR3

<400> SEQUENCE: 165

Arg Ser Phe Ser Ile Ala Val Cys Ala Thr Arg Ser Gly Ile Thr Arg
1               5                   10                  15
Ser Asn Phe Ala Tyr
                20

<210> SEQ ID NO 166
<211> LENGTH: 20

```
<212> TYPE: PRT
<213> ORGANISM: Artificial
<220> FEATURE:
<223> OTHER INFORMATION: AS63984 CDR3

<400> SEQUENCE: 166

Gly Gly Pro Val Thr Asn Ala Pro Arg Trp Tyr Pro Leu Arg Pro Pro
1               5                   10                  15
Gly Tyr Asn Tyr
            20

<210> SEQ ID NO 167
<211> LENGTH: 16
<212> TYPE: PRT
<213> ORGANISM: Artificial
<220> FEATURE:
<223> OTHER INFORMATION: AS63987 CDR3

<400> SEQUENCE: 167

Asp Arg Pro Phe Val Cys Asn Ile Ala Asn Met Arg Arg Ser Ser Asn
1               5                   10                  15

<210> SEQ ID NO 168
<211> LENGTH: 16
<212> TYPE: PRT
<213> ORGANISM: Artificial
<220> FEATURE:
<223> OTHER INFORMATION: AS63997 CDR3

<400> SEQUENCE: 168

Gly Tyr Leu Ser Gly Gly Ser Trp Asp Val Pro Gly Arg Tyr Asn Tyr
1               5                   10                  15

<210> SEQ ID NO 169
<211> LENGTH: 16
<212> TYPE: PRT
<213> ORGANISM: Artificial
<220> FEATURE:
<223> OTHER INFORMATION: AS64047 CDR3

<400> SEQUENCE: 169

Gly Phe Val Ser Gly Gly Arg Trp Asn Gln Ser Tyr Arg Tyr Lys Tyr
1               5                   10                  15

<210> SEQ ID NO 170
<211> LENGTH: 20
<212> TYPE: PRT
<213> ORGANISM: Artificial
<220> FEATURE:
<223> OTHER INFORMATION: AS64052 CDR3

<400> SEQUENCE: 170

Gly Gly Pro Pro Ala Asn Ala Asp Arg Trp Tyr Pro Leu Arg Pro Pro
1               5                   10                  15
Gly Tyr Asn Tyr
            20

<210> SEQ ID NO 171
<211> LENGTH: 17
<212> TYPE: PRT
<213> ORGANISM: Artificial
<220> FEATURE:
<223> OTHER INFORMATION: AS64062 CDR3

<400> SEQUENCE: 171

Val Val Pro Arg Gly Gly Ser Cys Arg Leu Asp Glu Arg Gly Tyr Tyr
```

His

<210> SEQ ID NO 172
<211> LENGTH: 14
<212> TYPE: PRT
<213> ORGANISM: Artificial
<220> FEATURE:
<223> OTHER INFORMATION: AS64072 CDR3

<400> SEQUENCE: 172

Glu Thr Thr Met Gly Trp Ala His Glu Arg Gly Tyr Arg Tyr
1               5                   10

<210> SEQ ID NO 173
<211> LENGTH: 18
<212> TYPE: PRT
<213> ORGANISM: Artificial
<220> FEATURE:
<223> OTHER INFORMATION: AS64097 CDR3

<400> SEQUENCE: 173

Gly Pro Asp Leu Gly Gly Ser Trp Cys Arg Pro Val Glu Arg Ala Phe
1               5                   10                  15

Thr Tyr

<210> SEQ ID NO 174
<211> LENGTH: 16
<212> TYPE: PRT
<213> ORGANISM: Artificial
<220> FEATURE:
<223> OTHER INFORMATION: AS64114 CDR3

<400> SEQUENCE: 174

Ala Ser Arg His Arg Leu Arg Leu Asn Asn Pro Arg Asp Tyr Asp Tyr
1               5                   10                  15

<210> SEQ ID NO 175
<211> LENGTH: 7
<212> TYPE: PRT
<213> ORGANISM: Artificial
<220> FEATURE:
<223> OTHER INFORMATION: AS64123 CDR3

<400> SEQUENCE: 175

Arg Phe Ser Glu Tyr Asn Tyr
1               5

<210> SEQ ID NO 176
<211> LENGTH: 20
<212> TYPE: PRT
<213> ORGANISM: Artificial
<220> FEATURE:
<223> OTHER INFORMATION: AS64130 CDR3

<400> SEQUENCE: 176

Gly Gly Pro Arg Thr Asn Asp Asp Arg Trp Tyr Pro Leu Arg Pro Pro
1               5                   10                  15

Gly Tyr Asn Tyr
            20

<210> SEQ ID NO 177
<211> LENGTH: 17
<212> TYPE: PRT
<213> ORGANISM: Artificial

```
<220> FEATURE:
<223> OTHER INFORMATION: AS64137 CDR3

<400> SEQUENCE: 177

Ala Ala Ala Ser Thr Asp Val Arg Leu Leu Asp Pro Gly Asp Phe Ala
1               5                   10                  15
Tyr

<210> SEQ ID NO 178
<211> LENGTH: 17
<212> TYPE: PRT
<213> ORGANISM: Artificial
<220> FEATURE:
<223> OTHER INFORMATION: AS64142 CDR3

<400> SEQUENCE: 178

Asp Thr Thr Ser Gly Tyr Cys Ser Gly Phe Trp Ser Thr Ser Arg Tyr
1               5                   10                  15
Ser

<210> SEQ ID NO 179
<211> LENGTH: 17
<212> TYPE: PRT
<213> ORGANISM: Artificial
<220> FEATURE:
<223> OTHER INFORMATION: AS64154 CDR3

<400> SEQUENCE: 179

Ser Ser Pro Arg Trp Gly Gly Thr Cys Arg Arg Trp Ser Gln Tyr Asn
1               5                   10                  15
Tyr

<210> SEQ ID NO 180
<211> LENGTH: 19
<212> TYPE: PRT
<213> ORGANISM: Artificial
<220> FEATURE:
<223> OTHER INFORMATION: AS64160 CDR3

<400> SEQUENCE: 180

Asp Phe Gly Arg Asp Lys Asn Tyr Leu Arg Pro Leu Leu Pro His Ala
1               5                   10                  15
Tyr Asn Tyr

<210> SEQ ID NO 181
<211> LENGTH: 9
<212> TYPE: PRT
<213> ORGANISM: Artificial
<220> FEATURE:
<223> OTHER INFORMATION: AS64228 CDR3

<400> SEQUENCE: 181

Leu Cys Trp Arg Glu Asn Val Asn Tyr
1               5

<210> SEQ ID NO 182
<211> LENGTH: 15
<212> TYPE: PRT
<213> ORGANISM: Artificial
<220> FEATURE:
<223> OTHER INFORMATION: AS64300 CDR3

<400> SEQUENCE: 182

Phe Asn Tyr Gly Gly Ala Trp Tyr Glu Glu Arg Ser Tyr Lys Tyr
```

```
<210> SEQ ID NO 183
<211> LENGTH: 16
<212> TYPE: PRT
<213> ORGANISM: Artificial
<220> FEATURE:
<223> OTHER INFORMATION: AS64380 CDR3

<400> SEQUENCE: 183

Ser Ser Arg His Arg Leu Gly Leu Asn Asn Pro Arg Asp Tyr Asp Tyr
1               5                   10                  15

<210> SEQ ID NO 184
<211> LENGTH: 16
<212> TYPE: PRT
<213> ORGANISM: Artificial
<220> FEATURE:
<223> OTHER INFORMATION: AS64395 CDR3

<400> SEQUENCE: 184

Ala Ala Ser Thr Ala Val Arg Leu Leu Asp Pro Gly Asp Phe Ala Tyr
1               5                   10                  15

<210> SEQ ID NO 185
<211> LENGTH: 7
<212> TYPE: PRT
<213> ORGANISM: Artificial
<220> FEATURE:
<223> OTHER INFORMATION: AS64443 CDR3

<400> SEQUENCE: 185

Arg Phe Pro Ala Val Thr Tyr
1               5

<210> SEQ ID NO 186
<211> LENGTH: 16
<212> TYPE: PRT
<213> ORGANISM: Artificial
<220> FEATURE:
<223> OTHER INFORMATION: AS64511 CDR3

<400> SEQUENCE: 186

Asn Leu Arg Ile Gly Gly Asp Trp Phe Asp Gly Arg Asp Phe Arg Ala
1               5                   10                  15

<210> SEQ ID NO 187
<211> LENGTH: 16
<212> TYPE: PRT
<213> ORGANISM: Artificial
<220> FEATURE:
<223> OTHER INFORMATION: AS64536 CDR3

<400> SEQUENCE: 187

Lys Trp Gly Leu Gly Gly Gly Leu Lys Ser Asp Thr Tyr Met Tyr
1               5                   10                  15

<210> SEQ ID NO 188
<211> LENGTH: 20
<212> TYPE: PRT
<213> ORGANISM: Artificial
<220> FEATURE:
<223> OTHER INFORMATION: AS64597 CDR3

<400> SEQUENCE: 188

Gly Gly Pro Pro Thr Asp Gly Asp Arg Trp Tyr Pro Leu Arg Pro Pro
1               5                   10                  15
```

```
Gly Tyr Asn Tyr
            20

<210> SEQ ID NO 189
<211> LENGTH: 10
<212> TYPE: PRT
<213> ORGANISM: Artificial
<220> FEATURE:
<223> OTHER INFORMATION: AS64617 CDR3

<400> SEQUENCE: 189

Ile Val Gly Arg Thr Cys Ser Leu Asn Tyr
1               5                   10

<210> SEQ ID NO 190
<211> LENGTH: 16
<212> TYPE: PRT
<213> ORGANISM: Artificial
<220> FEATURE:
<223> OTHER INFORMATION: AS64634 CDR3

<400> SEQUENCE: 190

Arg Arg Trp Val Ser Gly Thr Cys Tyr Trp Asp Ser Asp Phe His Tyr
1               5                   10                  15

<210> SEQ ID NO 191
<211> LENGTH: 16
<212> TYPE: PRT
<213> ORGANISM: Artificial
<220> FEATURE:
<223> OTHER INFORMATION: AS69498 CDR3

<400> SEQUENCE: 191

Ser Ser Arg His Arg Leu Arg Leu Ser Asp Pro Arg Asp Tyr Asp Tyr
1               5                   10                  15

<210> SEQ ID NO 192
<211> LENGTH: 17
<212> TYPE: PRT
<213> ORGANISM: Artificial
<220> FEATURE:
<223> OTHER INFORMATION: AS69500 CDR3

<400> SEQUENCE: 192

Arg Ala Phe Gln Val Gly Tyr Cys Tyr Leu Arg Thr Asp Val Tyr Asn
1               5                   10                  15

Tyr

<210> SEQ ID NO 193
<211> LENGTH: 16
<212> TYPE: PRT
<213> ORGANISM: Artificial
<220> FEATURE:
<223> OTHER INFORMATION: AS69527 CDR3

<400> SEQUENCE: 193

Arg Arg Trp Ala Cys Pro Arg Val Gly Ser Trp His Glu Phe Ala Tyr
1               5                   10                  15

<210> SEQ ID NO 194
<211> LENGTH: 16
<212> TYPE: PRT
<213> ORGANISM: Artificial
<220> FEATURE:
<223> OTHER INFORMATION: AS68280 CDR3
```

```
<400> SEQUENCE: 194

Ala Arg Gly Arg Phe Ile Asp Trp Thr Lys Ala Thr Gln Tyr Asp Tyr
1               5                   10                  15

<210> SEQ ID NO 195
<211> LENGTH: 20
<212> TYPE: PRT
<213> ORGANISM: Artificial
<220> FEATURE:
<223> OTHER INFORMATION: AS68355 CDR3

<400> SEQUENCE: 195

Ala Ile Val Gly Gly Phe Asn Ala Tyr Cys Ser Gly Gly Tyr Val Leu
1               5                   10                  15

Asp Phe Gly Ala
            20

<210> SEQ ID NO 196
<211> LENGTH: 24
<212> TYPE: PRT
<213> ORGANISM: Artificial
<220> FEATURE:
<223> OTHER INFORMATION: AS69443 CDR3

<400> SEQUENCE: 196

Asp Phe Leu Thr Gly Phe Tyr Tyr Ser Asp Ser Pro His Pro Ala Pro
1               5                   10                  15

Cys Ser Ala Ser Asp Phe Gly Tyr
            20

<210> SEQ ID NO 197
<211> LENGTH: 17
<212> TYPE: PRT
<213> ORGANISM: Artificial
<220> FEATURE:
<223> OTHER INFORMATION: AS75376 CDR3

<400> SEQUENCE: 197

Asp Pro Asn Pro Asp Tyr Met Leu Pro Phe Arg Pro Ser Arg Arg Ser
1               5                   10                  15

Trp

<210> SEQ ID NO 198
<211> LENGTH: 14
<212> TYPE: PRT
<213> ORGANISM: Artificial
<220> FEATURE:
<223> OTHER INFORMATION: AS75387 CDR3

<400> SEQUENCE: 198

Asp Leu Arg Leu Pro Arg Ala Gly Gly Cys Ala Tyr Ser Tyr
1               5                   10

<210> SEQ ID NO 199
<211> LENGTH: 13
<212> TYPE: PRT
<213> ORGANISM: Artificial
<220> FEATURE:
<223> OTHER INFORMATION: AS75695 CDR3

<400> SEQUENCE: 199

Asp Arg Arg Gly Arg Val Arg Arg Cys Glu Tyr Asn Ala
1               5                   10
```

```
<210> SEQ ID NO 200
<211> LENGTH: 17
<212> TYPE: PRT
<213> ORGANISM: Artificial
<220> FEATURE:
<223> OTHER INFORMATION: AS76169 CDR3

<400> SEQUENCE: 200

Asp Arg Gly Gly Tyr Ala Asn Ser Cys Ala Val Ala Ala Arg Tyr Asp
1               5                   10                  15
Tyr

<210> SEQ ID NO 201
<211> LENGTH: 16
<212> TYPE: PRT
<213> ORGANISM: Artificial
<220> FEATURE:
<223> OTHER INFORMATION: AS63931 CDR3

<400> SEQUENCE: 201

Gly Trp Leu Ser Gly Gly Ser Trp His Val Pro Gly Arg Tyr Asn Tyr
1               5                   10                  15

<210> SEQ ID NO 202
<211> LENGTH: 14
<212> TYPE: PRT
<213> ORGANISM: Artificial
<220> FEATURE:
<223> OTHER INFORMATION: AS63937 CDR3

<400> SEQUENCE: 202

Asp Ser Arg Arg Pro Cys Met Val Ala Ala Gly Tyr Thr Tyr
1               5                   10

<210> SEQ ID NO 203
<211> LENGTH: 17
<212> TYPE: PRT
<213> ORGANISM: Artificial
<220> FEATURE:
<223> OTHER INFORMATION: AS63948 CDR3

<400> SEQUENCE: 203

Ala Ser Pro Arg Trp Gly Gly Thr Cys Arg Arg Trp Ser Glu Tyr Asn
1               5                   10                  15
Tyr

<210> SEQ ID NO 204
<211> LENGTH: 15
<212> TYPE: PRT
<213> ORGANISM: Artificial
<220> FEATURE:
<223> OTHER INFORMATION: AS63956 CDR3

<400> SEQUENCE: 204

Tyr Gln Ala Lys Tyr Cys Ser Gly Pro Cys Ala Pro Pro Thr Asp
1               5                   10                  15

<210> SEQ ID NO 205
<211> LENGTH: 13
<212> TYPE: PRT
<213> ORGANISM: Artificial
<220> FEATURE:
<223> OTHER INFORMATION: AS63965 CDR3

<400> SEQUENCE: 205

Trp Cys Arg Glu Tyr Pro Gly Gly Ile Leu Asn Asn Gly
```

```
1               5                   10
```

<210> SEQ ID NO 206
<211> LENGTH: 10
<212> TYPE: PRT
<213> ORGANISM: Artificial
<220> FEATURE:
<223> OTHER INFORMATION: AS63993 CDR3

<400> SEQUENCE: 206

```
Arg Thr Asp Ser Glu His Ala Phe Lys Phe
1               5                   10
```

<210> SEQ ID NO 207
<211> LENGTH: 7
<212> TYPE: PRT
<213> ORGANISM: Artificial
<220> FEATURE:
<223> OTHER INFORMATION: AS63999 CDR3

<400> SEQUENCE: 207

```
Arg Tyr Thr Asp Tyr Asn Tyr
1               5
```

<210> SEQ ID NO 208
<211> LENGTH: 7
<212> TYPE: PRT
<213> ORGANISM: Artificial
<220> FEATURE:
<223> OTHER INFORMATION: AS64006 CDR3

<400> SEQUENCE: 208

```
Arg Ser Arg Thr Met Met Tyr
1               5
```

<210> SEQ ID NO 209
<211> LENGTH: 17
<212> TYPE: PRT
<213> ORGANISM: Artificial
<220> FEATURE:
<223> OTHER INFORMATION: AS64057 CDR3

<400> SEQUENCE: 209

```
Asp Thr Thr Ser Gly Ser Cys Ser Gly Phe Trp Ser Thr Ser Arg Tyr
1               5                   10                  15

Tyr
```

<210> SEQ ID NO 210
<211> LENGTH: 14
<212> TYPE: PRT
<213> ORGANISM: Artificial
<220> FEATURE:
<223> OTHER INFORMATION: AS64060 CDR3

<400> SEQUENCE: 210

```
Asp Pro Thr Ile Gly Cys Pro Gln Thr Tyr Arg Tyr Asn Tyr
1               5                   10
```

<210> SEQ ID NO 211
<211> LENGTH: 16
<212> TYPE: PRT
<213> ORGANISM: Artificial
<220> FEATURE:
<223> OTHER INFORMATION: AS64071 CDR3

<400> SEQUENCE: 211

```
Ser Thr Lys Asp Gln Phe Tyr Val Phe Asn Pro Ile Gly Tyr Asp Ser
1               5                   10                  15
```

<210> SEQ ID NO 212
<211> LENGTH: 21
<212> TYPE: PRT
<213> ORGANISM: Artificial
<220> FEATURE:
<223> OTHER INFORMATION: AS64093 CDR3

<400> SEQUENCE: 212

```
Arg Ser Phe Ser Ile Gly Val Cys Ala Thr Gln Ser Gly Ile Thr Trp
1               5                   10                  15

Ser Asn Phe Ala Tyr
            20
```

<210> SEQ ID NO 213
<211> LENGTH: 10
<212> TYPE: PRT
<213> ORGANISM: Artificial
<220> FEATURE:
<223> OTHER INFORMATION: AS64118 CDR3

<400> SEQUENCE: 213

```
Thr Trp Asp Ser Ser Cys Arg Phe Gln Tyr
1               5                   10
```

<210> SEQ ID NO 214
<211> LENGTH: 21
<212> TYPE: PRT
<213> ORGANISM: Artificial
<220> FEATURE:
<223> OTHER INFORMATION: AS64120 CDR3

<400> SEQUENCE: 214

```
Arg Ser Phe Ser Ile Ala Asp Cys Ala Thr Gln Ser Gly Ile Thr Arg
1               5                   10                  15

Ser Asn Phe Ala Tyr
            20
```

<210> SEQ ID NO 215
<211> LENGTH: 19
<212> TYPE: PRT
<213> ORGANISM: Artificial
<220> FEATURE:
<223> OTHER INFORMATION: AS64124 CDR3

<400> SEQUENCE: 215

```
Gly Arg Pro Tyr Ser Leu Pro Leu Pro Leu Pro Leu Glu Ser Gly Ala
1               5                   10                  15

Tyr Arg Tyr
```

<210> SEQ ID NO 216
<211> LENGTH: 13
<212> TYPE: PRT
<213> ORGANISM: Artificial
<220> FEATURE:
<223> OTHER INFORMATION: AS64135 CDR3

<400> SEQUENCE: 216

```
Asp Pro Met Gly Gly Ser Arg Thr Pro Cys Thr Ser Ala
1               5                   10
```

<210> SEQ ID NO 217
<211> LENGTH: 17

```
<212> TYPE: PRT
<213> ORGANISM: Artificial
<220> FEATURE:
<223> OTHER INFORMATION: AS64163 CDR3

<400> SEQUENCE: 217

Asp Pro Ser Val Cys Pro Gly Gly Met Trp Tyr Ser Lys Glu Tyr Arg
1               5                   10                  15

Tyr

<210> SEQ ID NO 218
<211> LENGTH: 17
<212> TYPE: PRT
<213> ORGANISM: Artificial
<220> FEATURE:
<223> OTHER INFORMATION: AS64182 CDR3

<400> SEQUENCE: 218

Ser Ser Pro His Trp Gly Gly Thr Cys Arg Arg Trp Ser Glu Tyr Lys
1               5                   10                  15

Tyr

<210> SEQ ID NO 219
<211> LENGTH: 13
<212> TYPE: PRT
<213> ORGANISM: Artificial
<220> FEATURE:
<223> OTHER INFORMATION: AS64183 CDR3

<400> SEQUENCE: 219

Asp Leu Ser Gly Gly Pro Ala Gly Cys Gly Tyr Thr His
1               5                   10

<210> SEQ ID NO 220
<211> LENGTH: 20
<212> TYPE: PRT
<213> ORGANISM: Artificial
<220> FEATURE:
<223> OTHER INFORMATION: AS64207 CDR3

<400> SEQUENCE: 220

Gly Gly Pro Pro Thr Asn Gly Ala Lys Trp Tyr Pro Leu Arg Pro Pro
1               5                   10                  15

Gly Tyr Asn Tyr
            20

<210> SEQ ID NO 221
<211> LENGTH: 13
<212> TYPE: PRT
<213> ORGANISM: Artificial
<220> FEATURE:
<223> OTHER INFORMATION: AS64276 CDR3

<400> SEQUENCE: 221

Ser Leu Gly Pro Gly Arg Gly Ala Cys Gly Tyr Asn Tyr
1               5                   10

<210> SEQ ID NO 222
<211> LENGTH: 13
<212> TYPE: PRT
<213> ORGANISM: Artificial
<220> FEATURE:
<223> OTHER INFORMATION: AS64336 CDR3

<400> SEQUENCE: 222
```

Arg Thr Gly Trp Ala Pro Arg Cys Ala Val Pro Gly Tyr
1               5                   10

<210> SEQ ID NO 223
<211> LENGTH: 18
<212> TYPE: PRT
<213> ORGANISM: Artificial
<220> FEATURE:
<223> OTHER INFORMATION: AS64346 CDR3

<400> SEQUENCE: 223

Val Gln Ser Lys Ser Ser Asn Tyr Val Leu Arg Asp Ala Ser Thr Tyr
1               5                   10                  15

Asn Tyr

<210> SEQ ID NO 224
<211> LENGTH: 7
<212> TYPE: PRT
<213> ORGANISM: Artificial
<220> FEATURE:
<223> OTHER INFORMATION: AS64420 CDR3

<400> SEQUENCE: 224

Arg Ser Arg Tyr Ala Thr Tyr
1               5

<210> SEQ ID NO 225
<211> LENGTH: 17
<212> TYPE: PRT
<213> ORGANISM: Artificial
<220> FEATURE:
<223> OTHER INFORMATION: AS64473 CDR3

<400> SEQUENCE: 225

Ser Ser Pro Gln Trp Gly Gly Thr Cys Arg Arg Trp Ser Glu Tyr Asn
1               5                   10                  15

Tyr

<210> SEQ ID NO 226
<211> LENGTH: 7
<212> TYPE: PRT
<213> ORGANISM: Artificial
<220> FEATURE:
<223> OTHER INFORMATION: AS64475 CDR3

<400> SEQUENCE: 226

Arg Asp Thr Ala Arg Thr Tyr
1               5

<210> SEQ ID NO 227
<211> LENGTH: 18
<212> TYPE: PRT
<213> ORGANISM: Artificial
<220> FEATURE:
<223> OTHER INFORMATION: AS64513 CDR3

<400> SEQUENCE: 227

Gly Tyr Tyr Ser Gly Ser Gly Pro Gly Tyr Leu Leu Pro Trp Arg Tyr
1               5                   10                  15

Asn Tyr

<210> SEQ ID NO 228
<211> LENGTH: 22
<212> TYPE: PRT
<213> ORGANISM: Artificial

-continued

```
<220> FEATURE:
<223> OTHER INFORMATION: AS64562 CDR3

<400> SEQUENCE: 228

Gly Phe Arg Pro Arg Gly Gly Tyr Thr Gly Asp Val Leu Ala Gln
1               5                   10                  15

Ala Ala Ala Tyr Asn Tyr
            20

<210> SEQ ID NO 229
<211> LENGTH: 17
<212> TYPE: PRT
<213> ORGANISM: Artificial
<220> FEATURE:
<223> OTHER INFORMATION: AS64583 CDR3

<400> SEQUENCE: 229

Lys Ala His Pro Asp Cys Ser Gly Asp Trp Ser Pro Ser Gly Tyr Glu
1               5                   10                  15

Tyr

<210> SEQ ID NO 230
<211> LENGTH: 7
<212> TYPE: PRT
<213> ORGANISM: Artificial
<220> FEATURE:
<223> OTHER INFORMATION: AS64594 CDR3

<400> SEQUENCE: 230

Arg Thr Gln Thr Arg Asn Tyr
1               5

<210> SEQ ID NO 231
<211> LENGTH: 22
<212> TYPE: PRT
<213> ORGANISM: Artificial
<220> FEATURE:
<223> OTHER INFORMATION: AS64605 CDR3

<400> SEQUENCE: 231

Arg Ser Asn Ser Tyr Ser Tyr Ser Ser Cys Asp Tyr Gly Pro Leu Thr
1               5                   10                  15

Arg Gly Gly Tyr Asn Phe
            20

<210> SEQ ID NO 232
<211> LENGTH: 7
<212> TYPE: PRT
<213> ORGANISM: Artificial
<220> FEATURE:
<223> OTHER INFORMATION: AS64606 CDR3

<400> SEQUENCE: 232

Arg Leu Asp Glu Lys Met Tyr
1               5

<210> SEQ ID NO 233
<211> LENGTH: 21
<212> TYPE: PRT
<213> ORGANISM: Artificial
<220> FEATURE:
<223> OTHER INFORMATION: AS68121 CDR3

<400> SEQUENCE: 233

Asp Pro Gly Ser Arg Thr Asp Asp Ser Cys Gly Thr Ser Tyr Asn Lys
```

```
1               5                   10                  15

Gly Asn Phe Gly Tyr
            20

<210> SEQ ID NO 234
<211> LENGTH: 20
<212> TYPE: PRT
<213> ORGANISM: Artificial
<220> FEATURE:
<223> OTHER INFORMATION: AS68170 CDR3

<400> SEQUENCE: 234

Ala Ser Asp Val Ala Val Gly Val Asn Ser Cys Gly Gly Arg Thr Ala
1               5                   10                  15

Gly Phe Asp Ala
            20

<210> SEQ ID NO 235
<211> LENGTH: 17
<212> TYPE: PRT
<213> ORGANISM: Artificial
<220> FEATURE:
<223> OTHER INFORMATION: AS63964 CDR3

<400> SEQUENCE: 235

Glu Val Val Asp Pro Thr Trp Gly Ser Arg Asp Gln Arg Arg Tyr Lys
1               5                   10                  15

Tyr

<210> SEQ ID NO 236
<211> LENGTH: 17
<212> TYPE: PRT
<213> ORGANISM: Artificial
<220> FEATURE:
<223> OTHER INFORMATION: AS64116 CDR3

<400> SEQUENCE: 236

Asp Arg Trp Asn Ser Phe Ala Asn Cys Gly Ala Trp Gly Arg Tyr Thr
1               5                   10                  15

Tyr

<210> SEQ ID NO 237
<211> LENGTH: 18
<212> TYPE: PRT
<213> ORGANISM: Artificial
<220> FEATURE:
<223> OTHER INFORMATION: AS68270 CDR3

<400> SEQUENCE: 237

Ala Ser Gly Trp Ile Val Pro Ser Arg Ser Leu Thr Ala Asn Leu Tyr
1               5                   10                  15

Arg Tyr

<210> SEQ ID NO 238
<211> LENGTH: 16
<212> TYPE: PRT
<213> ORGANISM: Artificial
<220> FEATURE:
<223> OTHER INFORMATION: AS68320 CDR3

<400> SEQUENCE: 238

Gly Arg Ala Gly Pro Trp Ala Leu Met Arg Pro Thr Glu Phe Gly Tyr
1               5                   10                  15
```

<210> SEQ ID NO 239
<211> LENGTH: 14
<212> TYPE: PRT
<213> ORGANISM: Artificial
<220> FEATURE:
<223> OTHER INFORMATION: AS68351 CDR3

<400> SEQUENCE: 239

Gly Ala Val Arg Leu Ser Thr Ser Ser Val Arg Asp Ser Ser
1               5                   10

<210> SEQ ID NO 240
<211> LENGTH: 7
<212> TYPE: PRT
<213> ORGANISM: Artificial
<220> FEATURE:
<223> OTHER INFORMATION: AS75378 CDR3

<400> SEQUENCE: 240

Arg Ser Tyr Glu Tyr Thr Tyr
1               5

<210> SEQ ID NO 241
<211> LENGTH: 16
<212> TYPE: PRT
<213> ORGANISM: Artificial
<220> FEATURE:
<223> OTHER INFORMATION: AS75383 CDR3

<400> SEQUENCE: 241

Asp Arg Arg Tyr Gly Arg Gln Trp Tyr Gln Pro Cys Glu Trp Asn Thr
1               5                   10                  15

<210> SEQ ID NO 242
<211> LENGTH: 20
<212> TYPE: PRT
<213> ORGANISM: Artificial
<220> FEATURE:
<223> OTHER INFORMATION: AS75751 CDR3

<400> SEQUENCE: 242

Gly Phe Gly Tyr Met Asn Val Ile Gln Ala Leu Asn Gly Met Arg Gln
1               5                   10                  15

Asn Pro Asp Tyr
            20

<210> SEQ ID NO 243
<211> LENGTH: 16
<212> TYPE: PRT
<213> ORGANISM: Artificial
<220> FEATURE:
<223> OTHER INFORMATION: AS76422 CDR3

<400> SEQUENCE: 243

Asp Arg Arg Asp Gly Arg Arg Trp Ser Gln Pro Cys Glu Trp Asn Thr
1               5                   10                  15

<210> SEQ ID NO 244
<211> LENGTH: 10
<212> TYPE: PRT
<213> ORGANISM: Artificial
<220> FEATURE:
<223> OTHER INFORMATION: AS64380VH4 CDR1

<400> SEQUENCE: 244

Gly Asn Thr Tyr Ser Ser Asn Tyr Met Gly
1               5                   10

```
1               5               10

<210> SEQ ID NO 245
<211> LENGTH: 10
<212> TYPE: PRT
<213> ORGANISM: Artificial
<220> FEATURE:
<223> OTHER INFORMATION: AS64380VH5 CDR1

<400> SEQUENCE: 245

Gly Asn Thr Tyr Ser Ser Asn Tyr Met Gly
1               5               10

<210> SEQ ID NO 246
<211> LENGTH: 10
<212> TYPE: PRT
<213> ORGANISM: Artificial
<220> FEATURE:
<223> OTHER INFORMATION: AS64380VH6 CDR1

<400> SEQUENCE: 246

Gly Asn Thr Tyr Ser Ser Asn Tyr Met Gly
1               5               10

<210> SEQ ID NO 247
<211> LENGTH: 10
<212> TYPE: PRT
<213> ORGANISM: Artificial
<220> FEATURE:
<223> OTHER INFORMATION: AS64380VH7 CDR1

<400> SEQUENCE: 247

Gly Asn Thr Tyr Ser Ser Asn Tyr Met Gly
1               5               10

<210> SEQ ID NO 248
<211> LENGTH: 10
<212> TYPE: PRT
<213> ORGANISM: Artificial
<220> FEATURE:
<223> OTHER INFORMATION: AS64511VH4 CDR1

<400> SEQUENCE: 248

Arg Ala Thr Tyr Ser Thr Asn Tyr Ile Ser
1               5               10

<210> SEQ ID NO 249
<211> LENGTH: 10
<212> TYPE: PRT
<213> ORGANISM: Artificial
<220> FEATURE:
<223> OTHER INFORMATION: AS64511VH5 CDR1

<400> SEQUENCE: 249

Arg Ala Thr Tyr Ser Thr Asn Tyr Ile Ser
1               5               10

<210> SEQ ID NO 250
<211> LENGTH: 10
<212> TYPE: PRT
<213> ORGANISM: Artificial
<220> FEATURE:
<223> OTHER INFORMATION: AS64511VH6 CDR1

<400> SEQUENCE: 250

Arg Ala Thr Tyr Ser Thr Asn Tyr Ile Ser
1               5               10
```

<210> SEQ ID NO 251
<211> LENGTH: 10
<212> TYPE: PRT
<213> ORGANISM: Artificial
<220> FEATURE:
<223> OTHER INFORMATION: AS63997VH4 CDR1

<400> SEQUENCE: 251

Phe Ser Gly Tyr Gly Val Ser Thr Met Ala
1               5                   10

<210> SEQ ID NO 252
<211> LENGTH: 10
<212> TYPE: PRT
<213> ORGANISM: Artificial
<220> FEATURE:
<223> OTHER INFORMATION: AS63997VH5 CDR1

<400> SEQUENCE: 252

Phe Ser Gly Tyr Gly Val Ser Thr Met Ala
1               5                   10

<210> SEQ ID NO 253
<211> LENGTH: 10
<212> TYPE: PRT
<213> ORGANISM: Artificial
<220> FEATURE:
<223> OTHER INFORMATION: AS63997VH6 CDR1

<400> SEQUENCE: 253

Phe Ser Gly Tyr Gly Val Ser Thr Met Ala
1               5                   10

<210> SEQ ID NO 254
<211> LENGTH: 17
<212> TYPE: PRT
<213> ORGANISM: Artificial
<220> FEATURE:
<223> OTHER INFORMATION: AS64380VH4 CDR2

<400> SEQUENCE: 254

Val Ile Tyr Thr Arg Gly Gly His Thr Tyr Tyr Val Asp Ser Val Arg
1               5                   10                  15

Gly

<210> SEQ ID NO 255
<211> LENGTH: 17
<212> TYPE: PRT
<213> ORGANISM: Artificial
<220> FEATURE:
<223> OTHER INFORMATION: AS64380VH5 CDR2

<400> SEQUENCE: 255

Val Ile Tyr Thr Arg Gly Gly His Thr Tyr Tyr Val Asp Ser Val Arg
1               5                   10                  15

Gly

<210> SEQ ID NO 256
<211> LENGTH: 17
<212> TYPE: PRT
<213> ORGANISM: Artificial
<220> FEATURE:
<223> OTHER INFORMATION: AS64380VH6 CDR2

<400> SEQUENCE: 256

```
Val Ile Tyr Thr Arg Gly Gly His Thr Tyr Tyr Val Asp Ser Val Arg
1               5                   10                  15

Gly

<210> SEQ ID NO 257
<211> LENGTH: 17
<212> TYPE: PRT
<213> ORGANISM: Artificial
<220> FEATURE:
<223> OTHER INFORMATION: AS64380VH7 CDR2

<400> SEQUENCE: 257

Val Ile Tyr Thr Arg Gly Gly His Thr Tyr Tyr Val Asp Ser Val Arg
1               5                   10                  15

Gly

<210> SEQ ID NO 258
<211> LENGTH: 17
<212> TYPE: PRT
<213> ORGANISM: Artificial
<220> FEATURE:
<223> OTHER INFORMATION: AS64511VH4 CDR2

<400> SEQUENCE: 258

Thr Ile Thr Thr Gly Asp Gly Glu Thr Ala Tyr Ala Asp Ser Val Lys
1               5                   10                  15

Gly

<210> SEQ ID NO 259
<211> LENGTH: 17
<212> TYPE: PRT
<213> ORGANISM: Artificial
<220> FEATURE:
<223> OTHER INFORMATION: AS64511VH5 CDR2

<400> SEQUENCE: 259

Thr Ile Thr Thr Gly Asp Gly Glu Thr Ala Tyr Ala Asp Ser Val Lys
1               5                   10                  15

Gly

<210> SEQ ID NO 260
<211> LENGTH: 17
<212> TYPE: PRT
<213> ORGANISM: Artificial
<220> FEATURE:
<223> OTHER INFORMATION: AS64511VH6 CDR2

<400> SEQUENCE: 260

Thr Ile Thr Thr Gly Asp Gly Glu Thr Ala Tyr Ala Asp Ser Val Lys
1               5                   10                  15

Gly

<210> SEQ ID NO 261
<211> LENGTH: 17
<212> TYPE: PRT
<213> ORGANISM: Artificial
<220> FEATURE:
<223> OTHER INFORMATION: AS63997VH4 CDR2

<400> SEQUENCE: 261

Ala Ile Thr Val Gly Ser Gly Asn Thr Tyr Tyr Ala Asp Ser Val Lys
1               5                   10                  15
```

Gly

<210> SEQ ID NO 262
<211> LENGTH: 17
<212> TYPE: PRT
<213> ORGANISM: Artificial
<220> FEATURE:
<223> OTHER INFORMATION: AS63997VH5 CDR2

<400> SEQUENCE: 262

Ala Ile Thr Val Gly Ser Gly Asn Thr Tyr Tyr Ala Asp Ser Val Lys
1               5                   10                  15

Gly

<210> SEQ ID NO 263
<211> LENGTH: 17
<212> TYPE: PRT
<213> ORGANISM: Artificial
<220> FEATURE:
<223> OTHER INFORMATION: AS63997VH6 CDR2

<400> SEQUENCE: 263

Ala Ile Thr Val Gly Ser Gly Asn Thr Tyr Tyr Ala Asp Ser Val Lys
1               5                   10                  15

Gly

<210> SEQ ID NO 264
<211> LENGTH: 16
<212> TYPE: PRT
<213> ORGANISM: Artificial
<220> FEATURE:
<223> OTHER INFORMATION: AS64380VH4 CDR3

<400> SEQUENCE: 264

Ser Ser Arg His Arg Leu Gly Leu Asn Asn Pro Arg Asp Tyr Asp Tyr
1               5                   10                  15

<210> SEQ ID NO 265
<211> LENGTH: 16
<212> TYPE: PRT
<213> ORGANISM: Artificial
<220> FEATURE:
<223> OTHER INFORMATION: AS64380VH5 CDR3

<400> SEQUENCE: 265

Ser Ser Arg His Arg Leu Gly Leu Asn Asn Pro Arg Asp Tyr Asp Tyr
1               5                   10                  15

<210> SEQ ID NO 266
<211> LENGTH: 16
<212> TYPE: PRT
<213> ORGANISM: Artificial
<220> FEATURE:
<223> OTHER INFORMATION: AS64380VH6 CDR3

<400> SEQUENCE: 266

Ser Ser Arg His Arg Leu Gly Leu Asn Asn Pro Arg Asp Tyr Asp Tyr
1               5                   10                  15

<210> SEQ ID NO 267
<211> LENGTH: 16
<212> TYPE: PRT
<213> ORGANISM: Artificial
<220> FEATURE:
<223> OTHER INFORMATION: AS64380VH7 CDR3

```
<400> SEQUENCE: 267

Ser Ser Arg His Arg Leu Gly Leu Asn Asn Pro Arg Asp Tyr Asp Tyr
1               5                   10                  15

<210> SEQ ID NO 268
<211> LENGTH: 16
<212> TYPE: PRT
<213> ORGANISM: Artificial
<220> FEATURE:
<223> OTHER INFORMATION: AS64511VH4 CDR3

<400> SEQUENCE: 268

Asn Leu Arg Ile Gly Gly Asp Trp Phe Asp Gly Arg Asp Phe Arg Ala
1               5                   10                  15

<210> SEQ ID NO 269
<211> LENGTH: 16
<212> TYPE: PRT
<213> ORGANISM: Artificial
<220> FEATURE:
<223> OTHER INFORMATION: AS64511VH5 CDR3

<400> SEQUENCE: 269

Asn Leu Arg Ile Gly Gly Asp Trp Phe Asp Gly Arg Asp Phe Arg Ala
1               5                   10                  15

<210> SEQ ID NO 270
<211> LENGTH: 16
<212> TYPE: PRT
<213> ORGANISM: Artificial
<220> FEATURE:
<223> OTHER INFORMATION: AS64511VH6 CDR3

<400> SEQUENCE: 270

Asn Leu Arg Ile Gly Gly Asp Trp Phe Asp Gly Arg Asp Phe Arg Ala
1               5                   10                  15

<210> SEQ ID NO 271
<211> LENGTH: 16
<212> TYPE: PRT
<213> ORGANISM: Artificial
<220> FEATURE:
<223> OTHER INFORMATION: AS63997VH4 CDR3

<400> SEQUENCE: 271

Gly Tyr Leu Ser Gly Gly Ser Trp Asp Val Pro Gly Arg Tyr Asn Tyr
1               5                   10                  15

<210> SEQ ID NO 272
<211> LENGTH: 16
<212> TYPE: PRT
<213> ORGANISM: Artificial
<220> FEATURE:
<223> OTHER INFORMATION: AS63997VH5 CDR3

<400> SEQUENCE: 272

Gly Tyr Leu Ser Gly Gly Ser Trp Asp Val Pro Gly Arg Tyr Asn Tyr
1               5                   10                  15

<210> SEQ ID NO 273
<211> LENGTH: 16
<212> TYPE: PRT
<213> ORGANISM: Artificial
<220> FEATURE:
<223> OTHER INFORMATION: AS63997VH6 CDR3

<400> SEQUENCE: 273
```

Gly Tyr Leu Ser Gly Gly Ser Trp Asp Val Pro Gly Arg Tyr Asn Tyr
1               5                   10                  15

<210> SEQ ID NO 274
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS63930

<400> SEQUENCE: 274

Glu Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Ser Gly Asn
            20                  25                  30

Tyr Met Ala Trp Phe Arg Gln Ala Pro Gly Asn Glu Arg Glu Gly Val
        35                  40                  45

Ala Val Val Tyr Asn Ile Asp Gly Gly Arg Phe Thr Thr Tyr Ala
    50                  55                  60

Asp Ser Val Lys Gly Arg Phe Thr Ile Ser Arg Gly Asn Asp Lys Asn
65                  70                  75                  80

Thr Val Tyr Leu Gln Met Asn Ser Leu Lys Pro Glu Asp Ser Gly Met
                85                  90                  95

Tyr Tyr Cys Ala Ala Glu Val Ala Asp Pro Thr Trp Gly Ser Arg Asp
            100                 105                 110

Gln Arg Arg Tyr Lys Tyr Trp Gly Gln Gly Thr Gln Val Thr Val Ser
            115                 120                 125

Ser

<210> SEQ ID NO 275
<211> LENGTH: 118
<212> TYPE: PRT
<213> ORGANISM: Artificial
<220> FEATURE:
<223> OTHER INFORMATION: Anti-DLL3 camel sdAb amino acid sequence
      AS63932

<400> SEQUENCE: 275

Gln Val Gln Leu Glu Glu Ser Gly Gly Gly Ser Val Gln Ala Gly Gly
1               5                   10                  15

Ser Leu Arg Leu Ser Cys Val Ala Ser Gly Tyr Thr Tyr Gly Ser Thr
            20                  25                  30

Phe Met Gly Trp Phe Arg Gln Asn Pro Gly Lys Glu Arg Glu Gly Val
        35                  40                  45

Ala Val Ile Tyr Thr Gly Gly Ser Thr Trp Tyr Ala Ser Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Tyr Gly Ser Gly Asn Val Asn Tyr Trp Gly Gln Gly Thr
            100                 105                 110

Gln Val Thr Val Ser Ser
            115

<210> SEQ ID NO 276
<211> LENGTH: 130

<212> TYPE: PRT
<213> ORGANISM: Artificial
<220> FEATURE:
<223> OTHER INFORMATION: Anti-DLL3 camel sdAb amino acid sequence
      AS63951

<400> SEQUENCE: 276

Gln Val His Leu Met Glu Ser Gly Gly Gly Ser Val Gln Ala Gly Gly
1               5                   10                  15

Ser Leu Arg Leu Ala Cys Glu Thr Ser Arg Asp Ile Tyr Gly Asn Asn
            20                  25                  30

Cys Met Ala Trp Phe Arg Gln Ala Pro Gly Lys Glu Arg Glu Gly Val
        35                  40                  45

Ala Ser Ile Tyr Pro Ala Gly Gly Arg Pro Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Arg Ser Phe Ser Ile Ala Val Cys Ala Thr Arg Ser Gly Ile
            100                 105                 110

Thr Arg Ser Asn Phe Ala Tyr Trp Gly Gln Gly Thr Gln Val Thr Val
        115                 120                 125

Ser Ser
130

<210> SEQ ID NO 277
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS63984

<400> SEQUENCE: 277

Gln Val Lys Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Asn
            20                  25                  30

Phe Met Gly Trp Phe Arg Gln Ala Pro Gly Lys Glu Arg Glu Gly Val
        35                  40                  45

Ala Thr Ile Val Ser Gly Gly Thr Thr Tyr Tyr Ala Asp Ser Val
    50                  55                  60

Arg Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Gly Gly Pro Val Thr Asn Ala Pro Arg Trp Tyr Pro Leu Arg
            100                 105                 110

Pro Pro Gly Tyr Asn Tyr Trp Gly Gln Gly Thr Gln Val Thr Val Ser
        115                 120                 125

Ser

<210> SEQ ID NO 278
<211> LENGTH: 122
<212> TYPE: PRT
<213> ORGANISM: Artificial
<220> FEATURE:
<223> OTHER INFORMATION: Anti-DLL3 camel sdAb amino acid sequence -continued

AS63987

<400> SEQUENCE: 278

Gln Val Arg Leu Val Glu Ser Gly Gly Gly Ser Val Gln Ala Gly Gly
1               5                   10                  15

Ser Leu Arg Leu Ser Cys Glu Ala Thr Gly Tyr Arg Asn Cys Met Ala
            20                  25                  30

Trp Phe Arg Gln Ala Pro Gly Lys Glu Arg Glu Gly Val Ala Val Ile
        35                  40                  45

Tyr Thr Pro Ser Gly Ile Thr Asp Tyr Ala Ser Ser Val Lys Gly Arg
    50                  55                  60

Phe Thr Ile Ser Gln Asn Asn Ala Arg Asn Thr Gln Tyr Leu Gln Met
65                  70                  75                  80

Asn Ser Leu Lys Pro Glu Asp Thr Ala Met Tyr Tyr Cys Ala Ala Asp
                85                  90                  95

Arg Pro Phe Val Cys Asn Ile Ala Asn Met Arg Arg Ser Ser Asn Trp
            100                 105                 110

Gly Arg Gly Thr Gln Val Thr Val Ser Ser
        115                 120

<210> SEQ ID NO 279
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS63997

<400> SEQUENCE: 279

Gln Val Arg Leu Val Glu Ser Gly Gly Gly Ser Val Gln Ala Gly Gly
1               5                   10                  15

Ser Leu Arg Leu Ser Cys Ala Gly Ser Phe Ser Gly Tyr Gly Val Ser
            20                  25                  30

Thr Met Ala Trp Phe Arg Gln Ala Pro Gly Lys Glu Arg Glu Gly Val
        35                  40                  45

Ala Ala Ile Thr Val Gly Ser Gly Asn Thr Tyr Tyr Ala Asp Ser Val
    50                  55                  60

Lys Gly Arg Phe Thr Ile Ser Arg Asp Asn Ala Lys Arg Thr Val Phe
65                  70                  75                  80

Leu Gln Met Asn Ser Leu Lys Pro Glu Asp Thr Ala Met Tyr Tyr Cys
                85                  90                  95

Ala Val Gly Tyr Leu Ser Gly Gly Ser Trp Asp Val Pro Gly Arg Tyr
            100                 105                 110

Asn Tyr Trp Gly Gln Gly Thr Gln Val Thr Val Ser Ser
        115                 120                 125

<210> SEQ ID NO 280
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64047

<400> SEQUENCE: 280

Gln Val His Leu Val Glu Ser Gly Gly Gly Ser Val Gln Ala Gly Gly
1               5                   10                  15

Ser Leu Arg Leu Ser Cys Ala Ala Ser Gln Tyr Val Tyr Arg Trp Asp
            20                  25                  30

```
Leu Met Gly Trp Phe Arg Gln Ala Pro Gly Lys Glu Arg Glu Ala Val
        35                  40                  45

Ala Ala Val Tyr Thr Gly Asp Gly Ile Thr Tyr Tyr Ala Asp Ser Val
 50                  55                  60

Lys Gly Arg Phe Ser Ile Ser Gln Asp Asn Ala Lys Asn Thr Val Tyr
 65                  70                  75                  80

Leu Gln Met Asn Ser Leu Lys Pro Glu Asp Thr Gly Met Tyr Phe Cys
                 85                  90                  95

Ala Ala Gly Phe Val Ser Gly Gly Arg Trp Asn Gln Ser Tyr Arg Tyr
            100                 105                 110

Lys Tyr Trp Gly Gln Gly Thr Gln Val Thr Val Ser Ser
        115                 120                 125
```

<210> SEQ ID NO 281
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS64052

<400> SEQUENCE: 281

```
Gln Val His Leu Met Glu Ser Gly Gly Gly Ser Val Gln Ala Gly Gly
 1               5                  10                  15

Ser Leu Arg Leu Ser Cys Ala Ala Ser Gly Tyr Thr Tyr Arg Ser Asn
                 20                  25                  30

Phe Met Gly Trp Phe Arg Gln Ala Pro Gly Lys Glu Arg Glu Gly Ile
        35                  40                  45

Ala Thr Ile His Ser Gly Val Ala Thr Thr Tyr Tyr Ala Asp Ser Val
 50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Gly Gly Pro Pro Ala Asn Ala Asp Arg Trp Tyr Pro Leu Arg
            100                 105                 110

Pro Pro Gly Tyr Asn Tyr Trp Gly Gln Gly Thr Gln Val Thr Val Ser
        115                 120                 125

Ser
```

<210> SEQ ID NO 282
<211> LENGTH: 127
<212> TYPE: PRT
<213> ORGANISM: Artificial
<220> FEATURE:
<223> OTHER INFORMATION: Anti-DLL3 camel sdAb amino acid sequence
      AS64062

<400> SEQUENCE: 282

```
Gln Val Arg Leu Val Glu Ser Gly Gly Gly Ser Val Gln Val Gly Gly
 1               5                  10                  15

Ser Leu Arg Leu Ser Cys Ala Ala Ser Arg Ser Pro Tyr Ser Ser Ser
                 20                  25                  30

Arg Cys Met Gly Trp Phe Arg Gln Ala Pro Gly Lys Glu Arg Glu Gly
        35                  40                  45

Val Ala Ala Leu Tyr Thr Gly Gly Gly Ser Thr Ser Tyr Ala Asp Ser
 50                  55                  60
```

```
Val Lys Gly Arg Phe Thr Ile Ser Gln Asp Asn Ala Lys Asn Thr Val
 65                  70                  75                  80

Tyr Leu Gln Met Asn Ser Leu Lys Pro Glu Asp Thr Ala Met Tyr Tyr
                 85                  90                  95

Cys Ala Ala Val Val Pro Arg Gly Gly Ser Cys Arg Leu Asp Glu Arg
                100                 105                 110

Gly Tyr Tyr His Trp Gly Gln Gly Thr Gln Val Thr Val Ser Ser
            115                 120                 125
```

<210> SEQ ID NO 283
<211> LENGTH: 123
<212> TYPE: PRT
<213> ORGANISM: Artificial
<220> FEATURE:
<223> OTHER INFORMATION: Anti-DLL3 camel sdAb amino acid sequence
      AS64072

<400> SEQUENCE: 283

```
Gln Val Gln Leu Val Glu Ser Gly Gly Gly Ser Val Gln Ala Gly Gly
 1               5                  10                  15

Phe Leu Arg Leu Ser Cys Ala Leu Ser Gly Tyr Ser Tyr Tyr Ile Asn
                20                  25                  30

Leu Met Ala Trp Phe Arg Gln Ala Pro Gly Lys Glu Arg Glu Ala Val
             35                  40                  45

Ala Ala His Gly Pro Val Ser Gly Thr Ala Tyr Tyr Thr Asp Ser Val
         50                  55                  60

Lys Gly Arg Phe Thr Ile Ser Arg Asp Pro Gly Lys Asn Thr Met Tyr
 65                  70                  75                  80

Leu Gln Met Phe Ser Leu Gln Pro Glu Asp Thr Ala Leu Tyr Tyr Cys
                 85                  90                  95

Ala Ala Glu Thr Thr Met Gly Trp Ala His Gly Arg Gly Tyr Arg Tyr
                100                 105                 110

Trp Gly Gln Gly Thr Gln Val Thr Val Ser Ser
            115                 120
```

<210> SEQ ID NO 284
<211> LENGTH: 127
<212> TYPE: PRT
<213> ORGANISM: Artificial
<220> FEATURE:
<223> OTHER INFORMATION: Anti-DLL3 camel sdAb amino acid sequence
      AS64097

<400> SEQUENCE: 284

```
Gln Val His Leu Met Glu Ser Gly Gly Gly Ser Val Gln Ala Gly Gly
 1               5                  10                  15

Ser Leu Arg Leu Ser Cys Glu Ala Ser Gly Tyr Thr Tyr Ser Arg Asn
                20                  25                  30

Cys Met Gly Trp Phe Arg Gln Ala Pro Gly Lys Glu Arg Glu Gly Val
             35                  40                  45

Ala Ala Ile Asn Thr Gly Gly Ser Thr Tyr Tyr Ala Asp Ser Leu
         50                  55                  60

Glu Gly Arg Phe Thr Ile Ser Gln Asp Asn Ala Lys Asn Thr Met Tyr
 65                  70                  75                  80

Leu Gln Met Asn Ser Leu Lys Pro Glu Asp Thr Ala Met Tyr Tyr Cys
                 85                  90                  95

Ala Ala Gly Pro Asp Leu Gly Gly Ser Trp Cys Arg Pro Val Glu Arg
                100                 105                 110
```

```
Ala Phe Thr Tyr Trp Gly Gln Gly Thr Gln Val Thr Val Ser Ser
        115                 120                 125
```

<210> SEQ ID NO 285
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64114

<400> SEQUENCE: 285

```
Gln Val Gln Leu Gln Glu Ser Gly Gly Gly Ser Val Gln Ala Gly Gly
1               5                   10                  15

Ser Leu Thr Leu Ser Cys Glu Ala Ser Gly Asn Thr Tyr Ser Thr Asn
                20                  25                  30

Tyr Met Gly Trp Phe Arg Gln Ala Pro Gly Lys Glu Arg Glu Val
            35                  40                  45

Ala Val Ile Tyr Thr Arg Gly Gly His Thr Tyr Tyr Val Asp Ser Val
    50                  55                  60

Arg Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ser Arg His Arg Leu Arg Leu Asn Asn Pro Arg Asp Tyr
            100                 105                 110

Asp Tyr Trp Gly Gln Gly Thr Gln Val Thr Val Ser Ser
        115                 120                 125
```

<210> SEQ ID NO 286
<211> LENGTH: 116
<212> TYPE: PRT
<213> ORGANISM: Artificial
<220> FEATURE:
<223> OTHER INFORMATION: Anti-DLL3 camel sdAb amino acid sequence
      AS64123

<400> SEQUENCE: 286

```
Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Thr Ser Asn
                20                  25                  30

Trp Leu Gly Trp Phe Arg Gln Ala Pro Gly Lys Glu Arg Glu Val
            35                  40                  45

Ala Ile Ile Tyr Thr Gly Ser Gly Ser Thr His Tyr Arg Ser Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Phe Ser Glu Tyr Asn Tyr Trp Gly Gln Gly Thr Gln Val
            100                 105                 110

Thr Val Ser Ser
        115
```

<210> SEQ ID NO 287
<211> LENGTH: 129
<212> TYPE: PRT
<213> ORGANISM: Artificial
<220> FEATURE:

<223> OTHER INFORMATION: Anti-DLL3 camel sdAb amino acid sequence
      AS64130

<400> SEQUENCE: 287

Glu Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Arg Ser Asn
            20                  25                  30

Phe Met Gly Trp Phe Arg Gln Ala Pro Ala Lys Glu Arg Glu Gly Val
        35                  40                  45

Ala Thr Ile Asp Ser Arg Gly Thr Ile Thr Tyr Tyr Ala Asp Ser Val
    50                  55                  60

Lys Gly Arg Phe Thr Ile Ser Gln Asp Asn Glu Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Gly Gly Pro Arg Thr Asn Asp Asp Arg Trp Tyr Pro Leu Arg
            100                 105                 110

Pro Pro Gly Tyr Asn Tyr Trp Gly Gln Gly Thr Gln Val Thr Val Ser
        115                 120                 125

Ser

<210> SEQ ID NO 288
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64137

<400> SEQUENCE: 288

Gln Val Arg Leu Val Glu Ser Gly Gly Gly Ser Val Gln Ala Gly Gly
1               5                   10                  15

Ser Leu Arg Leu Ser Cys Ala Ala Ser Gly Ser Thr Tyr Ser Thr Asn
            20                  25                  30

Phe Met Gly Trp Phe Arg Gln Ala Pro Gly Lys Glu Arg Glu Gly Val
        35                  40                  45

Ala Thr Leu Val Thr Trp Val Glu Arg Thr Ala Tyr Ala Asp Ser Val
    50                  55                  60

Lys Gly Arg Phe Thr Ile Ser Gln Asp Arg Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Ala Ala Ser Thr Asp Val Arg Leu Leu Asp Pro Gly Asp
            100                 105                 110

Phe Ala Tyr Trp Gly Gln Gly Thr Gln Val Thr Val Ser Ser
        115                 120                 125

<210> SEQ ID NO 289
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64142

<400> SEQUENCE: 289

Gln Val His Leu Met Glu Ser Gly Gly Gly Leu Val Gln Thr Gly Gly
1               5                   10                  15

```
Ser Leu Arg Leu Ser Cys Thr Ala Ser Gly Phe Thr Phe Asp Arg Asn
            20                  25                  30

Ala Met Arg Trp Tyr Arg Gln Ala Pro Gly Lys Glu Arg Glu Gly Val
            35                  40                  45

Ser Cys Ile Asp Trp Thr Gly Ala Asn Ile Ala Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Gly Met Tyr Tyr Cys
                85                  90                  95

Ala Ala Asp Thr Thr Ser Gly Tyr Cys Ser Gly Phe Trp Ser Thr Ser
                100                 105                 110

Arg Tyr Ser Trp Gly Gln Gly Thr Gln Val Thr Val Ser Ser
            115                 120                 125
```

<210> SEQ ID NO 290
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64154

<400> SEQUENCE: 290

```
Gln Val Gln Leu Lys Glu Ser Gly Gly Gly Ser Val Gln Ala Gly Gly
1               5                   10                  15

Ser Leu Arg Leu Ser Cys Thr Ala Ser Gly Tyr Thr Tyr Arg Tyr Leu
            20                  25                  30

Tyr Met Gly Trp Phe Arg Gln Thr Pro Gly Lys Glu Arg Glu Gly Val
            35                  40                  45

Ala Cys Ile Tyr Thr Gly Ser Gly Ser Thr Gly Tyr Ala Asp Ser Val
50                  55                  60

Lys Gly Arg Phe Thr Ile Ser Gln Asp Asn Ala Lys Asn Thr Val Tyr
65                  70                  75                  80

Leu Gln Met Asn Asn Leu Lys Pro Glu Asp Thr Ala Met Tyr Tyr Cys
                85                  90                  95

Ala Ala Ser Ser Pro Arg Trp Gly Thr Cys Arg Arg Trp Ser Gln
                100                 105                 110

Tyr Asn Tyr Trp Gly Gln Gly Thr Gln Val Thr Val Ser Ser
            115                 120                 125
```

<210> SEQ ID NO 291
<211> LENGTH: 128
<212> TYPE: PRT
<213> ORGANISM: Artificial
<220> FEATURE:
<223> OTHER INFORMATION: Anti-DLL3 camel sdAb amino acid sequence
      AS64160

<400> SEQUENCE: 291

```
Glu Val Gln Leu Val Glu Ser Gly Gly Gly Ser Val Gln Ala Gly Gly
1               5                   10                  15

Ser Leu Arg Leu Ser Cys Ala Ala Ser Val Tyr Thr Ser Ser Ser Tyr
            20                  25                  30

Cys Met Gly Trp Phe Arg Gln Ala Pro Gly Lys Glu Arg Glu Gly Val
            35                  40                  45

Ala Ala Met Cys Phe Gly Gly Leu Val Thr His Tyr Ala Asp Ser Val
50                  55                  60
```

```
Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asp Phe Gly Arg Asp Lys Asn Tyr Leu Arg Pro Leu Leu Pro
            100                 105                 110

His Ala Tyr Asn Tyr Trp Gly Gln Gly Thr Gln Val Thr Val Ser Ser
        115                 120                 125

<210> SEQ ID NO 292
<211> LENGTH: 117
<212> TYPE: PRT
<213> ORGANISM: Artificial
<220> FEATURE:
<223> OTHER INFORMATION: Anti-DLL3 camel sdAb amino acid sequence
      AS64228

<400> SEQUENCE: 292

Gln Val Gln Leu Lys Glu Ser Gly Gly Gly Ser Ile Gln Ala Gly Gly
1               5                   10                  15

Ser Leu Arg Leu Ser Cys Ala Ala Ser Gly Val Ser Tyr Asn Arg Cys
            20                  25                  30

Ser Met Gly Trp Tyr Arg Gln Ala Pro Gly Lys Gly Arg Glu Leu Val
        35                  40                  45

Ser Arg Ile Gln Pro Gly Gly Asn Thr Tyr Tyr Ala Asp Ser Val Lys
    50                  55                  60

Gly Arg Phe Thr Val Ser Gln Asp Asn Ala Lys Asn Thr Val Ser Leu
65                  70                  75                  80

Gln Met Asn Ser Leu Lys Pro Glu Asp Thr Ala Met Tyr Tyr Cys Asn
                85                  90                  95

Ala Leu Cys Trp Arg Glu Asn Val Asn Tyr Trp Gly Gln Gly Thr Gln
            100                 105                 110

Val Thr Val Ser Ser
        115

<210> SEQ ID NO 293
<211> LENGTH: 124
<212> TYPE: PRT
<213> ORGANISM: Artificial
<220> FEATURE:
<223> OTHER INFORMATION: Anti-DLL3 camel sdAb amino acid sequence
      AS64300

<400> SEQUENCE: 293

Gln Val His Leu Val Glu Ser Gly Gly Gly Ser Val Gln Thr Gly Gly
1               5                   10                  15

Ser Leu Arg Leu Ser Cys Ala Val Ser Gly Asp Ile Tyr Asn Leu Met
            20                  25                  30

Ser Met Ala Trp Phe Arg Arg Ala Pro Gly Lys Glu Arg Glu Gly Val
        35                  40                  45

Ala Tyr Ile Asn Thr Ile Ile Gly Asn Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Lys Pro Glu Asp Thr Ala Met Tyr Tyr Cys
                85                  90                  95

Ala Ala Phe Asn Tyr Gly Gly Ala Trp Tyr Glu Glu Arg Ser Tyr Lys
            100                 105                 110
```

```
Tyr Trp Gly Gln Gly Thr Gln Val Thr Val Ser Ser
        115                 120
```

<210> SEQ ID NO 294
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64380

<400> SEQUENCE: 294

```
Glu Val Gln Leu Val Glu Ser Gly Gly Gly Ser Val Gln Ala Gly Gly
1               5                   10                  15

Ser Leu Thr Leu Ser Cys Glu Ala Ser Gly Asn Thr Tyr Ser Ser Asn
            20                  25                  30

Tyr Met Gly Trp Phe Arg Gln Ala Pro Gly Lys Glu Arg Glu Val
        35                  40                  45

Ala Val Ile Tyr Thr Arg Gly Gly His Thr Tyr Tyr Val Asp Ser Val
    50                  55                  60

Arg Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ser Ser Arg His Arg Leu Gly Leu Asn Asn Pro Arg Asp Tyr
            100                 105                 110

Asp Tyr Trp Gly Gln Gly Thr Gln Val Thr Val Ser Ser
        115                 120                 125
```

<210> SEQ ID NO 295
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64395

<400> SEQUENCE: 295

```
Gln Val Arg Leu Val Glu Ser Gly Gly Gly Ser Val Gln Ala Gly Gly
1               5                   10                  15

Ser Leu Arg Leu Ser Cys Ala Ala Ser Gly Ser Thr Tyr Ser Thr Asn
            20                  25                  30

Phe Met Gly Trp Phe Arg Gln Ala Pro Gly Lys Glu Arg Glu Gly Val
        35                  40                  45

Ala Thr Leu Val Thr Trp Ala Glu Arg Thr Ala Tyr Ala Asp Ser Val
    50                  55                  60

Lys Gly Arg Phe Thr Ile Ser Gln Asp Arg Ala Lys Asn Thr Val Tyr
65                  70                  75                  80

Leu Gln Met Asn Gly Leu Lys Pro Glu Asp Thr Ala Met Tyr Tyr Cys
                85                  90                  95

Ala Ala Ala Ala Ser Thr Ala Val Arg Leu Leu Asp Pro Gly Asp Phe
            100                 105                 110

Ala Tyr Trp Gly Gln Gly Thr Gln Val Thr Val Ser Ser
        115                 120                 125
```

<210> SEQ ID NO 296
<211> LENGTH: 116
<212> TYPE: PRT
<213> ORGANISM: Artificial
<220> FEATURE:
<223> OTHER INFORMATION: Anti-DLL3 camel sdAb amino acid sequence
    AS64443

<400> SEQUENCE: 296

Gln Val His Leu Val Glu Ser Gly Gly Gly Ser Val Gln Ala Gly Gly
1               5                   10                  15

Ser Leu Arg Leu Ser Cys Ala Ala Ser Gly Tyr Thr Asp Ser Ser Val
            20                  25                  30

Tyr Ile Gly Trp Phe Arg Gln Ala Pro Gly Lys Glu Arg Glu Val
        35                  40                  45

Ala Ile Ile Tyr Thr Gly Gly Glu Ser Thr His Tyr Arg Ser Ser Val
50                  55                  60

Lys Gly Arg Phe Thr Val Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Arg Phe Pro Ala Val Thr Tyr Trp Gly Gln Gly Thr Gln Val
            100                 105                 110

Thr Val Ser Ser
        115

<210> SEQ ID NO 297
<211> LENGTH: 125
<212> TYPE: PRT
<213> ORGANISM: Artificial
<220> FEATURE:
<223> OTHER INFORMATION: Anti-DLL3 camel sdAb amino acid sequence
    AS64511

<400> SEQUENCE: 297

Gln Val Gln Leu Val Glu Ser Gly Gly Gly Ser Val Gln Ala Gly Gly
1               5                   10                  15

Ser Leu Arg Leu Ser Cys Ala Ala Ser Arg Ala Thr Tyr Ser Thr Asn
            20                  25                  30

Tyr Ile Ser Trp Phe Arg Gln Ala Pro Gly Lys Glu Arg Glu Ala Val
        35                  40                  45

Ala Thr Ile Thr Thr Gly Asp Gly Glu Thr Ala Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Asn Leu Arg Ile Gly Gly Asp Trp Phe Asp Gly Arg Asp Phe
            100                 105                 110

Arg Ala Trp Gly Gln Gly Thr Gln Val Thr Val Ser Ser
        115                 120                 125

<210> SEQ ID NO 298
<211> LENGTH: 125
<212> TYPE: PRT
<213> ORGANISM: Artificial
<220> FEATURE:
<223> OTHER INFORMATION: Anti-DLL3 camel sdAb amino acid sequence
    AS64536

<400> SEQUENCE: 298

Gln Val Lys Leu Val Glu Ser Gly Gly Gly Ser Val Gln Ala Gly Gly
1               5                   10                  15

Ser Leu Arg Leu Ser Cys Ala Ala Ser Arg Tyr Thr Asp Asn Phe Val
            20                  25                  30

Tyr Met Gly Trp Phe Arg Gln Ala Pro Gly Lys Glu Arg Glu Gly Val
        35                  40                  45

Ala Leu Ile Tyr Pro Gly Gly Ser Thr Tyr Ala Ser Ser Val
50                  55                  60

Lys Gly Arg Phe Thr Ile Ser Gln Asp Asn Ala Lys Gly Thr Val His
65                  70                  75                  80

Leu Gln Met Asn Asn Leu Lys Pro Glu Asp Thr Ala Met Tyr Tyr Cys
            85                  90                  95

Ala Ala Lys Trp Gly Leu Gly Gly Gly Leu Lys Ser Asp Thr Tyr
            100                 105                 110

Met Tyr Trp Gly Gln Gly Thr Gln Val Thr Val Ser Ser
        115                 120                 125

<210> SEQ ID NO 299
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS64597

<400> SEQUENCE: 299

Gln Val His Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Arg Val Asn
            20                  25                  30

Phe Met Gly Trp Phe Arg Gln Thr Pro Gly Lys Glu Arg Glu Gly Val
        35                  40                  45

Ala Thr Ile Asp Ser Gly Val Gly Thr Thr Tyr Tyr Ala Asp Ser Val
50                  55                  60

Lys Gly Arg Phe Thr Ile Ser His Asn Asn Ala Lys Asn Thr Ile Tyr
65                  70                  75                  80

Leu Gln Met Asn Ser Leu Lys Pro Glu Asp Thr Ala Met Tyr Tyr Cys
            85                  90                  95

Ala Ala Gly Gly Pro Pro Thr Asp Gly Asp Arg Trp Tyr Pro Leu Arg
            100                 105                 110

Pro Pro Gly Tyr Asn Tyr Trp Gly Gln Gly Thr Gln Val Thr Val Ser
        115                 120                 125

Ser

<210> SEQ ID NO 300
<211> LENGTH: 117
<212> TYPE: PRT
<213> ORGANISM: Artificial
<220> FEATURE:
<223> OTHER INFORMATION: Anti-DLL3 camel sdAb amino acid sequence
      AS64617

<400> SEQUENCE: 300

Gln Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Asp Arg Cys Ser
            20                  25                  30

Met Ala Trp Tyr Arg Gln Ala Pro Gly Lys Glu Arg Glu Leu Val Ser
        35                  40                  45

Arg Ile Ser Thr Ser Gly Phe Thr Asn Tyr Ala Ala Ser Val Lys Gly

```
                    50                  55                  60

Arg Phe Thr Ile Ser Gln Asp Asn Ala Lys Asn Thr Val Tyr Leu Gln
 65                  70                  75                  80

Met Asn Ser Leu Asn Pro Gly Asp Thr Gly Met Tyr Tyr Cys Ala Ile
                    85                  90                  95

Ile Val Gly Arg Thr Cys Ser Leu Asn Tyr Trp Gly Asn Gly Ile Leu
                100                 105                 110

Val Thr Val Ser Ser
            115

<210> SEQ ID NO 301
<211> LENGTH: 127
<212> TYPE: PRT
<213> ORGANISM: Artificial
<220> FEATURE:
<223> OTHER INFORMATION: Anti-DLL3 camel sdAb amino acid sequence
      AS64634

<400> SEQUENCE: 301

Gln Val Arg Leu Val Glu Ser Gly Gly Gly Ser Val Gln Ala Gly Gly
 1               5                  10                  15

Ser Leu Arg Leu Ser Cys Ala Ala Ser Gly Tyr Ser Phe Arg Gly Asp
                20                  25                  30

Phe Met Cys Met Gly Trp Phe Arg Gln Thr Pro Gly Lys Gly Arg Glu
                35                  40                  45

Gly Val Ala Val Phe Tyr Pro Gly Gly Gly Ser Thr Asn Tyr Ala Asp
                50                  55                  60

Ser Ala Lys Gly Arg Phe Thr Ile Ser Gln Asp Asn Ala Lys Asn Thr
 65                  70                  75                  80

Met Tyr Leu Gln Met Asn Thr Leu Lys Pro Glu Asp Thr Ala Met Tyr
                    85                  90                  95

Tyr Cys Ala Ala Arg Arg Trp Val Ser Gly Thr Cys Tyr Trp Asp Ser
                100                 105                 110

Asp Phe His Tyr Trp Gly Gln Gly Thr Gln Val Thr Val Ser Ser
                115                 120                 125

<210> SEQ ID NO 302
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS69498

<400> SEQUENCE: 302

Gln Val Gln Leu Gln Glu Ser Gly Gly Gly Ser Val Gln Ala Gly Gly
 1               5                  10                  15

Ser Leu Arg Leu Ser Cys Glu Ala Ser Gly Asn Thr Tyr Ser Ser Asn
                20                  25                  30

Tyr Met Ala Trp Phe Arg Gln Ala Pro Gly Lys Glu Arg Glu Val
                35                  40                  45

Ala Val Ile Tyr Thr Arg Gly Gly His Thr Tyr Tyr Ile Asp Ser Val
                50                  55                  60

Arg Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                    85                  90                  95

Ala Ala Ser Ser Arg His Arg Leu Arg Leu Ser Asp Pro Arg Asp Tyr
```

```
            100                 105                 110
Asp Tyr Trp Gly Gln Gly Thr Gln Val Thr Val Ser Ser
        115                 120                 125

<210> SEQ ID NO 303
<211> LENGTH: 127
<212> TYPE: PRT
<213> ORGANISM: Artificial
<220> FEATURE:
<223> OTHER INFORMATION: Anti-DLL3 camel sdAb amino acid sequence
      AS69500

<400> SEQUENCE: 303

Gln Val Arg Leu Val Glu Ser Gly Gly Gly Ser Val Gln Ala Gly Gly
1               5                   10                  15

Ser Leu Arg Leu Ser Cys Ala Ala Asp Arg Tyr Thr Tyr Ser Ser Ala
            20                  25                  30

Cys Met Gly Trp Phe Arg Gln Ala Pro Gly Lys Glu Arg Glu Gly Val
        35                  40                  45

Ala Ser Ile Phe Thr Gly Thr Gly Ser Thr Tyr Tyr Ala Asp Ser
    50                  55                  60

Val Lys Gly Arg Phe Thr Ile Ser Gln Asp Asn Ala Lys Asn Thr Val
65                  70                  75                  80

Tyr Leu Gln Met Asn Ser Leu Lys Pro Glu Asp Thr Ala Ile Tyr Tyr
                85                  90                  95

Cys Ala Ala Arg Ala Phe Gln Val Gly Tyr Cys Tyr Leu Arg Thr Asp
            100                 105                 110

Val Tyr Asn Tyr Trp Gly Gln Gly Thr Gln Val Thr Val Ser Ser
        115                 120                 125

<210> SEQ ID NO 304
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS69527

<400> SEQUENCE: 304

Glu Val Gln Leu Ala Glu Ser Gly Gly Gly Ser Val Gln Ala Gly Gly
1               5                   10                  15

Ser Leu Arg Leu Ser Cys Val Ala Ser Arg Tyr Thr Phe Ser Ser Thr
            20                  25                  30

Cys Met Ala Trp Phe Arg Gln Ala Pro Gly Lys Glu Arg Glu Val
        35                  40                  45

Ala Ala Ile Tyr Thr Asp Asp Gly Ser Thr Trp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Arg Trp Ala Cys Pro Arg Val Gly Ser Trp His Glu Phe
            100                 105                 110

Ala Tyr Trp Gly Gln Gly Thr Gln Val Thr Val Ser Ser
        115                 120                 125

<210> SEQ ID NO 305
<211> LENGTH: 125
<212> TYPE: PRT
```

<213> ORGANISM: Artificial
<220> FEATURE:
<223> OTHER INFORMATION: Anti-DLL3 camel sdAb amino acid sequence
    AS68280

<400> SEQUENCE: 305

Gln Val Gln Leu Val Glu Ser Gly Gly Gly Ser Val His Pro Gly Gly
1               5                   10                  15

Ser Leu Arg Leu Ser Cys Ala Ala Ser Gly Ser Thr Tyr Ser Ser Asn
            20                  25                  30

Tyr Leu Gly Trp Phe Arg Gln Ala Pro Gly Lys Gly Arg Asp Trp Val
        35                  40                  45

Ala Ala Ile Ser Thr Gly Asp Gly Ala Thr Ala Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Leu Glu Asp Ser Ala Met Tyr Tyr Cys
                85                  90                  95

Ala Ala Ala Arg Gly Arg Phe Ile Asp Trp Thr Lys Ala Thr Gln Tyr
            100                 105                 110

Asp Tyr Trp Gly Gln Gly Thr Gln Val Thr Val Ser Ser
        115                 120                 125

<210> SEQ ID NO 306
<211> LENGTH: 128
<212> TYPE: PRT
<213> ORGANISM: Artificial
<220> FEATURE:
<223> OTHER INFORMATION: Anti-DLL3 camel sdAb amino acid sequence
    AS68355

<400> SEQUENCE: 306

Gln Met Gln Leu Val Glu Ser Gly Gly Asp Ser Val Gln Ala Gly Gly
1               5                   10                  15

Ser Leu Arg Leu Ser Cys Ala Ala Ser Gly Tyr Thr Tyr Ser Gly Val
            20                  25                  30

Cys Met Gly Trp Phe Arg Gln Ala Pro Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Ile Val Gly Gly Phe Asn Ala Tyr Cys Ser Gly Gly Tyr Val
            100                 105                 110

Leu Asp Phe Gly Ala Trp Gly Gln Gly Thr Gln Val Thr Val Ser Ser
        115                 120                 125

<210> SEQ ID NO 307
<211> LENGTH: 132
<212> TYPE: PRT
<213> ORGANISM: Artificial
<220> FEATURE:
<223> OTHER INFORMATION: Anti-DLL3 camel sdAb amino acid sequence
    AS69443

<400> SEQUENCE: 307

Glu Val Gln Leu Ala Glu Ser Gly Gly Gly Ser Val Gln Ala Gly Gly
1               5                   10                  15

```
Ser Leu Arg Leu Ser Cys Ser Ala Ser Gly Phe Thr Phe Asp Asp Ser
            20                  25                  30

Asp Met Ala Trp Tyr Arg Gln Ala Pro Gly Asp Gly Cys Asp Leu Val
            35                  40                  45

Ser Thr Ile Ser Ser Asp Gly Ser Thr Tyr Tyr Ala Asp Ser Val Lys
 50                  55                  60

Gly Arg Phe Thr Ile Ser Gln Asp Asn Ala Lys Asn Thr Val Tyr Leu
 65                  70                  75                  80

Gln Met His Ser Leu Lys Pro Glu Asp Thr Ala Val Tyr Tyr Cys Ala
            85                  90                  95

Ala Asp Phe Leu Thr Gly Phe Tyr Tyr Ser Asp Ser Pro His Pro Ala
            100                 105                 110

Pro Cys Ser Ala Ser Asp Phe Gly Tyr Trp Gly Gln Gly Thr Gln Val
            115                 120                 125

Thr Val Ser Ser
        130
```

<210> SEQ ID NO 308
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS75376

<400> SEQUENCE: 308

```
Gln Val Gln Leu Lys Glu Ser Gly Gly Gly Ser Val Gln Ala Gly Gly
 1               5                   10                  15

Ser Leu Arg Leu Ser Cys Ala Ala Ser Gly Tyr Thr Tyr Ser Ser His
            20                  25                  30

Ser Met Gly Trp Phe Arg Gln Ala Pro Gly Lys Glu Arg Glu Gly Val
            35                  40                  45

Ala Val Ile Tyr Thr Gly Asp Gly Ser Thr Tyr Tyr Ala Asp Ser Val
            50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
            85                  90                  95

Ala Ala Asp Pro Asn Pro Asp Tyr Met Leu Pro Phe Arg Pro Ser Arg
            100                 105                 110

Arg Ser Trp Trp Gly Gln Gly Thr Gln Val Thr Val Ser Ser
            115                 120                 125
```

<210> SEQ ID NO 309
<211> LENGTH: 123
<212> TYPE: PRT
<213> ORGANISM: Artificial
<220> FEATURE:
<223> OTHER INFORMATION: Anti-DLL3 camel sdAb amino acid sequence
      AS75387

<400> SEQUENCE: 309

```
Gln Val His Leu Val Glu Ser Gly Gly Gly Ser Val Gln Ala Gly Gly
 1               5                   10                  15

Ser Leu Arg Leu Ser Cys Ala Ala Ser Gly Tyr Pro Tyr Ser Ser Pro
            20                  25                  30

Cys Met Ala Trp Phe Arg Gln Ala Pro Gly Lys Glu Arg Glu Gly Val
            35                  40                  45
```

-continued

```
Leu Val Ala Tyr Thr Gly Gly Asp Ile Gln Tyr Leu Thr Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Asp Leu Arg Leu Pro Arg Ala Gly Gly Cys Ala Tyr Ser Tyr
            100                 105                 110

Trp Gly Gln Gly Thr Gln Val Thr Val Ser Ser
        115                 120

<210> SEQ ID NO 310
<211> LENGTH: 121
<212> TYPE: PRT
<213> ORGANISM: Artificial
<220> FEATURE:
<223> OTHER INFORMATION: Anti-DLL3 camel sdAb amino acid sequence
      AS75695

<400> SEQUENCE: 310

Gln Val Arg Leu Val Glu Ser Gly Gly Gly Ser Val Gln Ala Gly Gly
 1               5                  10                  15

Ser Leu Arg Leu Ser Cys Val Ala Ser Gly Tyr Thr Val Ser Ala Tyr
             20                  25                  30

Cys Met Gly Trp Phe Arg Gln Val Leu Gly Lys Gly Arg Glu Arg Ile
         35                  40                  45

Ala Phe Ile Asp Ala Gly Gly Ala Thr Ile Tyr Ala Asp Pro Val Lys
     50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Val
                 85                  90                  95

Ala Asp Arg Arg Gly Arg Val Arg Cys Glu Tyr Asn Ala Trp Gly
            100                 105                 110

Gln Gly Thr Gln Val Thr Val Ser Ser
        115                 120

<210> SEQ ID NO 311
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS76169

<400> SEQUENCE: 311

Gln Val His Leu Met Glu Ser Gly Gly Gly Ser Val Gln Ala Gly Gly
 1               5                  10                  15

Ser Leu Arg Leu Ser Cys Ala Ala Ser Gly Tyr Ile Tyr Ser Ser Phe
             20                  25                  30

Cys Met Gly Trp Phe Arg Gln Ala Pro Gly Lys Glu Arg Glu Val Val
         35                  40                  45

Ala Tyr Ile Arg Asp Asn Ile Met Thr Ser Tyr Thr Asp Ser Val Lys
     50                  55                  60

Gly Arg Phe Thr Ile Ser Lys Asp Asn Ala Lys Arg Thr Leu Tyr Leu
 65                  70                  75                  80

Gln Met Asn Gly Leu Lys Pro Glu Asp Thr Gly Met Tyr Tyr Cys Ala
                 85                  90                  95
```

Val Asp Arg Gly Gly Tyr Ala Asn Ser Cys Ala Val Ala Ala Arg Tyr
            100                 105                 110

Asp Tyr Trp Gly Arg Gly Thr Gln Val Thr Val Ser Ser
        115                 120                 125

<210> SEQ ID NO 312
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS63931

<400> SEQUENCE: 312

Glu Val Gln Leu Ala Glu Ser Gly Gly Gly Ser Val Gln Ala Gly Gly
1               5                   10                  15

Ser Leu Arg Leu Ser Cys Ala Gly Ser Phe Ser Gly Tyr Gly Val Ser
            20                  25                  30

Thr Met Ala Trp Phe Arg Gln Ala Pro Gly Lys Glu Arg Glu Gly Val
        35                  40                  45

Ala Ala Ile Thr Val Gly Ser Gly Asn Thr Tyr Tyr Ala Asp Ser Val
    50                  55                  60

Thr Gly Arg Phe Thr Ile Ser Arg Asp Asn Ala Lys Arg Thr Val Tyr
65                  70                  75                  80

Leu Gln Met Asn Ser Leu Lys Pro Glu Asp Thr Ala Met Tyr Tyr Cys
                85                  90                  95

Ala Ala Gly Trp Leu Ser Gly Ser Trp His Val Pro Gly Arg Tyr
            100                 105                 110

Asn Tyr Trp Gly Gln Gly Thr Gln Val Thr Val Ser Ser
        115                 120                 125

<210> SEQ ID NO 313
<211> LENGTH: 123
<212> TYPE: PRT
<213> ORGANISM: Artificial
<220> FEATURE:
<223> OTHER INFORMATION: Anti-DLL3 camel sdAb amino acid sequence
      AS63937

<400> SEQUENCE: 313

Gln Val Lys Leu Val Glu Ser Gly Gly Gly Ser Val Gln Ala Gly Gly
1               5                   10                  15

Ser Leu Arg Leu Ser Cys Ala Ala Ser Gly Ser Thr Ile Ser Ser Arg
            20                  25                  30

Pro Met Ala Trp Phe Arg Gln Ala Pro Gly Lys Glu Arg Glu Gly Val
        35                  40                  45

Ala Cys Ile His Thr Gly Leu Gly Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Val Asn Ser Leu Lys Pro Glu Asp Thr Ala Met Tyr Tyr Cys
                85                  90                  95

Ala Ala Asp Ser Arg Arg Pro Cys Met Val Ala Ala Gly Tyr Thr Tyr
            100                 105                 110

Trp Gly Gln Gly Thr Gln Val Thr Val Ser Ser
        115                 120

<210> SEQ ID NO 314

<211> LENGTH: 126
<212> TYPE: PRT
<213> ORGANISM: Artificial
<220> FEATURE:
<223> OTHER INFORMATION: Anti-DLL3 camel sdAb amino acid sequence
      AS63948

<400> SEQUENCE: 314

Gln Val Gln Leu Val Glu Ser Gly Gly Gly Ser Val Gln Ala Gly Gly
1               5                   10                  15

Ser Leu Arg Leu Ser Cys Thr Ala Ser Gly Tyr Thr Tyr Arg Tyr Leu
                20                  25                  30

Tyr Met Gly Trp Phe Arg Gln Thr Pro Gly Lys Glu Arg Glu Gly Val
            35                  40                  45

Ala Cys Ile Tyr Thr Gly Ser Gly Ser Thr Gly Tyr Ala Asp Ser Val
        50                  55                  60

Lys Gly Arg Phe Thr Ile Ser Gln Asp Asn Ala Glu Asn Thr Val Tyr
65                  70                  75                  80

Leu Gln Met Asn Ser Leu Lys Pro Glu Asp Thr Ala Met Tyr Tyr Cys
                85                  90                  95

Ala Ala Ala Ser Pro Arg Trp Gly Gly Thr Cys Arg Arg Trp Ser Glu
            100                 105                 110

Tyr Asn Tyr Trp Gly Gln Gly Thr Gln Val Thr Val Ser Ser
        115                 120                 125

<210> SEQ ID NO 315
<211> LENGTH: 123
<212> TYPE: PRT
<213> ORGANISM: Artificial
<220> FEATURE:
<223> OTHER INFORMATION: Anti-DLL3 camel sdAb amino acid sequence
      AS63956

<400> SEQUENCE: 315

Gln Val His Leu Val Glu Ser Gly Gly Gly Leu Val Gln Ala Gly Gly
1               5                   10                  15

Ser Leu Arg Leu Ser Cys Ala Ala Ser Gly Phe Thr Tyr Ser Asn Cys
                20                  25                  30

Cys Met Arg Trp Tyr Arg Gln Ala Pro Gly Lys Ala Arg Glu Leu Val
            35                  40                  45

Ser Leu Ile Asn Ser Ser Gly Thr Tyr Tyr Ala Asp Ser Val Arg
        50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Met Tyr Tyr Cys Ala
                85                  90                  95

Ala Tyr Gln Ala Lys Tyr Cys Ser Gly Pro Cys Ala Pro Pro Thr Asp
            100                 105                 110

Trp Gly Gln Gly Thr Gln Val Thr Val Ser Ser
        115                 120

<210> SEQ ID NO 316
<211> LENGTH: 121
<212> TYPE: PRT
<213> ORGANISM: Artificial
<220> FEATURE:
<223> OTHER INFORMATION: Anti-DLL3 camel sdAb amino acid sequence
      AS63965

<400> SEQUENCE: 316

```
Gln Val Gln Leu Val Glu Ser Gly Gly Gly Ser Val Gln Ala Gly Gly
1               5                   10                  15

Ser Leu Arg Leu Ser Cys Val Ala Ser Gly Tyr Ser Gly Ser Cys
            20                  25                  30

Arg Met Gly Trp Tyr Arg Gln Ala Pro Gly Lys Glu Arg Glu Leu Val
            35                  40                  45

Ser Lys Val Ile Ser Asp Gly Thr Thr Val Tyr Ala Asp Ser Val Lys
50                  55                  60

Gly Arg Phe Thr Leu Ser Gln Gly Asn Ala Lys Asn Thr Val Tyr Leu
65                  70                  75                  80

Gln Met Ser Ser Leu Leu Pro Glu Asp Thr Ala Met Tyr Tyr Cys Asn
            85                  90                  95

Ala Trp Cys Arg Glu Tyr Pro Gly Gly Ile Leu Asn Asn Gly Trp Gly
            100                 105                 110

Gln Gly Thr Gln Val Thr Val Ser Ser
            115                 120
```

<210> SEQ ID NO 317
<211> LENGTH: 118
<212> TYPE: PRT
<213> ORGANISM: Artificial
<220> FEATURE:
<223> OTHER INFORMATION: Anti-DLL3 camel sdAb amino acid sequence AS63993

<400> SEQUENCE: 317

```
Gln Val Lys Leu Val Glu Ser Gly Gly Gly Leu Val Gln Ala Gly Gly
1               5                   10                  15

Ser Leu Arg Leu Ser Cys Thr Val Ser Gly Phe Thr Phe Asp Asp Leu
            20                  25                  30

Val Met Ala Trp Phe Arg Gln Ala Pro Gly Lys Glu Arg Gln Leu Val
            35                  40                  45

Ser Leu Val Ala Thr Ala Gly Asn Ser Val Tyr Ala Asp Ser Val Lys
50                  55                  60

Gly Arg Phe Thr Leu Ser Arg Asp Asn Ala His Ser Thr Ala Tyr Leu
65                  70                  75                  80

Gln Met Asn Gly Leu Lys Pro Glu Asp Thr Ala Met Tyr Tyr Cys Ala
            85                  90                  95

Ala Arg Thr Asp Ser Glu His Ala Phe Lys Phe Lys Trp Gly Gln Gly Thr
            100                 105                 110

Gln Val Thr Val Ser Ser
            115
```

<210> SEQ ID NO 318
<211> LENGTH: 116
<212> TYPE: PRT
<213> ORGANISM: Artificial
<220> FEATURE:
<223> OTHER INFORMATION: Anti-DLL3 camel sdAb amino acid sequence AS63999

<400> SEQUENCE: 318

```
Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Asn
            20                  25                  30

Trp Met Gly Trp Phe Arg Gln Ala Pro Gly Lys Glu Arg Glu Val
            35                  40                  45
```

```
Ala Ile Ile Tyr Thr Gly Gly Ile Ser Thr His Tyr Arg Ser Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Tyr Thr Asp Tyr Asn Tyr Trp Gly Gln Gly Thr Gln Val
            100                 105                 110

Thr Val Ser Ser
        115

<210> SEQ ID NO 319
<211> LENGTH: 116
<212> TYPE: PRT
<213> ORGANISM: Artificial
<220> FEATURE:
<223> OTHER INFORMATION: Anti-DLL3 camel sdAb amino acid sequence
      AS64006

<400> SEQUENCE: 319

Gln Val His Leu Val Glu Ser Gly Gly Gly Ser Val Gln Ala Gly Gly
1               5                   10                  15

Ser Leu Arg Leu Ser Cys Glu Val Ser Gly Tyr Thr Gly Asp Thr Thr
                20                  25                  30

Tyr Ile Gly Trp Phe Arg Gln Ala Pro Gly Lys Glu Arg Glu Gly Val
                35                  40                  45

Ala Leu Ile Tyr Thr Ser Gly Thr Ser Glu Tyr Tyr Ala Asp Ser Val
    50                  55                  60

Lys Gly Arg Phe Ile Ile Ser Arg Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Gly Ala Arg Ser Arg Thr Met Met Tyr Trp Gly Gln Gly Thr Gln Val
            100                 105                 110

Thr Val Ser Ser
        115

<210> SEQ ID NO 320
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64057

<400> SEQUENCE: 320

Gln Val Gln Leu Glu Glu Ser Gly Gly Gly Leu Val Gln Thr Gly Gly
1               5                   10                  15

Ser Leu Arg Leu Ser Cys Thr Ala Ser Gly Phe Thr Phe Asp Arg Asn
                20                  25                  30

Ala Met Arg Trp Tyr Arg Gln Ala Pro Gly Lys Glu Arg Glu Gly Val
                35                  40                  45

Ser Cys Ile Ser Trp Thr Gly Ala Asn Ile Ala Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Gly Met Tyr Tyr Cys
                85                  90                  95
```

```
Ala Ala Asp Thr Thr Ser Gly Ser Cys Ser Gly Phe Trp Ser Thr Ser
            100                 105                 110

Arg Tyr Tyr Trp Gly Gln Gly Thr Gln Val Thr Val Ser Ser
        115                 120                 125

<210> SEQ ID NO 321
<211> LENGTH: 122
<212> TYPE: PRT
<213> ORGANISM: Artificial
<220> FEATURE:
<223> OTHER INFORMATION: Anti-DLL3 camel sdAb amino acid sequence
      AS64060

<400> SEQUENCE: 321

Gln Val Lys Leu Val Glu Ser Gly Gly Gly Val Gln Ala Gly Gly
1               5                   10                  15

Ser Leu Arg Leu Ser Cys Ala Ala Ser Gly Ser Thr Tyr Cys Thr Tyr
                20                  25                  30

Arg Met Ser Trp Phe Arg Gln Ala Pro Gly Lys Glu Arg Glu Phe Val
                35                  40                  45

Ala Val Ile Asp Ser Gly Gly Ser Thr Ser Tyr Ala Asp Ser Val Lys
                50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Met Tyr Tyr Cys Lys
                85                  90                  95

Thr Asp Pro Thr Ile Gly Cys Pro Gln Thr Tyr Arg Tyr Asn Tyr Trp
                100                 105                 110

Gly Gln Gly Thr Gln Val Thr Val Ser Ser
                115                 120

<210> SEQ ID NO 322
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64071

<400> SEQUENCE: 322

Gln Val His Leu Met Glu Ser Gly Gly Gly Ser Val Gln Ala Gly Gly
1               5                   10                  15

Ser Leu Arg Leu Ser Cys Val Ala Ser Gly Asn Thr Tyr Arg Leu Asn
                20                  25                  30

Ser Met Gly Trp Phe Arg Gln Ala Pro Gly Lys Glu Arg Glu Gly Val
                35                  40                  45

Ala Phe Ile Val Met Ile Arg Gly Thr Thr Tyr Tyr Gly Ala Ser Val
                50                  55                  60

Lys Gly Arg Phe Thr Ile Ser Gln Asp Asn Ala Gln Thr Thr Val Tyr
65                  70                  75                  80

Leu Gln Met Ser Ser Leu Lys Pro Glu Asp Thr Ala Met Tyr Tyr Cys
                85                  90                  95

Ala Ala Ser Thr Lys Asp Gln Phe Tyr Val Phe Asn Pro Ile Gly Tyr
                100                 105                 110

Asp Ser Trp Gly Gln Gly Thr Gln Val Thr Val Ser Ser
                115                 120                 125

<210> SEQ ID NO 323
<211> LENGTH: 130
```

```
<212> TYPE: PRT
<213> ORGANISM: Artificial
<220> FEATURE:
<223> OTHER INFORMATION: Anti-DLL3 camel sdAb amino acid sequence
      AS64093

<400> SEQUENCE: 323

Gln Val His Leu Val Glu Ser Gly Gly Gly Ser Val Gln Ala Gly Gly
1               5                   10                  15

Ser Leu Arg Leu Ser Cys Ala Thr Ser Arg Tyr Ile Tyr Gly Asn Asn
            20                  25                  30

Cys Met Ala Trp Phe Arg Gln Ala Pro Gly Lys Glu Arg Glu Gly Val
        35                  40                  45

Ala Ser Ile Tyr Pro Ala Gly Gly Arg Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Ile Asp Ser Leu Lys Pro Glu Asp Thr Ala Met Tyr Tyr Cys
                85                  90                  95

Ala Ala Arg Ser Phe Ser Ile Gly Val Cys Ala Thr Gln Ser Gly Ile
            100                 105                 110

Thr Trp Ser Asn Phe Ala Tyr Trp Gly Gln Gly Thr Gln Val Thr Val
        115                 120                 125

Ser Ser
    130

<210> SEQ ID NO 324
<211> LENGTH: 117
<212> TYPE: PRT
<213> ORGANISM: Artificial
<220> FEATURE:
<223> OTHER INFORMATION: Anti-DLL3 camel sdAb amino acid sequence
      AS64118

<400> SEQUENCE: 324

Gln Val Gln Leu Ala Glu Ser Gly Gly Gly Ser Val Gln Ala Gly Gly
1               5                   10                  15

Ser Leu Arg Leu Ser Cys Ala Ala Ser Gly Tyr Thr Tyr Ser Ala Cys
            20                  25                  30

Arg Met Ala Trp Tyr Arg Gln Ala Pro Gly Lys Glu Arg Glu Leu Val
        35                  40                  45

Ser Phe Ile Asn Ser Ala Gly Ser Thr Tyr Tyr Ala Asp Ser Val Lys
    50                  55                  60

Gly Arg Phe Ala Ile Ser Arg Asp Asn Ala Lys Thr Thr Val Tyr Leu
65                  70                  75                  80

Gln Met Asn Ala Leu Lys Ala Glu Asp Thr Ala Ile Tyr Tyr Cys Asn
                85                  90                  95

Thr Trp Asp Ser Ser Cys Arg Phe Gln Tyr Trp Gly Gln Gly Thr Gln
            100                 105                 110

Val Thr Val Ser Ser
    115

<210> SEQ ID NO 325
<211> LENGTH: 130
<212> TYPE: PRT
<213> ORGANISM: Artificial
<220> FEATURE:
<223> OTHER INFORMATION: Anti-DLL3 camel sdAb amino acid sequence
      AS64120
```

<400> SEQUENCE: 325

```
Gln Val Arg Leu Val Glu Ser Gly Gly Gly Ser Val Gln Ala Gly Gly
1               5                   10                  15

Ser Leu Arg Leu Ser Cys Glu Thr Ser Arg Tyr Ile Tyr Gly Asn Asn
            20                  25                  30

Cys Met Ala Trp Phe Arg Gln Ala Pro Gly Lys Glu Arg Glu Gly Val
        35                  40                  45

Ala Ser Ile Tyr Pro Ala Gly Gly Arg Pro Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asp Ser Leu Lys Pro Glu Asp Thr Ala Met Tyr Tyr Cys
                85                  90                  95

Ala Ala Arg Ser Phe Ser Ile Ala Asp Cys Ala Thr Gln Ser Gly Ile
            100                 105                 110

Thr Arg Ser Asn Phe Ala Tyr Trp Gly Gln Gly Thr Gln Val Thr Val
        115                 120                 125

Ser Ser
130
```

<210> SEQ ID NO 326
<211> LENGTH: 128
<212> TYPE: PRT
<213> ORGANISM: Artificial
<220> FEATURE:
<223> OTHER INFORMATION: Anti-DLL3 camel sdAb amino acid sequence AS64124

<400> SEQUENCE: 326

```
Gln Val Lys Leu Val Glu Ser Gly Gly Gly Ser Val Gln Thr Gly Gly
1               5                   10                  15

Ser Leu Arg Leu Ser Cys Ala Val Ser Thr Tyr Thr Pro Ser Asn Asn
            20                  25                  30

Tyr Met Gly Trp Phe Arg Gln Ala Pro Gly Lys Glu Arg Glu Gly Val
        35                  40                  45

Ala Ala Ile Ala Thr Ile Gly Gly Thr Thr Arg Tyr Ala Asp Ser Val
    50                  55                  60

Lys Gly Arg Phe Thr Ile Ser Gln Asp Gly Ala Lys Asn Thr Ile Tyr
65                  70                  75                  80

Leu Gln Met Asn Gly Leu Lys Pro Glu Asp Thr Ala Met Tyr Tyr Cys
                85                  90                  95

Ala Ala Gly Arg Pro Tyr Ser Leu Pro Leu Pro Leu Pro Leu Glu Ser
            100                 105                 110

Gly Ala Tyr Arg Tyr Trp Gly Gln Gly Thr Gln Val Thr Val Ser Ser
        115                 120                 125
```

<210> SEQ ID NO 327
<211> LENGTH: 121
<212> TYPE: PRT
<213> ORGANISM: Artificial
<220> FEATURE:
<223> OTHER INFORMATION: Anti-DLL3 camel sdAb amino acid sequence AS64135

<400> SEQUENCE: 327

```
Gln Val Lys Leu Val Glu Ser Gly Gly Gly Ser Val Gln Ala Gly Gly
1               5                   10                  15

Ser Leu Arg Leu Ser Cys Val Ala Ser Thr Ser Thr Tyr Cys Arg Tyr
```

```
                    20                  25                  30

Tyr Met Arg Trp Tyr Arg Gln Ala Pro Gly Lys Glu Arg Glu Phe Val
                35                  40                  45

Ser Ala Met Gln Pro Asp Gly Thr Thr Ser Tyr Ser Asp Ser Val Lys
        50                  55                  60

Gly Arg Phe Thr Met Ser Gln Asp Arg Ala Asn Asn Met Leu Tyr Leu
65                  70                  75                  80

Gln Met Asn Ser Leu Arg Pro Glu Asp Thr Ala Met Tyr Tyr Cys Lys
                85                  90                  95

Arg Asp Pro Met Gly Gly Ser Arg Thr Pro Cys Thr Ser Ala Trp Gly
                100                 105                 110

Gln Gly Thr Gln Val Thr Val Ser Ser
                115                 120

<210> SEQ ID NO 328
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS64163

<400> SEQUENCE: 328

Gln Val Arg Leu Val Glu Ser Gly Gly Gly Ser Val Gln Ala Gly Gly
1               5                   10                  15

Ser Leu Arg Leu Ser Cys Ala Val Ser Gly Tyr Arg Tyr Arg Trp Asn
                20                  25                  30

Cys Met Ala Trp Phe Arg Gln Ala Pro Gly Lys Glu Arg Glu Gly Val
                35                  40                  45

Ala Ala Ile Ser Thr Gly Ser Gly Ser Thr Tyr Tyr Ala Gly Ser Val
        50                  55                  60

Lys Gly Arg Phe Thr Ile Ser Gln Asp Asn Ala Lys Asn Met Tyr Leu
65                  70                  75                  80

Gln Met Asn Ser Leu Lys Pro Glu Asp Thr Ala Met Tyr Tyr Cys Ala
                85                  90                  95

Ala Asp Pro Ser Val Cys Pro Gly Gly Met Trp Tyr Ser Lys Glu Tyr
                100                 105                 110

Arg Tyr Trp Gly Gln Gly Thr Gln Val Thr Val Ser Ser
                115                 120                 125

<210> SEQ ID NO 329
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64182

<400> SEQUENCE: 329

Gln Val His Leu Met Glu Ser Gly Gly Gly Ser Val Gln Ala Gly Gly
1               5                   10                  15

Ser Leu Arg Leu Ser Cys Thr Ala Ser Gly Gln Thr Ser Arg Tyr Leu
                20                  25                  30

Tyr Met Gly Trp Phe Arg Gln Thr Pro Gly Lys Glu Arg Glu Gly Val
                35                  40                  45

Ala Cys Ile Tyr Thr Gly Ser Gly Ser Thr Gly Tyr Ala Asp Ser Val
        50                  55                  60

Lys Gly Arg Phe Thr Ile Ser Gln Asp Asn Ala Lys Asn Thr Val Tyr
```

65                  70                  75                  80
Leu Gln Thr Asn Ser Leu Lys Pro Glu Asp Thr Ala Met Tyr Tyr Cys
                85                  90                  95

Ala Ala Ser Ser Pro His Trp Gly Gly Thr Cys Arg Arg Trp Ser Glu
            100                 105                 110

Tyr Lys Tyr Trp Gly Gln Gly Thr Gln Val Thr Val Ser Ser
        115                 120                 125

<210> SEQ ID NO 330
<211> LENGTH: 122
<212> TYPE: PRT
<213> ORGANISM: Artificial
<220> FEATURE:
<223> OTHER INFORMATION: Anti-DLL3 camel sdAb amino acid sequence
      AS64183

<400> SEQUENCE: 330

Gln Val His Leu Val Glu Ser Gly Gly Gly Ser Val Gln Ala Gly Gly
1               5                   10                  15

Ser Leu Arg Leu Ser Cys Ala Ala Ser Gly His Thr Tyr Ser Ala Asn
            20                  25                  30

Cys Met Ala Trp Phe Arg Arg Ala Pro Gly Lys Glu Arg Glu Trp Val
        35                  40                  45

Ala Ser Val Tyr Thr Asp Asp Ser Thr Met Tyr Thr Asp Ser Val
    50                  55                  60

Lys Gly Arg Phe Thr Ile Phe Gln Asp Asn Ala Lys Asn Thr Val Tyr
65                  70                  75                  80

Leu Gln Met Asn Ser Leu Lys Pro Glu Asp Thr Gly Met Tyr Ile Cys
                85                  90                  95

Ala Ala Asp Leu Ser Gly Gly Pro Ala Gly Cys Gly Tyr Thr His Trp
            100                 105                 110

Gly Gln Gly Thr Gln Val Thr Val Ser Ser
        115                 120

<210> SEQ ID NO 331
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS64207

<400> SEQUENCE: 331

Glu Val Gln Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Asn
            20                  25                  30

Phe Met Gly Trp Phe Arg Gln Ala Pro Gly Lys Glu Arg Glu Gly Val
        35                  40                  45

Ala Thr Ile Val Ser Gly Gly Thr Thr Tyr Tyr Ala Asp Ser Val
    50                  55                  60

Arg Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Gly Gly Pro Pro Thr Asn Gly Ala Lys Trp Tyr Pro Leu Arg
            100                 105                 110

Pro Pro Gly Tyr Asn Tyr Trp Gly Gln Gly Thr Gln Val Thr Val Ser

<210> SEQ ID NO 332
<211> LENGTH: 122
<212> TYPE: PRT
<213> ORGANISM: Artificial
<220> FEATURE:
<223> OTHER INFORMATION: Anti-DLL3 camel sdAb amino acid sequence AS64276

<400> SEQUENCE: 332

```
Gln Val His Leu Met Glu Ser Gly Gly Gly Ser Val Gln Ala Gly Gly
1               5                   10                  15

Ser Leu Ser Leu Ser Cys Val Val Ser Gly Tyr Thr Gly Ser Ser Arg
            20                  25                  30

Cys Met Ala Trp Phe Arg Gln Ala Pro Gly Lys Glu Arg Glu Ala Val
        35                  40                  45

Ala Gln Ile Phe Thr Gly Arg Gly Thr Thr Gly Tyr Ala Asp Ser Val
    50                  55                  60

Lys Gly Arg Phe Thr Ile Ser Gln Asp Asn Ala Lys Asn Thr Val Tyr
65                  70                  75                  80

Leu Arg Met Asn Ser Leu Arg Pro Glu Asp Thr Ala Ile Tyr Tyr Cys
                85                  90                  95

Ala Ala Ser Leu Gly Pro Gly Arg Gly Ala Cys Gly Tyr Asn Tyr Trp
            100                 105                 110

Gly Gln Gly Thr Gln Val Thr Val Ser Ser
        115                 120
```

<210> SEQ ID NO 333
<211> LENGTH: 121
<212> TYPE: PRT
<213> ORGANISM: Artificial
<220> FEATURE:
<223> OTHER INFORMATION: Anti-DLL3 camel sdAb amino acid sequence AS64336

<400> SEQUENCE: 333

```
Gln Val Gln Leu Val Glu Ser Gly Gly Gly Ser Val Gln Ala Gly Gly
1               5                   10                  15

Ser Leu Arg Leu Ser Cys Thr Thr Ser Gly Arg Thr Tyr Ser Ser Cys
            20                  25                  30

Ser Met Gly Trp Tyr Arg Gln Ala Pro Gly Lys Glu Arg Glu Leu Val
        35                  40                  45

Ser His Ile Phe Ser Asp Gly Ser Arg Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Met Tyr Tyr Cys Asn
                85                  90                  95

Arg Arg Thr Gly Trp Ala Pro Arg Cys Ala Val Pro Gly Tyr Trp Gly
            100                 105                 110

Gln Gly Thr Gln Val Thr Val Ser Ser
        115                 120
```

<210> SEQ ID NO 334
<211> LENGTH: 127
<212> TYPE: PRT
<213> ORGANISM: Artificial
<220> FEATURE:
<223> OTHER INFORMATION: Anti-DLL3 camel sdAb amino acid sequence
     AS64346

<400> SEQUENCE: 334

Gln Val His Leu Val Glu Ser Gly Gly Gly Ser Val Gln Ala Gly Gly
1               5                   10                  15

Ser Leu Arg Leu Ser Cys Ala Ala Ser Gly Tyr Thr Tyr Phe Met Gly
            20                  25                  30

Trp Phe Arg Gln Ala Pro Gln Lys Glu Arg Glu Trp Val Ala Thr Ile
        35                  40                  45

Gly Thr Gly Asp Ile Phe Asn Gly Ala Ala Tyr Tyr Val Asp Ser Val
    50                  55                  60

Lys Gly Arg Phe Ala Ile Ser Gln Asp Asn Ala Lys Asn Thr Val Tyr
65                  70                  75                  80

Leu Gln Met Asn Ser Leu Lys Pro Glu Asp Thr Ala Val Tyr Val Cys
                85                  90                  95

Ala Ala Val Gln Ser Lys Ser Ser Asn Tyr Val Leu Arg Asp Ala Ser
            100                 105                 110

Thr Tyr Asn Tyr Trp Gly Gln Gly Thr Gln Val Thr Val Ser Ser
        115                 120                 125

<210> SEQ ID NO 335
<211> LENGTH: 116
<212> TYPE: PRT
<213> ORGANISM: Artificial
<220> FEATURE:
<223> OTHER INFORMATION: Anti-DLL3 camel sdAb amino acid sequence
     AS64420

<400> SEQUENCE: 335

Glu Val Gln Leu Val Glu Ser Gly Gly Gly Ser Val Gln Ala Glu Gly
1               5                   10                  15

Ser Leu Arg Leu Ser Cys Ala Ala Ser Gly Asp Thr Ser Arg Ser Val
            20                  25                  30

Trp Met Gly Trp Ala Arg Gln Val Pro Gly Lys Glu Arg Glu Val Val
        35                  40                  45

Ala Thr Ile Ser Thr Ala Gly Gly Ser Thr Trp Tyr Thr Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Ile Tyr Tyr Cys
                85                  90                  95

Ala Ala Arg Ser Arg Tyr Ala Thr Tyr Trp Gly Gln Gly Thr Gln Val
            100                 105                 110

Thr Val Ser Ser
        115

<210> SEQ ID NO 336
<211> LENGTH: 126
<212> TYPE: PRT
<213> ORGANISM: Artificial
<220> FEATURE:
<223> OTHER INFORMATION: Anti-DLL3 camel sdAb amino acid sequence
     AS64473

<400> SEQUENCE: 336

Gln Val Arg Leu Val Glu Ser Gly Gly Gly Ser Val Gln Ala Gly Gly
1               5                   10                  15

```
Ser Leu Arg Leu Ser Cys Thr Ala Ser Gly Tyr Thr Tyr Arg Tyr Leu
            20                  25                  30

Tyr Met Ala Trp Phe Arg Gln Thr Pro Gly Lys Glu Arg Glu Gly Val
        35                  40                  45

Ala Cys Ile Tyr Thr Gly Ser Gly Thr Gly Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Asn Ala Glu Asp Thr Ala Met Tyr Tyr Cys
                85                  90                  95

Ala Ala Ser Ser Pro Gln Trp Gly Gly Thr Cys Arg Arg Trp Ser Glu
            100                 105                 110

Tyr Asn Tyr Trp Gly Gln Gly Thr Gln Val Thr Val Ser Ser
        115                 120                 125

<210> SEQ ID NO 337
<211> LENGTH: 116
<212> TYPE: PRT
<213> ORGANISM: Artificial
<220> FEATURE:
<223> OTHER INFORMATION: Anti-DLL3 camel sdAb amino acid sequence
      AS64475

<400> SEQUENCE: 337

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Trp Ser Arg Asn
            20                  25                  30

Trp Met Gly Trp Phe Arg Gln Ala Pro Gly Lys Glu Arg Glu Gly Phe
        35                  40                  45

Ala Thr Ile Thr Ile Ser Gly Ser Thr Trp Tyr Ala Asp Ser Val
    50                  55                  60

Lys Gly Arg Phe Thr Ile Ser Leu Asp Asn Ala Gly Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Asp Thr Ala Arg Thr Tyr Trp Gly Gln Gly Thr Gln Val
            100                 105                 110

Thr Val Ser Ser
        115

<210> SEQ ID NO 338
<211> LENGTH: 127
<212> TYPE: PRT
<213> ORGANISM: Artificial
<220> FEATURE:
<223> OTHER INFORMATION: Anti-DLL3 camel sdAb amino acid sequence
      AS64513

<400> SEQUENCE: 338

Glu Val Gln Leu Val Glu Ser Gly Gly Gly Ser Val Gln Ala Gly Gly
1               5                   10                  15

Ser Leu Arg Leu Ser Cys Val Ala Ser Asp Tyr Pro Tyr Ile Asp Asn
            20                  25                  30

Cys Met Gly Trp Phe Arg Gln Gly Pro Gly Lys Glu Arg Glu Gly Val
        35                  40                  45

Ala Ala Ala Cys Thr Gly Gly Gly Ser Thr Tyr Tyr Ala Asp Ser Val
    50                  55                  60
```

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Asp Val Tyr Tyr Cys
                 85                  90                  95

Ala Thr Gly Tyr Tyr Ser Gly Ser Gly Pro Gly Tyr Leu Leu Pro Trp
            100                 105                 110

Arg Tyr Asn Tyr Trp Gly Gln Gly Thr Gln Val Thr Val Ser Ser
        115                 120                 125

<210> SEQ ID NO 339
<211> LENGTH: 131
<212> TYPE: PRT
<213> ORGANISM: Artificial
<220> FEATURE:
<223> OTHER INFORMATION: Anti-DLL3 camel sdAb amino acid sequence
      AS64562

<400> SEQUENCE: 339

Glu Val Gln Leu Val Glu Ser Gly Gly Gly Ser Val Gln Ala Gly Gly
  1               5                  10                  15

Ser Leu Arg Leu Ser Cys Ala Ala Ser Gly Tyr Thr Ala Arg Arg Asp
             20                  25                  30

Phe Met Ala Trp Phe Arg Gln Val Pro Gly Lys Glu Arg Glu Gly Val
         35                  40                  45

Ala Val Ile His Thr Gly Gly Asp Thr Thr Tyr Tyr Ala Asp Ser Val
     50                  55                  60

Lys Gly Arg Phe Thr Ile Ser Arg Asp Asn Ala Gln Asn Ile Met Asn
 65                  70                  75                  80

Leu Gln Met Asn Ser Leu Lys Pro Glu Asp Thr Ala Met Tyr Tyr Cys
                 85                  90                  95

Ala Ala Gly Phe Arg Pro Arg Gly Gly Gly Tyr Thr Gly Asp Val Leu
            100                 105                 110

Ala Gln Ala Ala Ala Tyr Asn Tyr Trp Gly Gln Gly Thr Gln Val Thr
        115                 120                 125

Val Ser Ser
    130

<210> SEQ ID NO 340
<211> LENGTH: 126
<212> TYPE: PRT
<213> ORGANISM: Artificial
<220> FEATURE:
<223> OTHER INFORMATION: Anti-DLL3 camel sdAb amino acid sequence
      AS64583

<400> SEQUENCE: 340

Glu Val Gln Leu Ala Glu Ser Gly Gly Gly Leu Val Gln Ala Gly Gly
  1               5                  10                  15

Ser Leu Arg Leu Ser Cys Thr Ala Ser Gly Phe Thr Ile Ala Val Tyr
             20                  25                  30

Thr Met Gly Trp Phe Arg Gln Ala Pro Gly Lys Glu Arg Glu Gly Ile
         35                  40                  45

Ser Cys Thr Ser Trp Ala Gly Gly Arg Thr Tyr Thr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Met Tyr Tyr Cys
                 85                  90                  95
```

```
Ala Ala Lys Ala His Pro Asp Cys Ser Gly Asp Trp Ser Pro Ser Gly
            100                 105                 110

Tyr Glu Tyr Trp Gly Gln Gly Thr Gln Val Thr Val Ser Ser
        115                 120                 125

<210> SEQ ID NO 341
<211> LENGTH: 116
<212> TYPE: PRT
<213> ORGANISM: Artificial
<220> FEATURE:
<223> OTHER INFORMATION: Anti-DLL3 camel sdAb amino acid sequence
      AS64594

<400> SEQUENCE: 341

Gln Val His Leu Val Glu Ser Gly Gly Gly Val Gln Ala Gly Gly
1               5                   10                  15

Ser Leu Arg Leu Ser Cys Ala Ala Ser Gly Tyr Thr Tyr Asn Ser Asn
            20                  25                  30

Tyr Met Gly Trp Phe Arg Gln Ala Pro Gly Lys Glu Arg Glu Gly Val
        35                  40                  45

Ala Leu Ile Tyr Thr Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ser Val Arg Thr Gln Thr Arg Asn Tyr Trp Gly Gln Gly Thr Gln Val
            100                 105                 110

Thr Val Ser Ser
        115

<210> SEQ ID NO 342
<211> LENGTH: 131
<212> TYPE: PRT
<213> ORGANISM: Artificial
<220> FEATURE:
<223> OTHER INFORMATION: Anti-DLL3 camel sdAb amino acid sequence
      AS64605

<400> SEQUENCE: 342

Gln Val Lys Leu Val Glu Ser Gly Gly Gly Ser Val Gln Ala Gly Gly
1               5                   10                  15

Ser Leu Arg Leu Ser Cys Ala Val Ser Arg Tyr Pro Tyr Ser Ser Ile
            20                  25                  30

Cys Met Gly Trp Phe Arg Gln Ala Pro Gly Lys Glu Ser Glu Gly Val
        35                  40                  45

Ala Arg Ile Tyr Thr Gly Thr Gly Ser Thr Trp Tyr Thr Asp Ser Val
    50                  55                  60

Lys Gly Arg Phe Thr Ile Ala Arg Asp Asn Ala Gln Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Ser Asn Ser Tyr Ser Tyr Ser Cys Asp Tyr Gly Pro
            100                 105                 110

Leu Thr Arg Gly Gly Tyr Asn Phe Trp Gly Gln Gly Thr Gln Val Thr
        115                 120                 125

Val Ser Ser
        130
```

```
<210> SEQ ID NO 343
<211> LENGTH: 115
<212> TYPE: PRT
<213> ORGANISM: Artificial
<220> FEATURE:
<223> OTHER INFORMATION: Anti-DLL3 camel sdAb amino acid sequence
      AS64606

<400> SEQUENCE: 343

Glu Val Gln Leu Ala Glu Ser Gly Gly Gly Ser Val Gln Ala Gly
1               5                   10                  15

Ser Leu Arg Leu Ser Cys Ala Val Ser Gly Tyr Thr Ser Arg Ser Asn
            20                  25                  30

Tyr Met Gly Trp Phe Arg Gln Ala Pro Gly Lys Glu Arg Glu Gly Val
        35                  40                  45

Ala Leu Ile Tyr Thr Arg Gly Ser Thr Tyr Tyr Ala Ser Ser Val
    50                  55                  60

Lys Gly Arg Phe Thr Ile Ser Gln Asp Ser Ala Lys Lys Thr Tyr Leu
65                  70                  75                  80

Gln Met Asn Ser Val Lys Pro Glu Asp Thr Ala Met Tyr Tyr Cys Ala
                85                  90                  95

Leu Arg Leu Asp Glu Lys Met Tyr Trp Gly Gln Gly Thr Gln Val Thr
            100                 105                 110

Val Ser Ser
        115

<210> SEQ ID NO 344
<211> LENGTH: 133
<212> TYPE: PRT
<213> ORGANISM: Artificial
<220> FEATURE:
<223> OTHER INFORMATION: Anti-DLL3 camel sdAb amino acid sequence
      AS68121

<400> SEQUENCE: 344

Glu Val Gln Leu Ala Glu Ser Gly Gly Gly Ser Val Gln Ala Gly Gly
1               5                   10                  15

Ser Leu Arg Leu Ser Cys Asp Ala Ser Gly Tyr Thr Tyr Ser Arg Asn
            20                  25                  30

Cys Met Gly Trp Phe Arg Gln Ala Pro Gly Lys Glu Arg Glu Gly Val
        35                  40                  45

Ala Ala Phe Tyr Thr Asp Tyr Ile Arg Phe Gly Arg Thr Tyr Tyr Ala
    50                  55                  60

Asp Ser Val Lys Gly Arg Phe Thr Ile Phe Gln Asp Asn Ala Lys Asn
65                  70                  75                  80

Thr Val Tyr Leu Gln Met Asn Ser Leu Lys Pro Glu Asp Thr Ala Met
                85                  90                  95

Tyr Tyr Cys Ala Ala Asp Pro Gly Ser Arg Thr Asp Asp Ser Cys Gly
            100                 105                 110

Thr Ser Tyr Asn Lys Gly Asn Phe Gly Tyr Trp Gly Gln Gly Thr Gln
            115                 120                 125

Val Thr Val Ser Ser
    130

<210> SEQ ID NO 345
<211> LENGTH: 130
<212> TYPE: PRT
<213> ORGANISM: Artificial
<220> FEATURE:
```

<223> OTHER INFORMATION: Anti-DLL3 camel sdAb amino acid sequence
    AS68170

<400> SEQUENCE: 345

Gln Val Gln Leu Val Glu Ser Gly Gly Gly Ser Val Gln Ala Gly Gly
1               5                   10                  15

Ser Leu Arg Leu Ser Cys Thr Ala Ser Gly Tyr Thr Tyr Arg Ser Asn
            20                  25                  30

Cys Met Gly Trp Phe Arg Gln Ala Pro Gly Lys Glu Arg Glu Gly Val
        35                  40                  45

Ala Thr Ile Tyr Thr Gly Gly Arg Asn Leu Tyr Tyr Ala Asp Ser
    50                  55                  60

Val Lys Gly Arg Phe Thr Ile Ser Arg Asp Asn Ala Lys Asn Thr Leu
65                  70                  75                  80

Tyr Leu Gln Met Asn Ser Leu Lys Pro Glu Asp Ser Ala Arg Tyr Tyr
                85                  90                  95

Cys Ala Ala Ala Ser Asp Val Ala Val Gly Val Asn Ser Cys Gly Gly
            100                 105                 110

Arg Thr Ala Gly Phe Asp Ala Trp Gly Gln Gly Thr Gln Val Thr Val
        115                 120                 125

Ser Ser
    130

<210> SEQ ID NO 346
<211> LENGTH: 125
<212> TYPE: PRT
<213> ORGANISM: Artificial
<220> FEATURE:
<223> OTHER INFORMATION: Anti-DLL3 camel sdAb amino acid sequence
    AS63964

<400> SEQUENCE: 346

Gln Val Arg Leu Val Glu Ser Gly Gly Gly Ser Val Gln Ala Gly Gly
1               5                   10                  15

Ser Leu Arg Leu Ser Cys Ser Ala Ser Gly Tyr Thr Tyr Ser Tyr Asn
            20                  25                  30

Asn Met Gly Trp Phe Arg Gln Ala Pro Gly Asn Glu Arg Glu Gly Val
        35                  40                  45

Ala Ala Ile Ser Gly Gly Arg Phe Thr Ala Tyr Ala Asp Ser Val Lys
    50                  55                  60

Gly Arg Phe Thr Ile Ser Arg Asp Asn Ala Glu Asn Thr Leu Tyr Leu
65                  70                  75                  80

Gln Met Asn Asn Leu Lys Pro Glu Asp Thr Gly Met Tyr Tyr Cys Ala
                85                  90                  95

Ala Glu Val Val Asp Pro Thr Trp Gly Ser Arg Asp Gln Arg Arg Tyr
            100                 105                 110

Lys Tyr Trp Gly Gln Gly Thr Gln Val Thr Val Ser Ser
        115                 120                 125

<210> SEQ ID NO 347
<211> LENGTH: 124
<212> TYPE: PRT
<213> ORGANISM: Artificial
<220> FEATURE:
<223> OTHER INFORMATION: Anti-DLL3 camel sdAb amino acid sequence
    AS64116

<400> SEQUENCE: 347

Gln Val Lys Leu Val Glu Ser Gly Gly Gly Ser Val Gln Ala Gly Gly

-continued

```
  1               5                  10                 15
Ser Leu Arg Leu Ser Cys Ala Ala Ser Gly Tyr Ile Tyr Ser Cys Val
            20                  25                 30

Gly Trp Phe Arg Gln Ala Pro Gly Lys Glu Arg Glu Gly Val Ala Gly
            35                  40                 45

Ile Ser Thr Gly Gly Gly Thr Val Tyr Ala Asp Ser Val Lys Gly
            50                  55                 60

Gln Phe Thr Ile Ser Arg Asp Asn Ala Lys Asn Thr Val Tyr Leu Gln
 65                      70                 75                 80

Met Asp Ser Leu Lys Pro Glu Asp Thr Ala Met Tyr Tyr Cys Ala Ala
            85                  90                 95

Asp Arg Trp Asn Ser Phe Ala Asn Cys Gly Ala Trp Gly Arg Tyr Thr
            100                 105                110

Tyr Trp Gly Gln Gly Thr Gln Val Thr Val Ser Ser
            115                 120
```

<210> SEQ ID NO 348
<211> LENGTH: 130
<212> TYPE: PRT
<213> ORGANISM: Artificial
<220> FEATURE:
<223> OTHER INFORMATION: Anti-DLL3 camel sdAb amino acid sequence
      AS68270

<400> SEQUENCE: 348

```
Gln Val Gln Leu Ala Glu Ser Gly Gly Gly Ser Val Gln Ala Gly Gly
 1               5                  10                 15

Ser Leu Arg Leu Ser Cys Val Ala Ser Gly Tyr Pro Ser Ser Thr Tyr
            20                  25                 30

Tyr Met Leu Ser Met Ala Trp Phe Arg Gln Ala Pro Gly Lys Glu Arg
            35                  40                 45

Glu Gly Val Ala Ala Ile Thr Ser Gly Thr Gly Ser Thr Ser Tyr Ala
            50                  55                 60

Asp Ser Val Lys Asp Arg Phe Thr Ile Ser Lys Asp Tyr Ala Asn Asn
 65                      70                 75                 80

Thr Leu Tyr Leu His Ile Asn Asn Leu Lys Pro Glu Asp Thr Ala Met
            85                  90                 95

Tyr Tyr Cys Ala Ala Ala Ser Gly Trp Ile Val Pro Ser Arg Ser Leu
            100                 105                110

Thr Ala Asn Leu Tyr Arg Tyr Trp Gly Gln Gly Thr Gln Val Thr Val
            115                 120                125

Ser Ser
    130
```

<210> SEQ ID NO 349
<211> LENGTH: 125
<212> TYPE: PRT
<213> ORGANISM: Artificial
<220> FEATURE:
<223> OTHER INFORMATION: Anti-DLL3 camel sdAb amino acid sequence
      AS68320

<400> SEQUENCE: 349

```
Gln Val His Leu Val Glu Ser Gly Gly Asp Ser Val Gln Ala Gly Gly
 1               5                  10                 15

Ser Leu Arg Leu Ser Cys Ala Ala Ser Gly Tyr Thr Tyr Asn Thr Asn
            20                  25                 30

Tyr Met Gly Trp Phe Arg Gln Ala Pro Gly Lys Glu Arg Glu Gly Val
```

```
                35                  40                  45
Ala Ala Ile Tyr Arg His Ser Gly Asn Thr Ala Tyr Ala Asp Ser Val
        50                  55                  60
Lys Gly Arg Phe Thr Ile Ser Gln Asp Tyr Ala Lys Asn Thr Val Tyr
 65                  70                  75                  80
Leu Gln Met Asn Ser Leu Lys Pro Glu Asp Thr Ala Met Tyr Tyr Cys
                85                  90                  95
Ala Ala Gly Arg Ala Gly Pro Trp Ala Leu Met Arg Pro Thr Glu Phe
            100                 105                 110
Gly Tyr Trp Gly Gln Gly Thr Gln Val Thr Val Ser Ser
        115                 120                 125

<210> SEQ ID NO 350
<211> LENGTH: 123
<212> TYPE: PRT
<213> ORGANISM: Artificial
<220> FEATURE:
<223> OTHER INFORMATION: Anti-DLL3 camel sdAb amino acid sequence
      AS68351

<400> SEQUENCE: 350

Gln Val Gln Leu Glu Glu Ser Gly Gly Gly Leu Val Gln Pro Gly Gly
  1               5                  10                  15
Ser Leu Arg Leu Ser Cys Ala Ala Ser Gly Asp Thr Phe Arg Ala Tyr
                20                  25                  30
Tyr Met Asn Trp Val Arg Gln Ala Pro Gly Lys Gly Phe Glu Trp Val
            35                  40                  45
Ser Gly Ile Ser Ala Ser Gly Arg Thr Ser Tyr Ala Asp Ser Val
        50                  55                  60
Lys Gly Arg Phe Thr Ile Ser Arg Asp Asn Ala Lys Asn Thr Leu Tyr
 65                  70                  75                  80
Leu Gln Leu Asn Ser Leu Ser Thr Glu Asp Thr Gly Met Tyr Tyr Cys
                85                  90                  95
Val Lys Gly Ala Val Arg Leu Ser Thr Ser Ser Val Arg Asp Ser Ser
            100                 105                 110
Trp Gly Gln Gly Thr Gln Val Thr Val Ser Ser
        115                 120

<210> SEQ ID NO 351
<211> LENGTH: 116
<212> TYPE: PRT
<213> ORGANISM: Artificial
<220> FEATURE:
<223> OTHER INFORMATION: Anti-DLL3 camel sdAb amino acid sequence
      AS75378

<400> SEQUENCE: 351

Gln Val Gln Leu Glu Glu Ser Gly Gly Gly Ser Val Gln Ala Gly Gly
  1               5                  10                  15
Ser Leu Arg Leu Ser Cys Val Val Ser Gly Asn Thr Arg Ser Thr Thr
                20                  25                  30
Tyr Met Gly Trp Phe Arg Gln Ala Pro Gly Lys Glu Arg Glu Gly Val
            35                  40                  45
Ala Ile Val Tyr Thr Gly Gly Arg Asp Thr Tyr Tyr Ala Ala Ser Val
        50                  55                  60
Lys Gly Arg Phe Thr Ile Ser Gln Asp Asn Ala Lys Thr Thr Ile Tyr
 65                  70                  75                  80
Leu Gln Met Asn Ser Leu Glu Pro Glu Asp Thr Ala Met Tyr Tyr Cys
```

```
                        85                  90                  95

Ala Ala Arg Ser Tyr Glu Tyr Thr Tyr Trp Gly Arg Gly Thr Gln Val
            100                 105                 110

Thr Val Ser Ser
        115

<210> SEQ ID NO 352
<211> LENGTH: 124
<212> TYPE: PRT
<213> ORGANISM: Artificial
<220> FEATURE:
<223> OTHER INFORMATION: Anti-DLL3 camel sdAb amino acid sequence
      AS75383

<400> SEQUENCE: 352

Glu Val Gln Leu Ala Glu Ser Gly Gly Gly Ser Val Gln Ala Gly Gly
1               5                   10                  15

Ser Leu Arg Leu Ser Cys Val Ala Ser Gly Tyr Thr Phe Ser Ser Tyr
            20                  25                  30

Cys Leu Gly Trp Phe Arg Gln Ala Pro Gly Lys Gln Arg Gln Gly Val
        35                  40                  45

Ala Thr Phe Asn Asn Arg Gly Val Ala Asn Tyr His Asp Ser Val Lys
    50                  55                  60

Gly Arg Phe Thr Ala Ser Val Asp Asn Ala Lys Asn Thr Leu Leu Leu
65                  70                  75                  80

Gln Met Asn Ser Leu Glu Pro Asp Asp Thr Ala Met Tyr Tyr Cys Ala
                85                  90                  95

Ala Asp Arg Arg Tyr Gly Arg Gln Trp Tyr Gln Pro Cys Glu Trp Asn
            100                 105                 110

Thr Trp Gly Gln Gly Thr Gln Val Thr Val Ser Ser
        115                 120

<210> SEQ ID NO 353
<211> LENGTH: 129
<212> TYPE: PRT
<213> ORGANISM: Artificial
<220> FEATURE:
<223> OTHER INFORMATION: Anti-DLL3 camel sdAb amino acid sequence
      AS75751

<400> SEQUENCE: 353

Gln Val Arg Leu Val Glu Ser Gly Gly Gly Ser Val Gln Ala Gly Gly
1               5                   10                  15

Ser Leu Arg Leu Ser Cys Val Ala Ser Gly Tyr Phe Tyr Asn Thr Tyr
            20                  25                  30

Tyr Phe Met Gly Trp Phe Arg Gln Ala Pro Gly Lys Glu Arg Glu Gly
        35                  40                  45

Val Ala Ala Ile Asp Thr Asp Gly Arg Thr Ser Tyr Ala Asp Ser Val
    50                  55                  60

Lys Gly Arg Phe Thr Ile Ser Lys Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Gly Phe Gly Tyr Met Asn Val Ile Gln Ala Leu Asn Gly Met
            100                 105                 110

Arg Gln Asn Pro Asp Tyr Trp Gly Gln Gly Thr Gln Val Thr Val Ser
        115                 120                 125

Ser
```

<210> SEQ ID NO 354
<211> LENGTH: 124
<212> TYPE: PRT
<213> ORGANISM: Artificial
<220> FEATURE:
<223> OTHER INFORMATION: Anti-DLL3 camel sdAb amino acid sequence
      AS76422

<400> SEQUENCE: 354

Gln Val Lys Leu Val Glu Ser Gly Gly Gly Ser Val Gln Ala Gly Gly
1               5                   10                  15

Ser Leu Arg Leu Ser Cys Ala Ala Ser Gly Tyr Thr Phe Ala Gly Asn
            20                  25                  30

Cys Leu Gly Trp Phe Arg Gln Ala Pro Gly Lys Gly Arg Glu Gly Val
        35                  40                  45

Val Thr Tyr Asn Asn Phe Gly Val Ala Asn Tyr Ala Asp Ser Val Lys
    50                  55                  60

Gly Arg Phe Thr Val Ser Gln Asp Asn Ala Lys Asn Thr Leu Leu Leu
65                  70                  75                  80

Gln Met Asn Ser Leu Glu Pro Glu Asp Thr Ala Met Tyr Tyr Cys Ala
                85                  90                  95

Ala Asp Arg Arg Asp Gly Arg Arg Trp Ser Gln Pro Cys Glu Trp Asn
            100                 105                 110

Thr Trp Gly Gln Gly Thr Gln Val Thr Val Ser Ser
        115                 120

<210> SEQ ID NO 355
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64380VH4

<400> SEQUENCE: 355

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Thr Tyr Ser Ser Asn
            20                  25                  30

Tyr Met Gly Trp Phe Arg Gln Ala Pro Gly Lys Gly Leu Glu Val
        35                  40                  45

Ala Val Ile Tyr Thr Arg Gly Gly His Thr Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Ser Arg His Arg Leu Gly Leu Asn Asn Pro Arg Asp Tyr
            100                 105                 110

Asp Tyr Trp Gly Gln Gly Thr Leu Val Thr Val Ser Ser
        115                 120                 125

<210> SEQ ID NO 356
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64380VH5

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Thr Tyr Ser Ser Asn
            20                  25                  30

Tyr Met Gly Trp Phe Arg Gln Ala Pro Gly Lys Gly Leu Glu Glu Val
        35                  40                  45

Ala Val Ile Tyr Thr Arg Gly Gly His Thr Tyr Tyr Val Asp Ser Val
    50                  55                  60

Arg Gly Arg Phe Thr Ile Ser Gln Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ala Ser Ser Arg His Arg Leu Gly Leu Asn Asn Pro Arg Asp Tyr
            100                 105                 110

Asp Tyr Trp Gly Gln Gly Thr Leu Val Thr Val Ser Ser
        115                 120                 125

<210> SEQ ID NO 357
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64380VH6

<400> SEQUENCE: 357

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Thr Tyr Ser Ser Asn
            20                  25                  30

Tyr Met Gly Trp Phe Arg Gln Ala Pro Gly Lys Gly Leu Glu Glu Val
        35                  40                  45

Ala Val Ile Tyr Thr Arg Gly Gly His Thr Tyr Tyr Val Asp Ser Val
    50                  55                  60

Arg Gly Arg Phe Thr Ile Ser Gln Asp Asn Ala Lys Asn Ser Val Tyr
65                  70                  75                  80

Leu Gln Met Asn Ser Leu Arg Ala Glu Asp Thr Ala Met Tyr Tyr Cys
                85                  90                  95

Ala Ala Ser Ser Arg His Arg Leu Gly Leu Asn Asn Pro Arg Asp Tyr
            100                 105                 110

Asp Tyr Trp Gly Gln Gly Thr Leu Val Thr Val Ser Ser
        115                 120                 125

<210> SEQ ID NO 358
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64380VH7

<400> SEQUENCE: 358

Glu Val Gln Leu Val Glu Ser Gly Gly Gly Leu Val Gln Pro Gly Gly
1               5                   10                  15

Ser Leu Arg Leu Ser Cys Ala Ala Ser Gly Asn Thr Tyr Ser Ser Asn
            20                  25                  30

Tyr Met Gly Trp Phe Arg Gln Ala Pro Gly Lys Gly Arg Glu Val
            35                  40                  45

Ala Val Ile Tyr Thr Arg Gly His Thr Tyr Tyr Val Asp Ser Val
 50                  55                  60

Arg Gly Arg Phe Thr Ile Ser Gln Asp Asn Ala Lys Asn Ser Val Tyr
 65                  70                  75                  80

Leu Gln Met Asn Ser Leu Arg Ala Glu Asp Thr Ala Met Tyr Tyr Cys
                 85                  90                  95

Ala Ala Ser Ser Arg His Arg Leu Gly Leu Asn Asn Pro Arg Asp Tyr
                100                 105                 110

Asp Tyr Trp Gly Gln Gly Thr Leu Val Thr Val Ser Ser
        115                 120                 125

<210> SEQ ID NO 359
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64511VH4

<400> SEQUENCE: 359

Glu Val Gln Leu Val Glu Ser Gly Gly Gly Leu Val Gln Pro Gly Gly
1               5                   10                  15

Ser Leu Arg Leu Ser Cys Ala Ala Ser Arg Ala Thr Tyr Ser Thr Asn
            20                  25                  30

Tyr Ile Ser Trp Phe Arg Gln Ala Pro Gly Lys Gly Leu Glu Ala Val
            35                  40                  45

Ala Thr Ile Thr Thr Gly Asp Gly Glu Thr Ala Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Ala Asn Leu Arg Ile Gly Gly Asp Trp Phe Asp Gly Arg Asp Phe
                100                 105                 110

Arg Ala Trp Gly Gln Gly Thr Leu Val Thr Val Ser Ser
        115                 120                 125

<210> SEQ ID NO 360
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64511VH5

<400> SEQUENCE: 360

Glu Val Gln Leu Val Glu Ser Gly Gly Gly Leu Val Gln Pro Gly Gly
1               5                   10                  15

Ser Leu Arg Leu Ser Cys Ala Ala Ser Arg Ala Thr Tyr Ser Thr Asn
            20                  25                  30

Tyr Ile Ser Trp Phe Arg Gln Ala Pro Gly Lys Gly Leu Glu Ala Val
            35                  40                  45

Ala Thr Ile Thr Thr Gly Asp Gly Glu Thr Ala Tyr Ala Asp Ser Val
 50                  55                  60

Lys Gly Arg Phe Thr Ile Ser Arg Asp Asn Ala Lys Asn Ser Val Tyr
 65                  70                  75                  80

```
Leu Gln Met Asn Ser Leu Arg Ala Glu Asp Thr Ala Met Tyr Tyr Cys
                85                  90                  95

Ala Ala Asn Leu Arg Ile Gly Gly Asp Trp Phe Asp Gly Arg Asp Phe
            100                 105                 110

Arg Ala Trp Gly Gln Gly Thr Leu Val Thr Val Ser Ser
        115                 120                 125

<210> SEQ ID NO 361
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS64511VH6

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Ala Ser Arg Ala Thr Tyr Ser Thr Asn
            20                  25                  30

Tyr Ile Ser Trp Phe Arg Gln Ala Pro Gly Lys Gly Arg Glu Ala Val
        35                  40                  45

Ala Thr Ile Thr Thr Gly Asp Gly Glu Thr Ala Tyr Ala Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Met Tyr Tyr Cys
                85                  90                  95

Ala Ala Asn Leu Arg Ile Gly Gly Asp Trp Phe Asp Gly Arg Asp Phe
            100                 105                 110

Arg Ala Trp Gly Gln Gly Thr Leu Val Thr Val Ser Ser
        115                 120                 125

<210> SEQ ID NO 362
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS63931VH4

<400> SEQUENCE: 362

Gln Val Gln Leu Val Glu Ser Gly Gly Gly Val Val Gln Pro Gly Gly
1               5                   10                  15

Ser Leu Arg Leu Ser Cys Ala Gly Ser Phe Ser Gly Tyr Gly Val Ser
            20                  25                  30

Thr Met Ala Trp Phe Arg Gln Ala Pro Gly Lys Gly Leu Glu Gly Val
        35                  40                  45

Ala Ala Ile Thr Val Gly Ser Gly Asn Thr Tyr Tyr Ala Asp Ser Val
    50                  55                  60

Thr Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Trp Leu Ser Gly Gly Ser Trp His Val Pro Gly Arg Tyr
            100                 105                 110

Asn Tyr Trp Gly Gln Gly Thr Leu Val Thr Val Ser Ser
        115                 120                 125
```

<210> SEQ ID NO 363
<211> LENGTH: 125
<212> TYPE: PRT
<213> ORGANISM: Artificial
<220> FEATURE:
<223> OTHER INFORMATION: Anti-DLL3 humanized sdAb amino acid sequence AS63931VH5

<400> SEQUENCE: 363

```
Gln Val Gln Leu Val Glu Ser Gly Gly Gly Val Val Gln Pro Gly Gly
1               5                   10                  15

Ser Leu Arg Leu Ser Cys Ala Gly Ser Phe Ser Gly Tyr Gly Val Ser
            20                  25                  30

Thr Met Ala Trp Phe Arg Gln Ala Pro Gly Lys Gly Leu Glu Gly Val
        35                  40                  45

Ala Ala Ile Thr Val Gly Ser Gly Asn Thr Tyr Tyr Ala Asp Ser Val
    50                  55                  60

Thr Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Met Tyr Tyr Cys
                85                  90                  95

Ala Ala Gly Trp Leu Ser Gly Gly Ser Trp His Val Pro Gly Arg Tyr
            100                 105                 110

Asn Tyr Trp Gly Gln Gly Thr Leu Val Thr Val Ser Ser
        115                 120                 125
```

<210> SEQ ID NO 364
<211> LENGTH: 125
<212> TYPE: PRT
<213> ORGANISM: Artificial
<220> FEATURE:
<223> OTHER INFORMATION: Anti-DLL3 humanized sdAb amino acid sequence AS63931VH6

<400> SEQUENCE: 364

```
Gln Val Gln Leu Val Glu Ser Gly Gly Gly Val Val Gln Pro Gly Gly
1               5                   10                  15

Ser Leu Arg Leu Ser Cys Ala Gly Ser Phe Ser Gly Tyr Gly Val Ser
            20                  25                  30

Thr Met Ala Trp Phe Arg Gln Ala Pro Gly Lys Gly Arg Glu Gly Val
        35                  40                  45

Ala Ala Ile Thr Val Gly Ser Gly Asn Thr Tyr Tyr Ala Asp Ser Val
    50                  55                  60

Thr Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Met Tyr Tyr Cys
                85                  90                  95

Ala Ala Gly Trp Leu Ser Gly Gly Ser Trp His Val Pro Gly Arg Tyr
            100                 105                 110

Asn Tyr Trp Gly Gln Gly Thr Leu Val Thr Val Ser Ser
        115                 120                 125
```

<210> SEQ ID NO 365
<211> LENGTH: 125
<212> TYPE: PRT
<213> ORGANISM: Artificial
<220> FEATURE:
<223> OTHER INFORMATION: Anti-DLL3 humanized sdAb amino acid sequence AS63997VH4

```
<400> SEQUENCE: 365

Gln Val Gln Leu Val Glu Ser Gly Gly Gly Val Val Gln Pro Gly Gly
1               5                   10                  15

Ser Leu Arg Leu Ser Cys Ala Ala Ser Phe Ser Gly Tyr Gly Val Ser
            20                  25                  30

Thr Met Ala Trp Phe Arg Gln Ala Pro Gly Lys Gly Leu Glu Gly Val
        35                  40                  45

Ala Ala Ile Thr Val Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Gly Tyr Leu Ser Gly Gly Ser Trp Asp Val Pro Gly Arg Tyr
            100                 105                 110

Asn Tyr Trp Gly Gln Gly Thr Leu Val Thr Val Ser Ser
        115                 120                 125

<210> SEQ ID NO 366
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS63997VH5

<400> SEQUENCE: 366

Gln Val Gln Leu Val Glu Ser Gly Gly Gly Val Val Gln Pro Gly Gly
1               5                   10                  15

Ser Leu Arg Leu Ser Cys Ala Ala Ser Phe Ser Gly Tyr Gly Val Ser
            20                  25                  30

Thr Met Ala Trp Phe Arg Gln Ala Pro Gly Lys Gly Leu Glu Gly Val
        35                  40                  45

Ala Ala Ile Thr Val Gly Ser Gly Asn Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Met Tyr Tyr Cys
                85                  90                  95

Ala Val Gly Tyr Leu Ser Gly Gly Ser Trp Asp Val Pro Gly Arg Tyr
            100                 105                 110

Asn Tyr Trp Gly Gln Gly Thr Leu Val Thr Val Ser Ser
        115                 120                 125

<210> SEQ ID NO 367
<211> LENGTH: 125
<212> TYPE: PRT
<213> ORGANISM: Artificial
<220> FEATURE:
<223> OTHER INFORMATION: Anti-DLL3 humanized sdAb amino acid sequence
      AS63997VH6

<400> SEQUENCE: 367

Gln Val Gln Leu Val Glu Ser Gly Gly Gly Val Val Gln Pro Gly Gly
1               5                   10                  15

Ser Leu Arg Leu Ser Cys Ala Ala Ser Phe Ser Gly Tyr Gly Val Ser
            20                  25                  30

Thr Met Ala Trp Phe Arg Gln Ala Pro Gly Lys Gly Arg Glu Gly Val
```

```
                35                  40                  45
Ala Ala Ile Thr Val Gly Ser Gly Asn Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Met Tyr Tyr Cys
                85                  90                  95

Ala Val Gly Tyr Leu Ser Gly Ser Trp Asp Val Pro Gly Arg Tyr
            100                 105                 110

Asn Tyr Trp Gly Gln Gly Thr Leu Val Thr Val Ser Ser
        115                 120                 125

<210> SEQ ID NO 368
<211> LENGTH: 387
<212> TYPE: DNA
<213> ORGANISM: Artificial
<220> FEATURE:
<223> OTHER INFORMATION: Camel sdAb AS63930 Nucleic Acid Sequence

<400> SEQUENCE: 368
gaggtgcaac tggcggagtc tggggggagga tcggtgcagg ctggagggtc tctgagactc      60
tcctgtgcag cctctggata cacctacagt ggcaactata tggcctggtt ccgccaggct     120
ccagggaacg agcgcgaggg ggtcgcagtt gtttataata ttgacggtgg cggtcgtttc     180
actacctatg ccgactccgt gaagggccga ttcaccatct cccgaggcaa cgacaagaac     240
acggtgtatc tgcaaatgaa cagcctgaaa cctgaggata gtggcatgta ctactgtgcg     300
gcagaggtag ctgatccgac ctgggggtcg cgtgaccaaa gacgatataa gtactgggc     360 caggggaccc aggtcaccgt ctcctca                                          387

<210> SEQ ID NO 369
<211> LENGTH: 354
<212> TYPE: DNA
<213> ORGANISM: Artificial
<220> FEATURE:
<223> OTHER INFORMATION: Camel sdAb AS63932 Nucleic Acid Sequence

<400> SEQUENCE: 369
caggtgcaat tggaggagtc tggggggaggc tcggtgcagg ctggagggtc tctgagactc      60
tcctgtgtag cctctggata cacctacggt agcaccttca tgggctggtt ccgccagaat     120
ccagggaagg agcgcgaggg ggtcgcagtt atttatactg gtggtggtag tacatggtat     180
gccagctccg tgaagggccg attcaccatc tcccaggaca cgccaagaa cacggtgtat     240 ctgcaaatga acagcctgaa acctgaggac actgccatgt actactgtgc ggcgcgttac     300
gggtcgggaa acgttaacta ctggggccag gggacccagg tcaccgtctc ctca           354

<210> SEQ ID NO 370
<211> LENGTH: 390
<212> TYPE: DNA
<213> ORGANISM: Artificial
<220> FEATURE:
<223> OTHER INFORMATION: Camel sdAb AS63951 Nucleic Acid Sequence

<400> SEQUENCE: 370
caggtgcacc tgatggagtc tggggggaggc tcggtgcagg ctggagggtc tctgagactc      60
gcctgtgaaa cctctagaga catctacggt aacaactgca tggcctggtt ccgccaggct     120
ccagggaagg agcgcgaggg agtcgcgtct atttatcctg ctggtggtcg cccgtactat     180
```

```
gccgactccg tgaagggccg attcaccatc tcccaagaca acgccaagaa cacggtgtat    240
ctgcaaatgg acagcctgaa acctgaggac acggccatgt actactgcgc ggcacgctct    300
ttttcgatag cagtttgcgc gacgcgctct ggtattacca ggtctaattt tgcttactgg    360
ggccagggga cccaggtcac cgtctcctca                                     390
```

<210> SEQ ID NO 371
<211> LENGTH: 387
<212> TYPE: DNA
<213> ORGANISM: Artificial
<220> FEATURE:
<223> OTHER INFORMATION: Camel sdAb AS63984 Nucleic Acid Sequence

<400> SEQUENCE: 371

```
caggtgaagt tggtggagtc tgggggaggc tcggtgcagg ctggagggtc tctgagactc    60
tcctgtgcag cctctggata cacctacagt agcaacttca tgggctggtt ccgccaggct    120
ccagggaagg agcgcgaggg ggtcgcaact attgtttctg gtggtggtac cacatactat    180
gccgactccg tgaggggccg attcaccatc tcccaagaca acgccaagaa cacggtgtat    240
ctgcaaatga acagcctgaa acctgaggac actgccatgt actactgtgc ggcagggggc    300
cccgttacga acgcacctag atggtacccc ctccgacctc tggttataa ctactggggc    360 caggggaccc aggtcaccgt ctcctca                                        387
```

<210> SEQ ID NO 372
<211> LENGTH: 366
<212> TYPE: DNA
<213> ORGANISM: Artificial
<220> FEATURE:
<223> OTHER INFORMATION: Camel sdAb AS63987 Nucleic Acid Sequence

<400> SEQUENCE: 372

```
caggtgaggt tggtggagtc tgggggaggc tcggtgcagg ctggagggtc tctgagactc    60
tcctgtgaag ccactggata tagaaactgc atggcctggt tccgccaagc tccagggaag    120
gaacgcgagg gggtcgcagt tatttatact cctagtggta tcacggacta tgcaagctcc    180
gtgaagggcc gattcaccat ctcccaaaac aacgccagga acacgcagta tctgcaaatg    240
aacagcctga aacctgagga cactgccatg tactactgtg cggcagatcg acccttttgtt    300 tgtaatatag cgaatatgag aaggtcctcc aactgggggcc gggggaccca ggtcaccgtc    360
tcctca                                                               366
```

<210> SEQ ID NO 373
<211> LENGTH: 375
<212> TYPE: DNA
<213> ORGANISM: Artificial
<220> FEATURE:
<223> OTHER INFORMATION: Camel sdAb AS63997 Nucleic Acid Sequence

<400> SEQUENCE: 373

```
caggtgaggt tggtggagtc tgggggaggc tcggtgcagg ctggagggtc tctgagactc    60
tcctgtgcag gctcttctctc tggatacggc gtcagtacca tggcctggtt ccgccaggct    120
ccagggaagg agcgcgaggg ggtcgcagct attacagttg gtagtggaaa cacatactat    180
gccgactccg tgaagggccg attcaccatc tcccgagaca acgccaagag gacggtgttt    240
ttgcaaatga acagcctgaa acctgaggac actgccatgt actactgtgc ggtcggatac    300
ttgtcgggtg gtagttggga cgttcccgga aggtataact actggggcca ggggacccag    360
gtcaccgtct cctca                                                     375
```

<210> SEQ ID NO 374
<211> LENGTH: 375
<212> TYPE: DNA
<213> ORGANISM: Artificial
<220> FEATURE:
<223> OTHER INFORMATION: Camel sdAb AS64047 Nucleic Acid Sequence

<400> SEQUENCE: 374

| | | | | | |
|---|---|---|---|---|---|
| caggtgcacc | tggtggagtc | tgggggaggc | tcggtgcagg | ctggagggtc | tctgagactc | 60 |
| tcctgtgcag | cctctcagta | cgtttacagg | tgggacctca | tgggctggtt | ccgccaggct | 120 |
| ccagggaagg | agcgcgaggc | ggtcgctgct | gtttatactg | gtgatggtat | tacatactat | 180 |
| gccgactccg | tgaagggccg | attcagcatt | tcccaagaca | acgccaagaa | cacggtgtat | 240 |
| ctgcaaatga | acagcctgaa | acctgaggac | actggcatgt | acttctgtgc | ggcaggcttc | 300 |
| gtctctggtg | gtagatggaa | ccagtcatat | cgttataaat | actggggcca | ggggacccag | 360 |
| gtcaccgtct | cctca | | | | | 375 |

<210> SEQ ID NO 375
<211> LENGTH: 387
<212> TYPE: DNA
<213> ORGANISM: Artificial
<220> FEATURE:
<223> OTHER INFORMATION: Camel sdAb AS64052 Nucleic Acid Sequence

<400> SEQUENCE: 375

| | | | | | |
|---|---|---|---|---|---|
| caggtgcacc | tgatggagtc | tgggggaggc | tcggtgcagg | ctggagggtc | tctgagactc | 60 |
| tcctgtgcag | cctctggata | cacctaccgc | agcaacttca | tgggctggtt | ccgccaggct | 120 |
| ccagggaagg | agcgcgaggg | gatcgcaact | attcattctg | gtgtggctac | cacatactat | 180 |
| gccgactccg | tgaagggccg | attcaccatc | tcccaagaca | acgccaagaa | cacggtgtat | 240 |
| ctgcaaatga | acagcctgaa | acctgaggac | actgccatgt | actactgtgc | ggcaggggcc | 300 |
| cccctgcga | acgctgatag | atggtacccc | ctccgacctc | ctggttataa | ctactggggc | 360 |
| caggggaccc | aggtcaccgt | ctcctca | | | | 387 |

<210> SEQ ID NO 376
<211> LENGTH: 381
<212> TYPE: DNA
<213> ORGANISM: Artificial
<220> FEATURE:
<223> OTHER INFORMATION: Camel sdAb AS64062 Nucleic Acid Sequence

<400> SEQUENCE: 376

| | | | | | |
|---|---|---|---|---|---|
| caggtgaggt | tggtggagtc | tgggggaggc | tcggtgcagg | ttggagggtc | tctgagactc | 60 |
| tcctgtgcag | cctctagatc | tccctacagt | agcagtaggt | gcatgggtg | gttccgccag | 120 |
| gctccaggga | aggagcgcga | gggggtcgca | gctctttata | ctggtggtgg | tagcacatcc | 180 |
| tatgccgact | ccgtgaaggg | ccgattcacc | atctcccaag | acaacgccaa | gaatacggtg | 240 |
| tatctgcaaa | tgaacagcct | gaaacctgag | gacactgcca | tgtactactg | tgcggcagtt | 300 |
| gtccctaggg | gtggtagctg | ccgtcttgat | gaaagagggt | attaccactg | gggccagggg | 360 |
| acccaggtca | ccgtctcctc | a | | | | 381 |

<210> SEQ ID NO 377
<211> LENGTH: 369
<212> TYPE: DNA
<213> ORGANISM: Artificial
<220> FEATURE:

<223> OTHER INFORMATION: Camel sdAb AS64072 Nucleic Acid Sequence

<400> SEQUENCE: 377

```
caggtgcagc tggtggagtc tgggggaggc tcggtgcagg ccggagggtt tctgagactc      60
tcctgtgcac tctctggata cagctactat attaacttga tggcgtggtt ccgtcaggct     120
ccagggaagg agcgcgaggc agtcgcagct catggtcctg tgagtgggac agcatactat     180
accgactccg tgaagggccg attcaccatc tcccgagacc ccgcaagaa cacgatgtat      240
cttcaaatgt ttagcctgca accggaggac actgccctct actactgtgc ggcggaaacg     300
actatgggtt gggcccacga acgcgggtat aggtactggg gccaggggac ccaggtcacc     360
gtctcctca                                                             369
```

<210> SEQ ID NO 378
<211> LENGTH: 381
<212> TYPE: DNA
<213> ORGANISM: Artificial
<220> FEATURE:
<223> OTHER INFORMATION: Camel sdAb AS64097 Nucleic Acid Sequence

<400> SEQUENCE: 378

```
caggtgcacc tgatggagtc tgggggaggc tcggtgcagg ctggagggtc tctgagactc      60
tcctgtgaag cctctggata cacctacagt cgcaactgca tgggctggtt ccgccaggct     120
ccagggaagg agcgcgaggg ggtcgcagct attaacactg gtggtggtag cacatatt at    180
gccgactccc ttgagggccg attcaccatc tcccaagaca cgccaagaa tactatgtat      240
ctgcaaatga acagcctgaa acctgaggac actgccatgt actactgtgc ggcaggtccc     300
gatctcggtg gtagctggtg tcggcccgtt gagcgggctt ttacgtactg gggccagggg     360
acccaggtca ccgtctcctc a                                               381
```

<210> SEQ ID NO 379
<211> LENGTH: 375
<212> TYPE: DNA
<213> ORGANISM: Artificial
<220> FEATURE:
<223> OTHER INFORMATION: Camel sdAb AS64114 Nucleic Acid Sequence

<400> SEQUENCE: 379

```
caggtgcaac tgcaggagtc tgggggggc tcggtgcagg ctggagggtc tctgacactc       60
tcctgtgaag cctctggaaa cacctacagt actaattaca tgggctggtt ccgccaggct     120
ccagggaagg agcgcgaaga ggtcgcggtt atttacactc gtggtggtca cacatactat     180
gtcgactccg tgaggggccg attcaccatc tcccaagaca cgccaagaa cacggtgtat      240
ctgcaaatga acagcctgaa acctgaggac actgccatgt actactgtgc ggcagcttca     300
cgacatagac tccgtttaaa taacccacgg gactatgact actggggcca ggggacccag     360
gtcaccgtct cctca                                                      375
```

<210> SEQ ID NO 380
<211> LENGTH: 348
<212> TYPE: DNA
<213> ORGANISM: Artificial
<220> FEATURE:
<223> OTHER INFORMATION: Camel sdAb AS64123 Nucleic Acid Sequence

<400> SEQUENCE: 380

```
caggtgcaac tgcgagagtc tgggggaggc tcggtgcagg ctggagggtc tctgagactc      60
tcctgtgcag cctctggata cacttatacg agcaactggc tgggctggtt ccgccaggct     120
```

```
ccagggaagg agcgcgagga ggtcgcaatt atttatactg gtagtggtag tacacactat    180
cgcagctccg tgaagggccg attcaccatc tcccaagaca cgccaagaa  cacggtgtat    240 ctgcaaatga acagcctgaa acctgaggac actgccatgt actactgtgc ggcgcgtttc    300
tcagagtata attactgggg ccaggggacc caggtcaccg tctcctca                 348
```

<210> SEQ ID NO 381
<211> LENGTH: 387
<212> TYPE: DNA
<213> ORGANISM: Artificial
<220> FEATURE:
<223> OTHER INFORMATION: Camel sdAb AS64130 Nucleic Acid Sequence

<400> SEQUENCE: 381

```
gaggtgcaac tggcggagtc tggggagggc tcggtgcagg ctggagggtc tctgagactc    60
tcctgtgcag cctctggata cacctaccgt agcaacttca tgggctggtt ccgccaggct   120
ccggcgaagg agcgcgaggg ggtcgcaact attgattctc gtggtactat cacatactat   180
gccgactccg tgaagggccg attcaccatc tcccaagaca cgagaagaa  cacggtgtat   240 ctgcaaatga acagcctgaa acctgaggac actgccatgt actactgtgc ggcaggggc   300 ccccgcacga acgatgatag atggtacccc ctccgacctc ctggttataa ctactgggc   360 caggggaccc aggtcaccgt ctcctca                                        387
```

<210> SEQ ID NO 382
<211> LENGTH: 378
<212> TYPE: DNA
<213> ORGANISM: Artificial
<220> FEATURE:
<223> OTHER INFORMATION: Camel sdAb AS64137 Nucleic Acid Sequence

<400> SEQUENCE: 382

```
caggtgaggt tagtggagtc tggggagggc tcggtgcagg ctggagggtc tctgagactc    60
tcctgtgctg cctctggatc cacctacagt acaaacttca tgggctggtt ccgccaggct   120
ccagggaagg agcgcgaggg ggtcgcaacg ctggttactt gggttgaacg cacagcctat   180
gccgactccg tgaagggccg attcaccatc tcccaagacc cgccaagaa  cacggtgtat   240 ctacaaatga acagcctgaa acctgaggac actgccatgt actactgtgc ggcagccgcc   300
gcttccactg atgtacgtct cctcgacccg ggggactttg cttactgggg ccaggggacc   360
caggtcaccg tctcctca                                                  378
```

<210> SEQ ID NO 383
<211> LENGTH: 378
<212> TYPE: DNA
<213> ORGANISM: Artificial
<220> FEATURE:
<223> OTHER INFORMATION: Camel sdAb AS64142 Nucleic Acid Sequence

<400> SEQUENCE: 383

```
caggtgcacc tgatggagtc tggggaggc  ttggtgcaga caggggggtc tctgagactc    60
tcctgtacag cctctggatt cacttttgat cgtaatgcca tgcgctggta ccgccaggct   120
ccagggaagg agcgcgaggg ggtctcatgt attgattgga cgggtgcaaa tattgcctat   180
gcagactccg tgaagggccg attcaccatc tccagagaca cgccaagaa  cacgctgtat   240 ctgcaaatga acagcctgaa acctgaggac acgggcatgt attactgtgc ggcagatacg   300
acgtcggggt attgttcagg cttttggtct acagccggt  actcatgggg ccaggggacc   360
```

```
caggtcaccg tctcctca                                              378
```

<210> SEQ ID NO 384
<211> LENGTH: 378
<212> TYPE: DNA
<213> ORGANISM: Artificial
<220> FEATURE:
<223> OTHER INFORMATION: Camel sdAb AS64154 Nucleic Acid Sequence

<400> SEQUENCE: 384

```
caggtgcaat tgaaggagtc tgggggaggc tcggtgcagg ctggagggtc tctgagactc   60
tcctgtacag cctctggata cacctacaga tacctctaca tgggctggtt ccgccagact  120
ccagggaagg agcgcgaggg ggtcgcatgt atttatactg gtagtggtag cacagggtat  180
gccgactccg tgaagggccg attcaccatc tccaagaca acgccaagaa cacggtgtat  240
ctgcaaatga acaacctgaa acctgaggac actgccatgt actactgtgc ggcaagttcg  300
ccccggtggg gcggtacctg tcgacgctgg tctcagtata actactgggg ccaggggacc  360
caggtcaccg tctcctca                                                378
```

<210> SEQ ID NO 385
<211> LENGTH: 384
<212> TYPE: DNA
<213> ORGANISM: Artificial
<220> FEATURE:
<223> OTHER INFORMATION: Camel sdAb AS64160 Nucleic Acid Sequence

<400> SEQUENCE: 385

```
gaggtgcagc tggtggagtc tgggggaggc tcggtgcagg ctggagggtc tctgagactc   60
tcctgtgcgg cctctgtata caccagcagt agctactgca tgggctggtt ccgccaggct  120
ccagggaagg agcgcgaggg ggtcgcagct atgtgttttg gtggtcttgt cacacactat  180
gccgactccg tgaagggccg attcaccatc tccaagaca atgccaagaa cacggtgtat  240
ctgcaaatga acagcctgaa acctgaggac actgccatgt actactgtgc ggcagatttc  300
ggcagggata aaaactattt acgaccgtta ctgccccatg catataacta ctggggccaa  360
gggacccagg tcaccgtctc ctca                                         384
```

<210> SEQ ID NO 386
<211> LENGTH: 351
<212> TYPE: DNA
<213> ORGANISM: Artificial
<220> FEATURE:
<223> OTHER INFORMATION: Camel sdAb AS64228 Nucleic Acid Sequence

<400> SEQUENCE: 386

```
caggtgcaat tgaaggagtc tgggggaggt tcgatccagg ctggagggtc tctgagactc   60
tcctgtgcag cctctggagt ctcctacaat aggtgcagta tgggctggta ccgccaggct  120
ccagggaagg ggcgcgagtt ggtctcacgt attcagccgg tggtaatac atactatgca  180
gactccgtga agggccgatt caccgtctcc aagacaacg ccaagaacac agtatctcta  240
caaatgaaca gcctgaaacc tgaggacacg gccatgtatt actgtaacgc actgtgctgg  300
cgggagaatg ttaactactg gggccagggg acccaggtca ccgtctcctc a           351
```

<210> SEQ ID NO 387
<211> LENGTH: 372
<212> TYPE: DNA
<213> ORGANISM: Artificial
<220> FEATURE:
<223> OTHER INFORMATION: Camel sdAb AS64300 Nucleic Acid Sequence

<400> SEQUENCE: 387

| caggtgcacc tggtggagtc tgggggaggc tcggtgcaga ctggaggatc tctgagactc | 60 |
| tcctgtgcag tctctggaga catctataac ctcatgtcga tggcctggtt ccgccgggct | 120 |
| ccagggaagg agcgcgaggg ggtcgcatat attaatacta ttattggtaa cacatactat | 180 |
| actgactccg tgaagggccg attcaccatc tcccgcgata actccaagaa cactttgtat | 240 |
| ctgcaaatga caacctgaa acctgaggac acagccatgt actactgtgc ggcgttcaat | 300 |
| tacggaggtg cctggtacga ggaacgcagc tataaatact ggggccaggg gacccaggtc | 360 |
| accgtctcct ca | 372 |

<210> SEQ ID NO 388
<211> LENGTH: 375
<212> TYPE: DNA
<213> ORGANISM: Artificial
<220> FEATURE:
<223> OTHER INFORMATION: Camel sdAb AS64380 Nucleic Acid Sequence

<400> SEQUENCE: 388

| gaggtgcagc tggtggagtc tggggggggc tcggtgcagg ctggagggtc tctgacactc | 60 |
| tcctgtgaag cctctggaaa cacctacagt agtaattaca tgggctggtt ccgccaggct | 120 |
| ccagggaagg agcgcgagga ggtcgcggtt atttacactc gtggtggtca cacatactat | 180 |
| gtcgactccg tgaggggccg attcaccatc tcccaagaca acgccaagaa cacggtgtat | 240 |
| ctgcaaatga acagcctgaa acctgaggac actgccatgt actactgtgc ggcgtcttca | 300 |
| cgacatagac tcggttttaaa taacccacgg gactatgact actggggcca ggggacccag | 360 |
| gtcaccgtct cctca | 375 |

<210> SEQ ID NO 389
<211> LENGTH: 375
<212> TYPE: DNA
<213> ORGANISM: Artificial
<220> FEATURE:
<223> OTHER INFORMATION: Camel sdAb AS64395 Nucleic Acid Sequence

<400> SEQUENCE: 389

| caggtgaggt tggtggagtc tgggggaggc tcggtgcagg ctggagggtc tctgagactc | 60 |
| tcctgtgctg cctctggatc cacctacagt acaaacttca tgggctggtt ccgccaggct | 120 |
| ccagggaagg agcgcgaggg ggtcgcaacg cttgttactt gggctgaacg cacagcctat | 180 |
| gccgactccg tgaagggccg attcaccatc tcccaagacc gcgccaagaa cacggtgtat | 240 |
| ctacaaatga acggcctgaa acctgaggac actgccatgt actactgtgc ggcagccgct | 300 |
| tccactgctg tacgtctcct cgacccgggg gactttgctt actggggcca ggggacccag | 360 |
| gtcaccgtct cctca | 375 |

<210> SEQ ID NO 390
<211> LENGTH: 348
<212> TYPE: DNA
<213> ORGANISM: Artificial
<220> FEATURE:
<223> OTHER INFORMATION: Camel sdAb AS64443 Nucleic Acid Sequence

<400> SEQUENCE: 390

| caggtgcacc tggtggagtc tgggggaggc tcggtgcagg ctggagggtc tctgagactc | 60 |
| tcctgtgcag cctctggata taccgacagt agcgtctaca taggctggtt ccgccaggct | 120 |

```
ccagggaagg agcgcgagga ggtcgcgatt atttatactg gtggtgaaag cacacactat    180
cgcagctccg tgaagggccg attcaccgtc tcccaagaca cgccaagaa cacgctgtat    240
ctgcaaatga acagcctgaa acctgaggac acggccatgt attactgtgc agcacgattc    300
ccagctgtta cctactgggg ccaggggacc caggtcaccg tctcctca                348
```

<210> SEQ ID NO 391
<211> LENGTH: 375
<212> TYPE: DNA
<213> ORGANISM: Artificial
<220> FEATURE:
<223> OTHER INFORMATION: Camel sdAb AS64511 Nucleic Acid Sequence

<400> SEQUENCE: 391

```
caggtgcagc tggtggagtc tgggggaggc tcggtgcagg ctggagggtc tctgagactc     60
tcctgtgcag cctctagagc cacctacagt accaactaca taagctggtt ccgccaggct    120
ccagggaagg agcgcgaggc ggtcgcaaca attactactg gtgatggtga cacagcgtat    180
gccgactccg tgaagggccg attcaccatc tcccgagaca cgccaagaa cacggtctat    240
ctgcaaatga acagcctgaa acctgaggac actgccatgt actactgtgc ggcgaacttg    300
cgaatcggtg gcgactggtt cgacggacgc gattttcgtg cctggggcca ggggacccag    360
gtcaccgtct cctca                                                     375
```

<210> SEQ ID NO 392
<211> LENGTH: 375
<212> TYPE: DNA
<213> ORGANISM: Artificial
<220> FEATURE:
<223> OTHER INFORMATION: Camel sdAb AS64536 Nucleic Acid Sequence

<400> SEQUENCE: 392

```
caggtgaagt tggtggagtc tgggggaggc tcggtgcagg ctggagggtc tctgagactc     60
tcctgtgcag cctctagata caccgacaat ttcgtgtaca tgggctggtt ccgccaggct    120
ccagggaagg agcgcgaggg ggtcgcactg atttatcctg gtggtggtag cacctactat    180
gcctcctccg tgaagggccg attcaccatc tcccaagaca cgccaaggg cacggtgcat    240
ctgcaaatga acaacctgaa acctgaggac actgccatgt actactgtgc ggcaaaatgg    300
gggctgggcg gggggggcct gaaatcagat acgtatatgt actggggcca ggggacccag    360
gtcaccgtct cctca                                                     375
```

<210> SEQ ID NO 393
<211> LENGTH: 387
<212> TYPE: DNA
<213> ORGANISM: Artificial
<220> FEATURE:
<223> OTHER INFORMATION: Camel sdAb AS64597 Nucleic Acid Sequence

<400> SEQUENCE: 393

```
caggtgcacc tggtggagtc tgggggaggc tcggtgcagg ctggagggtc tctgagactc     60
tcctgtgcag cctctggata cacctaccgt gtcaacttca tgggctggtt ccgccagact    120
ccagggaagg agcgcgaggg ggtcgcaact attgattctg gtgtgggtac cacatactat    180
gccgactccg tgaagggccg attcaccatc tcccataaca cgccaagaa cacgatttat    240
ctgcaaatga acagcctgaa acctgaggac actgccatgt actactgtgc ggcaggggc    300
cccccctacgg acggtgatag atggtacccc ctccgacctc ctggttataa ctattggggc    360
caggggaccc aggtcaccgt ctcctca                                        387
```

<210> SEQ ID NO 394
<211> LENGTH: 351
<212> TYPE: DNA
<213> ORGANISM: Artificial
<220> FEATURE:
<223> OTHER INFORMATION: Camel sdAb AS64617 Nucleic Acid Sequence

<400> SEQUENCE: 394

| | |
|---|---|
| caggtgcagc tggtggagtc tgggggaggc tcggtgcagg ctggagggtc tctgagactc | 60 |
| tcctgtgcag cctctggata cactgataga tgcagcatgg cctggtaccg ccaggctcca | 120 |
| gggaaggagc gcgagttggt ctcgcgtatt agcacgagcg gtttcacaaa ctacgcagcc | 180 |
| tccgtgaagg gccgattcac catctcccaa gacaacgcca agaacacggt gtatctgcaa | 240 |
| atgaacagcc tgaaccccgg ggacacgggc atgtattact gtgccataat cgtaggacgt | 300 |
| acttgtagtt tgaactactg gggcaacggc atcctggtca ccgtctcctc a | 351 |

<210> SEQ ID NO 395
<211> LENGTH: 381
<212> TYPE: DNA
<213> ORGANISM: Artificial
<220> FEATURE:
<223> OTHER INFORMATION: Camel sdAb AS64634 Nucleic Acid Sequence

<400> SEQUENCE: 395

| | |
|---|---|
| caggtgaggt tggtggagtc tgggggaggc tcggtgcagg ctggagggtc tctgagactc | 60 |
| tcctgtgcag cctccggata cagtttttaga ggcgacttta tgtgtatggg ctggttccgc | 120 |
| cagactccag ggaaggggcg cgaggggggtc gcagtttttt atcctggtgg cggcagcaca | 180 |
| aactatgccg actccgcgaa gggccgattc accatctccc aagacaacgc caagaacacg | 240 |
| atgtatctgc aaatgaacac cctgaaacct gaggacactg ccatgtacta ctgtgcggct | 300 |
| cgacggtggg tcagtggtac ctgctactgg gatagtgact tcattactg gggccagggg | 360 |
| acccaggtca ccgtctcctc a | 381 |

<210> SEQ ID NO 396
<211> LENGTH: 375
<212> TYPE: DNA
<213> ORGANISM: Artificial
<220> FEATURE:
<223> OTHER INFORMATION: Camel sdAb AS69498 Nucleic Acid Sequence

<400> SEQUENCE: 396

| | |
|---|---|
| cagatgcagc tggtggagtc tgggggaggc tcggtgcagg ctggagggtc tctgagactc | 60 |
| tcctgtgcag cctctggaaa cacctacagt accaattaca tggcgtggtt ccgccaggct | 120 |
| ccagggaagg agcgcgagga ggtcgcggtt atttacactc gtggtggtca cacctactat | 180 |
| atcgactccg tgaggggccg attcaccatc tcccaagaca cgccaagaa cacggtgtat | 240 |
| ctgcaaataa acagcctgaa acctgaggac actgccatgt actactgtgc ggcgtcttca | 300 |
| cgaattagac tccattgaat cgacccacgg gactatcacg actggggcca ggggacccag | 360 |
| gtcaccgtct cctca | 375 |

<210> SEQ ID NO 397
<211> LENGTH: 381
<212> TYPE: DNA
<213> ORGANISM: Artificial
<220> FEATURE:
<223> OTHER INFORMATION: Camel sdAb AS69500 Nucleic Acid Sequence

```
<400> SEQUENCE: 397
caggtgaggt tagtggagtc tgggggaggc tcggtgcagg ctggagggtc tctgagactc      60
tcctgtgcag ccgacagata cacctacagt agcgcctgca tgggctggtt ccgccaggct     120
ccagggaagg agcgcgaggg ggtcgcctct attttactg gtactggtgg tagcacatac      180
tatgccgact ccgtgaaggg ccgattcacc atctcccaag acaacgccaa gaacacggtg     240
tatctgcaaa tgaacagcct gaaacctgag gacactgcca tatactactg tgcggcaagg     300
gccttccagg tcggttactg ctacctgcga accgatgtgt ataactactg gggccagggg     360
acccaggtca ccgtctcctc a                                                381

<210> SEQ ID NO 398
<211> LENGTH: 375
<212> TYPE: DNA
<213> ORGANISM: Artificial
<220> FEATURE:
<223> OTHER INFORMATION: Camel sdAb AS69527 Nucleic Acid Sequence

<400> SEQUENCE: 398
gaggtgcagc tggcggagtc tgggggaggc tcggtccagg ctggagggtc tctgagactc      60
tcctgtgtag cctctagata cacctttcagt agcacctgca tggcctggtt ccgccaggct    120
ccagggaagg agcgcgagga ggtcgcagct atttatactg atgatggtag cacatggtat     180
gccgactccg tgaagggccg attcaccatc tccagagaca cgccaagaa cacggtgtat     240 ctgcaaatga acagcctgaa acctgaggac actgctatgt actactgtgc ggcacgtagg     300
tgggcgtgcc ccagggttgg tagctggcat gagttcgcct actggggcca ggggacccag     360
gtcaccgtct cctca                                                      375

<210> SEQ ID NO 399
<211> LENGTH: 375
<212> TYPE: DNA
<213> ORGANISM: Artificial
<220> FEATURE:
<223> OTHER INFORMATION: Camel sdAb AS68280 Nucleic Acid Sequence

<400> SEQUENCE: 399
caggtgcaac tggtggagtc tgggggaggc tcggtgcacc ctggagggtc tctgagactc      60
tcctgtgcag cctctggatc cacctacagt tccaactacc tcggctggtt ccgccaggct     120
ccaggaaagg ggcgcgactg ggttgcggct attagcactg gtgacggtgc cacagcctat    180
gccgactccg tgaagggccg attcaccatc tccaagaca cgccaagaa cacggtgtat      240 ctgcaaatga acagcttgaa acttgaggac agtgccatgt actactgtgc ggcggctcgc    300
ggcagattta tcgattggac aaaggcaacc cagtatgact actggggcca ggggacccag    360
gtcaccgtct cctca                                                      375

<210> SEQ ID NO 400
<211> LENGTH: 384
<212> TYPE: DNA
<213> ORGANISM: Artificial
<220> FEATURE:
<223> OTHER INFORMATION: Camel sdAb AS68355 Nucleic Acid Sequence

<400> SEQUENCE: 400
cagatgcagc tggtggagtc tgggggagac tcggtgcagg ctggagggtc tctgagactc      60
tcctgtgcag cctctggata cacctacagc ggcgtctgca tgggctggtt ccgccaggct     120
ccagggaagg agcgcgaggg ggtcgcagct attgatagtg atggtagcac aagctacgca     180
```

```
gactccgtga agggccgatt caccatctcc aaagacaacg ccaagaacac tctgtatctg    240
caaatgaaca gcctgaaacc tgaggacact gccatgtact actgtgcggc agccattgtc    300 gggggttttta atgcatattg tagtggtggt tatgttctgg actttggtgc ctggggccag    360
gggacccagg tcaccgtctc ctca                                            384
```

<210> SEQ ID NO 401
<211> LENGTH: 396
<212> TYPE: DNA
<213> ORGANISM: Artificial
<220> FEATURE:
<223> OTHER INFORMATION: Camel sdAb AS69443 Nucleic Acid Sequence

<400> SEQUENCE: 401

```
gaggtgcagc tggcggagtc tggggggaggc tcggtgcagg ctggagggtc tctgagactc    60
tcctgttcag cctctggttt cacttttgat gattctgaca tggcctggta ccgccaggct   120
ccaggggatg ggtgcgactt ggtctcaact attagtagtg atggtagcac atactatgca   180
gactccgtga agggccgatt caccatctcc aagacaacg ccaagaacac ggtgtatctg    240
caaatgcaca gcctgaaacc tgaggacacg gccgtgtatt actgtgcggc agatttcctc   300
accggctttt actatagcga ctccccccat ccggccccctt gttctgcatc cgactttggt   360
tactggggcc aggggaccca ggtcaccgtc tcctca                              396
```

<210> SEQ ID NO 402
<211> LENGTH: 378
<212> TYPE: DNA
<213> ORGANISM: Artificial
<220> FEATURE:
<223> OTHER INFORMATION: Camel sdAb AS75376 Nucleic Acid Sequence

<400> SEQUENCE: 402

```
caggtgcaat tgaaggagtc tggggggaggc tcggtgcagg ctggagggtc tctgagactc    60
tcctgtgcag cctctggata cacctacagt agccactcca tgggctggtt ccgccaggct   120
ccagggaagg agcgcgaggg ggtcgcagtt atttatactg gtgatggtag cacatactat   180
gccgactccg tgaagggccg attcaccatc tcccaagaca cgccaagaa cacggtgtat    240 ctgcaaatga acagcctgaa acctgaggac actgccatgt actactgtgc ggcagatccg   300
aaccccgatt atatgcttcc gtttcggcc tcccgtaggt cgtggtgggg ccaggggacc    360
caggtcaccg tctcctca                                                  378
```

<210> SEQ ID NO 403
<211> LENGTH: 369
<212> TYPE: DNA
<213> ORGANISM: Artificial
<220> FEATURE:
<223> OTHER INFORMATION: Camel sdAb AS75387 Nucleic Acid Sequence

<400> SEQUENCE: 403

```
caggtgcacc tggtggagtc tggggggaggc tcggtgcagg ctggagggtc tctgagactc    60
tcctgtgcag cctctggata cccctacagt agcccctgca tggcctggtt tcgccaggct   120
ccagggaagg agcgcgaggg ggttttagtt gcttatactg gtggggacat tcaataccct   180
accgactccg tgaagggccg attcaccatc tcccgagaca cgccaagaa cacggtgtat    240 ctgcaaatga acagcctgaa acctgaggac actgccatgt actactgtgc ggcggatctg   300
cgattacctc gtgccggcgg ttgtgcgtat agctactggg gccagggggac ccaggtcacc    360
``` gtctcctca 369

<210> SEQ ID NO 404
<211> LENGTH: 363
<212> TYPE: DNA
<213> ORGANISM: Artificial
<220> FEATURE:
<223> OTHER INFORMATION: Camel sdAb AS75695 Nucleic Acid Sequence

<400> SEQUENCE: 404
caggtgaggt tggtggagtc tgggggaggc tcggtgcagg ctggagggtc tctgagactc     60
tcctgtgtag cctctggata caccgtcagt gcctactgta tgggctggtt ccgccaggtt    120
ctagggaagg ggcgcgagag gatcgcattt atcgatgccg ggggtgctac gatttacgca    180
gaccccgtga agggccgatt caccatctcc aaagacaacg ccaagaacac tctgtatctg    240
caaatgaaca gcctgaaacc tgaggacact gccatgtact actgtgttgc agatcgccgg    300
gggcgggtac gtcggtgcga gtataacgcc tggggccagg ggacccaggt caccgtctcc    360
tca                                                                 363

<210> SEQ ID NO 405
<211> LENGTH: 375
<212> TYPE: DNA
<213> ORGANISM: Artificial
<220> FEATURE:
<223> OTHER INFORMATION: Camel sdAb AS76169 Nucleic Acid Sequence

<400> SEQUENCE: 405
caggtgcacc tgatggagtc tgggggaggc tcggtgcagg ctggagggtc tctgagactc     60
tcctgtgcag cctctggata catttacagt agcttctgca tgggctggtt ccgccaggct    120
ccagggaagg agcgcgaggt ggtcgcgtat attcgcgata atattatgac aagttacaca    180
gactccgtga agggccgatt caccatctcc aaagacaacg ccaagagaac tctgtatcta    240
caaatgaacg gcctgaaacc tgaagatact ggcatgtact actgtgcggt agaccggggg    300
ggatacgcta atagttgcgc ggtagcggcc cggtatgatt actggggccg ggggacccag    360
gtcaccgtct cctca                                                    375

<210> SEQ ID NO 406
<211> LENGTH: 375
<212> TYPE: DNA
<213> ORGANISM: Artificial
<220> FEATURE:
<223> OTHER INFORMATION: Camel sdAb AS63931 Nucleic Acid Sequence

<400> SEQUENCE: 406
gaggtgcagc tggcggagtc tgggggaggc tcggtgcagg ctgggggtc tctgagactc     60
tcctgtgcag gctctttctc tggatacggc gtcagtacca tggcctggtt ccgccaggct    120
ccagggaagg agcgcgaggg ggtcgcagct attactgttg gtagtggaaa cacatactat    180
gccgactccg tgacgggccg attcaccatc tcccgagaca cgccaagag acggtgtat     240
ttgcaaatga acagcctgaa acctgaggac actgccatgt actactgtgc ggccggatgg    300
ttgtcgggtg gtagttggca cgttcccggc aggtataact actggggcca ggggacccag    360
gtcaccgtct cctca                                                    375

<210> SEQ ID NO 407
<211> LENGTH: 369
<212> TYPE: DNA
<213> ORGANISM: Artificial
<220> FEATURE:
<223> OTHER INFORMATION: Camel sdAb AS63937 Nucleic Acid Sequence

<400> SEQUENCE: 407

```
caggtgaagt tagtggagtc tgggggaggc tcggtgcagg ctggagggtc tctgagactc      60
tcctgtgcag cctctggatc caccatcagt agtcgcccga tggcctggtt ccgccaggct     120
ccagggaagg agcgcgaggg ggtcgcgtgt atacatactg gtcttggtag aacatactat     180
gccgactccg tgaagggccg attcaccatc tcccaagaca acgccaagaa cacggtgtat     240
ctgcaagtga acagcctgaa acctgaggac actgccatgt actactgtgc ggcagactcg     300
cggcggccgt gtatggtagc cgcagggtat acctactggg ccaggggac ccaggtcacc      360
gtctcctca                                                             369
```

<210> SEQ ID NO 408
<211> LENGTH: 378
<212> TYPE: DNA
<213> ORGANISM: Artificial
<220> FEATURE:
<223> OTHER INFORMATION: Camel sdAb AS63948 Nucleic Acid Sequence

<400> SEQUENCE: 408

```
caggtgcagc tggtggagtc tgggggaggc tcggtgcagg ctggagggtc tctgagactc      60
tcctgtacag cctctggata cacctataga tacctctaca tgggctggtt ccgccagact     120
ccagggaagg agcgcgaggg ggtcgcatgt atttatactg gtagtggtag cacagggtat     180
gccgactccg tgaagggccg attcaccatc tcccaagaca acgccgagaa cacggtgtat     240
ctgcaaatga acagcctgaa acctgaggac actgccatgt actactgtgc ggcagcttcg     300
ccccggtggg gtggtacctg tcgacggtgg tccgagtata actactgggg ccaggggacc     360
caggtcaccg tctcctca                                                   378
```

<210> SEQ ID NO 409
<211> LENGTH: 369
<212> TYPE: DNA
<213> ORGANISM: Artificial
<220> FEATURE:
<223> OTHER INFORMATION: Camel sdAb AS63956 Nucleic Acid Sequence

<400> SEQUENCE: 409

```
caggtgcacc tggtggagtc tgggggaggc ttggtgcagg ctggagggtc tctgagactc      60
tcctgtgcag cctccggatt cacctacagt aactgctgca tgaggtggta ccgccaggct     120
ccagggaagg cgcgcgagtt ggtctcatta attaatagta gtggtggcac atactatgca     180
gactctgtga ggggccgatt caccatctcc aaagacaacg ccaagaacac gctgtatctg     240
caaatgaaca gcctgaaacc tgaggacacg gccatgtatt actgtgcggc ttaccaagcc     300
aagtactgtt caggcccttg cgccccccca actgactggg gccaggggac ccaggtcacc     360
gtctcctca                                                             369
```

<210> SEQ ID NO 410
<211> LENGTH: 363
<212> TYPE: DNA
<213> ORGANISM: Artificial
<220> FEATURE:
<223> OTHER INFORMATION: Camel sdAb AS63965 Nucleic Acid Sequence

<400> SEQUENCE: 410

```
caggtgcagc tggtggagtc tgggggaggc tcggtgcagg ctggagggtc tctgagactc      60
```

```
tcctgtgtag cctctggata cagcagcggt agttgtcgca tgggctggta ccgccaggct    120
ccagggaagg agcgcgagtt ggtttcaaag gttattagtg atggtactac agtctatgca    180
gactccgtga agggccgatt caccctctcc caaggaaacg ccaagaacac ggtgtatctg    240
caaatgagta gcctgttacc tgaggacacg gccatgtatt actgtaatgc atggtgtagg    300
gagtatcccg gggggatcct gaataacggc tggggccagg ggacccaggt caccgtctcc    360
tca                                                                  363

<210> SEQ ID NO 411
<211> LENGTH: 354
<212> TYPE: DNA
<213> ORGANISM: Artificial
<220> FEATURE:
<223> OTHER INFORMATION: Camel sdAb AS63993 Nucleic Acid Sequence

<400> SEQUENCE: 411
caggtgaagt tggtggagtc tggggggggc ttggtgcagg caggggggtc tctgagactc     60
tcctgtacag tttctggatt cactttcgat gacctcgtca tggcctggtt ccgccaggct    120
ccagggaagg agcgccaact tgtctcgttg gttgcgactg ctggtaatag cgtctatgca    180
gactccgtga agggccgatt cacactctcc agagacaacg cccacagcac ggcgtatctg    240
caaatgaacg gcctgaaacc tgaggacacg gccatgtatt actgtgcggc acgtaccgat    300
tctgagcatg cgtttaagtt ctggggtcag gggacccagg tcaccgtctc ctca          354

<210> SEQ ID NO 412
<211> LENGTH: 348
<212> TYPE: DNA
<213> ORGANISM: Artificial
<220> FEATURE:
<223> OTHER INFORMATION: Camel sdAb AS63999 Nucleic Acid Sequence

<400> SEQUENCE: 412
gaggtgcaac tggtggagtc tgggggaggc tcggtgcagg ctggagggtc tctgagactc     60
tcctgtgcag cctctggata cacttacagt agcaactgga tgggctggtt ccgccaggct    120
ccagggaagg agcgcgagga ggtcgcaatt atttatactg gtggtattag tacacactat    180
cgcagctccg tgaagggccg attcaccatc tcccaagaca cgccaagaa cacggtgtat    240 ctgcaaatga acagcctgaa acctgaggac actgccatgt actactgtgc ggcgcgttat    300
acagactata actactgggg ccaggggacc caggtcaccg tctcctca                 348

<210> SEQ ID NO 413
<211> LENGTH: 348
<212> TYPE: DNA
<213> ORGANISM: Artificial
<220> FEATURE:
<223> OTHER INFORMATION: Camel sdAb AS64006 Nucleic Acid Sequence

<400> SEQUENCE: 413
caggtgcacc tggtggagtc tgggggaggc tcggtgcagg ctggagggtc tctgagactc     60
tcctgtgaag tctctggata caccggcgat acgacttaca taggctggtt ccgccaggct    120
ccagggaagg agcgcgaggg ggtcgcactt atttatacta gtggtactag cgagtactac    180
gccgactccg tgaagggccg attcatcatc tcccgagaca cgccaagaa cacggtgtat    240 ttacaaatga acagcctgaa acctgaggac actgccatgt actactgtgg cgcacggagc    300
cgcacgatga tgtactgggg ccaggggacc caggtcaccg tctcctca                 348
```

-continued

```
<210> SEQ ID NO 414
<211> LENGTH: 378
<212> TYPE: DNA
<213> ORGANISM: Artificial
<220> FEATURE:
<223> OTHER INFORMATION: Camel sdAb AS64057 Nucleic Acid Sequence

<400> SEQUENCE: 414
caggtgcaat tggaggagtc tgggggaggc ttggtgcaga caggggggtc tctgagactc      60
tcctgtacag cctctggatt cacttttgat cgtaatgcca tgcgctggta ccgccaggct     120
ccagggaagg agcgcgaggg ggtctcatgt attagttgga cgggtgcaaa tattgcctat     180
gcagactccg tgaagggccg attcaccatc tccagagaca cgccaagaa cacgctgtat      240 ctgcaaatga acagcctgaa acctgaggac acgggcatgt attactgtgc ggcagatacg     300
acgtcggggt cttgttcagg cttttggtct acgagccggt actactgggg ccaggggacc     360
caggtcaccg tctcctca                                                    378

<210> SEQ ID NO 415
<211> LENGTH: 366
<212> TYPE: DNA
<213> ORGANISM: Artificial
<220> FEATURE:
<223> OTHER INFORMATION: Camel sdAb AS64060 Nucleic Acid Sequence

<400> SEQUENCE: 415
caggtgaagt tagtggagtc tgggggaggc tcggtgcagg ctggagggtc tctgagactc      60
tcctgtgcag cctctggatc cacctactgt acctaccgta tgagctggtt ccgccaggct     120
ccagggaagg agcgcgagtt cgtcgcagtt attgatagtg gcggtagcac aagctacgca     180
gactccgtga agggccgatt caccatctcc gagacaacg ccaagaacac ggtgtatctg      240
caaatgaaca gcctgaaacc tgaggacacg gccatgtatt actgtaaaac agatccaacc     300
atcggctgcc cccagacata taggtataac tactggggcc aggggaccca ggtcaccgtc     360
tcctca                                                                 366

<210> SEQ ID NO 416
<211> LENGTH: 375
<212> TYPE: DNA
<213> ORGANISM: Artificial
<220> FEATURE:
<223> OTHER INFORMATION: Camel sdAb AS64071 Nucleic Acid Sequence

<400> SEQUENCE: 416
caggtgcacc tgatggagtc tgggggaggc tcggtgcagg ctggagggtc tctgagactc      60
tcctgtgtag cctctggaaa cacttacagg ctcaactcta tgggctggtt ccgccaggct     120
ccagggaagg agcgcgaggg ggtcgcattt attgttatga ttagaggtac cacatactat     180
ggcgcctccg taaagggccg attcaccatc tcccaagaca cgcccagac acggtgtat       240 ctgcaaatga gcagcctgaa accggaggac actgccatgt actactgtgc ggcatccact     300
aaggaccagt tttatgtatt taatcctatt gggtatgact cttggggcca ggggacccag     360
gtcaccgtct cctca                                                       375

<210> SEQ ID NO 417
<211> LENGTH: 390
<212> TYPE: DNA
<213> ORGANISM: Artificial
<220> FEATURE:
<223> OTHER INFORMATION: Camel sdAb AS64093 Nucleic Acid Sequence
```

<400> SEQUENCE: 417

```
caggtgcacc tggtggagtc tgggggaggc tcggtgcagg ctggagggtc tctgagactc    60
tcctgtgcaa cctctagata catctacggt aacaactgca tggcctggtt ccgccaggct   120
ccagggaagg agcgcgaggg agtcgcgtct atttatcctg ctggtggtcg cacgtactat   180
gccgactccg tgaagggccg attcaccatc tcccaagaca acgccaagaa cacggtgtat   240
ctgcaaattg acagcctgaa acctgaggac acggccatgt actactgcgc ggcacgctct   300
tttttcgatag gagtttgcgc gacgcagtct ggtattacct ggtctaattt tgcttactgg   360
ggccagggga cccaggtcac cgtctcctca                                     390
```

<210> SEQ ID NO 418
<211> LENGTH: 351
<212> TYPE: DNA
<213> ORGANISM: Artificial
<220> FEATURE:
<223> OTHER INFORMATION: Camel sdAb AS64118 Nucleic Acid Sequence

<400> SEQUENCE: 418

```
caggtgcaac tggcggagtc tgggggaggc tcggtgcagg ctggagggtc tctgagactc    60
tcctgtgcag cctctggata cacctacagt gcctgtagaa tggcctggta ccgccaggct   120
cccgggaagg agcgcgagtt ggtttcattt attaatagtg ctggtagcac atactatgcc   180
gactccgtga agggccgatt cgccatctcc gagacaacg ccaagacaac ggtgtatcta   240
caaatgaacg ccctgaaagc tgaggacacg gccatatatt actgtaacac atgggatagt   300
agctgccgct ttcagtactg gggccagggg acccaggtca ccgtctcctc a            351
```

<210> SEQ ID NO 419
<211> LENGTH: 404
<212> TYPE: DNA
<213> ORGANISM: Artificial
<220> FEATURE:
<223> OTHER INFORMATION: Camel sdAb AS64120 Nucleic Acid Sequence

<400> SEQUENCE: 419

```
caggtgaggt tggtggagtc tgggggaggc tcggtgcagg ctggagggtc tctgagactc    60
tcctgtgaaa cctctagata catctacggt aacaactgca tggcctggtt ccgccaggct   120
ccagggaagg agcgcgaggg agtcgcgtct atttatcctg ctggtggtcg cccgtactat   180
gccgactccg tgaagggccg attcaccatc tcccaaagac aacgccaaga acacggtgta   240
tctgcaaaat ggacagccct gaaaacctga ggacacggcc catgtactac tgcgcgggca   300
cgcttctttt ttcgatagca aattgcgcca acgcaatcct ggtattaacc agggccaaat   360
tttggcttac gggggccagg ggacccaggt caccttctc ctca                     404
```

<210> SEQ ID NO 420
<211> LENGTH: 384
<212> TYPE: DNA
<213> ORGANISM: Artificial
<220> FEATURE:
<223> OTHER INFORMATION: Camel sdAb AS64124 Nucleic Acid Sequence

<400> SEQUENCE: 420

```
caggtgaagt tggtggagtc tgggggaggc tcggtgcaga ctggagggtc tctgagactc    60
tcctgtgcag tctctacgta cacccccagt aacaactaca tgggctggtt ccgccaggct   120
ccagggaagg agcgcgaggg cgtcgcggct atcgctacta ttggtggtac cacacgttat   180
gccgactccg tgaagggccg attcaccatc tcccaagacg cgccaagaa cacgatatat   240
```

```
ctgcaaatga acggcctgaa accggaggac actgccatgt actactgtgc ggccgggcgg      300
ccatactcat tacccttacc cttacccttg gaaagcggtg cgtatcgcta ctggggccag      360
gggacccagg tcaccgtctc ctca                                             384
```

<210> SEQ ID NO 421
<211> LENGTH: 363
<212> TYPE: DNA
<213> ORGANISM: Artificial
<220> FEATURE:
<223> OTHER INFORMATION: Camel sdAb AS64135 Nucleic Acid Sequence

<400> SEQUENCE: 421

```
caggtgaagt tggtggagtc tgggggaggc tcggtgcagg ctggagggtc tctgagactc       60
tcctgtgtag cctctacatc aacctactgt aggtactaca tgcgctggta ccggcaggct      120
ccagggaaag agcgcgagtt cgtctcagcg atgcaacccg atggtacgac aagctactca      180
gactccgtga agggccgatt caccatgtcc aagacagag ccaacaatat gttgtatctg       240
caaatgaaca gcctgaggcc tgaggacacg gccatgtatt actgtaaaag agatccaatg      300
gggggttcaa ggaccccgtg cacctccgcc tggggccagg ggacccaggt caccgtctcc      360
tca                                                                    363
```

<210> SEQ ID NO 422
<211> LENGTH: 375
<212> TYPE: DNA
<213> ORGANISM: Artificial
<220> FEATURE:
<223> OTHER INFORMATION: Camel sdAb AS64163 Nucleic Acid Sequence

<400> SEQUENCE: 422

```
caggtgaggt tggtggagtc tgggggaggc tcggtgcagg ctggagggtc tctgagactc       60
tcctgtgcag tctctggata cagatataga tggaactgca tggcctggtt ccgccaggct      120
ccagggaagg agcgcgaggg ggtcgcagct atttctactg gaagcggaag cacatactat      180
gccggctccg tgaagggccg attcaccatc tcccaagaca acgccaagaa catgtatctg      240
caaatgaaca gcctgaaacc tgaggacact gccatgtact actgtgcggc agatccttcg      300
gtttgccccg gtggtatgtg gtactccaaa gagtataggt actggggcca ggggacccag      360
gtcaccgtct cctca                                                       375
```

<210> SEQ ID NO 423
<211> LENGTH: 378
<212> TYPE: DNA
<213> ORGANISM: Artificial
<220> FEATURE:
<223> OTHER INFORMATION: Camel sdAb AS64182 Nucleic Acid Sequence

<400> SEQUENCE: 423

```
caggtgcacc tgatggagtc tgggggaggc tcggtgcagg ctggagggtc tctgagactc       60
tcctgcacag cctctggaca gacctccaga tacctctaca tgggctggtt cgccagact       120 ccagggaagg agcgcgaggg ggtcgcatgt atttatactg gtagtggtag cacagggtat      180
gccgactccg tgaagggccg attcaccatc tcccaagaca acgccaagaa cacggtgtat      240
ctgcaaacga atagcctgaa acctgaggac actgccatgt actactgtgc ggcaagttcg      300
ccccattggg gcggtacctg tcgacgctgg tccgagtata agtactgggg ccaggggacc      360
caggtcaccg tctcctca                                                    378
```

<210> SEQ ID NO 424
<211> LENGTH: 366
<212> TYPE: DNA
<213> ORGANISM: Artificial
<220> FEATURE:
<223> OTHER INFORMATION: Camel sdAb AS64183 Nucleic Acid Sequence

<400> SEQUENCE: 424

| | | | | | |
|---|---|---|---|---|---|
| caggtgcacc | tggtggagtc | tgggggaggc | tcggtgcagg | ctggagggtc | tctgagactc | 60 |
| tcctgtgcag | cctctggaca | cacctacagt | gccaactgca | tggcctggtt | ccgccgggcc | 120 |
| ccagggaagg | agcgcgagtg | ggtcgcgtcg | gtttatactg | atgatgatag | cacaatgtat | 180 |
| accgactccg | tgaagggccg | attcaccatc | ttccaagaca | acgccaagaa | cacggtgtat | 240 |
| ctgcaaatga | acagcctgaa | acctgaggac | actggcatgt | acatctgtgc | ggcagattta | 300 |
| agcggaggac | cggccggttg | tgggtatacc | cactggggcc | aggggaccca | ggtcaccgtc | 360 |
| tcctca | | | | | | 366 |

<210> SEQ ID NO 425
<211> LENGTH: 387
<212> TYPE: DNA
<213> ORGANISM: Artificial
<220> FEATURE:
<223> OTHER INFORMATION: Camel sdAb AS64207 Nucleic Acid Sequence

<400> SEQUENCE: 425

| | | | | | |
|---|---|---|---|---|---|
| gaggtgcagc | tggtggagtc | tgggggaggc | tcggtgcagg | ctggagggtc | tctgagactc | 60 |
| tcctgtgcag | cctctggata | cacctacagt | agcaacttca | tggctggtt | ccgccaggct | 120 |
| ccagggaagg | agcgcgaggg | ggtcgcaact | attgtttctg | gtggtggtac | cacatactat | 180 |
| gccgactccg | tgaggggccg | attcaccatc | tcccaagaca | acgccaagaa | cacggtgtat | 240 |
| ctgcaaatga | acagcctgaa | acctgaggac | actgccatgt | actactgtgc | ggcaggggc | 300 |
| ccccctacga | acggtgctaa | gtggtacccc | ctccgacctc | ctggttataa | ctactggggc | 360 |
| caggggaccc | aggtcaccgt | ctcctca | | | | 387 |

<210> SEQ ID NO 426
<211> LENGTH: 366
<212> TYPE: DNA
<213> ORGANISM: Artificial
<220> FEATURE:
<223> OTHER INFORMATION: Camel sdAb AS64276 Nucleic Acid Sequence

<400> SEQUENCE: 426

| | | | | | |
|---|---|---|---|---|---|
| caggtgcacc | tgatggagtc | tgggggaggc | tcggtgcagg | ctggagggtc | tctgagcctc | 60 |
| tcctgtgtag | tctctggata | caccggcagt | agccgctgta | tggcctggtt | ccgccaggct | 120 |
| ccagggaagg | agcgcgaggc | ggtcgcacaa | atttttactg | gtcgtggtac | cacaggctat | 180 |
| gccgactccg | tgaagggccg | attcactatt | tcccaagaca | acgccaagaa | cacggtgtat | 240 |
| ctgcgaatga | acagtctgag | acctgaggac | actgccattt | actactgtgc | ggcgagtctc | 300 |
| ggcccgggac | gcggagcctg | tgggtataac | tactggggcc | aggggaccca | ggtcaccgtc | 360 |
| tcctca | | | | | | 366 |

<210> SEQ ID NO 427
<211> LENGTH: 363
<212> TYPE: DNA
<213> ORGANISM: Artificial
<220> FEATURE:
<223> OTHER INFORMATION: Camel sdAb AS64336 Nucleic Acid Sequence

<400> SEQUENCE: 427

```
caggtgcagc tggtggagtc tgggggaggc tcggtgcagg ctggagggtc tctaagactc    60
tcctgtacaa cctctggacg cacctacagt agctgcagca tgggctggta ccgccaggct   120
ccagggaagg agcgcgagtt ggtctcacat atttttagtg atggtagcag atactatgca   180
gactccgtga agggccgatt caccatctcc aagacaacg ccaagaacac ggtgtatctg    240
caaatgaaca gcctgaaacc tgaggacacg gccatgtatt actgtaaccg ccgtacgggt   300
tgggcaccaa ggtgcgctgt tcccggttac tggggccagg ggacccaggt caccgtctcc   360
tca                                                                  363
```

<210> SEQ ID NO 428
<211> LENGTH: 381
<212> TYPE: DNA
<213> ORGANISM: Artificial
<220> FEATURE:
<223> OTHER INFORMATION: Camel sdAb AS64346 Nucleic Acid Sequence

<400> SEQUENCE: 428

```
caggtgcacc tggtggagtc tgggggaggc tcggtgcagg ctggagggtc tctgagactc    60
tcctgtgcag cctctggata cacctatttc atgggctggt ccgccaggc tccacagaag    120
gagcgcgaat gggtcgcgac tattggtact ggtgatattt caatggcgc tgcttactat    180
gtcgactccg tgaagggccg attcgccatc tccaagaca acgccaagaa cacggtgtat   240
ctgcaaatga acagcctgaa acctgaagac actgccgtgt acgtctgtgc ggcagttcaa   300
tcgaaatcct caaactacgt gttgagagac gcatctacct acaactactg gggccagggg   360
acccaggtca ccgtctcctc a                                             381
```

<210> SEQ ID NO 429
<211> LENGTH: 348
<212> TYPE: DNA
<213> ORGANISM: Artificial
<220> FEATURE:
<223> OTHER INFORMATION: Camel sdAb AS64420 Nucleic Acid Sequence

<400> SEQUENCE: 429

```
gaggtgcagc tggtggagtc tgggggaggc tcggtgcagg ctgaagggtc tctgagactc    60
tcctgtgcag cctctggaga caccagtaga agcgtctgga tgggctgggc ccgccaggtt   120
ccagggaaag agcgcgaggt ggtcgcaacc attagtactg ccggtggtag tacatggtat   180
accgactccg tgaagggccg attcaccatc tccaagaca acgccaagaa cacggtgtac   240
ctgcaaatga acagcctgaa acctgaggac actgccatat actattgtgc ggccagaagc   300
agatatgcta cctactgggg ccaggggacc caggtcaccg tctcctca                348
```

<210> SEQ ID NO 430
<211> LENGTH: 378
<212> TYPE: DNA
<213> ORGANISM: Artificial
<220> FEATURE:
<223> OTHER INFORMATION: Camel sdAb AS64473 Nucleic Acid Sequence

<400> SEQUENCE: 430

```
caggtgaggt tggtggagtc tgggggaggc tcggtgcagg ctggagggtc tctgagactc    60
tcctgtacag cctctggata cacctacaga tacctctaca tggcctggtt ccgccagact   120
ccagggaagg agcgcgaggg ggtcgcatgt atttatactg gtagtggtac cacagggtat   180
```

-continued

```
gccgactccg tgaagggccg attcaccatc tcccaagaca acgccaagaa tacggtgtat      240
ctgcaaatga acagcctgaa cgctgaggac actgccatgt actactgtgc ggcaagttcg      300
ccccagtggg gcggtacctg tcgacgctgg tccgagtata actactgggg ccaggggacc      360
caggtcaccg tctcctca                                                    378
```

<210> SEQ ID NO 431
<211> LENGTH: 348
<212> TYPE: DNA
<213> ORGANISM: Artificial
<220> FEATURE:
<223> OTHER INFORMATION: Camel sdAb AS64475 Nucleic Acid Sequence

<400> SEQUENCE: 431

```
caggtgcaac tgcaggagtc tgggggaggc tcggtgcagg ctggagggtc tctgagactc       60
tcctgtgcag cctctggata cacctggagt cgcaactgga tgggctggtt ccgccaggct      120
ccagggaagg agcgcgaggg gttcgcaact attacaatta gtggtggtag cacatggtat      180
gccgactccg tgaagggccg attcaccatc tccctagaca acgccgggaa cacggtgtat      240
ctgcaaatga acagcctgaa acctgaggac actgccatgt actactgtgc ggcgcgggat      300
accgcgcgga cctactgggg ccagggtacc caggtcaccg tctcctca                   348
```

<210> SEQ ID NO 432
<211> LENGTH: 381
<212> TYPE: DNA
<213> ORGANISM: Artificial
<220> FEATURE:
<223> OTHER INFORMATION: Camel sdAb AS64513 Nucleic Acid Sequence

<400> SEQUENCE: 432

```
gaggtgcagc tggtggaatc tgggggaggc tcggtgcagg ctggagggtc tctgagactc       60
tcctgtgtag cctctgacta cccctacata gacaactgca tgggctggtt ccgccagggt      120
ccagggaagg agcgcgaggg ggtcgcagct gcgtgtactg gtggtggtag cacatattat      180
gccgactccg tgaagggccg attcaccatc tcccgagaca acgccaagaa cacggtgtat      240
ctgcaaatga acagcctgaa acctgaggac actgacgtgt actactgtgc gacaggctac      300
tatagcggct ctggtccggg gtatttactc ccatggaggt ataactactg gggccagggg      360
acccaggtca ccgtctcctc a                                                381
```

<210> SEQ ID NO 433
<211> LENGTH: 393
<212> TYPE: DNA
<213> ORGANISM: Artificial
<220> FEATURE:
<223> OTHER INFORMATION: Camel sdAb AS64562 Nucleic Acid Sequence

<400> SEQUENCE: 433

```
gaggtgcaac tggtggaatc tgggggaggc tcggtgcagg ctggagggtc tctgagactc       60
tcctgtgcag cctctggata caccgctagg cgcgacttca tggcctggtt ccgccaggtt      120
ccagggaagg agcgcgaggg ggtcgcagtc attcatactg gtggtgacac cacatactat      180
gccgactccg tgaagggccg attcaccatc tcccgcgaca acgcccagaa cataatgaat      240
ctgcaaatga acagccttaa acctgaggac actgccatgt actactgtgc ggcaggtttc      300
cgtccgcgtg gtggaggata cacgggtgac gtcttggccc aggctgcggc atacaactac      360
tggggccagg ggacccaggt caccgtctcc tca                                   393
```

```
<210> SEQ ID NO 434
<211> LENGTH: 378
<212> TYPE: DNA
<213> ORGANISM: Artificial
<220> FEATURE:
<223> OTHER INFORMATION: Camel sdAb AS64583 Nucleic Acid Sequence

<400> SEQUENCE: 434
gaggtgcagc tggcggagtc tgggggaggc ttggtgcagg caggggggtc tctgagactc      60
tcctgtacag cctctggatt cactattgct gtttatacca tgggctggtt ccgccaggct     120
ccagggaagg agcgcgaggg aatctcatgt actagctggg ctggtggtcg cacatacact     180
gcagactccg tgaagggccg attcaccatc tccagagaca cgccaagaa cacgctgtat      240 ctgcaaatga acagcctgaa acctgaggac acggccatgt attactgtgc ggcaaaggca     300
catcccgact gttcagggga ttggtcccca tctgggtatg aatactgggg ccaggggacc     360
caggtcaccg tctcctca                                                   378

<210> SEQ ID NO 435
<211> LENGTH: 348
<212> TYPE: DNA
<213> ORGANISM: Artificial
<220> FEATURE:
<223> OTHER INFORMATION: Camel sdAb AS64594 Nucleic Acid Sequence

<400> SEQUENCE: 435
caggtgcacc tggtggagtc tgggggaggc tcggtgcagg ctggagggtc tctgagactc      60
tcctgtgcag cctctggata cacctacaat agcaactaca tgggctggtt ccgccaggct     120
ccagggaagg agcgcgaggg ggtcgcactt atttatactg gtggtggtag cacatattat     180
gccgactccg tgaagggccg attcaccatc tcccgagaca cgccaaaaa cacggtgtat      240 ctgcaaatga acagcctgaa acctgaggac actgccatgt actactgttc ggtaagaacg     300
cagacgcgta actactgggg ccaggggacc caggtcaccg tctcctca                  348

<210> SEQ ID NO 436
<211> LENGTH: 393
<212> TYPE: DNA
<213> ORGANISM: Artificial
<220> FEATURE:
<223> OTHER INFORMATION: Camel sdAb AS64605 Nucleic Acid Sequence

<400> SEQUENCE: 436
caggtgaagt tggtggagtc tgggggaggc tcggtgcagg ctggagggtc tctgagactc      60
tcctgtgcag tttctagata tccctacagc agcatctgca tgggctggtt ccgccaggct     120
ccagggaagg agagcgaggg tgtcgcacgt atttatactg gtactggtag tacatggtat     180
accgactccg tgaagggccg attcaccatc gcccgagaca cgccagaa cacggtgtat       240 ctgcaaatga acagcctgaa acctgaggac actgccatgt actactgtgc ggcgcgtagc     300
aattcatatt catattcaag ttgtgattac ggccccctca cgagggggg gtataacttc      360 tggggccagg ggacccaggt caccgtctcc tca                                  393

<210> SEQ ID NO 437
<211> LENGTH: 345
<212> TYPE: DNA
<213> ORGANISM: Artificial
<220> FEATURE:
<223> OTHER INFORMATION: Camel sdAb AS64606 Nucleic Acid Sequence

<400> SEQUENCE: 437
```

```
gaggtgcagc tggcggagtc tggggggagga tcggtgcagg ctggagggtc tctgagactc      60
tcctgtgcag tctctggata caccagccgt agcaattaca tgggctggtt ccgccaggct     120
ccagggaagg agcgcgaggg ggtcgcgcta atttatactc gtggtggtag cacatactat     180
gcctcctccg tgaagggccg gttcaccatc tcccaagaca gtgccaagaa aacgtatctg     240
caaatgaaca gtgtgaaacc ggaggacact gccatgtact actgtgcttt gcgccttgat     300
gagaagatgt actggggcca ggggacccag gtcaccgtct cctca                     345

<210> SEQ ID NO 438
<211> LENGTH: 399
<212> TYPE: DNA
<213> ORGANISM: Artificial
<220> FEATURE:
<223> OTHER INFORMATION: Camel sdAb AS68121 Nucleic Acid Sequence

<400> SEQUENCE: 438
gaggtgcagc tggcggagtc tgggggaggc tcggtgcagg ctggagggtc tctgagactc      60
tcctgtgatg cctctggata cacctacagc cgcaactgca tgggctggtt ccgccaggct     120
ccagggaagg agcgcgaggg ggtcgcagcg ttctatactg attatattcg ttttgggcgc     180
acatattatg ccgactccgt gaagggccga ttcaccatct ccaagacaa cgccaagaac     240 acggtgtatc tgcaaatgaa cagcctgaaa cctgaggaca ctgccatgta ctactgtgcg     300
gcagatcctg ggagtcgtac agacgatagt tgtggtacct catacaacaa agggaatttt     360
ggttactggg gccaggggac ccaggtcacc gtctcctca                             399

<210> SEQ ID NO 439
<211> LENGTH: 390
<212> TYPE: DNA
<213> ORGANISM: Artificial
<220> FEATURE:
<223> OTHER INFORMATION: Camel sdAb AS68170 Nucleic Acid Sequence

<400> SEQUENCE: 439
caggtgcagc tggtggagtc tgggggaggc tcggtgcagg ctggagggtc gctgagactc      60
tcctgtacag cctctggata cacctacaga agcaactgta tgggctggtt ccgccaggct     120
ccagggaagg agcgcgaggg ggtcgcaaca atctatactg gtggtggtcg taatctatac     180
tatgccgact ccgtgaaggg ccgattcacc atctcccgag acaacgccaa gaacaccctg     240
tacctgcaaa tgaacagcct gaagcctgag gactctgcca ggtactactg tgcggccgcg     300
agtgacgtgg cagttggtgt taattcctgc ggggaagga ctgcggggtt tgacgcctgg     360
ggccagggga cccaggtcac cgtctcctca                                       390

<210> SEQ ID NO 440
<211> LENGTH: 375
<212> TYPE: DNA
<213> ORGANISM: Artificial
<220> FEATURE:
<223> OTHER INFORMATION: Camel sdAb AS63964 Nucleic Acid Sequence

<400> SEQUENCE: 440
caggtgaggt tagtggagtc tgggggagga tcggtacagg ctggagggtc tctgagactc      60
tcctgctcag cctctggata cacctacagt tacaacaata tgggctggtt ccgccaggct     120
ccagggaacg agcgcgaggg ggtcgcagct attagtggtg gtcgtttcac cgcctatgcc     180
gactccgtga agggccgatt caccatctcc cgagacaacg ccgagaacac gctgtatctg     240
caaatgaaca acctgaaacc tgaggacact gggatgtact actgtgcggc agaggtagtt     300
```

```
gatccgacct ggggggtcgcg tgaccaaaga cgatataagt actggggcca ggggacccag    360
gtcaccgtct cctca                                                      375

<210> SEQ ID NO 441
<211> LENGTH: 372
<212> TYPE: DNA
<213> ORGANISM: Artificial
<220> FEATURE:
<223> OTHER INFORMATION: Camel sdAb AS64116 Nucleic Acid Sequence

<400> SEQUENCE: 441
caggtgaagt tggtggagtc tgggggaggc tcggtgcagg ctggagggtc tctgagactc     60
tcgtgtgcag cctctggata catctacagt tgcgtgggct ggttccgcca ggctccaggg    120
aaggagcgcg aggggggtcgc aggtattagt actggtggtg gtggcacagt ctatgccgac   180
tccgtgaagg gccaattcac catctcccga dacaacgcca agaacacggt gtacctgcaa    240
atggacagcc tgaaacctga ggacactgcc atgtactact gtgcggcaga tcgatggaat    300
tcattcgcta attgcggtgc ctggggaagg tatacctact ggggccaggg gacccaggtc    360
accgtctcct ca                                                        372

<210> SEQ ID NO 442
<211> LENGTH: 390
<212> TYPE: DNA
<213> ORGANISM: Artificial
<220> FEATURE:
<223> OTHER INFORMATION: Camel sdAb AS68270 Nucleic Acid Sequence

<400> SEQUENCE: 442
caggtgcaac tggcggagtc tgggggaggc tcggtgcagg ctggagggtc tctgagactc     60
tcctgtgtag cctctggata cccctcttcc acctactaca tgctcagcat ggcgtggttc    120
cgccaggctc cagggaagga gcgcgagggg gtcgccgcta ttactagcgg tactgggagc    180
acaagctacg cagactccgt gaaggaccga ttcaccatct ccaaagacta cgccaacaac    240
actctgtatc tgcacataaa caacctgaaa cctgaggaca ctgccatgta ctactgtgcg    300
gcagcctcag gttggatcgt tcctagtagg tccctgaccg ccaacctata taggtattgg    360
ggccagggga cccaggtcac cgtctcctca                                     390

<210> SEQ ID NO 443
<211> LENGTH: 375
<212> TYPE: DNA
<213> ORGANISM: Artificial
<220> FEATURE:
<223> OTHER INFORMATION: Camel sdAb AS68320 Nucleic Acid Sequence

<400> SEQUENCE: 443
caggtgcacc tggtggagtc tgggggagac tcggtgcagg ctggagggtc cctgagactc     60
tcctgtgcag cctctggata cacctacaat accaactaca tgggctggtt ccgccaggct    120
ccagggaagg agcgcgaggg ggtcgcagct atttatagac atagtggtaa cacagcctat    180
gccgactccg tgaagggccg attcaccatc tcccaagact acgccaagaa caccgtgtat    240
ctgcaaatga acagcctgaa acctgaggac actgccatgt actactgtgc ggcagggcgc    300
gctggtccct gggccctgat gcgcccgact gagtttggtt actggggcca ggggacccag    360
gtcaccgtct cctca                                                     375

<210> SEQ ID NO 444
```

<211> LENGTH: 369
<212> TYPE: DNA
<213> ORGANISM: Artificial
<220> FEATURE:
<223> OTHER INFORMATION: Camel sdAb AS68351 Nucleic Acid Sequence

<400> SEQUENCE: 444

```
caggtgcaat tggaggagtc tgggggaggc ttggtgcagc ctggggggtc tctgagactc      60
tcctgtgcgg cctctggaga cacatttcgt gcctattaca tgaactgggt ccgccaggct     120
ccagggaagg gattcgagtg ggtctcaggt attagcgcca gtggcggccg tacgtcatac     180
gcagactccg tgaagggccg attcaccatc tccagagaca cgccaaaaa cacgctgtat      240
ctgcaattga acagcctgag cactgaggac acgggcatgt attattgtgt aaagggagct     300
gtccgtctct cgacatcgtc agtacgggat cgtcctgggg ccaggggac ccaggtcacc      360
gtctcctca                                                             369
```

<210> SEQ ID NO 445
<211> LENGTH: 348
<212> TYPE: DNA
<213> ORGANISM: Artificial
<220> FEATURE:
<223> OTHER INFORMATION: Camel sdAb AS75378 Nucleic Acid Sequence

<400> SEQUENCE: 445

```
caggtgcaat tggaggagtc tgggggaggc tcggtgcagg ctggagggtc tctgagactc      60
tcctgtgtag tctctggaaa cacccgcagt accacgtaca tgggctggtt ccgccaggct     120
ccagggaagg agcgcgaggg ggtcgcaata gtttatactg gtggtcgtga cacatactat     180
gccgcctccg tgaagggccg attcaccatc tcccaagaca cgccaagac aacgatctat      240
ctgcaaatga acagtctgga acctgaggac actgccatgt actactgtgc ggcacgctca     300
tatgagtata cctactgggg tcgggggacc caggtcaccg tctcctca                  348
```

<210> SEQ ID NO 446
<211> LENGTH: 372
<212> TYPE: DNA
<213> ORGANISM: Artificial
<220> FEATURE:
<223> OTHER INFORMATION: Camel sdAb AS75383 Nucleic Acid Sequence

<400> SEQUENCE: 446

```
gaggtgcaac tggcggagtc tgggggaggc tcggtgcagg ctggagggtc tctgagactc      60
tcctgtgtag cctctggata caccttcagt agctactgct gggctggtt ccgccaggct      120
ccagggaagc agcgccaggg ggtcgcaacg tttaataata gaggtgtcgc aaactaccac     180
gattccgtga agggccgatt caccgcctcc gtagacaacg ccaagaacac tctgcttctg     240
caaatgaaca gcctggaacc tgacgacacg gccatgtact actgtcggc ggatcgccgg      300
tacggtcgtc agtggtatca gccttgcgag tggaacacct ggggccaggg gacccaggtc     360
accgtctcct ca                                                         372
```

<210> SEQ ID NO 447
<211> LENGTH: 387
<212> TYPE: DNA
<213> ORGANISM: Artificial
<220> FEATURE:
<223> OTHER INFORMATION: Camel sdAb AS75751 Nucleic Acid Sequence

<400> SEQUENCE: 447

```
caggtgaggt tggtggagtc tgggggaggc tcggtgcagg ctggagggtc tctgagactc      60
```

```
tcctgtgtag cctctggata cttctacaat acctactact ttatgggctg gttccgccag    120
gctccaggga aggagcgcga gggggtcgca gctattgata ctgatggtag aacaagttac    180
gcagactccg tgaagggccg attcaccatc tccaaagaca acgccaagaa cactctgtat    240
ctgcaaatga acagcctgaa acctgaggac actgccatgt actactgtgc ggcaggtttt    300
ggctatatga atgttattca ggctcttaat ggcatgagac agaatcccga ctactgggc     360 caggggaccc aggtcaccgt ctcctca                                       387
```

<210> SEQ ID NO 448
<211> LENGTH: 372
<212> TYPE: DNA
<213> ORGANISM: Artificial
<220> FEATURE:
<223> OTHER INFORMATION: Camel sdAb AS76422 Nucleic Acid Sequence

<400> SEQUENCE: 448

```
caggtgaagt tggtggagtc tgggggaggc tcggtgcagg ctggagggtc tctgagactc     60
tcctgtgcag cctctggata caccttcgct ggcaactgct gggctggtt tcgccaggct    120 ccagggaagg ggcgcgaggg ggtcgtaacg tacaataact tcggtgtcgc caactacgcc    180
gattccgtga agggccgatt caccgtctcc aagacaacg ccaagaacac tctgcttctg    240
caaatgaaca gcctggaacc tgaggacact gccatgtact actgtgcggc ggaccgccgg    300
gacggtcgtc gctggtctca gccttgcgag tggaataact ggggccaggg gacccaggtc    360
accgtctcct ca                                                       372
```

<210> SEQ ID NO 449
<211> LENGTH: 375
<212> TYPE: DNA
<213> ORGANISM: Artificial
<220> FEATURE:
<223> OTHER INFORMATION: Humanized sdAb AS64380VH4 Nucleic Acid Sequence

<400> SEQUENCE: 449

```
gaggtgcagc tggtggagag cggaggagga ctggtgcagc caggaggcag cctgaggctg     60
tcctgcgcag catctggaaa cacctacagc tccaattata tgggatggtt caggcaggca    120
cctggcaagg gactggagga ggtggccgtg atctacacca ggggaggaca cacatactat    180
gtggactccg tgcggggacg gttcaccatc agcaggata acgccaagaa cagcctgtat    240
ctgcagatga actctctgag agccgaggac acagccgtgt actattgtgc agcatctagc    300
aggcacaggc tgggcctgaa caatccaagg gactacgatt attggggcca gggcaccctg    360
gtgacagtgt cctct                                                    375
```

<210> SEQ ID NO 450
<211> LENGTH: 375
<212> TYPE: DNA
<213> ORGANISM: Artificial
<220> FEATURE:
<223> OTHER INFORMATION: Humanized sdAb AS64380VH5 Nucleic Acid Sequence

<400> SEQUENCE: 450

```
gaggtgcagc tggtggagag cggaggagga ctggtgcagc caggaggcag cctgaggctg     60
tcctgcgcag catctggaaa cacctacagc tccaattata tgggatggtt caggcaggca    120
cctggcaagg gcctggagga ggtggccgtg atctacacca gaggcggcca cacatactat    180
gtggactccg tgcggggacg gttcaccatc agccaggata acgccaagaa cagcctgtat    240
```

-continued

| | |
|---|---|
| ctgcagatga actctctgag ggccgaggac acagccgtgt actattgtgc agcatctagc | 300 |
| aggcacaggc tgggcctgaa caatccaagg gactacgatt attggggcca gggcaccctg | 360 |
| gtgacagtgt cctct | 375 |

<210> SEQ ID NO 451
<211> LENGTH: 375
<212> TYPE: DNA
<213> ORGANISM: Artificial
<220> FEATURE:
<223> OTHER INFORMATION: Humanized sdAb AS64380VH6 Nucleic Acid Sequence

<400> SEQUENCE: 451

| | |
|---|---|
| gaggtgcagc tggtggagag cggaggagga ctggtgcagc caggaggcag cctgaggctg | 60 |
| tcctgcgcag catctggaaa cacctacagc tccaattata tgggatggtt caggcaggca | 120 |
| cctggcaagg gcctggagga ggtggccgtg atctacacca gaggcggcca cacatactat | 180 |
| gtggactccg tgcggggacg gttcaccatc agccaggata cgccaagaa cagcgtgtat | 240 |
| ctgcagatga actctctgag ggccgaggac acagccatgt actattgtgc agcatctagc | 300 |
| aggcacaggc tgggcctgaa caatccaagg gactacgatt attggggcca gggcaccctg | 360 |
| gtgacagtgt cctct | 375 |

<210> SEQ ID NO 452
<211> LENGTH: 375
<212> TYPE: DNA
<213> ORGANISM: Artificial
<220> FEATURE:
<223> OTHER INFORMATION: Humanized sdAb AS64380VH7 Nucleic Acid Sequence

<400> SEQUENCE: 452

| | |
|---|---|
| gaggtgcagc tggtggagag cggaggagga ctggtgcagc caggaggcag cctgaggctg | 60 |
| tcctgcgcag catctggaaa cacctacagc tccaattata tgggatggtt caggcaggca | 120 |
| cctggcaagg gaagagagga ggtggccgtg atctacacca gggaggaca cacatactat | 180 |
| gtggactccg tgcggggacg gttcaccatc agccaggata cgccaagaa cagcgtgtat | 240 |
| ctgcagatga actctctgag ggccgaggac acagccatgt actattgtgc agcatctagc | 300 |
| aggcacaggc tgggcctgaa caatccaagg gactacgatt attggggcca gggcaccctg | 360 |
| gtgacagtgt cctct | 375 |

<210> SEQ ID NO 453
<211> LENGTH: 375
<212> TYPE: DNA
<213> ORGANISM: Artificial
<220> FEATURE:
<223> OTHER INFORMATION: Humanized sdAb AS64511VH4 Nucleic Acid Sequence

<400> SEQUENCE: 453

| | |
|---|---|
| gaggtgcagc tggtggagtc cggaggagga ctggtgcagc caggaggctc tctgaggctg | 60 |
| agctgcgcag catccagagc aacctactct acaaactata tcagctggtt caggcaggca | 120 |
| cctggcaagg gactggaggc agtggcaacc atcaccacag gcgatggcga gacagcctac | 180 |
| gccgactctg tgaagggcag gtttaccatc tcccgcgata cgccaagaa cagcctgtat | 240 |
| ctgcagatga acagcctgag ggccgaggac acagccgtgt actattgtgc agcaaatctg | 300 |
| aggatcggag gcgactggtt cgatggaagg gactttagag catggggaca gggaaccctg | 360 |
| gtgacagtga gctcc | 375 |

<210> SEQ ID NO 454
<211> LENGTH: 375
<212> TYPE: DNA
<213> ORGANISM: Artificial
<220> FEATURE:
<223> OTHER INFORMATION: Humanized sdAb AS64511VH5 Nucleic Acid Sequence

<400> SEQUENCE: 454

```
gaggtgcagc tggtggagtc cggaggagga ctggtgcagc caggaggctc tctgaggctg      60
agctgcgcag catccagagc aacctactct acaaactata tcagctggtt caggcaggca     120
cctggcaagg gactggaggc agtggcaacc atcaccacag gcgatggcga gacagcctac     180
gccgactctg tgaagggcag gtttaccatc tcccgcgata cgccaagaa cagcgtgtat     240
ctgcagatga acagcctgag ggccgaggac acagccatgt actattgtgc agcaaatctg     300
aggatcggag gcgactggtt cgatggaagg gactttagag catggggaca gggaaccctg     360
gtgacagtga gctcc                                                       375
```

<210> SEQ ID NO 455
<211> LENGTH: 375
<212> TYPE: DNA
<213> ORGANISM: Artificial
<220> FEATURE:
<223> OTHER INFORMATION: Humanized sdAb AS64511VH6 Nucleic Acid Sequence

<400> SEQUENCE: 455

```
gaggtgcagc tggtggagtc cggaggagga ctggtgcagc caggaggctc tctgaggctg      60
agctgcgcag catccagagc aacctactct acaaactata tcagctggtt caggcaggca     120
cctggcaagg gaagggaggc agtggccacc atcaccacag gcgatggcga gacagcctac     180
gccgactctg tgaagggcag gtttaccatc tcccgcgata cgccaagaa cagcgtgtat     240
ctgcagatga acagcctgcg ggccgaggac acagccatgt actattgtgc agcaaatctg     300
aggatcggag gcgactggtt cgatggaagg gactttagag catggggaca gggaaccctg     360
gtgacagtga gctcc                                                       375
```

<210> SEQ ID NO 456
<211> LENGTH: 375
<212> TYPE: DNA
<213> ORGANISM: Artificial
<220> FEATURE:
<223> OTHER INFORMATION: Humanized sdAb AS63931VH4 Nucleic Acid Sequence

<400> SEQUENCE: 456

```
caggtgcagc tggtggagag cggaggagga gtggtgcagc caggaggcag cctgaggctg      60
tcctgcgcag gctctttcag cggatacggc gtgtccacca tggcatggtt taggcaggca     120
cctggcaagg gactggaggg agtggcagca atcaccgtgg gatccggaaa cacatactat     180
gccgactctg tgaccggccg gttcacaatc tctagagata cagcaagaa taccctgtat     240
ctgcagatga acagcctgcg ggccgaggac acagccgtgt actattgtgc agcaggatgg     300
ctgtccggag gatcttggca cgtgcccggc aggtacaact attggggcca gggcaccctg     360
gtgacagtga gctcc                                                       375
```

<210> SEQ ID NO 457
<211> LENGTH: 375
<212> TYPE: DNA
<213> ORGANISM: Artificial
<220> FEATURE:
<223> OTHER INFORMATION: Humanized sdAb AS63931VH5 Nucleic Acid Sequence

<400> SEQUENCE: 457

```
caggtgcagc tggtggagag cggaggagga gtggtgcagc caggaggcag cctgaggctg    60
tcctgcgcag gctctttcag cggatacggc gtgtccacca tggcatggtt taggcaggca   120
cctggcaagg gactggaggg agtggcagca atcaccgtgg atccggaaa cacatactat    180
gccgactctg tgaccggccg gttcacaatc tctagagata acagcaagaa taccgtgtat   240
ctgcagatga acagcctgcg ggccgaggac acagccatgt actattgtgc agcaggatgg   300
ctgtccggag gatcttggca cgtgcccggc aggtacaact attggggcca gggcaccctg   360
gtgacagtga gctcc                                                    375
```

<210> SEQ ID NO 458
<211> LENGTH: 375
<212> TYPE: DNA
<213> ORGANISM: Artificial
<220> FEATURE:
<223> OTHER INFORMATION: Humanized sdAb AS63931VH6 Nucleic Acid Sequence

<400> SEQUENCE: 458

```
caggtgcagc tggtggagag cggaggagga gtggtgcagc caggaggcag cctgaggctg    60
tcctgcgcag gctctttcag cggatacggc gtgtccacca tggcctggtt taggcaggca   120
cctggcaagg gaagggaggg agtggcagca atcaccgtgg atccggaaa cacatactat    180
gccgactctg tgaccggccg gttcacaatc tctagagata acagcaagaa taccgtgtat   240
ctgcagatga acagcctgcg ggccgaggac acagccatgt actattgtgc agcaggatgg   300
ctgtccggag gatcttggca cgtgcccggc aggtacaact attggggcca gggcaccctg   360
gtgacagtga gctcc                                                    375
```

<210> SEQ ID NO 459
<211> LENGTH: 375
<212> TYPE: DNA
<213> ORGANISM: Artificial
<220> FEATURE:
<223> OTHER INFORMATION: Humanized sdAb AS63997VH4 Nucleic Acid Sequence

<400> SEQUENCE: 459

```
caggtgcagc tggtggagag cggaggagga gtggtgcagc caggaggcag cctgaggctg    60
tcctgcgcag cctctttcag cggatacggc gtgtccacca tggcatggtt taggcaggca   120
cctggcaagg gactggaggg agtggcagca atcaccgtgg atccggaaa cacatactat    180
gccgactctg tgaagggccg gttcaccatc tctagagata acagcaagaa tacactgtac   240
ctgcagatga acagcctgcg ggccgaggac acagccgtgt actattgtgc cgtgggctat   300
ctgtccggag gatcttggga tgtgccagga aggtacaact attggggcca gggcaccctg   360
gtgacagtga gctcc                                                    375
```

<210> SEQ ID NO 460
<211> LENGTH: 375
<212> TYPE: DNA
<213> ORGANISM: Artificial
<220> FEATURE:
<223> OTHER INFORMATION: Humanized sdAb AS63997VH5 Nucleic Acid Sequence

<400> SEQUENCE: 460

```
caggtgcagc tggtggagag cggaggagga gtggtgcagc caggaggcag cctgaggctg    60
tcctgcgcag cctctttcag cggatacggc gtgtccacca tggcatggtt taggcaggca   120
cctggcaagg gactggaggg agtggcagca atcaccgtgg atccggaaa cacatactat    180
```

```
gccgactctg tgaagggccg gttcaccatc tctagagata acagcaagaa tacagtgtac      240
ctgcagatga acagcctgcg ggccgaggac acagccatgt actattgtgc cgtgggctat      300
ctgtccggag gatcttggga tgtgccagga aggtacaact attggggcca gggcaccctg      360
gtgacagtga gctcc                                                       375

<210> SEQ ID NO 461
<211> LENGTH: 375
<212> TYPE: DNA
<213> ORGANISM: Artificial
<220> FEATURE:
<223> OTHER INFORMATION: Humanized sdAb AS63997VH6 Nucleic Acid Sequence

<400> SEQUENCE: 461
caggtgcagc tggtggagag cggaggagga gtggtgcagc caggaggcag cctgaggctg       60
tcctgcgcag cctctttcag cggatacggc gtgtccacca tggcctggtt taggcaggca      120
cctggcaagg gaagggaggg agtggcagca atcaccgtgg gatccggaaa cacatactat      180
gccgactctg tgaagggccg gttcaccatc tctagagata acagcaagaa tacagtgtac      240
ctgcagatga acagcctgcg ggccgaggac acagccatgt actattgtgc cgtgggctat      300
ctgtccggag gatcttggga tgtgccagga aggtacaact attggggcca gggcaccctg      360
gtgacagtga gctcc                                                       375

<210> SEQ ID NO 462
<211> LENGTH: 15
<212> TYPE: PRT
<213> ORGANISM: Artificial
<220> FEATURE:
<223> OTHER INFORMATION: Linker amino acid sequence

<400> SEQUENCE: 462

Gly Gly Gly Gly Ser Gly Gly Gly Gly Ser Gly Gly Gly Gly Ser
1               5                   10                  15

<210> SEQ ID NO 463
<211> LENGTH: 10
<212> TYPE: PRT
<213> ORGANISM: Artificial
<220> FEATURE:
<223> OTHER INFORMATION: Linker amino acid sequence

<400> SEQUENCE: 463

Gly Gly Gly Gly Ser Gly Gly Gly Gly Ser
1               5                   10

<210> SEQ ID NO 464
<211> LENGTH: 5
<212> TYPE: PRT
<213> ORGANISM: Artificial
<220> FEATURE:
<223> OTHER INFORMATION: Linker amino acid sequence

<400> SEQUENCE: 464

Gly Gly Gly Gly Ser
1               5

<210> SEQ ID NO 465
<211> LENGTH: 21
<212> TYPE: PRT
<213> ORGANISM: Artificial
<220> FEATURE:
<223> OTHER INFORMATION: CD8&A signal peptide amino acid sequence
```

<400> SEQUENCE: 465

Met Ala Leu Pro Val Thr Ala Leu Leu Leu Pro Leu Ala Leu Leu
1               5                   10                  15

His Ala Ala Arg Pro
            20

<210> SEQ ID NO 466
<211> LENGTH: 69
<212> TYPE: PRT
<213> ORGANISM: Artificial
<220> FEATURE:
<223> OTHER INFORMATION: CD8&A hinge amino acid sequence

<400> SEQUENCE: 466

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 467
<211> LENGTH: 24
<212> TYPE: PRT
<213> ORGANISM: Artificial
<220> FEATURE:
<223> OTHER INFORMATION: CD8&A transmembrane domain amino acid sequence

<400> SEQUENCE: 467

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 468
<211> LENGTH: 42
<212> TYPE: PRT
<213> ORGANISM: Artificial
<220> FEATURE:
<223> OTHER INFORMATION: 4-1BB intracellular domain amino acid sequence

<400> SEQUENCE: 468

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 469
<211> LENGTH: 41
<212> TYPE: PRT
<213> ORGANISM: Artificial
<220> FEATURE:
<223> OTHER INFORMATION: CD28 intracellular domain amino acid sequence

<400> SEQUENCE: 469

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 470
<211> LENGTH: 112
<212> TYPE: PRT
<213> ORGANISM: Artificial
<220> FEATURE:
<223> OTHER INFORMATION: CD3&F intracellular domain amino acid sequence

<400> SEQUENCE: 470

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 471
<211> LENGTH: 25
<212> TYPE: PRT
<213> ORGANISM: Artificial
<220> FEATURE:
<223> OTHER INFORMATION: F2A element amino acid sequence

<400> SEQUENCE: 471

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 472
<211> LENGTH: 22
<212> TYPE: PRT
<213> ORGANISM: Artificial
<220> FEATURE:
<223> OTHER INFORMATION: P2A element amino acid sequence

<400> SEQUENCE: 472

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 473
<211> LENGTH: 257
<212> TYPE: PRT
<213> ORGANISM: Artificial
<220> FEATURE:
<223> OTHER INFORMATION: CAR3 anti-DLL3 scFv amino acid sequence
```

<400> SEQUENCE: 473

```
Met Ala Leu Pro Val Thr Ala Leu Leu Leu Pro Leu Ala Leu Leu Leu
1               5                   10                  15

His Ala Ala Arg Pro Ala Ile Gln Leu Thr Gln Ser Pro Ser Ser Leu
            20                  25                  30

Ser Ala Ser Val Gly Asp Arg Val Thr Ile Thr Cys Arg Ala Ser Glu
        35                  40                  45

Asn Ile Tyr Tyr Asn Leu Ala Trp Tyr Gln Gln Lys Pro Gly Lys Ala
    50                  55                  60

Pro Lys Leu Leu Ile Tyr Thr Ala Asn Ser Leu Glu Asp Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Lys Gln Ala Tyr
            100                 105                 110

Asp Val Pro Pro Thr Phe Gly Gly Gly Thr Lys Leu Glu Ile Lys Gly
        115                 120                 125

Gly Gly Gly Ser Gly Gly Gly Gly Ser Gly Gly Gly Gly Ser Gln Val
    130                 135                 140

Gln Leu Val Gln Ser Gly Ala Glu Val Lys Lys Pro Gly Ala Ser Val
145                 150                 155                 160

Lys Val Ser Cys Lys Ala Ser Gly Tyr Thr Phe Thr Arg Tyr Trp Ile
                165                 170                 175

His Trp Ile Arg Gln Ala Pro Gly Gln Gly Leu Glu Trp Met Gly Tyr
            180                 185                 190

Ile Asn Pro Thr Val Tyr Thr Glu Phe Asn Gln Asn Phe Lys Asp Arg
        195                 200                 205

Val Thr Met Thr Arg Asp Thr Ser Thr Ser Thr Val Tyr Met Glu Leu
    210                 215                 220

Ser Ser Leu Arg Ser Glu Asp Thr Ala Val Tyr Tyr Cys Ala Arg Gly
225                 230                 235                 240

Gly Ser Asn Phe Phe Asp Tyr Trp Gln Gly Thr Thr Val Thr Val Ser
                245                 250                 255

Ser
```

<210> SEQ ID NO 474
<211> LENGTH: 27
<212> TYPE: PRT
<213> ORGANISM: Artificial
<220> FEATURE:
<223> OTHER INFORMATION: CD28 transmembrane domain amino acid sequence

<400> SEQUENCE: 474

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 475
<211> LENGTH: 39
<212> TYPE: PRT
<213> ORGANISM: Artificial
<220> FEATURE:
<223> OTHER INFORMATION: CD28 hinge

<400> SEQUENCE: 475

-continued

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35

<210> SEQ ID NO 476
<211> LENGTH: 369
<212> TYPE: PRT
<213> ORGANISM: Artificial
<220> FEATURE:
<223> OTHER INFORMATION: Camel anti-DLL3 CAR sequence CAS63997

<400> SEQUENCE: 476

Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Ala Gly Gly Ser Leu Arg Leu Ser Cys Ala Gly Ser Phe Ser
        35                  40                  45

Gly Tyr Gly Val Ser Thr Met Ala Trp Phe Arg Gln Ala Pro Gly Lys
    50                  55                  60

Glu Arg Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ala
                85                  90                  95

Lys Arg Thr Val Phe Leu Gln Met Asn Ser Leu Lys Pro Glu Asp Thr
            100                 105                 110

Ala Met Tyr Tyr Cys Ala Val Gly Tyr Leu Ser Gly Gly Ser Trp Asp
        115                 120                 125

Val Pro Gly Arg Tyr Asn Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 477
<211> LENGTH: 369
<212> TYPE: PRT
<213> ORGANISM: Artificial
<220> FEATURE:
<223> OTHER INFORMATION: Camel anti-DLL3 CAR sequence CAS64380

<400> SEQUENCE: 477

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Ser
            20                  25                  30

Val Gln Ala Gly Gly Ser Leu Thr Leu Ser Cys Glu Ala Ser Gly Asn
        35                  40                  45

Thr Tyr Ser Ser Asn Tyr Met Gly Trp Phe Arg Gln Ala Pro Gly Lys
    50                  55                  60

Glu Arg Glu Glu Val Ala Val Ile Tyr Thr Arg Gly Gly His Thr Tyr
65                  70                  75                  80

Tyr Val Asp Ser Val Arg Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Ala Ser Ser Arg His Arg Leu Gly Leu Asn
        115                 120                 125

Asn Pro Arg Asp Tyr Asp Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln

```
305                 310                 315                 320
Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
                340                 345                 350

Ala Thr Lys Asp Thr Tyr Asp Ala Leu His Met Gln Ala Leu Pro Pro
                355                 360                 365

Arg

<210> SEQ ID NO 478
<211> LENGTH: 369
<212> TYPE: PRT
<213> ORGANISM: Artificial
<220> FEATURE:
<223> OTHER INFORMATION: Camel anti-DLL3 CAR sequence CAS64511

<400> SEQUENCE: 478

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
                20                  25                  30

Val Gln Ala Gly Gly Ser Leu Arg Leu Ser Cys Ala Ala Ser Arg Ala
                35                  40                  45

Thr Tyr Ser Thr Asn Tyr Ile Ser Trp Phe Arg Gln Ala Pro Gly Lys
    50                  55                  60

Glu Arg Glu Ala Val Ala Thr Ile Thr Thr Gly Asp Gly Glu Thr Ala
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
                100                 105                 110

Ala Met Tyr Tyr Cys Ala Ala Asn Leu Arg Ile Gly Gly Asp Trp Phe
                115                 120                 125

Asp Gly Arg Asp Phe Arg Ala Trp Gly Gln Gly Thr Gln Val Thr Val
                130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
                195                 200                 205

Leu Val Ile Thr Leu Tyr Cys Lys Arg Gly Arg Lys Lys Leu Leu Tyr
                210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
                260                 265                 270

Gly Gln Asn Gln Leu Tyr Asn Glu Leu Asn Leu Gly Arg Arg Glu Glu
                275                 280                 285

Tyr Asp Val Leu Asp Lys Arg Arg Gly Arg Asp Pro Glu Met Gly Gly
                290                 295                 300
```

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
            325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 479
<211> LENGTH: 361
<212> TYPE: PRT
<213> ORGANISM: Artificial
<220> FEATURE:
<223> OTHER INFORMATION: Camel anti-DLL3 CAR sequence CAS64617

<400> SEQUENCE: 479

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Asp Arg Cys Ser Met Ala Trp Tyr Arg Gln Ala Pro Gly Lys Glu
    50                  55                  60

Arg Glu Leu Val Ser Arg Ile Ser Thr Ser Gly Phe Thr Asn Tyr Ala
65                  70                  75                  80

Ala Ser Val Lys Gly Arg Phe Thr Ile Ser Gln Asp Asn Ala Lys Asn
                85                  90                  95

Thr Val Tyr Leu Gln Met Asn Ser Leu Asn Pro Gly Asp Thr Gly Met
            100                 105                 110

Tyr Tyr Cys Ala Ile Ile Val Gly Arg Thr Cys Ser Leu Asn Tyr Trp
        115                 120                 125

Gly Asn Gly Ile Leu Val Thr Val Ser Ser Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Lys Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
                340                 345                 350

Leu His Met Gln Ala Leu Pro Pro Arg
                355                 360

<210> SEQ ID NO 480
<211> LENGTH: 376
<212> TYPE: PRT
<213> ORGANISM: Artificial
<220> FEATURE:
<223> OTHER INFORMATION: Camel anti-DLL3 CAR sequence CAS69443

<400> SEQUENCE: 480

Met Ala Leu Pro Val Thr Ala Leu Leu Leu Pro Leu Ala Leu Leu Leu
1               5                   10                  15

His Ala Ala Arg Pro Glu Val Gln Leu Ala Glu Ser Gly Gly Gly Ser
                20                  25                  30

Val Gln Ala Gly Gly Ser Leu Arg Leu Ser Cys Ser Ala Ser Gly Phe
            35                  40                  45

Thr Phe Asp Asp Ser Asp Met Ala Trp Tyr Arg Gln Ala Pro Gly Asp
    50                  55                  60

Gly Cys Asp Leu Val Ser Thr Ile Ser Ser Asp Gly Ser Thr Tyr Tyr
65                  70                  75                  80

Ala Asp Ser Val Lys Gly Arg Phe Thr Ile Ser Gln Asp Asn Ala Lys
                85                  90                  95

Asn Thr Val Tyr Leu Gln Met His Ser Leu Lys Pro Glu Asp Thr Ala
                100                 105                 110

Val Tyr Tyr Cys Ala Ala Asp Phe Leu Thr Gly Phe Tyr Tyr Ser Asp
            115                 120                 125

Ser Pro His Pro Ala Pro Cys Ser Ala Ser Asp Phe Gly Tyr Trp Gly
    130                 135                 140

Gln Gly Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
                180                 185                 190

Leu Asp Phe Ala Cys Asp Ile Tyr Ile Trp Ala Pro Leu Ala Gly Thr
            195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
                260                 265                 270

Asp Ala Pro Ala Tyr Lys Gln Gly Gln Asn Gln Leu Tyr Asn Glu Leu
            275                 280                 285

```
Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
                340                 345                 350

Leu Tyr Gln Gly Leu Ser Thr Ala Thr Lys Asp Thr Tyr Asp Ala Leu
            355                 360                 365

His Met Gln Ala Leu Pro Pro Arg
    370                 375

<210> SEQ ID NO 481
<211> LENGTH: 369
<212> TYPE: PRT
<213> ORGANISM: Artificial
<220> FEATURE:
<223> OTHER INFORMATION: Camel anti-DLL3 CAR sequence CAS63931

<400> SEQUENCE: 481

Met Ala Leu Pro Val Thr Ala Leu Leu Leu Pro Leu Ala Leu Leu Leu
1               5                   10                  15

His Ala Ala Arg Pro Glu Val Gln Leu Ala Glu Ser Gly Gly Gly Ser
                20                  25                  30

Val Gln Ala Gly Gly Ser Leu Arg Leu Ser Cys Ala Gly Ser Phe Ser
            35                  40                  45

Gly Tyr Gly Val Ser Thr Met Ala Trp Phe Arg Gln Ala Pro Gly Lys
        50                  55                  60

Glu Arg Glu Gly Val Ala Ala Ile Thr Val Gly Ser Gly Asn Thr Tyr
65                  70                  75                  80

Tyr Ala Asp Ser Val Thr Gly Arg Phe Thr Ile Ser Arg Asp Asn Ala
                85                  90                  95

Lys Arg Thr Val Tyr Leu Gln Met Asn Ser Leu Lys Pro Glu Asp Thr
                100                 105                 110

Ala Met Tyr Tyr Cys Ala Ala Gly Trp Leu Ser Gly Ser Trp His
                115                 120                 125

Val Pro Gly Arg Tyr Asn Tyr Trp Gly Gln Gly Thr Gln Val Thr Val
        130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
        210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
                260                 265                 270
```

```
Gly Gln Asn Gln Leu Tyr Asn Glu Leu Asn Leu Gly Arg Arg Glu Glu
            275                 280                 285

Tyr Asp Val Leu Asp Lys Arg Gly Arg Asp Pro Glu Met Gly Gly
290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
            355                 360                 365

Arg

<210> SEQ ID NO 482
<211> LENGTH: 369
<212> TYPE: PRT
<213> ORGANISM: Artificial
<220> FEATURE:
<223> OTHER INFORMATION: Camel anti-DLL3 CAR sequence CAS64047

<400> SEQUENCE: 482

Met Ala Leu Pro Val Thr Ala Leu Leu Leu Pro Leu Ala Leu Leu Leu
1               5                   10                  15

His Ala Ala Arg Pro Gln Val His Leu Val Glu Ser Gly Gly Gly Ser
                20                  25                  30

Val Gln Ala Gly Gly Ser Leu Arg Leu Ser Cys Ala Ala Ser Gln Tyr
            35                  40                  45

Val Tyr Arg Trp Asp Leu Met Gly Trp Phe Arg Gln Ala Pro Gly Lys
        50                  55                  60

Glu Arg Glu Ala Val Ala Val Tyr Thr Gly Asp Gly Ile Thr Tyr
65                  70                  75                  80

Tyr Ala Asp Ser Val Lys Gly Arg Phe Ser Ile Ser Gln Asp Asn Ala
                85                  90                  95

Lys Asn Thr Val Tyr Leu Gln Met Asn Ser Leu Lys Pro Glu Asp Thr
            100                 105                 110

Gly Met Tyr Phe Cys Ala Ala Gly Phe Val Ser Gly Gly Arg Trp Asn
        115                 120                 125

Gln Ser Tyr Arg Tyr Lys Tyr Trp Gly Gln Gly Thr Gln Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
```

```
                  260                 265                 270
Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
        290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 483
<211> LENGTH: 373
<212> TYPE: PRT
<213> ORGANISM: Artificial
<220> FEATURE:
<223> OTHER INFORMATION: Camel anti-DLL3 CAR sequence CAS64052

<400> SEQUENCE: 483

Met Ala Leu Pro Val Thr Ala Leu Leu Leu Pro Leu Ala Leu Leu Leu
1               5                   10                  15

His Ala Ala Arg Pro Gln Val His Leu Met Glu Ser Gly Gly Gly Ser
            20                  25                  30

Val Gln Ala Gly Gly Ser Leu Arg Leu Ser Cys Ala Ala Ser Gly Tyr
        35                  40                  45

Thr Tyr Arg Ser Asn Phe Met Gly Trp Phe Arg Gln Ala Pro Gly Lys
    50                  55                  60

Glu Arg Glu Gly Ile Ala Thr Ile His Ser Gly Val Ala Thr Thr Tyr
65                  70                  75                  80

Tyr Ala Asp Ser Val Lys Gly Arg Phe Thr Ile Ser Gln Asp Asn Ala
                85                  90                  95

Lys Asn Thr Val Tyr Leu Gln Met Asn Ser Leu Lys Pro Glu Asp Thr
            100                 105                 110

Ala Met Tyr Tyr Cys Ala Ala Gly Gly Pro Pro Ala Asn Ala Asp Arg
        115                 120                 125

Trp Tyr Pro Leu Arg Pro Pro Gly Tyr Asn Tyr Trp Gly Gln Gly Thr
    130                 135                 140

Gln Val Thr Val Ser Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Ile Tyr Ile Trp Ala Pro Leu Ala Gly Thr Cys Gly Val
        195                 200                 205

Leu Leu Leu Ser Leu Val Ile Thr Leu Tyr Cys Lys Arg Gly Arg Lys
    210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                245                 250                 255
```

```
Gly Gly Cys Glu Leu Arg Val Lys Phe Ser Arg Ser Ala Asp Ala Pro
            260                 265                 270

Ala Tyr Lys Gln Gly Gln Asn Gln Leu Tyr Asn Glu Leu Asn Leu Gly
        275                 280                 285

Arg Arg Glu Glu Tyr Asp Val Leu Asp Lys Arg Arg Gly Arg Asp Pro
    290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                325                 330                 335

Met Lys Gly Glu Arg Arg Arg Gly Lys Gly His Asp Gly Leu Tyr Gln
            340                 345                 350

Gly Leu Ser Thr Ala Thr Lys Asp Thr Tyr Asp Ala Leu His Met Gln
        355                 360                 365

Ala Leu Pro Pro Arg
    370

<210> SEQ ID NO 484
<211> LENGTH: 371
<212> TYPE: PRT
<213> ORGANISM: Artificial
<220> FEATURE:
<223> OTHER INFORMATION: Camel anti-DLL3 CAR sequence CAS64062

<400> SEQUENCE: 484

Met Ala Leu Pro Val Thr Ala Leu Leu Leu Pro Leu Ala Leu Leu Leu
1               5                   10                  15

His Ala Ala Arg Pro Gln Val Arg Leu Val Glu Ser Gly Gly Gly Ser
            20                  25                  30

Val Gln Val Gly Gly Ser Leu Arg Leu Ser Cys Ala Ala Ser Arg Ser
        35                  40                  45

Pro Tyr Ser Ser Ser Arg Cys Met Gly Trp Phe Arg Gln Ala Pro Gly
    50                  55                  60

Lys Glu Arg Glu Gly Val Ala Ala Leu Tyr Thr Gly Gly Ser Thr
65                  70                  75                  80

Ser Tyr Ala Asp Ser Val Lys Gly Arg Phe Thr Ile Ser Gln Asp Asn
                85                  90                  95

Ala Lys Asn Thr Val Tyr Leu Gln Met Asn Ser Leu Lys Pro Glu Asp
            100                 105                 110

Thr Ala Met Tyr Tyr Cys Ala Ala Val Val Pro Arg Gly Gly Ser Cys
        115                 120                 125

Arg Leu Asp Glu Arg Gly Tyr Tyr His Trp Gly Gln Gly Thr Gln Val
    130                 135                 140

Thr Val Ser Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
        195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240
```

Glu Glu Asp Gly Cys Ser Cys Arg Phe Pro Glu Glu Glu Gly Gly
                245                 250                 255

Cys Glu Leu Arg Val Lys Phe Ser Arg Ser Ala Asp Ala Pro Ala Tyr
            260                 265                 270

Lys Gln Gly Gln Asn Gln Leu Tyr Asn Glu Leu Asn Leu Gly Arg Arg
        275                 280                 285

Glu Glu Tyr Asp Val Leu Asp Lys Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg
    370

<210> SEQ ID NO 485
<211> LENGTH: 369
<212> TYPE: PRT
<213> ORGANISM: Artificial
<220> FEATURE:
<223> OTHER INFORMATION: Humanized anti-DLL3 CAR sequence CAS64380VH4

<400> SEQUENCE: 485

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Asn
        35                  40                  45

Thr Tyr Ser Ser Asn Tyr Met Gly Trp Phe Arg Gln Ala Pro Gly Lys
    50                  55                  60

Gly Leu Glu Glu Val Ala Val Ile Tyr Thr Arg Gly Gly His Thr Tyr
65                  70                  75                  80

Tyr Val Asp Ser Val Arg Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Ser Arg His Arg Leu Gly Leu Asn
        115                 120                 125

Asn Pro Arg Asp Tyr Asp Tyr Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

-continued

```
Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
                260                 265                 270

Gly Gln Asn Gln Leu Tyr Asn Glu Leu Asn Leu Gly Arg Arg Glu Glu
                275                 280                 285

Tyr Asp Val Leu Asp Lys Arg Arg Gly Arg Asp Pro Glu Met Gly Gly
                290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
                340                 345                 350

Ala Thr Lys Asp Thr Tyr Asp Ala Leu His Met Gln Ala Leu Pro Pro
                355                 360                 365

Arg
```

<210> SEQ ID NO 486
<211> LENGTH: 369
<212> TYPE: PRT
<213> ORGANISM: Artificial
<220> FEATURE:
<223> OTHER INFORMATION: Humanized anti-DLL3 CAR sequence CAS64380VH5

<400> SEQUENCE: 486

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Pro Gly Gly Ser Leu Arg Leu Ser Cys Ala Ala Ser Gly Asn
            35                  40                  45

Thr Tyr Ser Ser Asn Tyr Met Gly Trp Phe Arg Gln Ala Pro Gly Lys
    50                  55                  60

Gly Leu Glu Glu Val Ala Val Ile Tyr Thr Arg Gly Gly His Thr Tyr
65                  70                  75                  80

Tyr Val Asp Ser Val Arg Gly Arg Phe Thr Ile Ser Gln Asp Asn Ala
                85                  90                  95

Lys Asn Ser Leu Tyr Leu Gln Met Asn Ser Leu Arg Ala Glu Asp Thr
                100                 105                 110

Ala Val Tyr Tyr Cys Ala Ala Ser Ser Arg His Arg Leu Gly Leu Asn
                115                 120                 125

Asn Pro Arg Asp Tyr Asp Tyr Trp Gly Gln Gly Thr Leu Val Thr Val
                130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
                195                 200                 205
```

```
Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
                260                 265                 270

Gly Gln Asn Gln Leu Tyr Asn Glu Leu Asn Leu Gly Arg Arg Glu Glu
                275                 280                 285

Tyr Asp Val Leu Asp Lys Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
                340                 345                 350

Ala Thr Lys Asp Thr Tyr Asp Ala Leu His Met Gln Ala Leu Pro Pro
                355                 360                 365

Arg

<210> SEQ ID NO 487
<211> LENGTH: 369
<212> TYPE: PRT
<213> ORGANISM: Artificial
<220> FEATURE:
<223> OTHER INFORMATION: Humanized anti-DLL3 CAR sequence CAS64380VH6

<400> SEQUENCE: 487

Met Ala Leu Pro Val Thr Ala Leu Leu Leu Pro Leu Ala Leu Leu Leu
1                   5                   10                  15

His Ala Ala Arg Pro Glu Val Gln Leu Val Glu Ser Gly Gly Gly Leu
                20                  25                  30

Val Gln Pro Gly Gly Ser Leu Arg Leu Ser Cys Ala Ala Ser Gly Asn
            35                  40                  45

Thr Tyr Ser Ser Asn Tyr Met Gly Trp Phe Arg Gln Ala Pro Gly Lys
    50                  55                  60

Gly Leu Glu Glu Val Ala Val Ile Tyr Thr Arg Gly His Thr Tyr
65                  70                  75                  80

Tyr Val Asp Ser Val Arg Gly Arg Phe Thr Ile Ser Gln Asp Asn Ala
                85                  90                  95

Lys Asn Ser Val Tyr Leu Gln Met Asn Ser Leu Arg Ala Glu Asp Thr
                100                 105                 110

Ala Met Tyr Tyr Cys Ala Ala Ser Ser Arg His Arg Leu Gly Leu Asn
            115                 120                 125

Asn Pro Arg Asp Tyr Asp Tyr Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
```

```
                195                 200                 205
Leu Val Ile Thr Leu Tyr Cys Lys Arg Gly Arg Lys Lys Leu Leu Tyr
    210                 215                 220
Ile Phe Lys Gln Pro Phe Met Arg Pro Val Gln Thr Thr Gln Glu Glu
225                 230                 235                 240
Asp Gly Cys Ser Cys Arg Phe Pro Glu Glu Glu Glu Gly Gly Cys Glu
                245                 250                 255
Leu Arg Val Lys Phe Ser Arg Ser Ala Asp Ala Pro Ala Tyr Lys Gln
            260                 265                 270
Gly Gln Asn Gln Leu Tyr Asn Glu Leu Asn Leu Gly Arg Arg Glu Glu
        275                 280                 285
Tyr Asp Val Leu Asp Lys Arg Gly Arg Asp Pro Glu Met Gly Gly
    290                 295                 300
Lys Pro Arg Arg Lys Asn Pro Gln Glu Gly Leu Tyr Asn Glu Leu Gln
305                 310                 315                 320
Lys Asp Lys Met Ala Glu Ala Tyr Ser Glu Ile Gly Met Lys Gly Glu
                325                 330                 335
Arg Arg Arg Gly Lys Gly His Asp Gly Leu Tyr Gln Gly Leu Ser Thr
            340                 345                 350
Ala Thr Lys Asp Thr Tyr Asp Ala Leu His Met Gln Ala Leu Pro Pro
        355                 360                 365
Arg

<210> SEQ ID NO 488
<211> LENGTH: 369
<212> TYPE: PRT
<213> ORGANISM: Artificial
<220> FEATURE:
<223> OTHER INFORMATION: Humanized anti-DLL3 CAR sequence CAS64380VH7

<400> SEQUENCE: 488

Met Ala Leu Pro Val Thr Ala Leu Leu Leu Pro Leu Ala Leu Leu Leu
1               5                   10                  15
His Ala Ala Arg Pro Glu Val Gln Leu Val Glu Ser Gly Gly Gly Leu
            20                  25                  30
Val Gln Pro Gly Gly Ser Leu Arg Leu Ser Cys Ala Ala Ser Gly Asn
        35                  40                  45
Thr Tyr Ser Ser Asn Tyr Met Gly Trp Phe Arg Gln Ala Pro Gly Lys
    50                  55                  60
Gly Arg Glu Glu Val Ala Val Ile Tyr Thr Arg Gly His Thr Tyr
65                  70                  75                  80
Tyr Val Asp Ser Val Arg Gly Arg Phe Thr Ile Ser Gln Asp Asn Ala
                85                  90                  95
Lys Asn Ser Val Tyr Leu Gln Met Asn Ser Leu Arg Ala Glu Asp Thr
            100                 105                 110
Ala Met Tyr Tyr Cys Ala Ala Ser Ser Arg His Arg Leu Gly Leu Asn
        115                 120                 125
Asn Pro Arg Asp Tyr Asp Tyr Trp Gly Gln Gly Thr Leu Val Thr Val
    130                 135                 140
Ser Ser Thr Thr Thr Pro Ala Pro Arg Pro Pro Thr Pro Ala Pro Thr
145                 150                 155                 160
Ile Ala Ser Gln Pro Leu Ser Leu Arg Pro Glu Ala Cys Arg Pro Ala
                165                 170                 175
Ala Gly Gly Ala Val His Thr Arg Gly Leu Asp Phe Ala Cys Asp Ile
            180                 185                 190
```

Tyr Ile Trp Ala Pro Leu Ala Gly Thr Cys Gly Val Leu Leu Leu Ser
            195                 200                 205

Leu Val Ile Thr Leu Tyr Cys Lys Arg Gly Arg Lys Lys Leu Leu Tyr
            210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
            290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
            355                 360                 365

Arg

<210> SEQ ID NO 489
<211> LENGTH: 369
<212> TYPE: PRT
<213> ORGANISM: Artificial
<220> FEATURE:
<223> OTHER INFORMATION: Humanized anti-DLL3 CAR sequence CAS64511VH4

<400> SEQUENCE: 489

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Arg Ala
        35                  40                  45

Thr Tyr Ser Thr Asn Tyr Ile Ser Trp Phe Arg Gln Ala Pro Gly Lys
    50                  55                  60

Gly Leu Glu Ala Val Ala Thr Ile Thr Thr Gly Asp Gly Glu Thr Ala
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Asn Leu Arg Ile Gly Gly Asp Trp Phe
        115                 120                 125

Asp Gly Arg Asp Phe Arg Ala Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
            195                 200                 205

Leu Val Ile Thr Leu Tyr Cys Lys Arg Gly Arg Lys Lys Leu Leu Tyr
210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
            245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
            290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
            325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
            355                 360                 365

Arg

<210> SEQ ID NO 490
<211> LENGTH: 369
<212> TYPE: PRT
<213> ORGANISM: Artificial
<220> FEATURE:
<223> OTHER INFORMATION: Humanized anti-DLL3 CAR sequence CAS64511VH5

<400> SEQUENCE: 490

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Arg Ala
        35                  40                  45

Thr Tyr Ser Thr Asn Tyr Ile Ser Trp Phe Arg Gln Ala Pro Gly Lys
    50                  55                  60

Gly Leu Glu Ala Val Ala Thr Ile Thr Thr Gly Asp Gly Glu Thr Ala
65                  70                  75                  80

Tyr Ala Asp Ser Val Lys Gly Arg Phe Thr Ile Ser Arg Asp Asn Ala
                85                  90                  95

Lys Asn Ser Val Tyr Leu Gln Met Asn Ser Leu Arg Ala Glu Asp Thr
            100                 105                 110

Ala Met Tyr Tyr Cys Ala Ala Asn Leu Arg Ile Gly Gly Asp Trp Phe
        115                 120                 125

Asp Gly Arg Asp Phe Arg Ala Trp Gly Gln Gly Thr Leu Val Thr Val
    130                 135                 140

Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala

```
            165                 170                 175
Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
            195                 200                 205

Leu Val Ile Thr Leu Tyr Cys Lys Arg Gly Arg Lys Lys Leu Leu Tyr
            210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
            245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
            290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
            325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
            355                 360                 365

Arg

<210> SEQ ID NO 491
<211> LENGTH: 369
<212> TYPE: PRT
<213> ORGANISM: Artificial
<220> FEATURE:
<223> OTHER INFORMATION: Humanized anti-DLL3 CAR sequence CAS64511VH6

<400> SEQUENCE: 491

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Arg Ala
            35                  40                  45

Thr Tyr Ser Thr Asn Tyr Ile Ser Trp Phe Arg Gln Ala Pro Gly Lys
        50                  55                  60

Gly Arg Glu Ala Val Ala Thr Ile Thr Thr Gly Asp Gly Glu Thr Ala
65                  70                  75                  80

Tyr Ala Asp Ser Val Lys Gly Arg Phe Thr Ile Ser Arg Asp Asn Ala
            85                  90                  95

Lys Asn Ser Val Tyr Leu Gln Met Asn Ser Leu Arg Ala Glu Asp Thr
            100                 105                 110

Ala Met Tyr Tyr Cys Ala Ala Asn Leu Arg Ile Gly Gly Asp Trp Phe
            115                 120                 125

Asp Gly Arg Asp Phe Arg Ala Trp Gly Gln Gly Thr Leu Val Thr Val
            130                 135                 140

Ser Ser Thr Thr Thr Pro Ala Pro Arg Pro Pro Thr Pro Ala Pro Thr
145                 150                 155                 160
```

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 492
<211> LENGTH: 369
<212> TYPE: PRT
<213> ORGANISM: Artificial
<220> FEATURE:
<223> OTHER INFORMATION: Humanized anti-DLL3 CAR sequence CAS63997VH4

<400> SEQUENCE: 492

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Leu Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Val Gly Tyr Leu Ser Gly Ser Trp Asp
        115                 120                 125

Val Pro Gly Arg Tyr Asn Tyr Trp Gly Gln Gly Thr Leu Val Thr Val
    130                 135                 140

Ser Ser Thr Thr Thr Pro Ala Pro Arg Pro Thr Pro Ala Pro Thr
145                 150                 155                 160

Ile Ala Ser Gln Pro Leu Ser Leu Arg Pro Glu Ala Cys Arg Pro Ala
            165                 170                 175

Ala Gly Gly Ala Val His Thr Arg Gly Leu Asp Phe Ala Cys Asp Ile
                180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
        210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
            245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
        290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 493
<211> LENGTH: 369
<212> TYPE: PRT
<213> ORGANISM: Artificial
<220> FEATURE:
<223> OTHER INFORMATION: Humanized anti-DLL3 CAR sequence CAS63997VH5

<400> SEQUENCE: 493

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Leu Glu Gly Val Ala Ala Ile Thr Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Gly Ser Trp Asp
        115                 120                 125

Val Pro Gly Arg Tyr Asn Tyr Trp Gly Gln Gly Thr Leu Val Thr Val

```
                    130                 135                 140
Ser Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
                260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
        290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
                340                 345                 350

Ala Thr Lys Asp Thr Tyr Asp Ala Leu His Met Gln Ala Leu Pro Pro
            355                 360                 365

Arg

<210> SEQ ID NO 494
<211> LENGTH: 369
<212> TYPE: PRT
<213> ORGANISM: Artificial
<220> FEATURE:
<223> OTHER INFORMATION: Humanized anti-DLL3 CAR sequence CAS63997VH6

<400> SEQUENCE: 494

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Arg Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Gly Ser Trp Asp
        115                 120                 125
```

Val Pro Gly Arg Tyr Asn Tyr Trp Gly Gln Gly Thr Leu Val Thr Val
            130                 135                 140

Ser Ser Thr Thr Thr Pro Ala Pro Arg Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 495
<211> LENGTH: 11
<212> TYPE: PRT
<213> ORGANISM: Artificial
<220> FEATURE:
<223> OTHER INFORMATION: Anti-DLL3 human scFv CDR1 sequence AS56704

<400> SEQUENCE: 495

Arg Ala Ser Gln Ser Val Ser Ser Ala Val Ala
1               5                   10

<210> SEQ ID NO 496
<211> LENGTH: 7
<212> TYPE: PRT
<213> ORGANISM: Artificial
<220> FEATURE:
<223> OTHER INFORMATION: Anti-DLL3 human scFv CDR2 sequence AS56704

<400> SEQUENCE: 496

Ser Ala Ser Ser Leu Tyr Ser
1               5

<210> SEQ ID NO 497
<211> LENGTH: 9
<212> TYPE: PRT
<213> ORGANISM: Artificial

```
<220> FEATURE:
<223> OTHER INFORMATION: Anti-DLL3 human scFv CDR3 sequence AS56704

<400> SEQUENCE: 497

Gln Gln Ala Ser Trp Ser Pro Ile Thr
1               5

<210> SEQ ID NO 498
<211> LENGTH: 10
<212> TYPE: PRT
<213> ORGANISM: Artificial
<220> FEATURE:
<223> OTHER INFORMATION: Anti-DLL3 human scFv VH CDR1 sequence AS56704

<400> SEQUENCE: 498

Gly Phe Asn Ile Ser Ser Ser Tyr Met His
1               5                   10

<210> SEQ ID NO 499
<211> LENGTH: 17
<212> TYPE: PRT
<213> ORGANISM: Artificial
<220> FEATURE:
<223> OTHER INFORMATION: Anti-DLL3 human scFv VH CDR2 sequence AS56704

<400> SEQUENCE: 499

Tyr Ile Tyr Pro Ser Tyr Gly Tyr Thr Ser Tyr Ala Asp Ser Val Lys
1               5                   10                  15

Gly

<210> SEQ ID NO 500
<211> LENGTH: 10
<212> TYPE: PRT
<213> ORGANISM: Artificial
<220> FEATURE:
<223> OTHER INFORMATION: Anti-DLL3 human scFv VH CDR3 sequence AS56704

<400> SEQUENCE: 500

Gly Gly Tyr Tyr Tyr His Gly Met Asp Tyr
1               5                   10

<210> SEQ ID NO 501
<211> LENGTH: 11
<212> TYPE: PRT
<213> ORGANISM: Artificial
<220> FEATURE:
<223> OTHER INFORMATION: Anti-DLL3 human scFv VL CDR1 sequence AS56788

<400> SEQUENCE: 501

Arg Ala Ser Gln Ser Val Ser Ser Ala Val Ala
1               5                   10

<210> SEQ ID NO 502
<211> LENGTH: 7
<212> TYPE: PRT
<213> ORGANISM: Artificial
<220> FEATURE:
<223> OTHER INFORMATION: Anti-DLL3 human scFv VL CDR2 sequence AS56788

<400> SEQUENCE: 502

Ser Ala Ser Ser Leu Tyr Ser
1               5

<210> SEQ ID NO 503
<211> LENGTH: 10
<212> TYPE: PRT
```

```
<213> ORGANISM: Artificial
<220> FEATURE:
<223> OTHER INFORMATION: Anti-DLL3 human scFv VL CDR3 sequence AS56788

<400> SEQUENCE: 503

Gln Gln His Tyr Ala Pro Ser Leu Ile Thr
1               5                   10

<210> SEQ ID NO 504
<211> LENGTH: 10
<212> TYPE: PRT
<213> ORGANISM: Artificial
<220> FEATURE:
<223> OTHER INFORMATION: Anti-DLL3 human scFv VH CDR1 sequence AS56788

<400> SEQUENCE: 504

Gly Phe Asn Ile Ser Ser Tyr Ser Met His
1               5                   10

<210> SEQ ID NO 505
<211> LENGTH: 17
<212> TYPE: PRT
<213> ORGANISM: Artificial
<220> FEATURE:
<223> OTHER INFORMATION: Anti-DLL3 human scFv VH CDR2 sequence AS56788

<400> SEQUENCE: 505

Tyr Ile Ser Ser Tyr Tyr Gly Tyr Thr Tyr Tyr Ala Asp Ser Val Lys
1               5                   10                  15

Gly

<210> SEQ ID NO 506
<211> LENGTH: 9
<212> TYPE: PRT
<213> ORGANISM: Artificial
<220> FEATURE:
<223> OTHER INFORMATION: Anti-DLL3 human scFv VH CDR3 sequence AS56788

<400> SEQUENCE: 506

Tyr Ser Tyr Tyr Tyr Gly Met Asp Tyr
1               5

<210> SEQ ID NO 507
<211> LENGTH: 107
<212> TYPE: PRT
<213> ORGANISM: Artificial
<220> FEATURE:
<223> OTHER INFORMATION: Anti-DLL3 human scFv VL amino acid sequence
      AS56704

<400> SEQUENCE: 507

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
                20                  25                  30

Val Ala Trp Tyr Gln Gln Lys Pro Gly Lys Ala Pro Lys Leu Leu Ile
            35                  40                  45

Tyr Ser Ala Ser Ser Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Trp Ser Pro Ile
                85                  90                  95
```

Thr Phe Gly Gln Gly Thr Lys Val Glu Ile Lys
            100                 105

<210> SEQ ID NO 508
<211> LENGTH: 119
<212> TYPE: PRT
<213> ORGANISM: Artificial
<220> FEATURE:
<223> OTHER INFORMATION: Anti-DLL3 human scFv VH amino acid sequence
      AS56704

<400> SEQUENCE: 508

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Ser Ser Ser
            20                  25                  30

Tyr Met His Trp Val Arg Gln Ala Pro Gly Lys Gly Leu Glu Trp Val
        35                  40                  45

Ala Tyr Ile Tyr Pro Ser Tyr Gly Tyr Thr Ser Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Tyr Tyr His Gly Met Asp Tyr Trp Gly Gln Gly
            100                 105                 110

Thr Leu Val Thr Val Ser Ser
        115

<210> SEQ ID NO 509
<211> LENGTH: 108
<212> TYPE: PRT
<213> ORGANISM: Artificial
<220> FEATURE:
<223> OTHER INFORMATION: Anti-DLL3 human scFv VL amino acid sequence
      AS56788

<400> SEQUENCE: 509

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ala Pro Ser Leu
                85                  90                  95

Ile Thr Phe Gly Gln Gly Thr Lys Val Glu Ile Lys
            100                 105

<210> SEQ ID NO 510
<211> LENGTH: 118
<212> TYPE: PRT
<213> ORGANISM: Artificial
<220> FEATURE:
<223> OTHER INFORMATION: Anti-DLL3 human scFv VH amino acid sequence
      AS56788

<400> SEQUENCE: 510

| | | | | | | | | | | | | | | |
|---|---|---|---|---|---|---|---|---|---|---|---|---|---|---|
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Ser Ser Tyr
            20                  25                  30

Ser Met His Trp Val Arg Gln Ala Pro Gly Lys Gly Leu Glu Trp Val
        35                  40                  45

Ala Tyr Ile Ser Ser Tyr Tyr Gly Tyr Thr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Ser Tyr Tyr Tyr Gly Met Asp Tyr Trp Gly Gln Gly Thr
            100                 105                 110

Leu Val Thr Val Ser Ser
        115

<210> SEQ ID NO 511
<211> LENGTH: 321
<212> TYPE: DNA
<213> ORGANISM: Artificial
<220> FEATURE:
<223> OTHER INFORMATION: Nucleic Acid Sequence for VL domain of
      anti-DLL3 human scFv AS56704

<400> SEQUENCE: 511
gacatccaga tgacccagag cccgagcagc ctgagcgcga gcgttggtga ccgtgttacc    60
attacctgcc gtgcgagcca gagcgttagc agcgcggtgg cgtggtacca gcaaaagccg   120
ggtaaagcgc cgaagctgct gatctatagc gcgagcagcc tgtatagcgg cgttccgagc   180
cgtttcagcg gtagccgtag cggcaccgac tttaccctga ccattagcag cctgcagccg   240
gaagatttcg caacttatta ctgtcagcaa gcttcttggt ctccgatcac gttcggacag   300
ggcaccaaag ttgagattaa a                                             321

<210> SEQ ID NO 512
<211> LENGTH: 357
<212> TYPE: DNA
<213> ORGANISM: Artificial
<220> FEATURE:
<223> OTHER INFORMATION: Nucleic Acid Sequence for VH domain of
      anti-DLL3 human scFv AS56704

<400> SEQUENCE: 512
gaggttcaac tggtggagag cggtggtggt ctggttcagc cgggtggtag cctgcgtctg    60
agctgcgcag cttctggctt caacatctct tcttcttata tgcactgggt gcgtcaggcg   120
ccgggtaaag gcctggaatg ggttgcatat atttatcctt cttatggcta tacttcttat   180
gccgatagcg tcaagggccg tttcaccatc agcgcggata ccagcaaaaa caccgcatac   240
ctgcaaatga acagcctgcg tgcggaagat accgccgtct attattgtgc tcgcggtggt   300
tactactacc atggtatgga ctactggggt caaggcaccc tggttaccgt gagcagc     357

<210> SEQ ID NO 513
<211> LENGTH: 324
<212> TYPE: DNA
<213> ORGANISM: Artificial
<220> FEATURE:
<223> OTHER INFORMATION: Nucleic Acid Sequence for VL domain of anti-DLL3 human scFv AS56788

<400> SEQUENCE: 513

```
gacatccaga tgacccagag cccgagcagc ctgagcgcga gcgttggtga ccgtgttacc     60
attacctgcc gtgcgagcca gagcgttagc agcgcggtgg cgtggtacca gcaaaagccg    120
ggtaaagcgc cgaagctgct gatctatagc gcgagcagcc tgtatagcgg cgttccgagc    180
cgtttcagcg gtagccgtag cggcaccgac tttaccctga ccattagcag cctgcagccg    240
gaagatttcg caacttatta ctgtcagcaa cattacgctc cgtctctgat cacgttcgga    300
cagggcacca agttgagat taaa                                            324
```

<210> SEQ ID NO 514
<211> LENGTH: 354
<212> TYPE: DNA
<213> ORGANISM: Artificial
<220> FEATURE:
<223> OTHER INFORMATION: Nucleic Acid Sequence for VH domain of
      anti-DLL3 human scFv AS56788

<400> SEQUENCE: 514

```
gaggttcaac tggtggagag cggtggtggt ctggttcagc cgggtggtag cctgcgtctg     60
agctgcgcag cttctggctt caacatctct tcttattcta tgcactgggt gcgtcaggcg    120
ccgggtaaag gcctggaatg ggttgcatat atttcttctt attatggcta tactattat    180
gccgatagcg tcaagggccg tttcaccatc agcgcggata ccagcaaaaa caccgcatac    240
ctgcaaatga acagcctgcg tgcggaagat accgccgtct attattgtgc tcgctactct    300
tactactacg gtatggacta ctggggtcaa ggcaccctgg ttaccgtgag cagc           354
```

<210> SEQ ID NO 515
<211> LENGTH: 485
<212> TYPE: PRT
<213> ORGANISM: Artificial
<220> FEATURE:
<223> OTHER INFORMATION: Human anti-DLL3 scFv CAR sequences CAS56704

<400> SEQUENCE: 515

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Val Ser Ser Ala Val Ala Trp Tyr Gln Gln Lys Pro Gly Lys Ala
    50                  55                  60

Pro Lys Leu Leu Ile Tyr Ser Ala Ser Ser Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln Ala
            100                 105                 110

Ser Trp Ser Pro Ile Thr Phe Gly Gln Gly Thr Lys Val Glu Ile Lys
        115                 120                 125

Gly Gly Gly Gly Ser Gly Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160
```

```
Leu Arg Leu Ser Cys Ala Ala Ser Gly Phe Asn Ile Ser Ser Tyr
                165                 170                 175

Met His Trp Val Arg Gln Ala Pro Gly Lys Gly Leu Glu Trp Val Ala
            180                 185                 190

Tyr Ile Tyr Pro Ser Tyr Gly Tyr Thr Ser Tyr Ala Asp Ser Val Lys
        195                 200                 205

Gly Arg Phe Thr Ile Ser Ala Asp Thr Ser Lys Asn Thr Ala Tyr Leu
    210                 215                 220

Gln Met Asn Ser Leu Arg Ala Glu Asp Thr Ala Val Tyr Tyr Cys Ala
225                 230                 235                 240

Arg Gly Gly Tyr Tyr Tyr His Gly Met Asp Tyr Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 516
<211> LENGTH: 485
<212> TYPE: PRT
<213> ORGANISM: Artificial
<220> FEATURE:
<223> OTHER INFORMATION: Human anti-DLL3 scFv CAR sequences CAS56788

<400> SEQUENCE: 516

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30
```

-continued

```
Ser Ala Ser Val Gly Asp Arg Val Thr Ile Thr Cys Arg Ala Ser Gln
         35                  40                  45

Ser Val Ser Ser Ala Val Ala Trp Tyr Gln Gln Lys Pro Gly Lys Ala
 50                  55                  60

Pro Lys Leu Leu Ile Tyr Ser Ala Ser Ser Leu Tyr Ser Gly Val Pro
 65                  70                  75                  80

Ser Arg Phe Ser Gly Ser Arg Ser Gly Thr Asp Phe Thr Leu Thr Ile
                 85                  90                  95

Ser Ser Leu Gln Pro Glu Asp Phe Ala Thr Tyr Tyr Cys Gln Gln His
                100                 105                 110

Tyr Ala Pro Ser Leu Ile Thr Phe Gly Gln Gly Thr Lys Val Glu Ile
                115                 120                 125

Lys Gly Gly Gly Gly Ser Gly Gly Gly Gly Ser Gly Gly Gly Gly Ser
        130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Asn Ile Ser Ser Tyr
                165                 170                 175

Ser Met His Trp Val Arg Gln Ala Pro Gly Lys Gly Leu Glu Trp Val
                180                 185                 190

Ala Tyr Ile Ser Ser Tyr Tyr Gly Tyr Thr Tyr Tyr Ala Asp Ser Val
                195                 200                 205

Lys Gly Arg Phe Thr Ile Ser Ala Asp Thr Ser Lys Asn Thr Ala Tyr
                210                 215                 220

Leu Gln Met Asn Ser Leu Arg Ala Glu Asp Thr Ala Val Tyr Tyr Cys
225                 230                 235                 240

Ala Arg Tyr Ser Tyr Tyr Tyr Gly Met Asp Tyr Trp Gly Gln Gly Thr
                245                 250                 255

Leu Val Thr Val Ser Ser Thr Thr Thr Pro Ala Pro Arg Pro Pro Thr
                260                 265                 270

Pro Ala Pro Thr Ile Ala Ser Gln Pro Leu Ser Leu Arg Pro Glu Ala
                275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
                355                 360                 365

Gly Gly Cys Glu Leu Arg Val Lys Phe Ser Arg Ser Ala Asp Ala Pro
        370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
```

-continued

```
                450                 455                 460
Gly Leu Ser Thr Ala Thr Lys Asp Thr Tyr Asp Ala Leu His Met Gln
465                 470                 475                 480

Ala Leu Pro Pro Arg
                485

<210> SEQ ID NO 517
<211> LENGTH: 476
<212> TYPE: PRT
<213> ORGANISM: Artificial
<220> FEATURE:
<223> OTHER INFORMATION: 1H2.1 amino acid sequence

<400> SEQUENCE: 517

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Asp
            35                  40                  45

Ser Ile Ser Ser Tyr Tyr Trp Thr Trp Ile Arg Gln Pro Pro Gly Lys
        50                  55                  60

Gly Leu Glu Trp Ile Gly Tyr Ile Tyr Tyr Ser Gly Thr Thr Asn Tyr
65                  70                  75                  80

Asn Pro Ser Leu Lys Ser Arg Val Thr Ile Ser Val Asp Thr Ser Lys
                85                  90                  95

Ser Gln Phe Ser Leu Lys Leu Ser Val Thr Ala Ala Asp Thr Ala
            100                 105                 110

Val Tyr Tyr Cys Ala Ser Ile Ala Val Arg Gly Phe Phe Asp Tyr
        115                 120                 125

Trp Gly Gln Gly Thr Leu Val Thr Val Ser Ser Gly Gly Gly Gly Ser
            130                 135                 140

Gly Gly Gly Gly Ser Gly Gly Gly Ser Glu Ile Val Leu Thr Gln
145                 150                 155                 160

Ser Pro Gly Thr Leu Ser Leu Ser Pro Gly Glu Arg Ala Thr Leu Ser
                165                 170                 175

Cys Arg Ala Ser Gln Ser Val Ser Ser Ser Tyr Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Asp Arg Phe Ser Gly Ser Gly Ser Gly Thr
210                 215                 220

Asp Phe Thr Leu Thr Ile Ser Arg Leu Glu Pro Glu Asp Phe Ala Val
225                 230                 235                 240

Tyr Tyr Cys Gln Gln Tyr Gly Thr Ser Pro Leu Thr Phe Gly Gly Gly
                245                 250                 255

Thr Lys Val Glu Ile Lys Arg Ala Ala Ala Leu Asp Asn Glu Lys Ser
            260                 265                 270

Asn Gly Thr Ile Ile His Val Lys Gly Lys His Leu Cys Pro Ser Pro
        275                 280                 285

Leu Phe Pro Gly Pro Ser Lys Pro Phe Trp Val Leu Val Val Val Gly
            290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
```

```
            325                 330                 335
Asn Met Thr Pro Arg Pro Gly Pro Thr Arg Lys His Tyr Gln Pro
            340                 345                 350

Tyr Ala Pro Pro Arg Asp Phe Ala Ala Tyr Arg Ser Arg Val Lys Phe
            355                 360                 365

Ser Arg Ser Ala Asp Ala Pro Ala Tyr Gln Gln Gly Gln Asn Gln Leu
            370                 375                 380

Tyr Asn Glu Leu Asn Leu Gly Arg Arg Glu Tyr Asp Val Leu Asp
385                 390                 395                 400

Lys Arg Arg Gly Arg Asp Pro Glu Met Gly Gly Lys Pro Arg Arg Lys
                    405                 410                 415

Asn Pro Gln Glu Gly Leu Tyr Asn Glu Leu Gln Lys Asp Lys Met Ala
                    420                 425                 430

Glu Ala Tyr Ser Glu Ile Gly Met Lys Gly Glu Arg Arg Arg Gly Lys
                    435                 440                 445

Gly His Asp Gly Leu Tyr Gln Gly Leu Ser Thr Ala Thr Lys Asp Thr
                    450                 455                 460

Tyr Asp Ala Leu His Met Gln Ala Leu Pro Pro Arg
465                 470                 475

<210> SEQ ID NO 518
<211> LENGTH: 509
<212> TYPE: PRT
<213> ORGANISM: Artificial
<220> FEATURE:
<223> OTHER INFORMATION: T1 amino acid sequence

<400> SEQUENCE: 518

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Pro Gly Gly Ser Leu Arg Leu Ser Cys Ala Ala Ser Gly Asn
            35                  40                  45

Thr Tyr Ser Ser Asn Tyr Met Gly Trp Phe Arg Gln Ala Pro Gly Lys
        50                  55                  60

Gly Leu Glu Glu Val Ala Val Ile Tyr Thr Arg Gly Gly His Thr Tyr
65                  70                  75                  80

Tyr Val Asp Ser Val Arg Gly Arg Phe Thr Ile Ser Gln Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Ala Ser Ser Arg His Arg Leu Gly Leu Asn
        115                 120                 125

Asn Pro Arg Asp Tyr Asp Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Ala Ser Gly Asn Thr Tyr Ser Ser
            180                 185                 190

Asn Tyr Met Gly Trp Phe Arg Gln Ala Pro Gly Lys Gly Leu Glu Glu
        195                 200                 205

Val Ala Val Ile Tyr Thr Arg Gly Gly His Thr Tyr Tyr Val Asp Ser
```

```
            210                 215                 220
Val Arg Gly Arg Phe Thr Ile Ser Gln Asp Asn Ala Lys Asn Ser Leu
225                 230                 235                 240

Tyr Leu Gln Met Asn Ser Leu Arg Ala Glu Asp Thr Ala Val Tyr Tyr
                245                 250                 255

Cys Ala Ala Ser Ser Arg His Arg Leu Gly Leu Asn Asn Pro Arg Asp
                260                 265                 270

Tyr Asp Tyr Trp Gly Gln Gly Thr Leu Val Thr Val Ser Ser Thr Thr
            275                 280                 285

Thr Pro Ala Pro Arg Pro Pro Thr Pro Ala Pro Thr Ile Ala Ser Gln
        290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
                340                 345                 350

Leu Tyr Cys Lys Arg Gly Arg Lys Lys Leu Leu Tyr Ile Phe Lys Gln
            355                 360                 365

Pro Phe Met Arg Pro Val Gln Thr Thr Gln Glu Glu Asp Gly Cys Ser
        370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
                420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 519
<211> LENGTH: 509
<212> TYPE: PRT
<213> ORGANISM: Artificial
<220> FEATURE:
<223> OTHER INFORMATION: T2 amino acid sequence

<400> SEQUENCE: 519

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Gly Ser Leu Arg Leu Ser Cys Ala Ala Ser Phe Ser
            35                  40                  45

Gly Tyr Gly Val Ser Thr Met Ala Trp Phe Arg Gln Ala Pro Gly Lys
        50                  55                  60

Gly Leu Glu Gly Val Ala Ala Ile Thr Val Gly Ser Gly Asn Thr Tyr
```

-continued

```
                65                  70                  75                  80
Tyr Ala Asp Ser Val Lys Gly Arg Phe Thr Ile Ser Arg Asp Asn Ser
                    85                  90                  95
Lys Asn Thr Val Tyr Leu Gln Met Asn Ser Leu Arg Ala Glu Asp Thr
                    100                 105                 110
Ala Met Tyr Tyr Cys Ala Val Gly Tyr Leu Ser Gly Ser Trp Asp
                115                 120                 125
Val Pro Gly Arg Tyr Asn Tyr Trp Gly Gln Gly Thr Leu Val Thr Val
            130                 135                 140
Ser Ser Gly Gly Gly Gly Ser Gly Gly Gly Gly Ser Gly Gly Gly Gly
145                 150                 155                 160
Ser Gln Val Gln Leu Val Glu Ser Gly Gly Val Val Gln Pro Gly
                    165                 170                 175
Gly Ser Leu Arg Leu Ser Cys Ala Ala Ser Phe Ser Tyr Gly Val
                180                 185                 190
Ser Thr Met Ala Trp Phe Arg Gln Ala Pro Gly Lys Gly Leu Glu Gly
            195                 200                 205
Val Ala Ala Ile Thr Val Gly Ser Gly Asn Thr Tyr Tyr Ala Asp Ser
    210                 215                 220
Val Lys Gly Arg Phe Thr Ile Ser Arg Asp Asn Ser Lys Asn Thr Val
225                 230                 235                 240
Tyr Leu Gln Met Asn Ser Leu Arg Ala Glu Asp Thr Ala Met Tyr Tyr
                245                 250                 255
Cys Ala Val Gly Tyr Leu Ser Gly Ser Trp Asp Val Pro Gly Arg
            260                 265                 270
Tyr Asn Tyr Trp Gly Gln Gly Thr Leu Val Thr Val Ser Ser Thr Thr
        275                 280                 285
Thr Pro Ala Pro Arg Pro Pro Thr Pro Ala Pro Thr Ile Ala Ser Gln
    290                 295                 300
Pro Leu Ser Leu Arg Pro Glu Ala Cys Arg Pro Ala Ala Gly Gly Ala
305                 310                 315                 320
Val His Thr Arg Gly Leu Asp Phe Ala Cys Asp Ile Tyr Ile Trp Ala
                325                 330                 335
Pro Leu Ala Gly Thr Cys Gly Val Leu Leu Leu Ser Leu Val Ile Thr
            340                 345                 350
Leu Tyr Cys Lys Arg Gly Arg Lys Lys Leu Leu Tyr Ile Phe Lys Gln
        355                 360                 365
Pro Phe Met Arg Pro Val Gln Thr Thr Gln Glu Glu Asp Gly Cys Ser
    370                 375                 380
Cys Arg Phe Pro Glu Glu Glu Gly Gly Cys Glu Leu Arg Val Lys
385                 390                 395                 400
Phe Ser Arg Ser Ala Asp Ala Pro Ala Tyr Lys Gln Gly Gln Asn Gln
                405                 410                 415
Leu Tyr Asn Glu Leu Asn Leu Gly Arg Arg Glu Glu Tyr Asp Val Leu
            420                 425                 430
Asp Lys Arg Arg Gly Arg Asp Pro Glu Met Gly Gly Lys Pro Arg Arg
        435                 440                 445
Lys Asn Pro Gln Glu Gly Leu Tyr Asn Glu Leu Gln Lys Asp Lys Met
    450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
                485                 490                 495
```

Thr Tyr Asp Ala Leu His Met Gln Ala Leu Pro Pro Arg
            500                 505

<210> SEQ ID NO 520
<211> LENGTH: 509
<212> TYPE: PRT
<213> ORGANISM: Artificial
<220> FEATURE:
<223> OTHER INFORMATION: T3 amino acid sequence

<400> SEQUENCE: 520

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
50                  55                  60

Gly Leu Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Gly Ser Trp Asp
        115                 120                 125

Val Pro Gly Arg Tyr Asn Tyr Trp Gly Gln Gly Thr Leu Val Thr Val
130                 135                 140

Ser Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Ala Ser Gly Asn Thr Tyr Ser Ser
            180                 185                 190

Asn Tyr Met Gly Trp Phe Arg Gln Ala Pro Gly Lys Gly Leu Glu Glu
        195                 200                 205

Val Ala Val Ile Tyr Thr Arg Gly Gly His Thr Tyr Tyr Val Asp Ser
210                 215                 220

Val Arg Gly Arg Phe Thr Ile Ser Gln Asp Asn Ala Lys Asn Ser Leu
225                 230                 235                 240

Tyr Leu Gln Met Asn Ser Leu Arg Ala Glu Asp Thr Ala Val Tyr Tyr
                245                 250                 255

Cys Ala Ala Ser Ser Arg His Arg Leu Gly Leu Asn Asn Pro Arg Asp
            260                 265                 270

Tyr Asp Tyr Trp Gly Gln Gly Thr Leu Val Thr Val Ser Ser Thr Thr
        275                 280                 285

Thr Pro Ala Pro Arg Pro Pro Thr Pro Ala Pro Thr Ile Ala Ser Gln
290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
            340                 345                 350

```
Leu Tyr Cys Lys Arg Gly Arg Lys Leu Leu Tyr Ile Phe Lys Gln
            355                 360                 365

Pro Phe Met Arg Pro Val Gln Thr Thr Gln Glu Glu Asp Gly Cys Ser
    370                 375                 380

Cys Arg Phe Pro Glu Glu Glu Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 521
<211> LENGTH: 775
<212> TYPE: PRT
<213> ORGANISM: Artificial
<220> FEATURE:
<223> OTHER INFORMATION: T3-PD-1DNR amino acid sequence

<400> SEQUENCE: 521

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Leu Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Ser Trp Asp
            115                 120                 125

Val Pro Gly Arg Tyr Asn Tyr Trp Gly Gln Gly Thr Leu Val Thr Val
        130                 135                 140

Ser Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Ala Ser Gly Asn Thr Tyr Ser Ser
            180                 185                 190

Asn Tyr Met Gly Trp Phe Arg Gln Ala Pro Gly Lys Gly Leu Glu Glu
        195                 200                 205
```

```
Val Ala Val Ile Tyr Thr Arg Gly Gly His Thr Tyr Val Asp Ser
    210                 215                 220
Val Arg Gly Arg Phe Thr Ile Ser Gln Asp Asn Ala Lys Asn Ser Leu
225                 230                 235                 240
Tyr Leu Gln Met Asn Ser Leu Arg Ala Glu Asp Thr Ala Val Tyr Tyr
                245                 250                 255
Cys Ala Ala Ser Ser Arg His Arg Leu Gly Leu Asn Asn Pro Arg Asp
                260                 265                 270
Tyr Asp Tyr Trp Gly Gln Gly Thr Leu Val Thr Val Ser Ser Thr Thr
            275                 280                 285
Thr Pro Ala Pro Arg Pro Pro Thr Pro Ala Pro Thr Ile Ala Ser Gln
    290                 295                 300
Pro Leu Ser Leu Arg Pro Glu Ala Cys Arg Pro Ala Ala Gly Gly Ala
305                 310                 315                 320
Val His Thr Arg Gly Leu Asp Phe Ala Cys Asp Ile Tyr Ile Trp Ala
                325                 330                 335
Pro Leu Ala Gly Thr Cys Gly Val Leu Leu Leu Ser Leu Val Ile Thr
                340                 345                 350
Leu Tyr Cys Lys Arg Gly Arg Lys Lys Leu Leu Tyr Ile Phe Lys Gln
    355                 360                 365
Pro Phe Met Arg Pro Val Gln Thr Thr Gln Glu Glu Asp Gly Cys Ser
    370                 375                 380
Cys Arg Phe Pro Glu Glu Glu Gly Gly Cys Glu Leu Arg Val Lys
385                 390                 395                 400
Phe Ser Arg Ser Ala Asp Ala Pro Ala Tyr Lys Gln Gly Gln Asn Gln
                405                 410                 415
Leu Tyr Asn Glu Leu Asn Leu Gly Arg Arg Glu Glu Tyr Asp Val Leu
                420                 425                 430
Asp Lys Arg Arg Gly Arg Asp Pro Glu Met Gly Gly Lys Pro Arg Arg
            435                 440                 445
Lys Asn Pro Gln Glu Gly Leu Tyr Asn Glu Leu Gln Lys Asp Lys Met
    450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
                485                 490                 495
Thr Tyr Asp Ala Leu His Met Gln Ala Leu Pro Pro Arg Gly Ser Gly
                500                 505                 510
Ala Thr Asn Phe Ser Leu Leu Lys Gln Ala Gly Asp Val Glu Glu Asn
    515                 520                 525
Pro Gly Pro Met Gln Ile Pro Gln Ala Pro Trp Pro Val Val Trp Ala
    530                 535                 540
Val Leu Gln Leu Gly Trp Arg Pro Gly Trp Phe Leu Asp Ser Pro Asp
545                 550                 555                 560
Arg Pro Trp Asn Pro Pro Thr Phe Ser Pro Ala Leu Leu Val Val Thr
                565                 570                 575
Glu Gly Asp Asn Ala Thr Phe Thr Cys Ser Phe Ser Asn Thr Ser Glu
                580                 585                 590
Ser Phe Val Leu Asn Trp Tyr Arg Met Ser Pro Ser Asn Gln Thr Asp
    595                 600                 605
Lys Leu Ala Ala Phe Pro Glu Asp Arg Ser Gln Pro Gly Gln Asp Cys
    610                 615                 620
```

Arg Phe Arg Val Thr Gln Leu Pro Asn Gly Arg Asp Phe His Met Ser
625                 630                 635                 640

Val Val Arg Ala Arg Arg Asn Asp Ser Gly Thr Tyr Leu Cys Gly Ala
            645                 650                 655

Ile Ser Leu Ala Pro Lys Ala Gln Ile Lys Glu Ser Leu Arg Ala Glu
            660                 665                 670

Leu Arg Val Thr Glu Arg Arg Ala Glu Val Pro Thr Ala His Pro Ser
            675                 680                 685

Pro Ser Pro Arg Pro Ala Gly Gln Ala Ala Pro Thr Thr Thr Pro
690                 695                 700

Ala Pro Arg Pro Pro Thr Pro Ala Pro Thr Ile Ala Ser Gln Pro Leu
705                 710                 715                 720

Ser Leu Arg Pro Glu Ala Cys Arg Pro Ala Ala Gly Gly Ala Val His
            725                 730                 735

Thr Arg Gly Leu Asp Phe Ala Cys Asp Ile Tyr Ile Trp Ala Pro Leu
            740                 745                 750

Ala Gly Thr Cys Gly Val Leu Leu Leu Ser Leu Val Ile Thr Leu Tyr
            755                 760                 765

Cys Asn His Arg Arg Ile Gln
770                 775

<210> SEQ ID NO 522
<211> LENGTH: 766
<212> TYPE: PRT
<213> ORGANISM: Artificial
<220> FEATURE:
<223> OTHER INFORMATION: T3-PD-1CSR amino acid sequence

<400> SEQUENCE: 522

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Leu Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Gly Ser Trp Asp
        115                 120                 125

Val Pro Gly Arg Tyr Asn Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Pro Gly
                165                 170                 175

Gly Ser Leu Arg Leu Ser Cys Ala Ala Ser Gly Asn Thr Tyr Ser Ser
            180                 185                 190

Asn Tyr Met Gly Trp Phe Arg Gln Ala Pro Gly Lys Gly Leu Glu Glu
        195                 200                 205

Val Ala Val Ile Tyr Thr Arg Gly Gly His Thr Tyr Val Asp Ser
210             215                 220

Val Arg Gly Arg Phe Thr Ile Ser Gln Asp Asn Ala Lys Asn Ser Leu
225                 230                 235                 240

Tyr Leu Gln Met Asn Ser Leu Arg Ala Glu Asp Thr Ala Val Tyr Tyr
            245                 250                 255

Cys Ala Ala Ser Ser Arg His Arg Leu Gly Leu Asn Asn Pro Arg Asp
        260                 265                 270

Tyr Asp Tyr Trp Gly Gln Gly Thr Leu Val Thr Val Ser Ser Thr Thr
        275                 280                 285

Thr Pro Ala Pro Arg Pro Pro Thr Pro Ala Pro Thr Ile Ala Ser Gln
290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
                340                 345                 350

Leu Tyr Cys Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
        370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
        420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg Gly Ser Gly
            500                 505                 510

Ala Thr Asn Phe Ser Leu Leu Lys Gln Ala Gly Asp Val Glu Glu Asn
            515                 520                 525

Pro Gly Pro Met Gln Ile Pro Gln Ala Pro Trp Pro Val Val Trp Ala
        530                 535                 540

Val Leu Gln Leu Gly Trp Arg Pro Gly Trp Phe Leu Asp Ser Pro Asp
545                 550                 555                 560

Arg Pro Trp Asn Pro Pro Thr Phe Ser Pro Ala Leu Leu Val Val Thr
                565                 570                 575

Glu Gly Asp Asn Ala Thr Phe Thr Cys Ser Phe Ser Asn Thr Ser Glu
            580                 585                 590

Ser Phe Val Leu Asn Trp Tyr Arg Met Ser Pro Ser Asn Gln Thr Asp
        595                 600                 605

Lys Leu Ala Ala Phe Pro Glu Asp Arg Ser Gln Pro Gly Gln Asp Cys
610                 615                 620

Arg Phe Arg Val Thr Gln Leu Pro Asn Gly Arg Asp Phe His Met Ser

```
                625                 630                 635                 640
Val Val Arg Ala Arg Arg Asn Asp Ser Gly Thr Tyr Leu Cys Gly Ala
                        645                 650                 655

Ile Ser Leu Ala Pro Lys Ala Gln Ile Lys Glu Ser Leu Arg Ala Glu
                660                 665                 670

Leu Arg Val Thr Glu Arg Arg Ala Glu Val Pro Thr Ala His Cys Pro
            675                 680                 685

Ser Pro Leu Phe Pro Gly Pro Ser Lys Pro Phe Trp Val Leu Val Val
        690                 695                 700

Val Gly Gly Val Leu Ala Cys Tyr Ser Leu Leu Val Thr Val Ala Phe
705                 710                 715                 720

Ile Ile Phe Trp Val Arg Ser Lys Arg Ser Arg Leu Leu His Ser Asp
                    725                 730                 735

Tyr Met Asn Met Thr Pro Arg Arg Pro Gly Pro Thr Arg Lys His Tyr
                740                 745                 750

Gln Pro Tyr Ala Pro Pro Arg Asp Phe Ala Ala Tyr Arg Ser
            755                 760                 765

<210> SEQ ID NO 523
<211> LENGTH: 244
<212> TYPE: PRT
<213> ORGANISM: Artificial
<220> FEATURE:
<223> OTHER INFORMATION: PD-1DNR amino acid sequence

<400> SEQUENCE: 523

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Ala Ala Pro Thr Thr Thr Pro Ala Pro Arg
                165                 170                 175

Pro Pro Thr Pro Ala Pro Thr Ile Ala Ser Gln Pro Leu Ser Leu Arg
            180                 185                 190

Pro Glu Ala Cys Arg Pro Ala Ala Gly Gly Ala Val His Thr Arg Gly
        195                 200                 205

Leu Asp Phe Ala Cys Asp Ile Tyr Ile Trp Ala Pro Leu Ala Gly Thr
    210                 215                 220

Cys Gly Val Leu Leu Leu Ser Leu Val Ile Thr Leu Tyr Cys Asn His
```

-continued

```
               225                 230                 235                 240

Arg Arg Ile Gln

<210> SEQ ID NO 524
<211> LENGTH: 235
<212> TYPE: PRT
<213> ORGANISM: Artificial
<220> FEATURE:
<223> OTHER INFORMATION: PD-1CSR amino acid sequence

<400> SEQUENCE: 524

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Cys Pro Ser Pro Leu
145                 150                 155                 160

Phe Pro Gly Pro Ser Lys Pro Phe Trp Val Leu Val Val Val Gly Gly
                165                 170                 175

Val Leu Ala Cys Tyr Ser Leu Leu Val Thr Val Ala Phe Ile Ile Phe
            180                 185                 190

Trp Val Arg Ser Lys Arg Ser Arg Leu Leu His Ser Asp Tyr Met Asn
        195                 200                 205

Met Thr Pro Arg Arg Pro Gly Pro Thr Arg Lys His Tyr Gln Pro Tyr
    210                 215                 220

Ala Pro Pro Arg Asp Phe Ala Ala Tyr Arg Ser
225                 230                 235

<210> SEQ ID NO 525
<211> LENGTH: 730
<212> TYPE: PRT
<213> ORGANISM: Artificial
<220> FEATURE:
<223> OTHER INFORMATION: T3-P2A-TGF-&B-DNR amino acid sequence

<400> SEQUENCE: 525

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
```

```
              50                  55                  60
Gly Leu Glu Gly Val Ala Ala Ile Thr Val Gly Ser Gly Asn Thr Tyr
 65                  70                  75                  80

Tyr Ala Asp Ser Val Lys Gly Arg Phe Thr Ile Ser Arg Asp Asn Ser
                     85                  90                  95

Lys Asn Thr Val Tyr Leu Gln Met Asn Ser Leu Arg Ala Glu Asp Thr
                100                 105                 110

Ala Met Tyr Tyr Cys Ala Val Gly Tyr Leu Ser Gly Gly Ser Trp Asp
            115                 120                 125

Val Pro Gly Arg Tyr Asn Tyr Trp Gly Gln Gly Thr Leu Val Thr Val
130                 135                 140

Ser Ser Gly Gly Gly Gly Ser Gly Gly Gly Ser Gly Gly Gly Gly Gly
145                 150                 155                 160

Ser Glu Val Gln Leu Val Glu Ser Gly Gly Leu Val Gln Pro Gly Gly
                165                 170                 175

Gly Ser Leu Arg Leu Ser Cys Ala Ala Ser Gly Asn Thr Tyr Ser Ser
                180                 185                 190

Asn Tyr Met Gly Trp Phe Arg Gln Ala Pro Gly Lys Gly Leu Glu Glu
                195                 200                 205

Val Ala Val Ile Tyr Thr Arg Gly Gly His Thr Tyr Tyr Val Asp Ser
        210                 215                 220

Val Arg Gly Arg Phe Thr Ile Ser Gln Asp Asn Ala Lys Asn Ser Leu
225                 230                 235                 240

Tyr Leu Gln Met Asn Ser Leu Arg Ala Glu Asp Thr Ala Val Tyr Tyr
                245                 250                 255

Cys Ala Ala Ser Ser Arg His Arg Leu Gly Leu Asn Asn Pro Arg Asp
                260                 265                 270

Tyr Asp Tyr Trp Gly Gln Gly Thr Leu Val Thr Val Ser Ser Thr Thr
            275                 280                 285

Thr Pro Ala Pro Arg Pro Pro Thr Pro Ala Pro Thr Ile Ala Ser Gln
        290                 295                 300

Pro Leu Ser Leu Arg Pro Glu Ala Cys Arg Pro Ala Ala Gly Gly Ala
305                 310                 315                 320

Val His Thr Arg Gly Leu Asp Phe Ala Cys Asp Ile Tyr Ile Trp Ala
                325                 330                 335

Pro Leu Ala Gly Thr Cys Gly Val Leu Leu Leu Ser Leu Val Ile Thr
                340                 345                 350

Leu Tyr Cys Lys Arg Gly Arg Lys Lys Leu Leu Tyr Ile Phe Lys Gln
            355                 360                 365

Pro Phe Met Arg Pro Val Gln Thr Thr Gln Glu Glu Asp Gly Cys Ser
370                 375                 380

Cys Arg Phe Pro Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
            435                 440                 445

Lys Asn Pro Gln Glu Gly Leu Tyr Asn Glu Leu Gln Lys Asp Lys Met
        450                 455                 460

Ala Glu Ala Tyr Ser Glu Ile Gly Met Lys Gly Glu Arg Arg Arg Gly
465                 470                 475                 480
```

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg Gly Ser Gly
                500                 505                 510

Ala Thr Asn Phe Ser Leu Leu Lys Gln Ala Gly Asp Val Glu Glu Asn
                515                 520                 525

Pro Gly Pro Met Gly Arg Gly Leu Leu Arg Gly Leu Trp Pro Leu His
                530                 535                 540

Ile Val Leu Trp Thr Arg Ile Ala Ser Thr Ile Pro Pro His Val Gln
545                 550                 555                 560

Lys Ser Val Asn Asn Asp Met Ile Val Thr Asp Asn Gly Ala Val
                565                 570                 575

Lys Phe Pro Gln Leu Cys Lys Phe Cys Asp Val Arg Phe Ser Thr Cys
                580                 585                 590

Asp Asn Gln Lys Ser Cys Met Ser Asn Cys Ser Ile Thr Ser Ile Cys
                595                 600                 605

Glu Lys Pro Gln Glu Val Cys Val Ala Val Trp Arg Lys Asn Asp Glu
                610                 615                 620

Asn Ile Thr Leu Glu Thr Val Cys His Asp Pro Lys Leu Pro Tyr His
625                 630                 635                 640

Asp Phe Ile Leu Glu Asp Ala Ala Ser Pro Lys Cys Ile Met Lys Glu
                645                 650                 655

Lys Lys Lys Pro Gly Glu Thr Phe Phe Met Cys Ser Cys Ser Ser Asp
                660                 665                 670

Glu Cys Asn Asp Asn Ile Ile Phe Ser Glu Glu Tyr Asn Thr Ser Asn
                675                 680                 685

Pro Asp Leu Leu Leu Val Ile Phe Gln Val Thr Gly Ile Ser Leu Leu
                690                 695                 700

Pro Pro Leu Gly Val Ala Ile Ser Val Ile Ile Phe Tyr Cys Tyr
705                 710                 715                 720

Arg Val Asn Arg Gln Gln Lys Leu Ser Ser
                725                 730

<210> SEQ ID NO 526
<211> LENGTH: 730
<212> TYPE: PRT
<213> ORGANISM: Artificial
<220> FEATURE:
<223> OTHER INFORMATION: TGF-&B-DNR-P2A-T3 amino acid sequence

<400> SEQUENCE: 526

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Gly Ala Val Lys Phe Pro
                35                  40                  45

Gln Leu Cys Lys Phe Cys Asp Val Arg Phe Ser Thr Cys Asp Asn Gln
                50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
                100                 105                 110

-continued

```
Leu Glu Asp Ala Ala Ser Pro Lys Cys Ile Met Lys Glu Lys Lys
    115                 120                 125
Pro Gly Glu Thr Phe Phe Met Cys Ser Cys Ser Ser Asp Glu Cys Asn
130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Phe Tyr Cys Tyr Arg Val Asn
                180                 185                 190
Arg Gln Gln Lys Leu Ser Ser Gly Ser Gly Ala Thr Asn Phe Ser Leu
                195                 200                 205
Leu Lys Gln Ala Gly Asp Val Glu Glu Asn Pro Gly Pro Met Ala Leu
    210                 215                 220
Pro Val Thr Ala Leu Leu Leu Pro Leu Ala Leu Leu Leu His Ala Ala
225                 230                 235                 240
Arg Pro Gln Val Gln Leu Val Glu Ser Gly Gly Val Val Gln Pro
                245                 250                 255
Gly Gly Ser Leu Arg Leu Ser Cys Ala Ala Ser Phe Ser Gly Tyr Gly
                260                 265                 270
Val Ser Thr Met Ala Trp Phe Arg Gln Ala Pro Gly Lys Gly Leu Glu
        275                 280                 285
Gly Val Ala Ala Ile Thr Val Gly Ser Gly Asn Thr Tyr Tyr Ala Asp
        290                 295                 300
Ser Val Lys Gly Arg Phe Thr Ile Ser Arg Asp Asn Ser Lys Asn Thr
305                 310                 315                 320
Val Tyr Leu Gln Met Asn Ser Leu Arg Ala Glu Asp Thr Ala Met Tyr
                325                 330                 335
Tyr Cys Ala Val Gly Tyr Leu Ser Gly Gly Ser Trp Asp Val Pro Gly
                340                 345                 350
Arg Tyr Asn Tyr Trp Gly Gln Gly Thr Leu Val Thr Val Ser Ser Gly
                355                 360                 365
Gly Gly Gly Ser Gly Gly Gly Ser Gly Gly Gly Ser Glu Val
    370                 375                 380
Gln Leu Val Glu Ser Gly Gly Gly Leu Val Gln Pro Gly Gly Ser Leu
385                 390                 395                 400
Arg Leu Ser Cys Ala Ala Ser Gly Asn Thr Tyr Ser Ser Asn Tyr Met
                405                 410                 415
Gly Trp Phe Arg Gln Ala Pro Gly Lys Gly Leu Glu Val Ala Val
                420                 425                 430
Ile Tyr Thr Arg Gly Gly His Thr Tyr Tyr Val Asp Ser Val Arg Gly
                435                 440                 445
Arg Phe Thr Ile Ser Gln Asp Asn Ala Lys Asn Ser Leu Tyr Leu Gln
    450                 455                 460
Met Asn Ser Leu Arg Ala Glu Asp Thr Ala Val Tyr Tyr Cys Ala Ala
465                 470                 475                 480
Ser Ser Arg His Arg Leu Gly Leu Asn Asn Pro Arg Asp Tyr Asp Tyr
                485                 490                 495
Trp Gly Gln Gly Thr Leu Val Thr Val Ser Ser Thr Thr Pro Ala
                500                 505                 510
Pro Arg Pro Pro Thr Pro Ala Pro Thr Ile Ala Ser Gln Pro Leu Ser
    515                 520                 525
```

Leu Arg Pro Glu Ala Cys Arg Pro Ala Ala Gly Gly Ala Val His Thr
530             535                 540

Arg Gly Leu Asp Phe Ala Cys Asp Ile Tyr Ile Trp Ala Pro Leu Ala
545                 550                 555                 560

Gly Thr Cys Gly Val Leu Leu Leu Ser Leu Val Ile Thr Leu Tyr Cys
                565                 570                 575

Lys Arg Gly Arg Lys Leu Leu Tyr Ile Phe Lys Gln Pro Phe Met
            580                 585                 590

Arg Pro Val Gln Thr Thr Gln Glu Glu Asp Gly Cys Ser Cys Arg Phe
                595                 600                 605

Pro Glu Glu Glu Glu Gly Gly Cys Glu Leu Arg Val Lys Phe Ser Arg
            610                 615                 620

Ser Ala Asp Ala Pro Ala Tyr Lys Gln Gly Gln Asn Gln Leu Tyr Asn
625                 630                 635                 640

Glu Leu Asn Leu Gly Arg Arg Glu Tyr Asp Val Leu Asp Lys Arg
                645                 650                 655

Arg Gly Arg Asp Pro Glu Met Gly Gly Lys Pro Arg Arg Lys Asn Pro
            660                 665                 670

Gln Glu Gly Leu Tyr Asn Glu Leu Gln Lys Asp Lys Met Ala Glu Ala
                675                 680                 685

Tyr Ser Glu Ile Gly Met Lys Gly Glu Arg Arg Arg Gly Lys Gly His
            690                 695                 700

Asp Gly Leu Tyr Gln Gly Leu Ser Thr Ala Thr Lys Asp Thr Tyr Asp
705                 710                 715                 720

Ala Leu His Met Gln Ala Leu Pro Pro Arg
            725                 730

<210> SEQ ID NO 527
<211> LENGTH: 729
<212> TYPE: PRT
<213> ORGANISM: Artificial
<220> FEATURE:
<223> OTHER INFORMATION: T3-T2A-TGF-&B-DNR amino acid sequence

<400> SEQUENCE: 527

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Gly Ser Leu Arg Leu Ser Cys Ala Ala Ser Phe Ser
        35                  40                  45

Gly Tyr Gly Val Ser Thr Met Ala Trp Phe Arg Gln Ala Pro Gly Lys
    50                  55                  60

Gly Leu Glu Gly Val Ala Ala Ile Thr Val Gly Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Met Tyr Tyr Cys Ala Val Gly Tyr Leu Ser Gly Gly Ser Trp Asp
        115                 120                 125

Val Pro Gly Arg Tyr Asn Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

```
Ser Glu Val Gln Leu Val Glu Ser Gly Gly Gly Leu Val Gln Pro Gly
                165                 170                 175
Gly Ser Leu Arg Leu Ser Cys Ala Ala Ser Gly Asn Thr Tyr Ser Ser
            180                 185                 190
Asn Tyr Met Gly Trp Phe Arg Gln Ala Pro Gly Lys Gly Leu Glu Glu
        195                 200                 205
Val Ala Val Ile Tyr Thr Arg Gly His Thr Tyr Tyr Val Asp Ser
210                 215                 220
Val Arg Gly Arg Phe Thr Ile Ser Gln Asp Asn Ala Lys Asn Ser Leu
225                 230                 235                 240
Tyr Leu Gln Met Asn Ser Leu Arg Ala Glu Asp Thr Ala Val Tyr Tyr
                245                 250                 255
Cys Ala Ala Ser Ser Arg His Arg Leu Gly Leu Asn Asn Pro Arg Asp
            260                 265                 270
Tyr Asp Tyr Trp Gly Gln Gly Thr Leu Val Thr Val Ser Ser Thr Thr
        275                 280                 285
Thr Pro Ala Pro Arg Pro Pro Thr Pro Ala Pro Thr Ile Ala Ser Gln
290                 295                 300
Pro Leu Ser Leu Arg Pro Glu Ala Cys Arg Pro Ala Ala Gly Gly Ala
305                 310                 315                 320
Val His Thr Arg Gly Leu Asp Phe Ala Cys Asp Ile Tyr Ile Trp Ala
                325                 330                 335
Pro Leu Ala Gly Thr Cys Gly Val Leu Leu Leu Ser Leu Val Ile Thr
            340                 345                 350
Leu Tyr Cys Lys Arg Gly Arg Lys Lys Leu Leu Tyr Ile Phe Lys Gln
        355                 360                 365
Pro Phe Met Arg Pro Val Gln Thr Thr Gln Glu Glu Asp Gly Cys Ser
370                 375                 380
Cys Arg Phe Pro Glu Glu Glu Glu Gly Gly Cys Glu Leu Arg Val Lys
385                 390                 395                 400
Phe Ser Arg Ser Ala Asp Ala Pro Ala Tyr Lys Gln Gly Gln Asn Gln
                405                 410                 415
Leu Tyr Asn Glu Leu Asn Leu Gly Arg Arg Glu Glu Tyr Asp Val Leu
            420                 425                 430
Asp Lys Arg Arg Gly Arg Asp Pro Glu Met Gly Gly Lys Pro Arg Arg
        435                 440                 445
Lys Asn Pro Gln Glu Gly Leu Tyr Asn Glu Leu Gln Lys Asp Lys Met
450                 455                 460
Ala Glu Ala Tyr Ser Glu Ile Gly Met Lys Gly Glu Arg Arg Arg Gly
465                 470                 475                 480
Lys Gly His Asp Gly Leu Tyr Gln Gly Leu Ser Thr Ala Thr Lys Asp
                485                 490                 495
Thr Tyr Asp Ala Leu His Met Gln Ala Leu Pro Pro Arg Gly Ser Gly
            500                 505                 510
Glu Gly Arg Gly Ser Leu Leu Thr Cys Gly Asp Val Glu Glu Asn Pro
        515                 520                 525
Gly Pro Met Gly Arg Gly Leu Leu Arg Gly Leu Trp Pro Leu His Ile
530                 535                 540
Val Leu Trp Thr Arg Ile Ala Ser Thr Ile Pro Pro His Val Gln Lys
545                 550                 555                 560
Ser Val Asn Asn Asp Met Ile Val Thr Asp Asn Asn Gly Ala Val Lys
                565                 570                 575
Phe Pro Gln Leu Cys Lys Phe Cys Asp Val Arg Phe Ser Thr Cys Asp
```

```
                    580             585             590
Asn Gln Lys Ser Cys Met Ser Asn Cys Ser Ile Thr Ser Ile Cys Glu
                595             600             605
Lys Pro Gln Glu Val Cys Val Ala Val Trp Arg Lys Asn Asp Glu Asn
            610             615             620
Ile Thr Leu Glu Thr Val Cys His Asp Pro Lys Leu Pro Tyr His Asp
625             630             635             640
Phe Ile Leu Glu Asp Ala Ala Ser Pro Lys Cys Ile Met Lys Glu Lys
                645             650             655
Lys Lys Pro Gly Glu Thr Phe Phe Met Cys Ser Cys Ser Ser Asp Glu
            660             665             670
Cys Asn Asp Asn Ile Ile Phe Ser Glu Glu Tyr Asn Thr Ser Asn Pro
            675             680             685
Asp Leu Leu Leu Val Ile Phe Gln Val Thr Gly Ile Ser Leu Leu Pro
            690             695             700
Pro Leu Gly Val Ala Ile Ser Val Ile Ile Ile Phe Tyr Cys Tyr Arg
705             710             715             720
Val Asn Arg Gln Gln Lys Leu Ser Ser
                725

<210> SEQ ID NO 528
<211> LENGTH: 729
<212> TYPE: PRT
<213> ORGANISM: Artificial
<220> FEATURE:
<223> OTHER INFORMATION: TGF-&B-DNR-T2A-T3 amino acid sequence

<400> SEQUENCE: 528

Met Gly Arg Gly Leu Leu Arg Gly Leu Trp Pro Leu His Ile Val Leu
1               5                   10                  15
Trp Thr Arg Ile Ala Ser Thr Ile Pro Pro His Val Gln Lys Ser Val
                20                  25                  30
Asn Asn Asp Met Ile Val Thr Asp Asn Asn Gly Ala Val Lys Phe Pro
            35                  40                  45
Gln Leu Cys Lys Phe Cys Asp Val Arg Phe Ser Thr Cys Asp Asn Gln
        50                  55                  60
Lys Ser Cys Met Ser Asn Cys Ser Ile Thr Ser Ile Cys Glu Lys Pro
65              70                  75                  80
Gln Glu Val Cys Val Ala Val Trp Arg Lys Asn Asp Glu Asn Ile Thr
                85                  90                  95
Leu Glu Thr Val Cys His Asp Pro Lys Leu Pro Tyr His Asp Phe Ile
            100                 105                 110
Leu Glu Asp Ala Ala Ser Pro Lys Cys Ile Met Lys Glu Lys Lys Lys
        115                 120                 125
Pro Gly Glu Thr Phe Phe Met Cys Ser Cys Ser Ser Asp Glu Cys Asn
    130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Ile Phe Tyr Cys Tyr Arg Val Asn
            180                 185                 190
Arg Gln Gln Lys Leu Ser Ser Gly Ser Gly Glu Gly Arg Gly Ser Leu
        195                 200                 205
Leu Thr Cys Gly Asp Val Glu Glu Asn Pro Gly Pro Met Ala Leu Pro
```

```
                210                 215                 220
Val Thr Ala Leu Leu Leu Pro Leu Ala Leu Leu Leu His Ala Ala Arg
225                 230                 235                 240

Pro Gln Val Gln Leu Val Glu Ser Gly Gly Gly Val Val Gln Pro Gly
                245                 250                 255

Gly Ser Leu Arg Leu Ser Cys Ala Ala Ser Phe Ser Gly Tyr Gly Val
                260                 265                 270

Ser Thr Met Ala Trp Phe Arg Gln Ala Pro Gly Lys Gly Leu Glu Gly
                275                 280                 285

Val Ala Ala Ile Thr Val Gly Ser Gly Asn Thr Tyr Tyr Ala Asp Ser
                290                 295                 300

Val Lys Gly Arg Phe Thr Ile Ser Arg Asp Asn Ser Lys Asn Thr Val
305                 310                 315                 320

Tyr Leu Gln Met Asn Ser Leu Arg Ala Glu Asp Thr Ala Met Tyr Tyr
                325                 330                 335

Cys Ala Val Gly Tyr Leu Ser Gly Gly Ser Trp Asp Val Pro Gly Arg
                340                 345                 350

Tyr Asn Tyr Trp Gly Gln Gly Thr Leu Val Thr Val Ser Ser Gly Gly
                355                 360                 365

Gly Gly Ser Gly Gly Gly Ser Gly Gly Gly Ser Glu Val Gln
370                 375                 380

Leu Val Glu Ser Gly Gly Gly Leu Val Gln Pro Gly Gly Ser Leu Arg
385                 390                 395                 400

Leu Ser Cys Ala Ala Ser Gly Asn Thr Tyr Ser Ser Asn Tyr Met Gly
                405                 410                 415

Trp Phe Arg Gln Ala Pro Gly Lys Gly Leu Glu Glu Val Ala Val Ile
                420                 425                 430

Tyr Thr Arg Gly Gly His Thr Tyr Tyr Val Asp Ser Val Arg Gly Arg
                435                 440                 445

Phe Thr Ile Ser Gln Asp Asn Ala Lys Asn Ser Leu Tyr Leu Gln Met
                450                 455                 460

Asn Ser Leu Arg Ala Glu Asp Thr Ala Val Tyr Tyr Cys Ala Ala Ser
465                 470                 475                 480

Ser Arg His Arg Leu Gly Leu Asn Asn Pro Arg Asp Tyr Asp Tyr Trp
                485                 490                 495

Gly Gln Gly Thr Leu Val Thr Val Ser Ser Thr Thr Thr Pro Ala Pro
                500                 505                 510

Arg Pro Pro Thr Pro Ala Pro Thr Ile Ala Ser Gln Pro Leu Ser Leu
                515                 520                 525

Arg Pro Glu Ala Cys Arg Pro Ala Ala Gly Gly Ala Val His Thr Arg
                530                 535                 540

Gly Leu Asp Phe Ala Cys Asp Ile Tyr Ile Trp Ala Pro Leu Ala Gly
545                 550                 555                 560

Thr Cys Gly Val Leu Leu Leu Ser Leu Val Ile Thr Leu Tyr Cys Lys
                565                 570                 575

Arg Gly Arg Lys Lys Leu Leu Tyr Ile Phe Lys Gln Pro Phe Met Arg
                580                 585                 590

Pro Val Gln Thr Thr Gln Glu Glu Asp Gly Cys Ser Cys Arg Phe Pro
                595                 600                 605

Glu Glu Glu Glu Gly Gly Cys Glu Leu Arg Val Lys Phe Ser Arg Ser
                610                 615                 620

Ala Asp Ala Pro Ala Tyr Lys Gln Gly Gln Asn Gln Leu Tyr Asn Glu
625                 630                 635                 640
```

```
Leu Asn Leu Gly Arg Arg Glu Glu Tyr Asp Val Leu Asp Lys Arg Arg
                645                 650                 655

Gly Arg Asp Pro Glu Met Gly Gly Lys Pro Arg Arg Lys Asn Pro Gln
            660                 665                 670

Glu Gly Leu Tyr Asn Glu Leu Gln Lys Asp Lys Met Ala Glu Ala Tyr
            675                 680                 685

Ser Glu Ile Gly Met Lys Gly Glu Arg Arg Gly Lys Gly His Asp
            690                 695                 700

Gly Leu Tyr Gln Gly Leu Ser Thr Ala Thr Lys Asp Thr Tyr Asp Ala
705                 710                 715                 720

Leu His Met Gln Ala Leu Pro Pro Arg
                725
```

```
<210> SEQ ID NO 529
<211> LENGTH: 199
<212> TYPE: PRT
<213> ORGANISM: Artificial
<220> FEATURE:
<223> OTHER INFORMATION: TGF-&B-DNR amino acid sequence

<400> SEQUENCE: 529

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser
                195
```

ANTI-DLL3 CHIMERIC ANTIGEN RECEPTORS AND USES THEREOF

CROSS REFERENCE TO RELATED APPLICATIONS

This application is a National Stage Application under 35 U.S.C. § 371 and claims the benefit of International Application No. PCT/CN2020/102717, filed on Jul. 17, 2020, which claims the benefit of International Application No. PCT/CN2020/090587, filed on May 15, 2020, and International Application No. PCT/CN2019/096360, filed on Jul. 17, 2019. The entire contents of the foregoing applications are incorporated herein by reference.

FIELD OF THE INVENTION

The present invention relates to chimeric antigen receptors (CARs) targeting DLL3 and binding proteins specific for DLL3. The present invention also concerns nucleic acid sequences encoding the CARs or the binding proteins, modified immune cells expressing the CARs, as well as their uses for treating DLL3 associated disorders.

BACKGROUND

Advances in cellular immunotherapy have provided a promising approach for the treatment of various tumors. One such treatment involves genetic engineering of immune cells, particularly T cells, to express chimeric antigen receptors (CARs) on the cell surface. Chimeric antigen receptors are proteins which, in their usual format, graft the specificity of a monoclonal antibody (mAb) to the effector function of a T cell. Once the CARs are expressed in a T cell, the CAR modified T cell (CAR-T or CAR-T cell) acquires some properties, such as antigen specific recognition, antitumor reactivity and proliferation, and thus can act as "living drugs" to eradicate targeted tumor cells. In principal, any antigens (e.g., cell surface molecules) can be targeted by these CAR-T cells. CAR-T cell therapy can override tolerance to self-antigens and provide a treatment which is not reliant on the MHC status of a patient. Using T cells engineered to express chimeric antigen receptors targeting CD19, recent trials have demonstrated remarkable clinical responses in leukaemia and lymphoma patients.

CARs are expressed as transmembrane proteins, including an antigen-specific binding site, a transmembrane region, and a signaling cytoplasmic domain (e.g., a CD3ζ chain). The antigen-specific binding site is usually a monoclonal antibody-derived single chain variable fragment (scFv) consisting of a heavy and light chain joined by a flexible linker. Recently CAR constructs have incorporated additional cytoplasmic domains from co-stimulatory molecules such as CD28 or 4-1 BB to enhance T cell survival in vivo. Other genetic modifications have also been made to CARs, e.g. the addition of cytokine genes or genes to avoid immunosuppressive mechanisms at the tumor site.

DLL3 (delta-like ligand 3) protein has been found to be clinically associated with various proliferative disorders, including tumors exhibiting neuroendocrine features, such as small-cell lung cancer (SCLC). SCLC, originating from neuroendocrine progenitor cells, comprises approximately 15% of all lung cancers, and has one of the lowest 5-year survival rates at 6% (Alvarado-Luna et al., 2016, *Transl Lung Cancer Res* 5:26-38; Siegel et al., 2017, *CA Cancer J Clin* 67:7-30). This is because it is highly aggressive, with about two-thirds of patients having metastatic diseases at diagnosis, and is highly refractory to conventional treatment (e.g., platinum-based chemotherapy).

There is a need for improved therapeutic approaches to treat SCLC and other DLL3-expressing cancers.

SUMMARY

In one aspect, the present disclosure provides a chimeric antigen receptor (CAR) targeting DLL3 (anti-DLL3 CAR). The anti-DLL3 CAR comprises a DLL3 binding domain, wherein the DLL3 binding domain comprises or is derived from a single domain antibody (sdAb) or a single chain variable fragment (scFv).

In some embodiments, the sdAb comprises a polypeptide that comprises a CDR1 comprising the amino acid sequence of any one of SEQ ID NOs: 1-81 or a variant thereof comprising up to about 3 amino acid substitutions in the CDR1, a CDR2 comprising the amino acid sequence of any one of SEQ ID NOs: 82-162 or a variant thereof comprising up to about 3 amino acid substitutions in the CDR2, and a CDR3 comprising the amino acid sequence of any one of SEQ ID NOs: 163-243 or a variant thereof comprising up to about 3 amino acid substitutions in the CDR3.

In some embodiments, the sdAb comprises a polypeptide that comprises a CDR1 comprising the amino acid sequence of any one of SEQ ID NOs: 1-81, a CDR2 comprising the amino acid sequence of any one of SEQ ID NOs: 82-162 and a CDR3 comprising the amino acid sequence of any one of SEQ ID NOs: 163-243, or a variant of the polypeptide comprising up to about 3 amino acid substitutions in the CDR1, CDR2 and CDR3.

In some embodiments, the sdAb comprises a polypeptide comprising any one of the following:

(1) a CDR1 comprising the amino acid sequence of SEQ ID NO: 6, or a variant thereof comprising up to about 3 amino acid substitutions; a CDR2 comprising the amino acid sequence of SEQ ID NO: 87, or a variant thereof comprising up to about 3 amino acid substitutions; and a CDR3 comprising the amino acid sequence of SEQ ID NO: 168, or a variant thereof comprising up to about 3 amino acid substitutions;

(2) a CDR1 comprising the amino acid sequence of SEQ ID NO: 21, or a variant thereof comprising up to about 3 amino acid substitutions; a CDR2 comprising the amino acid sequence of SEQ ID NO: 102, or a variant thereof comprising up to about 3 amino acid substitutions; and a CDR3 comprising the amino acid sequence of SEQ ID NO: 183, or a variant thereof comprising up to about 3 amino acid substitutions;

(3) a CDR1 comprising the amino acid sequence of SEQ ID NO: 24, or a variant thereof comprising up to about 3 amino acid substitutions; a CDR2 comprising the amino acid sequence of SEQ ID NO: 105, or a variant thereof comprising up to about 3 amino acid substitutions; and a CDR3 comprising the amino acid sequence of SEQ ID NO: 186, or a variant thereof comprising up to about 3 amino acid substitutions;

(4) a CDR1 comprising the amino acid sequence of SEQ ID NO: 27, or a variant thereof comprising up to about 3 amino acid substitutions; a CDR2 comprising the amino acid sequence of SEQ ID NO: 108, or a variant thereof comprising up to about 3 amino acid substitutions; and a CDR3 comprising the amino acid sequence of SEQ ID NO: 189, or a variant thereof comprising up to about 3 amino acid substitutions;

(5) a CDR1 comprising the amino acid sequence of SEQ ID NO: 34, or a variant thereof comprising up to about 3 amino acid substitutions; a CDR2 comprising the amino acid sequence of SEQ ID NO: 115, or a variant thereof comprising up to about 3 amino acid substitutions; and a CDR3 comprising the amino acid sequence of SEQ ID NO: 196, or a variant thereof comprising up to about 3 amino acid substitutions;

(6) a CDR1 comprising the amino acid sequence of SEQ ID NO: 39, or a variant thereof comprising up to about 3 amino acid substitutions; a CDR2 comprising the amino acid sequence of SEQ ID NO: 120, or a variant thereof comprising up to about 3 amino acid substitutions; and a CDR3 comprising the amino acid sequence of SEQ ID NO: 201, or a variant thereof comprising up to about 3 amino acid substitutions;

(7) a CDR1 comprising the amino acid sequence of SEQ ID NO: 7, or a variant thereof comprising up to about 3 amino acid substitutions; a CDR2 comprising the amino acid sequence of SEQ ID NO: 88, or a variant thereof comprising up to about 3 amino acid substitutions; and a CDR3 comprising the amino acid sequence of SEQ ID NO: 169, or a variant thereof comprising up to about 3 amino acid substitutions;

(8) a CDR1 comprising the amino acid sequence of SEQ ID NO: 8, or a variant thereof comprising up to about 3 amino acid substitutions; a CDR2 comprising the amino acid sequence of SEQ ID NO: 89, or a variant thereof comprising up to about 3 amino acid substitutions; and a CDR3 comprising the amino acid sequence of SEQ ID NO: 170, or a variant thereof comprising up to about 3 amino acid substitutions; or (9) a CDR1 comprising the amino acid sequence of SEQ ID NO: 9, or a variant thereof comprising up to about 3 amino acid substitutions; a CDR2 comprising the amino acid sequence of SEQ ID NO: 90, or a variant thereof comprising up to about 3 amino acid substitutions; and a CDR3 comprising the amino acid sequence of SEQ ID NO: 171, or a variant thereof comprising up to about 3 amino acid substitutions.

In some embodiments, the sdAb comprises a polypeptide comprising any one of the following:

(1) a CDR1 comprising the amino acid sequence of SEQ ID NO: 6; a CDR2 comprising the amino acid sequence of SEQ ID NO: 87; and a CDR3 comprising the amino acid sequence of SEQ ID NO: 168;

(2) a CDR1 comprising the amino acid sequence of SEQ ID NO: 21; a CDR2 comprising the amino acid sequence of SEQ ID NO: 102; and a CDR3 comprising the amino acid sequence of SEQ ID NO: 183;

(3) a CDR1 comprising the amino acid sequence of SEQ ID NO: 24; a CDR2 comprising the amino acid sequence of SEQ ID NO: 105; and a CDR3 comprising the amino acid sequence of SEQ ID NO: 186;

(4) a CDR1 comprising the amino acid sequence of SEQ ID NO: 27; a CDR2 comprising the amino acid sequence of SEQ ID NO: 108; and a CDR3 comprising the amino acid sequence of SEQ ID NO: 189;

(5) a CDR1 comprising the amino acid sequence of SEQ ID NO: 34; a CDR 2 comprising the amino acid sequence of SEQ ID NO: 115; and a CDR 3 comprising the amino acid sequence of SEQ ID NO: 196;

(6) a CDR1 comprising the amino acid sequence of SEQ ID NO: 39; a CDR2 comprising the amino acid sequence of SEQ ID NO: 120; and a CDR3 comprising the amino acid sequence of SEQ ID NO: 201;

(7) a CDR1 comprising the amino acid sequence of SEQ ID NO: 7; a CDR2 comprising the amino acid sequence of SEQ ID NO: 88; and a CDR 3 comprising the amino acid sequence of SEQ ID NO: 169;

(8) a CDR1 comprising the amino acid sequence of SEQ ID NO: 8; a CDR2 comprising the amino acid sequence of SEQ ID NO: 89; and a CDR 3 comprising the amino acid sequence of SEQ ID NO: 170; or (9) a CDR1 comprising the amino acid sequence of SEQ ID NO: 9; a CDR 2 comprising the amino acid sequence of SEQ ID NO: 90; and a CDR 3 comprising the amino acid sequence of SEQ ID NO: 171.

In some embodiments, the sdAb is a camel sdAb raised against human or rhesus DLL3.

In some embodiments, the sdAb comprises an amino acid sequence having at least about 95% sequence identity to the amino acid sequence of any one of SEQ ID NOs: 274-354.

In some embodiments, the sdAb is humanized through CDR grafting.

In some embodiments, the humanized sdAb comprises an amino acid sequence having at least about 95% sequence identity to the amino acid sequence of any one of SEQ ID NOs: 355-367.

In some embodiments, the scFv comprises a heavy chain variable region (VH) and a light chain variable region (VL), wherein the VH domain of the scFv comprises a CDR1 set forth in SEQ ID NO: 498 or 504 or a variant thereof comprising up to about 3 amino acid substitutions in the CDR1, a CDR2 set forth in SEQ ID NO: 499 or 505 or a variant thereof comprising up to about 3 amino acid substitutions in the CDR2, and a CDR3 set forth in SEQ ID NO: 500 or 506 or a variant thereof comprising up to about 3 amino acid substitutions in the CDR3, and the VL domain of the scFv comprises a CDR1 set forth in SEQ ID NO: 495 or 501 or a variant thereof comprising up to about 3 amino acid substitutions in the CDR1, a CDR2 set forth in SEQ ID NO: 496 or 502 or a variant thereof comprising up to about 3 amino acid substitutions in the CDR2, and a CDR3 set forth in SEQ ID NO: 497 or 503 or a variant thereof comprising up to about 3 amino acid substitutions in the CDR3.

In some embodiments, the VH domain of the scFv comprises a CDR1 set forth in SEQ ID NO: 498, a CDR2 set forth in SEQ ID NO: 499, and a CDR3 set forth in SEQ ID NO: 500, and the VL domain of the scFv comprises a CDR1 set forth in SEQ ID NO: 495, a CDR2 set forth in SEQ ID NO: 496, and a CDR3 set forth in SEQ ID NO: 497; or the VH domain of the scFv comprises a CDR1 set forth in SEQ ID NO: 504, a CDR2 set forth in SEQ ID NO: 505, and a CDR3 set forth in SEQ ID NO: 506, and the VL domain of the scFv comprises a CDR1 set forth in SEQ ID NO: 501, a CDR2 set forth in SEQ ID NO: 502, and a CDR3 set forth in SEQ ID NO: 503.

In some embodiments, the VH domain of the scFv comprises an amino acid sequence having at least about 95% sequence identity to the amino acid sequence set forth in SEQ ID NO: 508, and the VL domain of the scFv comprises an amino acid sequence having at least about 95% sequence identity to the amino acid sequence set forth in SEQ ID NO: 507; or the VH domain of the scFv comprises an amino acid sequence having at least about 95% sequence identity to the amino acid sequence set forth in SEQ ID NO: 510, and the VL domain of the scFv comprises an amino acid sequence having at least about 95% sequence identity to the amino acid sequence set forth in SEQ ID NO: 509.

In some embodiments, the scFv is obtained from a synthetic human Fab phage library.

In some embodiments, the DLL3 is human or rhesus DLL3.

In some embodiments, the anti-DLL3 CAR comprises, from N-terminus to C-terminus, a signal peptide, the DLL3 binding domain, a hinge domain, a transmembrane domain, and an intracellular signaling domain.

In some embodiments, the intracellular signaling domain is derived from CD3ζ, FcRγ, FcRβ, CD3γ, CD3δ, CD3ε, CD5, CD22, CD79a, CD79b, or CD66d.

In some embodiments, the intracellular signaling domain further comprises an intracellular co-stimulatory sequence.

In some embodiments, the intracellular co-stimulatory sequence is derived from a co-stimulatory molecule selected from the group consisting of CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof.

In some embodiments, the CAR comprises an amino acid sequence having at least about 95% sequence identity to an amino acid sequence selected from the group consisting of SEQ ID NOs: 476-484, SEQ ID NOs: 485-494 or SEQ ID NOs: 515-516.

In some embodiments, the DLL3 binding domain comprises two sdAbs linked to each other.

In some embodiments, each of the sdAbs independently comprises an amino acid sequence having at least about 95% sequence identity to SEQ ID NO:356 or SEQ ID NO:366.

In some embodiments, the CAR comprises an amino acid sequence having at least about 95% sequence identity to an amino acid sequence selected from the group consisting of SEQ ID NOs: 518-520.

In some embodiments, the CAR comprises an amino acid sequence of SEQ ID NO: 520.

In another aspect, the present disclosure provides a DLL3 binding protein comprising a single domain antibody (sdAb) moiety that specifically binds to DLL3, wherein the sdAb moiety comprises a polypeptide that comprises a CDR1 comprising the amino acid sequence of any one of SEQ ID NOs: 1-81 or a variant thereof comprising up to about 3 amino acid substitutions in the CDR1, a CDR2 comprising the amino acid sequence of any one of SEQ ID NOs: 82-162 or a variant thereof comprising up to about 3 amino acid substitutions in the CDR2, and a CDR3 comprising the amino acid sequence of any one of SEQ ID NOs: 163-243 or a variant thereof comprising up to about 3 amino acid substitutions in the CDR3.

In some embodiments, the sdAb moiety comprises a polypeptide that comprises a CDR1 comprising the amino acid sequence of any one of SEQ ID NOs: 1-81, a CDR2 comprising the amino acid sequence of any one of SEQ ID NOs: 82-162 and a CDR3 comprising the amino acid sequence of any one of SEQ ID NOs: 163-243, or a variant of the polypeptide comprising up to about 3 amino acid substitutions in the CDR1, CDR2 and CDR3.

In some embodiments, the sdAb moiety comprises a polypeptide comprising any one of the following:
(1) a CDR1 comprising the amino acid sequence of SEQ ID NO: 6, or a variant thereof comprising up to about 3 amino acid substitutions; a CDR 2 comprising the amino acid sequence of SEQ ID NO: 87, or a variant thereof comprising up to about 3 amino acid substitutions; and a CDR 3 comprising the amino acid sequence of SEQ ID NO: 168, or a variant thereof comprising up to about 3 amino acid substitutions;
(2) a CDR1 comprising the amino acid sequence of SEQ ID NO: 21, or a variant thereof comprising up to about 3 amino acid substitutions; a CDR2 comprising the amino acid sequence of SEQ ID NO: 102, or a variant thereof comprising up to about 3 amino acid substitutions; and a CDR3 comprising the amino acid sequence of SEQ ID NO: 183, or a variant thereof comprising up to about 3 amino acid substitutions;
(3) a CDR1 comprising the amino acid sequence of SEQ ID NO: 24, or a variant thereof comprising up to about 3 amino acid substitutions; a CDR2 comprising the amino acid sequence of SEQ ID NO: 105, or a variant thereof comprising up to about 3 amino acid substitutions; and a CDR3 comprising the amino acid sequence of SEQ ID NO: 186, or a variant thereof comprising up to about 3 amino acid substitutions;
(4) a CDR1 comprising the amino acid sequence of SEQ ID NO: 27, or a variant thereof comprising up to about 3 amino acid substitutions; a CDR2 comprising the amino acid sequence of SEQ ID NO: 108, or a variant thereof comprising up to about 3 amino acid substitutions; and a CDR3 comprising the amino acid sequence of SEQ ID NO: 189, or a variant thereof comprising up to about 3 amino acid substitutions;
(5) a CDR1 comprising the amino acid sequence of SEQ ID NO: 34, or a variant thereof comprising up to about 3 amino acid substitutions; a CDR2 comprising the amino acid sequence of SEQ ID NO: 115, or a variant thereof comprising up to about 3 amino acid substitutions; and a CDR3 comprising the amino acid sequence of SEQ ID NO: 196, or a variant thereof comprising up to about 3 amino acid substitutions;
(6) a CDR1 comprising the amino acid sequence of SEQ ID NO: 39, or a variant thereof comprising up to about 3 amino acid substitutions; a CDR2 comprising the amino acid sequence of SEQ ID NO: 120, or a variant thereof comprising up to about 3 amino acid substitutions; and a CDR 3 comprising the amino acid sequence of SEQ ID NO: 201, or a variant thereof comprising up to about 3 amino acid substitutions;
(7) a CDR1 comprising the amino acid sequence of SEQ ID NO: 7, or a variant thereof comprising up to about 3 amino acid substitutions; a CDR2 comprising the amino acid sequence of SEQ ID NO: 88, or a variant thereof comprising up to about 3 amino acid substitutions; and a CDR 3 comprising the amino acid sequence of SEQ ID NO: 169, or a variant thereof comprising up to about 3 amino acid substitutions;
(8) a CDR1 comprising the amino acid sequence of SEQ ID NO: 8, or a variant thereof comprising up to about 3 amino acid substitutions; a CDR 2 comprising the amino acid sequence of SEQ ID NO: 89, or a variant thereof comprising up to about 3 amino acid substitutions; and a CDR3 comprising the amino acid sequence of SEQ ID NO: 170, or a variant thereof comprising up to about 3 amino acid substitutions; or
(9) a CDR1 comprising the amino acid sequence of SEQ ID NO: 9, or a variant thereof comprising up to about 3 amino acid substitutions; a CDR2 comprising the amino acid sequence of SEQ ID NO: 90, or a variant thereof comprising up to about 3 amino acid substitutions; and a CDR 3 comprising the amino acid sequence of SEQ ID NO: 171, or a variant thereof comprising up to about 3 amino acid substitutions.

In some embodiments, the sdAb moiety comprises a polypeptide comprising any one of the following:
(1) a CDR1 comprising the amino acid sequence of SEQ ID NO: 6; a CDR2 comprising the amino acid sequence of SEQ ID NO: 87; and a CDR 3 comprising the amino acid sequence of SEQ ID NO: 168;

(2) a CDR1 comprising the amino acid sequence of SEQ ID NO: 21; a CDR 2 comprising the amino acid sequence of SEQ ID NO: 102; and a CDR 3 comprising the amino acid sequence of SEQ ID NO: 183;

(3) a CDR1 comprising the amino acid sequence of SEQ ID NO: 24; a CDR2 comprising the amino acid sequence of SEQ ID NO: 105; and a CDR 3 comprising the amino acid sequence of SEQ ID NO: 186;

(4) a CDR1 comprising the amino acid sequence of SEQ ID NO: 27; a CDR 2 comprising the amino acid sequence of SEQ ID NO: 108; and a CDR3 comprising the amino acid sequence of SEQ ID NO: 189;

(5) a CDR1 comprising the amino acid sequence of SEQ ID NO: 34; a CDR2 comprising the amino acid sequence of SEQ ID NO: 115; and a CDR3 comprising the amino acid sequence of SEQ ID NO: 196;

(6) a CDR1 comprising the amino acid sequence of SEQ ID NO: 39; a CDR2 comprising the amino acid sequence of SEQ ID NO: 120; and a CDR3 comprising the amino acid sequence of SEQ ID NO: 201;

(7) a CDR1 comprising the amino acid sequence of SEQ ID NO: 7; a CDR2 comprising the amino acid sequence of SEQ ID NO: 88; and a CDR3 comprising the amino acid sequence of SEQ ID NO: 169;

(8) a CDR1 comprising the amino acid sequence of SEQ ID NO: 8; a CDR2 comprising the amino acid sequence of SEQ ID NO: 89; and a CDR3 comprising the amino acid sequence of SEQ ID NO: 170; or (9) a CDR1 comprising the amino acid sequence of SEQ ID NO: 9; a CDR2 comprising the amino acid sequence of SEQ ID NO: 90; and a CDR3 comprising the amino acid sequence of SEQ ID NO: 171.

In some embodiments, the sdAb moiety is a camel sdAb raised against human or rhesus DLL3.

In some embodiments, the sdAb moiety comprises an amino acid sequence having at least about 95% sequence identity to the amino acid sequence of any one of SEQ ID NOs: 274-354.

In some embodiments, the sdAb moiety is humanized through CDR grafting.

In some embodiments, the humanized sdAb comprises an amino acid sequence having at least about 95% sequence identity to the amino acid sequence of any one of SEQ ID NOs: 355-367.

In some embodiments, the DLL3 is human or rhesus DLL3.

In another aspect, the present disclosure provides a DLL3 binding protein comprising a single chain variable fragment (scFv) moiety that specifically binds to DLL3, wherein the scFv moiety comprises a heavy chain variable region (VH) and a light chain variable region (VL), wherein the VH domain of the scFv moiety comprises a CDR1 set forth in SEQ ID NO: 498 or 504 or a variant thereof comprising up to about 3 amino acid substitutions in the CDR1, a CDR2 set forth in SEQ ID NO: 499 or 505 or a variant thereof comprising up to about 3 amino acid substitutions in the CDR2, and a CDR3 set forth in SEQ ID NO: 500 or 506 or a variant thereof comprising up to about 3 amino acid substitutions in the CDR3, and the VL domain of the scFv moiety comprises a CDR1 set forth in SEQ ID NO: 495 or 501 or a variant thereof comprising up to about 3 amino acid substitutions in the CDR1, a CDR2 set forth in SEQ ID NO: 496 or 502 or a variant thereof comprising up to about 3 amino acid substitutions in the CDR2, and a CDR3 set forth in SEQ ID NO: 497 or 503 or a variant thereof comprising up to about 3 amino acid substitutions in the CDR3.

In some embodiments, the scFv moiety comprises a heavy chain variable region (VH) and a light chain variable region (VL), wherein the VH domain of the scFv moiety comprises a CDR1 set forth in SEQ ID NO: 498, a CDR2 set forth in SEQ ID NO: 499, and a CDR3 set forth in SEQ ID NO: 500, and the VL domain of the scFv moiety comprises a CDR1 set forth in SEQ ID NO: 495, a CDR2 set forth in SEQ ID NO: 496, and a CDR3 set forth in SEQ ID NO: 497; or the VH domain of the scFv moiety comprises a CDR1 set forth in SEQ ID NO: 504, a CDR2 set forth in SEQ ID NO: 505, and a CDR3 set forth in SEQ ID NO: 506, and the VL domain of the scFv moiety comprises a CDR1 set forth in SEQ ID NO: 501, a CDR2 set forth in SEQ ID NO: 502, and a CDR3 set forth in SEQ ID NO: 503.

In some embodiments, the VH domain of the scFv moiety comprises an amino acid sequence having at least about 95% sequence identity to the amino acid sequence set forth in SEQ ID NO: 508, and the VL domain of the scFv moiety comprises an amino acid sequence having at least about 95% sequence identity to the amino acid sequence set forth in SEQ ID NO: 507; or the VH domain of the scFv moiety comprises an amino acid sequence having at least about 95% sequence identity to the amino acid sequence set forth in SEQ ID NO: 510, and the VL domain of the scFv moiety comprises an amino acid sequence having at least about 95% sequence identity to the amino acid sequence set forth in SEQ ID NO: 509.

In some embodiments, the scFv moiety is obtained from a synthetic human Fab phage library.

In some embodiments, the DLL3 is human or rhesus DLL3.

In another aspect, the present disclosure provides an isolated nucleic acid molecule encoding an anti-DLL3 CAR or a DLL3 binding protein as described above.

In some embodiments, the isolated nucleic acid molecule comprises a polynucleotide sequence selected from the group consisting of SEQ ID NOs: 368-448 which encodes a camel single domain antibody (sdAb).

In some embodiments, the isolated nucleic acid molecule comprises a polynucleotide sequence selected from the group consisting of SEQ ID NOs: 449-461 which encodes a humanized camel sdAb.

In some embodiments, the isolated nucleic acid molecule comprises a polynucleotide sequence selected from the group consisting of SEQ ID NOs: 511-514 which encodes a VL or VH domain of a human scFv.

In some embodiments, the nucleic acid molecule further comprises a polynucleotide sequence encoding a Chimeric Switch Receptor (CSR) or a Dominant Negative Receptor (DNR).

In some embodiments, the nucleic acid molecule further comprises a polynucleotide sequence encoding a PD-1 Dominant Negative Receptor (PD-1 DNR), a PD-1 Chimeric Switch Receptor (PD-1 CSR), or a TGF-β Dominant Negative Receptor (TGF-β DNR).

In some embodiments, the PD-1 DNR comprises an amino acid sequence having at least about 95% sequence identity to SEQ ID NO: 523.

In some embodiments, the PD-1 CSR comprises an amino acid sequence having at least about 95% sequence identity to SEQ ID NO: 524.

In some embodiments, the TGF-β DNR comprises an amino acid sequence having at least about 95% sequence identity to SEQ ID NO: 529.

In some embodiments, the polynucleotide sequence encoding the PD-1 DNR, the PD-1 CSR or the TGF-β DNR is linked to the polynucleotide sequence encoding the CAR through a polynucleotide sequence encoding a 2A self-cleaving peptide.

In some embodiments, the 2A self-cleaving peptide is a T2A peptide or a P2A peptide.

In some embodiments, the nucleic acid molecule comprises, in the 5' to 3' direction, a polynucleotide sequence encoding the CAR, a polynucleotide sequence encoding the 2A self-cleaving peptide, and a polynucleotide sequence encoding the PD-1 DNR, the PD-1 CSR or the TGF-β DNR.

In some embodiments, the nucleic acid molecule encoding a peptide having at least about 95% sequence identity to SEQ ID NO: 521 or 522, or the nucleic acid molecule encoding a peptide having at least about 95% sequence identity to an amino acid sequence selected from the group consisting of SEQ ID NOs: 525-528.

In another aspect, the present disclosure provides an expression vector comprising an isolated nucleic acid molecule as described above.

In another aspect, the present disclosure provides an engineered immune cell comprising an isolated nucleic acid molecule as described above.

In some embodiments, the engineered immune cell is selected from the group consisting of a cytotoxic T cell, a helper T cell, a natural killer T cell, a γδ T cell, a NKT cell and a Nature Killer cell.

In another aspect, the present disclosure provides an engineered immune cell expressing an anti-DLL3 CAR as described above.

In some embodiments, the engineered immune cell also expresses a CSR or a DNR.

In some embodiments, the CSR is a PD-1 CSR, the DNR is a PD-1 DNR or a TGF-β DNR.

In some embodiments, the PD-1 DNR comprises an amino acid sequence having at least about 95% sequence identity to SEQ ID NO: 523.

In some embodiments, the PD-1 CSR comprises an amino acid sequence having at least about 95% sequence identity to SEQ ID NO: 524.

In some embodiments, the TGF-β DNR comprises an amino acid sequence having at least about 95% sequence identity to SEQ ID NO: 529.

In some embodiments, the CAR and the CSR, or the CAR and the DNR, are co-expressed through a 2A self-cleaving peptide.

In some embodiments, the 2A self-cleaving peptide is a T2A peptide or a P2A peptide.

In some embodiments, the engineered immune cell expresses the CAR and the PD-1 DNR, and is stimulated by a cell expressing DLL3 and PD-L1.

In some embodiments, the engineered immune cell expresses the CAR and the PD-1 CSR, and is stimulated by a cell expressing DLL3 and PD-L1.

In some embodiments, the engineered immune cell expresses the CAR and the TGF-β DNR, and is stimulated by a cell expressing DLL3 in the present of TGF-β.

In some embodiments, the engineered immune cell is selected from the group consisting of a cytotoxic T cell, a helper T cell, a natural killer T cell, a γδ T cell, a NKT cell and a Nature Killer cell.

In another aspect, the present disclosure provides a pharmaceutical composition comprising an anti-DLL3 CAR, an isolated DLL3 binding protein, an expression vector, or an engineered immune cell as described above, and a physiologically acceptable excipient.

In another aspect, the present disclosure provides a method for treating a DLL3 associated disorder in a subject, comprising administrating to the subject a therapeutically effective amount of engineered immune cells as described above or a therapeutically effective amount of a pharmaceutical composition as described above.

In another aspect, the present disclosure provides the use of an anti-DLL3 CAR, an isolated DLL3 binding protein, an expression vector, or an engineered immune cell as described above for the preparation of a medicament for treating a DLL3 associated disorder.

In another aspect, the present disclosure provides a medicament for use in treating a DLL3 associated disorder comprising an anti-DLL3 CAR, a DLL3 binding protein, an expression vector, or an engineered immune cell as described above.

In some embodiments, the DLL3 associated disorder is a cancer selected from the group consisting of lung cancer, melanoma, breast cancer, prostate cancer, colon cancer, renal cell carcinoma, ovarian cancer, neuroblastoma, rhabdomyosarcoma, leukemia and lymphoma.

In some embodiments, the cancer expresses DLL3 and PD-L1.

In some embodiments, the cancer has a higher expression level of TGF-β compared to corresponding normal tissue.

In some embodiments, the DLL3 associated disorder is small cell lung cancer.

BRIEF DESCRIPTION OF THE DRAWINGS

FIG. 4 shows fold expansions of T cells expressing exemplary monospecific CARs comprising various camel anti-DLL3 sdAbs, after long-term stimulation with small cell lung cancer cell line SHP-77.

FIG. 5 shows the results of in vivo anti-tumor efficacy of the CAR-T cells expressing CARs with camel anti-DLL3 sdAbs in a SHP-77 tumor model. In this model, each mouse was infused with a dose of 1.0 million CAR-T cells.

DETAILED DESCRIPTION

Figure 1:
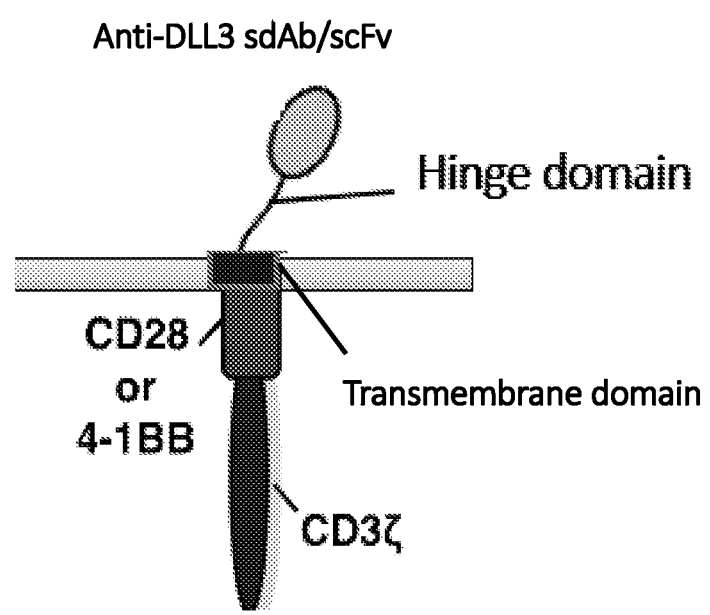
FIG. 1 shows schematic representation of a $V_HH$ based CAR construct. Sequences which can be used in the construct are listed in SEQ ID NOs: 462-472, 474 and 475.

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

The articles "a" and "an" are used herein to refer to one or to more than one (i.e., to at least one) of the grammatical object of the article. By way of example, "an element" means one element or more than one element.

The term "binding protein" as used herein refers to a molecule or a portion of a molecule which binds a target molecule (e.g., DLL3). In some embodiments, the binding protein comprises an antibody. In some embodiments, the binding protein comprises an antigen-binding fragment of an antibody. In some embodiments, the binding protein can further comprise a small molecular weight component, such as a small-molecule drug or toxin. The binding protein can also be an antibody or an antigen-binding fragment thereof. In some embodiments, the binding protein comprises the ligand-binding domain of a receptor. In some embodiments, the binding protein comprises the extracellular domain of a transmembrane receptor. The binding protein can also be the ligand-binding domain of a receptor, or the extracellular domain of a transmembrane receptor. In some embodiments, the binding protein comprises a single domain antibody (sdAb) or a single chain variable fragment (scFv). In some embodiments, the binding protein can be an sdAb or a scFv. A DLL3 binding protein can be a DLL3 binding domain. In some embodiment, the DLL3 binding protein comprises an antibody or an antigen-binding fragment of an antibody which binds DLL3. In some embodiments, the DLL3 binding protein can be an antibody or an antigen-binding fragment of an antibody. In some embodiments, the DLL3 binding protein comprises a single domain antibody (sdAb) or a single chain variable fragment (scFv) which binds DLL3. In some embodiments, the DLL3 binding protein can be an sdAb or a scFv.

The term "antibody" generally refers to any immunoglobulin (Ig) molecule comprised of four polypeptide chains, two heavy (H) chains and two light (L) chains, or any functional fragment thereof, which retains the essential epitope binding features of the Ig molecule. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, lgG4, IgA1 and lgA2) or subclass. In a broad meaning, the term "antibody" further refers to scFv or sdAb which is not derived from an immunoglobulin molecule with four polypeptide chains.

An antibody fragment is a portion of an antibody, for example as F(ab')$_2$, Fab, Fv, scFv, sdAb, and the like. Functional fragments of a full length antibody retain the target specificity of a full length antibody. Recombinant functional antibody fragments, such as scFv (single chain variable chain fragments), have therefore been used to develop therapeutics as an alternative to therapeutics based on mAbs. scFv fragments (~25 kDa) consist of the two variable domains, VH and VL. Naturally, VH and VL domains are non-covalently associated via hydrophobic interaction and tend to dissociate. However, stable fragments can be engineered by linking the domains with a hydrophilic flexible linker to create a scFv.

As used herein, the term "single domain antibody" (sdAb) has its general meaning in the art and refers to the single heavy chain variable domain of antibodies of the type that can be found in Camelid mammals and are naturally devoid of light chains. Such single-domain antibody is also called V$_H$H or "Nanobody". The amino acid sequence and structure of a single-domain antibody can be considered to be comprised of four framework regions (FR1, FR2, FR3, and FR4), and three complementary determining regions (CDR1, CDR2, and CDR3). Accordingly, the single-domain antibody can be defined as an amino acid sequence with the general structure: FR1-CDR1-FR2-CDR2-FR3-CDR3-FR4, which is similar to variable domain VH or VL. The use of sdAbs as single antigen-binding proteins or as an antigen-binding domain in larger proteins or polypeptides offer a number of significant advantages over the use of conventional antibodies or antibody fragments (e.g., scFv). The advantages of sdAbs include: only a single domain is required to bind an antigen with high affinity and with high selectivity; sdAbs are highly stable to denaturing agents or conditions including heat, pH, and proteases; and sdAbs can access targets and epitopes not accessible to conventional antibodies. Typically, sdAbs are produced in camelids such as llamas, but can also be synthetically generated using techniques that are well known in the art.

As used herein, the term "humanized sdAb" means an sdAb that has had one or more amino acid residues in the amino acid sequence of the naturally occurring $V_HH$ sequence replaced by one or more of the amino acid residues that occur at the corresponding position in a VH domain from a conventional 4-chain antibody from a human. This can be performed by methods that are well known in the art. For example, the FRs of the sdAbs can be replaced by human variable FRs. Humanized sdAbs thus have less antigenicity when administrated into human bodies.

As used herein, the term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

"DLL3", also known as "delta-like ligand 3", is a transmembrane protein involved in Notch signaling pathway. The Notch signaling pathway, first identified in *C. elegans* and *Drosophila* and subsequently shown to be evolutionarily conserved from invertebrates to vertebrates, participates in a series of fundamental biological processes including normal embryonic development, adult tissue homeostasis, and stein cell maintenance. In *Drosophila*, Notch signaling is mediated primarily by one Notch receptor gene and two ligand genes, known as Serrate and Delta (Wharton et al., 1985; Rebay et al., 1991). In humans, there are four known Notch receptors and five DSL (Delta-Serrate LAG2) ligands—two homologs of Serrate, known as Jagged1 and Jagged 2, and three homologs of Delta, termed delta-like ligands or DLL1, DLL3 and DLL4. In humans, the DLL3 gene is located on chromosome 19q13, and consists of 8 exons spanning 9.5 kb. Alternate splicing within the last exon gives rise to two protein isoforms. Both share overall 100% identity across their extracellular domains and their transmembrane domains, differing only in that the longer isoform contains an extended cytoplasmic tail.

As used herein, the term "specifically bind" or "specific binding" or any synonym thereof refers to the ability of a polypeptide, such as a single domain antibody (sdAb), to specifically recognize and detectably bind, as assayed by standard in vitro assays, to a DLL3 molecule. For example, binding, as used herein, is measured by the capacity of an anti-DLL3 polypeptide of the invention to recognize a DLL3 molecule on the surface of a cell using well described antigen-antibody binding assays, flow cytometry, and other assays known to those of skill in the art.

As used herein, the term "expression vector" is a nucleic acid construct or sequence, generated recombinantly or synthetically, with specific nucleic acid elements that permit transcription and/or expression of another nucleic acid in a host cell. An expression vector can be part of a plasmid, virus, or nucleic acid fragment. In one example, an expression vector is a DNA vector, such as a plasmid, that comprises at least one promoter sequence and at least one terminator sequence (e.g., a polyadenylation sequence), and optionally an origin of replication (ori) sequence, and optionally a selection or selectable marker sequence. Optionally, the expression vector may further comprise at least one nucleotide coding sequence of interest that codes for at least one polypeptide, wherein the at least one promoter sequence is operably linked with the at least one coding sequence. The term "expression" includes any step involved in the production of the polypeptide including, but not limited to, transcription, post-transcriptional modification, translation, post-translational modification, and/or secretion.

The term "isolated" refers to a material that is substantially or essentially free from components that normally accompany it in its native state. The material can be a cell or a macromolecule such as a protein or nucleic acid. For example, an "isolated nucleic acid," as used herein, refers to a polynucleotide, which has been purified from the sequences which flank it in a naturally-occurring state, e.g., a DNA fragment which has been removed from the sequences that are normally adjacent to the fragment. Alternatively, an "isolated antibody" or an "isolated polypeptide" and the like, as used herein, refer to in vitro isolation and/or purification of an antibody or polypeptide molecule from its natural cellular environment, and from association with other components of the cell.

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an hypervariable region (HVR) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr-. Op. Struct. Biol. 2:593-596 (1992). See also, for example, Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982, 321 and 7,087,409.

"sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The dissociation constant ($K_D$ or $K_d$) is used as an indicator showing affinity of antibodies to antigens. For example, easy analysis is possible by the Scatchard method using antibodies marked with a variety of marker agents, as well as by using BiacoreX (made by Amersham Biosciences), which is an over-the-counter, measuring kit, or similar kit, according to the user's manual and experiment operation method attached with the kit. The $K_D$ value that can be derived using these methods is expressed in units of M (Mols).

"Chimeric Switch Receptor (CSR)" as used herein refers to a receptor which is created to reverse the outcomes of its original signaling pathway in order to confer an immune cell (e.g., a CAR T cell) with a desired activity, such as, the ability to overcome the immunosuppressive tumor microenvironment and to allow it to have greater in vivo persistence. In some embodiments, a CSR can exploit the inhibitory molecules expressed by a cancer cell to further stimulate the CAR T cell. In a non-limiting example, a CAR T cell can be engineered to express a CSR composed of the extracellular ligand binding domain of the human inhibitory receptor programmed cell death protein 1 (PD-1) fused to the transmembrane and cytoplasmic co-stimulatory signaling domains of CD28. When the CAR T cell is administrated into a subject with a cancer expressing DLL3 and programmed cell death ligand 1 (PD-L1), the expressed CAR can bind to the DLL3 and the expressed switch receptor can bind to PD-L1. The nature of the PD-1/CD28 chimeric switch receptor fusion protein prevents the normal PD1/PD-L1-mediated T-cell suppression and, instead, promotes signaling through the CD28 domain, which results in the stimulation of the CAR T cell. Thus, exchanging the transmembrane and intracellular domain of PD-1 with that of CD28 converts PD-L1 into a co-stimulation ligand of the CAR T cell. This will induce enhanced toxicity against PD-L1-expressing cancer cells. In other embodiments, a CSR can also be used to inhibit the effects of a CAR T cell on unintended target cells.

"Dominant Negative Receptor (DNR)" as used herein refers to a receptor which is able to bind its ligand but will not induce a signaling cascade inside the cell. A DNR usually has an intact ligand binding region but is missing an intracellular enzymatic region. It may be a mutated form of a full length receptor or a truncated form of the receptor. Following CAR T cell immunotherapy, some cancers, especially solid caners may upregulate inhibitory ligands that bind to inhibitory receptors on CAR T cells. This adaptive resistance compromises the efficacy of chimeric CAR T cell therapies. Some cancers, particularly solid cancer, are known to secrete transforming growth factor β (TGF-β), creating an immunosuppressive milieu. TGF-β is known to induce or promote metastasis and to potently suppress the immune system. Therefore, in some embodiments, we use a truncated version of the TGF-β receptor TGFBRII as a TGF-β DNR to improve the antitumor performance of the CAR T cells disclosed herein. In some embodiments, the CAR and the TGF-β DNR are co-expressed on a T cell's surface by using a 2A self-cleaving peptide. In some embodiments, the CAR and the TGF-β DNR are separately expressed on a T cell's surface by using two expression vectors. We find TGF-β DNR, when introduced into the anti-DLL3 CAR T cells disclosed herein, is able to enhance the cytotoxicity of the CAR T cells against some DLL3 positive cancer cells, such as SCLC cells. Similarly, in some embodiments, we use a truncated version of the PD-1 receptor as a PD-1 DNR to improve the antitumor performance of the CAR T cells disclosed herein.

As used herein, "treatment" or "treating," includes any beneficial or desirable effect on the symptoms or pathology of a disease or pathological condition, and may include even minimal reductions in one or more measurable markers of the disease or condition being treated, e.g., cancer, autoimmune disease, immune disorder, etc. Treatment can optionally involve delaying of the progression of the disease or condition. "Treatment" does not necessarily indicate complete eradication or cure of the disease or condition, or associated symptoms thereof.

Some aspects of the present invention relate to a DLL3 binding protein, which has binding specificity for human or rhesus DLL3 protein.

In some embodiments, the DLL3 binding protein comprising a single domain antibody ("sdAb") moiety that specifically binds to DLL3, wherein the sdAb moiety comprises a polypeptide that comprises a CDR1 comprising the amino acid sequence of any one of SEQ ID NOs: 1-81 or a variant thereof comprising up to about 3 amino acid substitutions in the CDR1, a CDR2 comprising the amino acid sequence of any one of SEQ ID NOs: 82-162 or a variant thereof comprising up to about 3 amino acid substitutions in the CDR2, and a CDR3 comprising the amino acid sequence of any one of SEQ ID NOs: 163-243 or a variant thereof comprising up to about 3 amino acid substitutions in the CDR3.

In some embodiments, the sdAb comprises a polypeptide that comprises a CDR1 comprising the amino acid sequence of any one of SEQ ID NOs: 1-81, a CDR2 comprising the amino acid sequence of any one of SEQ ID NOs: 82-162; and a CDR3 comprising the amino acid sequence of any one of SEQ ID NOs: 163-243, or a variant of the polypeptide comprising up to about 3 amino acid substitutions in the CDR regions. In some embodiments, the anti-DLL3 antibody is or comprises a single domain antibody (sdAb), which is produced from camel after been immunized with human or rhesus DLL3 proteins. In some embodiments, the sdAb comprises a CDR set (i.e., a combination of CDR1, CDR2, and CDR3) as listed in each row of Table 1.

In some embodiments, the sdAb comprises a polypeptide comprising any one of the following:

(1) a CDR1 comprising the amino acid sequence of SEQ ID NO: 6, or a variant thereof comprising up to about 3 amino acid substitutions; a CDR 2 comprising the amino acid sequence of SEQ ID NO: 87, or a variant thereof comprising up to about 3 amino acid substitutions; and a CDR 3 comprising the amino acid sequence of SEQ ID NO: 168, or a variant thereof comprising up to about 3 amino acid substitutions;

(2) a CDR1 comprising the amino acid sequence of SEQ ID NO: 21, or a variant thereof comprising up to about 3 amino acid substitutions; a CDR2 comprising the amino acid sequence of SEQ ID NO: 102, or a variant thereof comprising up to about 3 amino acid substitutions; and a CDR3 comprising the amino acid sequence of SEQ ID NO: 183, or a variant thereof comprising up to about 3 amino acid substitutions;

(3) a CDR1 comprising the amino acid sequence of SEQ ID NO: 24, or a variant thereof comprising up to about 3 amino acid substitutions; a CDR2 comprising the amino acid sequence of SEQ ID NO: 105, or a variant thereof comprising up to about 3 amino acid substitutions; and a CDR3 comprising the amino acid sequence of SEQ ID NO: 186, or a variant thereof comprising up to about 3 amino acid substitutions;
(4) a CDR1 comprising the amino acid sequence of SEQ ID NO: 27, or a variant thereof comprising up to about 3 amino acid substitutions; a CDR2 comprising the amino acid sequence of SEQ ID NO: 108, or a variant thereof comprising up to about 3 amino acid substitutions; and a CDR3 comprising the amino acid sequence of SEQ ID NO: 189, or a variant thereof comprising up to about 3 amino acid substitutions;
(5) a CDR1 comprising the amino acid sequence of SEQ ID NO: 34, or a variant thereof comprising up to about 3 amino acid substitutions; a CDR2 comprising the amino acid sequence of SEQ ID NO: 115, or a variant thereof comprising up to about 3 amino acid substitutions; and a CDR3 comprising the amino acid sequence of SEQ ID NO: 196, or a variant thereof comprising up to about 3 amino acid substitutions;
(6) a CDR1 comprising the amino acid sequence of SEQ ID NO: 39, or a variant thereof comprising up to about 3 amino acid substitutions; a CDR2 comprising the amino acid sequence of SEQ ID NO: 120, or a variant thereof comprising up to about 3 amino acid substitutions; and a CDR 3 comprising the amino acid sequence of SEQ ID NO: 201, or a variant thereof comprising up to about 3 amino acid substitutions;
(7) a CDR1 comprising the amino acid sequence of SEQ ID NO: 7, or a variant thereof comprising up to about 3 amino acid substitutions; a CDR2 comprising the amino acid sequence of SEQ ID NO: 88, or a variant thereof comprising up to about 3 amino acid substitutions; and a CDR 3 comprising the amino acid sequence of SEQ ID NO: 169, or a variant thereof comprising up to about 3 amino acid substitutions;
(8) a CDR1 comprising the amino acid sequence of SEQ ID NO: 8, or a variant thereof comprising up to about 3 amino acid substitutions; a CDR 2 comprising the amino acid sequence of SEQ ID NO: 89, or a variant thereof comprising up to about 3 amino acid substitutions; and a CDR3 comprising the amino acid sequence of SEQ ID NO: 170, or a variant thereof comprising up to about 3 amino acid substitutions; or
(9) a CDR1 comprising the amino acid sequence of SEQ ID NO: 9, or a variant thereof comprising up to about 3 amino acid substitutions; a CDR2 comprising the amino acid sequence of SEQ ID NO: 90, or a variant thereof comprising up to about 3 amino acid substitutions; and a CDR 3 comprising the amino acid sequence of SEQ ID NO: 171, or a variant thereof comprising up to about 3 amino acid substitutions.

In some embodiments, the sdAb comprises a polypeptide comprising any one of the following:
(1) a CDR1 comprising the amino acid sequence of SEQ ID NO: 6; a CDR2 comprising the amino acid sequence of SEQ ID NO: 87; and a CDR 3 comprising the amino acid sequence of SEQ ID NO: 168;
(2) a CDR1 comprising the amino acid sequence of SEQ ID NO: 21; a CDR 2 comprising the amino acid sequence of SEQ ID NO: 102; and a CDR 3 comprising the amino acid sequence of SEQ ID NO: 183;
(3) a CDR1 comprising the amino acid sequence of SEQ ID NO: 24; a CDR2 comprising the amino acid sequence of SEQ ID NO: 105; and a CDR 3 comprising the amino acid sequence of SEQ ID NO: 186;
(4) a CDR1 comprising the amino acid sequence of SEQ ID NO: 27; a CDR 2 comprising the amino acid sequence of SEQ ID NO: 108; and a CDR3 comprising the amino acid sequence of SEQ ID NO: 189;
(5) a CDR1 comprising the amino acid sequence of SEQ ID NO: 34; a CDR2 comprising the amino acid sequence of SEQ ID NO: 115; and a CDR3 comprising the amino acid sequence of SEQ ID NO: 196;
(6) a CDR1 comprising the amino acid sequence of SEQ ID NO: 39; a CDR2 comprising the amino acid sequence of SEQ ID NO: 120; and a CDR3 comprising the amino acid sequence of SEQ ID NO: 201;
(7) a CDR1 comprising the amino acid sequence of SEQ ID NO: 7; a CDR2 comprising the amino acid sequence of SEQ ID NO: 88; and a CDR3 comprising the amino acid sequence of SEQ ID NO: 169;
(8) a CDR1 comprising the amino acid sequence of SEQ ID NO: 8; a CDR2 comprising the amino acid sequence of SEQ ID NO: 89; and a CDR3 comprising the amino acid sequence of SEQ ID NO: 170; or
(9) a CDR1 comprising the amino acid sequence of SEQ ID NO: 9; a CDR2 comprising the amino acid sequence of SEQ ID NO: 90; and a CDR3 comprising the amino acid sequence of SEQ ID NO: 171.

In some embodiments, the sdAb comprises an amino acid sequence having at least about 95% (e.g., about 96%, 97%, 98%, 99% or 100%) sequence identity to the amino acid sequence of any one of SEQ ID NOs: 274-354. In some embodiments, the sdAb comprises the amino acid sequence of any one of SEQ ID NOs: 274-354. In other embodiments, the sdAb is humanized, and comprises an amino acid sequence having at least about 95% (e.g., about 96%, 97%, 98%, 99% or 100%) sequence identity to the amino acid sequence of any one of SEQ ID NOs: 355-367. In some embodiments, the sdAb comprises the amino acid sequence of any one of SEQ ID NOs: 355-367. A humanized antibody can be produced using a variety of techniques known in the art, including but not limited to, CDR-grafting (see, e.g., U.S. Pat. Nos. 5,225,539, 5,530,101, and 5,585,089), veneering or resurfacing (see, e.g., European Patent Nos. EP 592,106 and EP 519,596), and chain shuffling (see, e.g., U.S. Pat. No. 5,565,332). Generally, during humanization, the CDR residues of a receptor antibody (e.g., a human antibody) are replaced with CDR residues of a donor antibody (e.g., a rodent antibody), to retain the antigen-binding specificity while minimizing the in vivo immunogenicity. Often, framework residues in the framework regions will also be substituted with the corresponding residue from the donor antibody to alter, for example improve, antigen binding. These framework substitutions, e.g., conservative substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323).

In some cases, the sdAb can be fused with a human IgG hinge fragment and a Fc fragment to form a heave chain antibody (HCAb). In some cases, the sdAb can be fused with another sdAb or scFv which is specific for an antigen other than DLL3 to form a bispecific antibody. In some cases, the sdAb can be fused with two or more sdAbs or scFvs which are specific for an antigen other than DLL3 to form a multispecific antibody. In other cases, the sdAb can be chemically modified to carry a drug molecule. Thus the anti-DLL3 sdAb can be used in vivo to lead the drug molecule to a DLL3-expressing cell.

In some embodiments, the DLL3 binding protein is or comprises a single chain variable fragment (scFv) that specifically bind DLL3. In some cases, the scFv is isolated from a synthetic human Fab or scFv phage library through repeated rounds of phage panning, with each round of panning involving the processes of binding, removal of nonspecific phages, and the elution and amplification of bound phages for the next round. In some embodiments, the DLL3 binding protein comprising a scFv moiety that specifically binds to DLL3, wherein the scFv comprises a heavy chain variable region (VH) and a light chain variable region (VL), wherein the VH domain of the scFv comprises CDR1 set forth in SEQ ID NO: 498 or 504, CDR2 set forth in SEQ ID NO: 499 or 505, and CDR3 set forth in SEQ ID NO: 500 or 506, and the VL domain of the scFv comprises CDR1 set forth in SEQ ID NO: 495 or 501, CDR2 set forth in SEQ ID NO: 496 or 502, and CDR3 set forth in SEQ ID NO: 497 or 503. In some embodiments, the DLL3 binding protein comprising scFv moiety that specifically binds to DLL3, wherein the scFv comprises a heavy chain variable region (VH) and a light chain variable region (VL), wherein the VH domain of the scFv comprises CDR1 set forth in SEQ ID NO: 498, CDR2 set forth in SEQ ID NO: 499, and CDR3 set forth in SEQ ID NO: 500, and the VL domain of the scFv comprises CDR1 set forth in SEQ ID NO: 495, CDR2 set forth in SEQ ID NO: 496, and CDR3 set forth in SEQ ID NO: 497; or the VH domain of the scFv comprises CDR1 set forth in SEQ ID NO: 504, CDR2 set forth in SEQ ID NO: 505, and CDR3 set forth in SEQ ID NO: 506, and the VL domain of the scFv comprises CDR1 set forth in SEQ ID NO: 501, CDR2 set forth in SEQ ID NO: 502, and CDR3 set forth in SEQ ID NO: 503.

In some cases, the scFv can be fused with another sdAb or scFv which is specific for an antigen other than DLL3 to form a bispecific antibody. In some cases, the scFv can be fused with two or more sdAbs or scFvs which are specific for an antigen other than DLL3 to form a multispecific antibody. In other cases, the scFv can be chemically modified to carry a drug molecule. Thus the anti-DLL3 scFv can be used in vivo to lead the drug molecule to a DLL3-expressing cell.

Some aspects of the present invention relate to a CAR or a CAR-T cell comprising a DLL3 binding domain (anti-DLL3 CAR or anti-DLL3 CAR-T cells).

A CAR of the present invention comprises an extracellular domain, a transmembrane domain and an intracellular domain. In some embodiments, the CAR further includes a signal peptide at N-terminus, and a hinge region between the extracellular domain and the transmembrane domain. The extracellular domain includes a target-specific binding element (also referred to as an antigen recognition domain or antigen binding domain). The intracellular domain, or otherwise the cytoplasmic domain, often includes one or more co-stimulatory signaling domains and a CD3ζ chain portion. The co-stimulatory signaling domain refers to a portion of the CAR including the intracellular domain of a co-stimulatory molecule.

Antigen recognition or antigen targeting by a CAR molecule most commonly involves the use of an antibody or antibody fragment. In accordance with the present invention, the antigen binding domain is an antibody or antibody fragment that specifically binds to DLL3. Preferably, the antigen binding domain of the CAR of the invention is an anti-DLL3 scFv or sdAb as mentioned above.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of), for example, the alpha, beta or zeta chain of the T-cell receptor, CD8α chain.

The intracellular signaling domain of the CAR of the invention is responsible for activation of at least one of the normal effector functions of an immune cell. The term "effector function" refers to a specialized function of a cell. Effector function of a T cell, for example, may be cytolytic activity or helper activity including the secretion of cytokines. Thus, the term "intracellular domain" refers to the portion of a protein which transduces the effector function signal and directs the cell to perform a specialized function. While usually the entire cytoplasmic domain can be employed, in many cases it is not necessary to use the entire chain. To the extent that a truncated portion of a cytoplasmic domain is used, such truncated portion may be used in place of an intact chain as long as it transduces the effector function signal. The term intracellular domain is thus meant to include any truncated portion of a cytoplasmic domain sufficient to transduce the effector function signal. Preferred examples of cytoplasmic domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability. In some embodiments, the intracellular signaling domain is derived from CD3ζ, FcRγ, FcRβ, CD3γ, CD3δ, CD3ε, CD5, CD22, CD79a, CD79b, or CD66d.

Often, signals generated through the TCR alone are insufficient for full activation of the T cell. Accordingly, a secondary or co-stimulatory signal is used. Thus, T cell activation can be said to be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences). The co-stimulatory signaling sequence refers to a portion of the CAR including the intracellular domain of a co-stimulatory molecule. A co-stimulatory molecule is a cell surface molecule other than an antigen receptor or their ligands that is required for an efficient response of lymphocytes to an antigen. Examples of such molecules include CD27, CD28, 4-1BB, OX40, CD40, PD-1, LFA-1, ICOS, CD2, CD7, LIGHT, NKG2C, B7-H3, TNFRSF9, TNFRSF4, TNFRSF8, CD40LG, ITGB2, KLRC2, TNFRSF18, TNFRSF14, HAVCR1, LGALS9, DAP10, DAP12, CD83, ligands of CD83 and combinations thereof.

The hinge region between the extracellular domain and the transmembrane domain of the CAR generally means any oligo- or polypeptide that functions to link the transmembrane domain to the extracellular domain in the polypeptide chain. The hinge region may be up to 300 amino acids, preferably 2 to 100 amino acids and most preferably 2 to 10 amino acids.

In addition to the antigen binding domain, transmembrane domain, cytoplasmic domain, and hinge region, the CAR of the present invention can also include a signal peptide sequence linked to the N-terminus of the CAR. Signal peptide sequences exist at the N-terminus of many secretory proteins and membrane proteins, and typically have a length of 15 to 30 amino acids. Since many of the protein molecules mentioned above have signal peptide sequences, these signal peptides can be used as a signal peptide for the CAR of this invention.

In some embodiments, the CAR comprising a DLL3 binding domain, wherein the DLL3 binding domain comprises or is derived from a single domain antibody (sdAb) or a single chain variable fragment (scFv).

In some embodiments, the CAR comprising a DLL3 binding domain, wherein the DLL3 binding domain comprises or is derived from a single domain antibody (sdAb), wherein the sdAb comprises a CDR1 comprising the amino acid sequence of any one of SEQ ID NOs: 1-81 or a variant thereof comprising up to about 3 amino acid substitutions in the CDR1; a CDR2 comprising the amino acid sequence of any one of SEQ ID NOs: 82-162 or a variant thereof comprising up to about 3 amino acid substitutions in the CDR2; and a CDR3 comprising the amino acid sequence of any one of SEQ ID NOs: 163-243 or a variant thereof comprising up to about 3 amino acid substitutions in the CDR3. In some embodiments, the CAR comprising a DLL3 binding domain, wherein the DLL3 binding domain comprises or is derived from a single domain antibody (sdAb), wherein the sdAb comprises a CDR1 comprising the amino acid sequence of any one of SEQ ID NOs: 1-81; a CDR2 comprising the amino acid sequence of any one of SEQ ID NOs: 82-162; and a CDR3 comprising the amino acid sequence of any one of SEQ ID NOs: 163-243.

In some embodiments, the CAR comprising a DLL3 binding domain, wherein the DLL3 binding domain comprises an sdAb comprising any one of the following:

(1) a CDR1 comprising the amino acid sequence of SEQ ID NO: 6, or a variant thereof comprising up to about 3 amino acid substitutions; a CDR2 comprising the amino acid sequence of SEQ ID NO: 87, or a variant thereof comprising up to about 3 amino acid substitutions; and a CDR3 comprising the amino acid sequence of SEQ ID NO: 168, or a variant thereof comprising up to about 3 amino acid substitutions;

(2) a CDR1 comprising the amino acid sequence of SEQ ID NO: 21, or a variant thereof comprising up to about 3 amino acid substitutions; a CDR2 comprising the amino acid sequence of SEQ ID NO: 102, or a variant thereof comprising up to about 3 amino acid substitutions; and a CDR3 comprising the amino acid sequence of SEQ ID NO: 183, or a variant thereof comprising up to about 3 amino acid substitutions;

(3) a CDR1 comprising the amino acid sequence of SEQ ID NO: 24, or a variant thereof comprising up to about 3 amino acid substitutions; a CDR2 comprising the amino acid sequence of SEQ ID NO: 105, or a variant thereof comprising up to about 3 amino acid substitutions; and a CDR3 comprising the amino acid sequence of SEQ ID NO: 186, or a variant thereof comprising up to about 3 amino acid substitutions;

(4) a CDR1 comprising the amino acid sequence of SEQ ID NO: 27, or a variant thereof comprising up to about 3 amino acid substitutions; a CDR2 comprising the amino acid sequence of SEQ ID NO: 108, or a variant thereof comprising up to about 3 amino acid substitutions; and a CDR3 comprising the amino acid sequence of SEQ ID NO: 189, or a variant thereof comprising up to about 3 amino acid substitutions;

(5) a CDR1 comprising the amino acid sequence of SEQ ID NO: 34, or a variant thereof comprising up to about 3 amino acid substitutions; a CDR2 comprising the amino acid sequence of SEQ ID NO: 115, or a variant thereof comprising up to about 3 amino acid substitutions; and a CDR3 comprising the amino acid sequence of SEQ ID NO: 196, or a variant thereof comprising up to about 3 amino acid substitutions;

(6) a CDR1 comprising the amino acid sequence of SEQ ID NO: 39, or a variant thereof comprising up to about 3 amino acid substitutions; a CDR2 comprising the amino acid sequence of SEQ ID NO: 120, or a variant thereof comprising up to about 3 amino acid substitutions; and a CDR3 comprising the amino acid sequence of SEQ ID NO: 201, or a variant thereof comprising up to about 3 amino acid substitutions;

(7) a CDR1 comprising the amino acid sequence of SEQ ID NO: 7, or a variant thereof comprising up to about 3 amino acid substitutions; a CDR2 comprising the amino acid sequence of SEQ ID NO: 88, or a variant thereof comprising up to about 3 amino acid substitutions; and a CDR3 comprising the amino acid sequence of SEQ ID NO: 169, or a variant thereof comprising up to about 3 amino acid substitutions;

(8) a CDR1 comprising the amino acid sequence of SEQ ID NO: 8, or a variant thereof comprising up to about 3 amino acid substitutions; a CDR2 comprising the amino acid sequence of SEQ ID NO: 89, or a variant thereof comprising up to about 3 amino acid substitutions; and a CDR3 comprising the amino acid sequence of SEQ ID NO: 170, or a variant thereof comprising up to about 3 amino acid substitutions; or (9) a CDR1 comprising the amino acid sequence of SEQ ID NO: 9, or a variant thereof comprising up to about 3 amino acid substitutions; a CDR2 comprising the amino acid sequence of SEQ ID NO: 90, or a variant thereof comprising up to about 3 amino acid substitutions; and a CDR3 comprising the amino acid sequence of SEQ ID NO: 171, or a variant thereof comprising up to about 3 amino acid substitutions.

In some embodiments, the CAR comprising a DLL3 binding domain, wherein the DLL3 binding domain comprises an sdAb comprising any one of the following:

(1) a CDR1 comprising the amino acid sequence of SEQ ID NO: 6; a CDR2 comprising the amino acid sequence of SEQ ID NO: 87; and a CDR3 comprising the amino acid sequence of SEQ ID NO: 168;

(2) a CDR1 comprising the amino acid sequence of SEQ ID NO: 21; a CDR2 comprising the amino acid sequence of SEQ ID NO: 102; and a CDR3 comprising the amino acid sequence of SEQ ID NO: 183;

(3) a CDR1 comprising the amino acid sequence of SEQ ID NO: 24; a CDR2 comprising the amino acid sequence of SEQ ID NO: 105; and a CDR3 comprising the amino acid sequence of SEQ ID NO: 186;

(4) a CDR1 comprising the amino acid sequence of SEQ ID NO: 27; a CDR2 comprising the amino acid sequence of SEQ ID NO: 108; and a CDR3 comprising the amino acid sequence of SEQ ID NO: 189;

(5) a CDR1 comprising the amino acid sequence of SEQ ID NO: 34; a CDR 2 comprising the amino acid sequence of SEQ ID NO: 115; and a CDR 3 comprising the amino acid sequence of SEQ ID NO: 196;

(6) a CDR1 comprising the amino acid sequence of SEQ ID NO: 39; a CDR2 comprising the amino acid sequence of SEQ ID NO: 120; and a CDR 3 comprising the amino acid sequence of SEQ ID NO: 201;

(7) a CDR1 comprising the amino acid sequence of SEQ ID NO: 7; a CDR2 comprising the amino acid sequence of SEQ ID NO: 88; and a CDR 3 comprising the amino acid sequence of SEQ ID NO: 169;

(8) a CDR1 comprising the amino acid sequence of SEQ ID NO: 8; a CDR2 comprising the amino acid sequence of SEQ ID NO: 89; and a CDR 3 comprising the amino acid sequence of SEQ ID NO: 170; or (9) a CDR1 comprising the amino acid sequence of SEQ ID NO: 9; a CDR 2 comprising the amino acid sequence of SEQ ID NO: 90; and a CDR 3 comprising the amino acid sequence of SEQ ID NO: 171.

In some embodiments, the CAR comprising a DLL3 binding domain, wherein the DLL3 binding domain comprises a camel sdAb, wherein the sdAb comprises an amino acid sequence having at least about 95% (e.g. 96%, 97%, 98%, 99% or 100%) sequence identity to the amino acid sequence of any one of SEQ ID NOs: 274-354. In some embodiments, the CAR comprising a DLL3 binding domain, wherein the DLL3 binding domain comprises a camel sdAb comprising an amino acid of any one of SEQ ID NOs: 274-354. In some embodiments, the CAR comprising a DLL3 binding domain, wherein the DLL3 binding domain comprises a humanized sdAb, wherein the sdAb comprises an amino acid sequence having at least about 95% (e.g. 96%, 97%, 98%, 99% or 100%) sequence identity to the amino acid sequence of any one of SEQ ID NOs: 355-367. In some embodiments, the CAR comprising a DLL3 binding domain, wherein the DLL3 binding domain comprises a humanized sdAb comprising an amino acid sequence of any one of SEQ ID NOs: 355-367.

In some embodiments, the CAR comprising a DLL3 binding domain, wherein the DLL3 binding domain comprises or is derived from a single chain variable fragment (scFv), wherein the VH domain of the scFv comprises CDR1 set forth in SEQ ID NO: 498, CDR2 set forth in SEQ ID NO: 499, and CDR3 set forth in SEQ ID NO: 500, and the VL domain of the scFv comprises CDR1 set forth in SEQ ID NO: 495, CDR2 set forth in SEQ ID NO: 496, and CDR3 set forth in SEQ ID NO: 497; or the VH domain of the scFv comprises CDR1 set forth in SEQ ID NO: 504, CDR2 set forth in SEQ ID NO: 505, and CDR3 set forth in SEQ ID NO: 506, and the VL domain of the scFv comprises CDR1 set forth in SEQ ID NO: 501, CDR2 set forth in SEQ ID NO: 502, and CDR3 set forth in SEQ ID NO: 503. In some embodiments, the VH domain of the scFv comprises an amino acid sequence set forth in SEQ ID NO: 508, and the VL domain of the scFv comprises an amino acid sequence set forth in SEQ ID NO: 507; or the VH domain of the scFv comprises an amino acid sequence set forth in SEQ ID NO: 510, and the VL domain of the scFv comprises an amino acid sequence set forth in SEQ ID NO: 509.

In some embodiments, the CAR of the present invention comprises a camel sdAb provided herein as the DLL3 binding domain and comprises an amino acid sequence having at least about 95% (e.g. 96%, 97%, 98%, 99% or 100%) sequence identity to the amino acid sequence of any one of SEQ ID NOs: 476-484. In some embodiments, the CAR of the present invention comprises a camel sdAb provided herein as the DLL3 binding domain and has an amino acid sequence selected from the group consisting of SEQ ID NOs: 476-484. In some embodiments, the CAR of the present invention comprises a humanized sdAb provided herein as the DLL3 binding domain and comprises an amino acid sequence having at least about 95% (e.g. 96%, 97%, 98%, 99% or 100%) sequence identity to the amino acid sequence of any one of SEQ ID NOs: 485-494. In other embodiments, the CAR of the present invention comprises a humanized sdAb provided herein as the DLL3 binding domain and has an amino acid sequence selected from the group consisting of SEQ ID NOs: 485-494.

In some embodiments, the CAR of the present invention comprises a human scFv provided herein as the DLL3 binding domain and comprises an amino acid sequence having at least about 95% (e.g. 96%, 97%, 98%, 99% or 100%) sequence identity to the amino acid sequence of any one of SEQ ID NOs: 515-516. In some embodiments, the CAR of the present invention comprises a human scFv provided herein as the DLL3 binding domain and has an amino acid sequence selected from the group consisting of SEQ ID NOs: 515-516.

In some embodiments, the CAR of the present invention comprises, from N-terminus to C-terminus, a signal peptide, the DLL3 binding domain, a hinge region, a transmembrane domain, and a cytoplasmic signaling domain. In particular embodiments, the CAR of the present invention comprises, from N-terminus to C-terminus, a CD8α signal peptide as set forth in SEQ ID NO: 465, the DLL3 binding domain, a CD8α hinge domain as set forth in SEQ ID NO: 466, a CD8α transmembrane domain as set forth in SEQ ID NO: 467, a CD137 cytoplasmic domain as set forth in SEQ ID NO: 468, a CD28 cytoplasmic domain as set forth in SEQ ID NO: 469, and a CD3ζ cytoplasmic domain as set forth in SEQ ID NO: 470.

Some aspects of the present invention relates to an isolated nucleic acid molecule which encodes the sdAb, scFv, or CAR of the present invention. In some embodiments, the nucleic acid molecule encodes a camel sdAb and comprises a polynucleotide sequence selected from the group consisting of SEQ ID NOs: 368-448. In some embodiments, the nucleic acid molecule encodes a humanized sdAb and comprises a polynucleotide sequence selected from the group consisting of SEQ ID NOs: 449-461. In some embodiments, the nucleic acid molecule encodes a VH and a VL domain of a scFv, wherein the VH domain encoding sequence comprises a polynucleotide sequence of SEQ ID NOs: 512 or 514, the VL domain encoding sequence comprises a polynucleotide sequence of SEQ ID NOs: 511 or 513.

Some aspects of present application relates to an engineered immune cell, comprising any one of the CARs provided above, or any one of the isolated nucleic acids described above, or any one of the vectors described above. In some embodiments, the engineered immune cell is a cytotoxic T cell, a helper T cell, a natural killer T cell, a γδ T cell, a NKT cell and a Nature Killer cell. In some embodiments, the cells comprise an expression vector which carries an isolated nucleic acid molecule of the present invention. Genetically modifying a cell with an expression vector to express a polypeptide encoded by a portion of the nucleic acid molecule is a genetic technique well known in the art.

Some aspects of the present invention relates to uses of the DLL3 binding proteins, anti-DLL3 CARs, nucleic acid molecules or CAR-T cells of the present invention. In some embodiments, the CAR-T cells of the present invention are formulated as a pharmaceutical composition with a physiologically acceptable excipient. As used herein, "physiologically acceptable excipient" includes without limitation any adjuvant, carrier, diluent, preservative, dispersing agent, suspending agent, stabilizer, isotonic agent, solvent, surfactant, or emulsifier as being acceptable for use in humans or domestic animals. In some embodiments, the CAR-T cells of the present invention or the pharmaceutical composition comprising the same is used to treat a DLL3-related disorder in a subject. Accordingly, a method for treating a DLL3-related disorder is provided, which comprises administrating to a subject suffering from a DLL3 associated disorder a therapeutically effective amount of the CAR-T cells or the pharmaceutical composition of the present invention. A "therapeutically effective amount" of antibodies, CAR-T cells or a pharmaceutical composition may vary according to factors such as the disease state, age, sex, and weight of a subject (e.g., a patient). The term "therapeutically effective amount" may include an amount that is effective to "treat" a subject. When a therapeutic amount is indicated, the precise amount contemplated in particular embodiments, to be administered, can be determined by a physician in view of the condition of the subject. In some embodiments, the DLL3 associated disorder is a cancer expressing DLL3 as cell surface proteins, such as, melanoma, breast cancer, prostate cancer, colon cancer, renal cell carcinoma, ovarian cancer, neuroblastoma, rhabdomyosarcoma, leukemia and lymphoma. Preferably, the DLL3 associated disorder is a lung cancer, especially small cell lung cancer (SCLC).

EXAMPLES

The examples described herein are not intended to represent that the experiments below are all or the only experiments performed. Efforts have been made to ensure accuracy with respect to numbers used (for example, amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1. Animal Immunization and Antibody Library Construction

This example demonstrated that the immunized camel showed good immune response towards human or rhesus DLL3 protein and the acquired immunized library showed superior quality.

Animal Immunization

Immunogens comprising extracellular domain of human DLL3 protein (aa27-466) having an N-terminal FLAG tag (AdipoGen, AG-40B-0151) or/and DLL3-expressing plasmid or DLL3-expressing cells (CHO-K1/DLL3 or/and CHO-K1/EGF4) were mixed with adjuvant or PBS and injected to camels. Typically, the camels were immunized for 2-4 times with 1-week to 2-week intervals. After multiple rounds of immunization, immune reactions against the target antigen DLL3 were assessed by serum titration through both enzyme-linked immune sorbent assay (ELISA) and flow cytometric assay.

Phage Display Library Construction

Total RNA was extracted from lymphocytes of immunized camel using TRIZOL® Reagent according to the manufacturer's protocol. cDNA was synthesized based on RNA template with an oligo(dT)20 primer using PRIMESCRIPT™ 1st Strand cDNA Synthesis Kit according to the manufacturer's protocol. $V_HHs$ were amplified from camel cDNA for generation of $V_HH$ phage library.

Example 2. Generation of Anti-DLL3 Antibodies

Anti-DLL3 antibodies provided herein include single domain antibodies (sdAbs) generated from an immunized camel or human Fab isolated from synthetic human Fab library.

Phage Display

A phage display library was constructed with the sdAbs obtained by immunization (Immunogens comprising extracellular domain of human DLL3 protein (aa27-466) having an N-terminal FLAG tag (AdipoGen, AG-40B-0151) or/and DLL3-expressing plasmid or DLL3-expressing cells (CHO-K1/DLL3 or/and CHO-K1/EGF4)). Another human Fab phage display library was synthesized. Both phage libraries were rescued and stored after filter sterilization at 4° C. for further use. Bound phages were isolated with the above-mentioned two phage libraries using protein-based panning as well as cell-based panning. At least one round of panning was carried for both protein- and cell-based panning approaches using both libraries until the percentage of DLL3-specific phage clones reached 30%. Output phages of each round were assessed for the number of total output clones, percentage of DLL3 positive clones by ELISA and sequence diversity of DLL3-specific clones. Based on these results the best panning outputs were selected for high-throughput screening.

High-Throughput Screening

The selected output phages were used to infect exponentially growing E. coli cells. Double-strand DNA of the output phages was extracted. The sdAb/Fab insert were cut from the phagemid vector and inserted into an antibody fragment expression vector for high-throughput screening. The resulting plasmid was used to transform exponentially growing E. coli cells, which were subsequently plated and grown overnight at 37° C. Thousands of colonies were picked individually and grown in 96 deep well plates containing 1 mL 2×YT medium. The expression of antibody fragment was induced by adding 1 mM IPTG.

The sdAb/Fab proteins in the supernatant were analyzed for their ability to bind DLL3 ECD protein by ELISA and DLL3 expressing SHP-77 cell lines (American Type Culture Collection (ATCC)® CRL-2195™) and CHO-K1/human DLL3 (in-house generation) by FACS. All binders were sequenced. The redundant sequences were removed. All together, 81 camel sdAbs and 2 human Fab binders that bound both human and rhesus DLL3 proteins and cell lines were obtained. All these binders have unique amino acid sequences.

Some of these unique binders were subjected to further characterization by surface plasmon resonance (SPR) on a BIAcore T200 instrument (GE Healthcare). The experiment was carried out as follows: the crude sdAb/Fab proteins were captured through an affinity tag onto the sensorchip. High-concentration (100 nM) of human DLL3 flowed over the sensorchip surface, and were allowed to bind the antibody fragments for 300 s followed by injection of running buffer to allow the dissociation of the complex formed. On-rate (ka) and off-rate (kd) were roughly calculated based on one association and dissociation curve, and were used to estimate the equilibrium dissociation constant ($K_D$). The binding affinities of some of these unique binders were shown in Table 7.

CDR sequences of anti-DLL3 camel sdAbs were listed in Table 1 and CDR sequences of anti-DLL3 human scFvs were listed in Table 2.

TABLE 1

Anti-DLL3 camel sdAb CDR sequences

| sdAb | ID | CDR1 Sequence | ID | CDR2 Sequence | ID | CDR3 Sequence |
|---|---|---|---|---|---|---|
| AS63930 | 1 | GYTYS GNYMA | 82 | VVYNI DGGGR FTTYA DSVKG | 163 | EVADP TWGSR DQRRY KY |

TABLE 1-continued

Anti-DLL3 camel sdAb CDR sequences

| sdAb | ID | CDR1 Sequence | ID | CDR2 Sequence | ID | CDR3 Sequence |
|---|---|---|---|---|---|---|
| AS63932 | 2 | GYTYGSTFMG | 83 | VIYTGGGSTWYASSVKG | 164 | RYGSGNVNY |
| AS63951 | 3 | RDIYGNNCMA | 84 | SIYPAGGRPYYADSVKG | 165 | RSFSIAVCATRSGITRSNFAY |
| AS63984 | 4 | GYTYSSNFMG | 85 | TIVSGGGTTYYADSVRG | 166 | GGPVTNAPRWYPLRPPGYNY |
| AS63987 | 5 | GYRNCMA | 86 | VIYTPSGITDYASSVKG | 167 | DRPFVCNIANMRRSSN |
| AS63997 | 6 | FSGYGVSTMA | 87 | AITVGSGNTYYADSVKG | 168 | GYLSGGSWDVPGRYNY |
| AS64047 | 7 | QYVYRWDLMG | 88 | AVYTGDGITYYADSVKG | 169 | GFVSGGRWNQSYRYKY |
| AS64052 | 8 | GYTYRSNFMG | 89 | TIHSGVATTYYADSVKG | 170 | GGPPANADRWYPLRPPGYNY |
| AS64062 | 9 | RSPYSSSRCMG | 90 | ALYTGGGSTSYADSVKG | 171 | VVPRGGSCRLDERGYYH |
| AS64072 | 10 | GYSYYINLMA | 91 | AHGPVSGTAYYTDSVKG | 172 | ETTMGWAJIERGYRY |
| AS64097 | 11 | GYTYSRNCMG | 92 | AINTGGGSTYYADSLEG | 173 | GPDLGGSWCRPVERAFTY |
| AS64114 | 12 | GNTYSTNYMG | 93 | VIYTRGGHTYYVDSVRG | 174 | ASRHRLRLNNPRDYDY |
| AS64123 | 13 | GYTYTSNWLG | 94 | IIYTGSGSTHYRSSVKG | 175 | RFSEYNY |
| AS64130 | 14 | GYTYRSNFMG | 95 | TIDSRGTITYYADSVKG | 176 | GGPRTNDDRWYPLRPPGYNY |
| AS64137 | 15 | GSTYSTNFMG | 96 | TLVTWVERTAYADSVKG | 177 | AASTDVRLLDPGDFAY |
| AS64142 | 16 | GFTFDRNAMR | 97 | CIDWTGANIAYADSVKG | 178 | DTTSGYCSGFWSTSRYS |
| AS64154 | 17 | GYTYRYLYMG | 98 | CIYTGSGSTGYADSVKG | 179 | SSPRWGGTCRRWSQYNY |
| AS64160 | 18 | VYTSSSYCMG | 99 | AMCFGGLVTHYADSVKG | 180 | DFGRDKNYLRPLLPHAYNY |
| AS64228 | 19 | GVSYNRCSMG | 100 | RIQPGGNTYYADSVKG | 181 | LCWRENVNY |
| AS64300 | 20 | GDIYNLMSMA | 101 | YINTIIGNTYYTDSVKG | 182 | FNYGGAWYEERSYKY |
| AS64380 | 21 | GNTYSSNYMG | 102 | VIYTRGGHTYYVDSVRG | 183 | SSRHRLGLNNPRDYDY |
| AS64395 | 22 | GSTYSTNFMG | 103 | TLVTWAERTAYADSVKG | 184 | AASTAVRLLDPGDFAY |
| AS64443 | 23 | GYTDSSVYIG | 104 | IIYTGGESTHYRSSVKG | 185 | RFPAVTY |
| AS64511 | 24 | RATYSTNYIS | 105 | TITTGDGETAYADSVKG | 186 | NLRIGGDWFDGRDFRA |
| AS64536 | 25 | RYTDNFVYMG | 106 | LIYPGGGSTYYASSVKG | 187 | KWGLGGGGLKSDTYMY |
| AS64597 | 26 | GYTYRVNFMG | 107 | TIDSGVGTTYYADSVKG | 188 | GGPPTDGDRWYPLRPPGYNY |
| AS64617 | 27 | GYTDRCSMA | 108 | RISTSGFTNYAASVKG | 189 | IVGRTCSLNY |
| AS64634 | 28 | GYSFRGDFMCMG | 109 | VFYPGGGSTNYADSAKG | 190 | RRWVSGTCYWDSDFHY |
| AS69498 | 29 | GNTYSSNYMA | 110 | VIYTRGGHTYYIDSVRG | 191 | SSRHRLRLSDPRDYDY |
| AS69500 | 30 | RYTYSSACMG | 111 | SIFTGTGGSTYYADSVKG | 192 | RAFQVGYCYLRTDVYNY |

TABLE 1-continued

Anti-DLL3 camel sdAb CDR sequences

| sdAb | ID | CDR1 Sequence | ID | CDR2 Sequence | ID | CDR3 Sequence |
|---|---|---|---|---|---|---|
| AS69527 | 31 | RYTFSSTCMA | 112 | AIYTDDGSTWYADSVKG | 193 | RRWACPRVGSWHEFAY |
| AS68280 | 32 | GSTYSSNYLG | 113 | AISTGDGATAYADSVKG | 194 | ARGRFIDWTKATQYDY |
| AS68355 | 33 | GYTYSGVCMG | 114 | AIDSDGSTSYADSVKG | 195 | AIVGGFNAYCSGGYVLDFGA |
| AS69443 | 34 | GFTFDDSDMA | 115 | TISSDGSTYYADSVKG | 196 | DFLTGFYYSDSPHPAPCSASDFGY |
| AS75376 | 35 | GYTYSSHSMG | 116 | VIYTGDGSTYYADSVKG | 197 | DPNPDYMLPFRPSRRSW |
| AS75387 | 36 | GYPYSSPCMA | 117 | VAYTGGDIQYLTDSVKG | 198 | DLRLPRAGGCAYSY |
| AS75695 | 37 | GYTVSAYCMG | 118 | FIDAGGATIYADPVKG | 199 | DRRGRVRRCEYNA |
| AS76169 | 38 | GYIYSSFCMG | 119 | YIRDNIMTSYTDSVKG | 200 | DRGGYANSCAVAARYDY |
| AS63931 | 39 | FSGYGVSTMA | 120 | AITVGSGNTYYADSVTG | 201 | GWLSGGSWHVPGRYNY |
| AS63937 | 40 | GSTISSRPMA | 121 | CIHTGLGRTYYADSVKG | 202 | DSRRPCMVAAGYTY |
| AS63948 | 41 | GYTYRYLYMG | 122 | CIYTGSGSTGYADSVKG | 203 | ASPRWGGTCRRWSEYNY |
| AS63956 | 42 | GFTYSNCCMR | 123 | LINSSGGTYYADSVRG | 204 | YQAKYCSGPCAPPTD |
| AS63965 | 43 | GYSSGSCRMG | 124 | KVISDGTTVYADSVKG | 205 | WCREYPGGILNNG |
| AS63993 | 44 | GFTFDDLVMA | 125 | LVATAGNSVYADSVKG | 206 | RTDSEHAFKF |
| AS63999 | 45 | GYTYSSNWMG | 126 | IIYTGGISTHYRSSVKG | 207 | RYTDYNY |
| AS64006 | 46 | GYTGDTTYIG | 127 | LIYTSGTSEYYADSVKG | 208 | RSRTMMY |
| AS64057 | 47 | GFTFDRNAMR | 128 | CISWTGANIAYADSVKG | 209 | DTTSGSCSGFWSTSRYY |
| AS64060 | 48 | GSTYCTYRMS | 129 | VIDSGGSTSYADSVKG | 210 | DPTIGCPQTYRYNY |
| AS64071 | 49 | GNTYRLNSMG | 130 | FIVMIRGTTYYGASVKG | 211 | STKDQFYVFNPIGYDS |
| AS64093 | 50 | RYIYGNNCMA | 131 | SIYPAGGRTYYADSVKG | 212 | RSFSIGVCATQSGITWSNFAY |
| AS64118 | 51 | GYTYSACRMA | 132 | FINSAGSTYYADSVKG | 213 | TWDSSCRFQY |
| AS64120 | 52 | RYIYGNNCMA | 133 | SIYPAGGRPYYADSVKG | 214 | RSFSIADCATQSGITRSNFAY |
| AS64124 | 53 | TYTPSNNYMG | 134 | AIATIGGTTRYADSVKG | 215 | GRPYSLPLPLPLESGAYRY |
| AS64135 | 54 | TSTYCRYYMR | 135 | AMQPDGTTSYSDSVKG | 216 | DPMGGSRTPCTSA |
| AS64163 | 55 | GYRYRWNCMA | 136 | AISTGSGSTYYAGSVKG | 217 | DPSVCPGGMWYSKEYRY |
| AS64182 | 56 | GQTSRYLYMG | 137 | CIYTGSGSTGYADSVKG | 218 | SSPHWGGTCRRWSEYKY |

TABLE 1-continued

Anti-DLL3 camel sdAb CDR sequences

| sdAb | ID | CDR1 Sequence | ID | CDR2 Sequence | ID | CDR3 Sequence |
|---|---|---|---|---|---|---|
| AS64183 | 57 | GHTYSANCMA | 138 | SVYTDDDSTMYTDSVKG | 219 | DLSGGPAGCGYTH |
| AS64207 | 58 | GYTYSSNFMG | 139 | TIVSGGGTTYYADSVRG | 220 | GGPPTNGAKWYPLRPPGYNY |
| AS64276 | 59 | GYTGSSRCMA | 140 | QIFTGRGTTGYADSVKG | 221 | SLGPGRGACGYNY |
| AS64336 | 60 | GRTYSSCSMG | 141 | HIFSDGSRYYADSVKG | 222 | RTGWAPRCAVPGY |
| AS64346 | 61 | GYTYFMG | 142 | TIGTGDIFNGAAYYVDSVKG | 223 | VQSKSSNYVLRDASTYNY |
| AS64420 | 62 | GDTSRSVWMG | 143 | TISTAGGSTWYTDSVKG | 224 | RSRYATY |
| AS64473 | 63 | GYTYRYLYMA | 144 | CIYTGSGTTGYADSVKG | 225 | SSPQWGGTCRRWSEYNY |
| AS64475 | 64 | GYTWSRNWMG | 145 | TITISGGSTWYADSVKG | 226 | RDTARTY |
| AS64513 | 65 | DYPYIDNCMG | 146 | AACTGGGSTYYADSVKG | 227 | GYYSGSGPGYLLPWRYNY |
| AS64562 | 66 | GYTARRDFMA | 147 | VIHTGGDTTYYADSVKG | 228 | GFRPRGGGYTGDVLAQAAAYNY |
| AS64583 | 67 | GFTIAVYTMG | 148 | CTSWAGGRTYTADSVKG | 229 | KAHPDCSGDWSPSGYEY |
| AS64594 | 68 | GYTYNSNYMG | 149 | LIYTGGSTYYADSVKG | 230 | RTQTRNY |
| AS64605 | 69 | RYPYSSICMG | 150 | RIYTGTGSTWYTDSVKG | 231 | RSNSYSYSCDYGPLTRGGYNF |
| AS64606 | 70 | GYTSRSNYMG | 151 | AFYLIYTRGGSTYYASSVKG | 232 | RLDEKMY |
| AS68121 | 71 | GYTYSRNCMG | 152 | TDYIRFGRTYYADSVKG | 233 | DPGSRTDDSCGTSYNKGNFGY |
| AS68170 | 72 | GYTYRSNCMG | 153 | TIYTGGGRNLYYADSVKG | 234 | ASDVAVGVNSCGGRTAGFDA |
| AS63964 | 73 | GYTYSYNNMG | 154 | AISGGRFTAYADSVKG | 235 | EVVDPTWGSRDQRRYKY |
| AS64116 | 74 | GYIYSCVG | 155 | GISTGGGGTVYADSVKG | 236 | DRWNSFANCGAWGRYTY |
| AS68270 | 75 | GYPSSTYYMLSMA | 156 | AITSGTGSTSYADSVKD | 237 | ASGWIVPSRSLTANLYRY |
| AS68320 | 76 | GYTYNTNYMG | 157 | AIYRHSGNTAYADSVKG | 238 | GRAGPWALMRPTEFGY |
| AS68351 | 77 | GDTFRAYYMN | 158 | GISASGGRTSYADSVKG | 239 | GAVRLSTSSVRDSS |
| AS75378 | 78 | GNTRSTTYMG | 159 | IVYTGGRDTYYAASVKG | 240 | RSYEYTY |
| AS75383 | 79 | GYTFSSYCLG | 160 | TFNNRGVANYHDSVKG | 241 | DRRYGRQWYQPCEWNT |
| AS75751 | 80 | GYFYNTYYFMG | 161 | AIDTDGRTSYADSVKG | 242 | GFGYMNVIQALNGMRQNPDY |

TABLE 1-continued

Anti-DLL3 camel sdAb CDR sequences

| sdAb | CDR1 ID | CDR1 Sequence | CDR2 ID | CDR2 Sequence | CDR3 ID | CDR3 Sequence |
|---|---|---|---|---|---|---|
| AS76422 | 81 | GYTFAGNCLG | 162 | TYNNFGVANYADSVKG | 243 | DRRDGRRWSQPCEWNT |

TABLE 2

Anti-DLL3 human scFv CDR sequences

| Ab | CDR1 ID | CDR1 Sequence | CDR2 ID | CDR2 Sequence | CDR3 ID | CDR3 Sequence |
|---|---|---|---|---|---|---|
| AS56704 | 495 | VL: RASQVSSAVA | 496 | VL: SASSLYS | 497 | VL: QQASWSPIT |
|  | 498 | VH: GFNISSYMH | 499 | VH: YIYPSYGYTSYADSVKG | 500 | VH: GGYYYGMDY |
| AS56788 | 501 | VL: RASQSVSSAVA | 502 | VL: SASSLYS | 503 | VL: QQHYAPSLIT |
|  | 504 | VH: GFNISSSYMH | 505 | VH: YISSYYGYADSVKG | 506 | VH: YSYYYGMDY |
| AS56788 | 501 | VL: RASQSVSSAVA | 502 | VL: SASSLYS | 503 | VL: QQHYAPSLIT |
|  | 504 | VH: GFNISSYSMH | 505 | VH: Y1SSYYGYTYYADSVKG | 506 | VH: YSYYYGMDY |

Anti-DLL3 sdAb amino acid sequences were listed in Table 3. CDRs of the sdAb were underlined. Nucleic acid sequences encoding the anti-DLL3 sdAbs were shown in SEQ ID NOs: 368-448.

TABLE 3

Anti-DLL3 camel sdAb amino acid sequences

| SEQ ID | Camel sdAb | Amino Acid Sequence |
|---|---|---|
| 274 | AS63930 | EVQLAESGGGSVQAGGSLRLSCAASGYTYSGNYMAWFRQAPGNEREGVAVVYNIDGGGRFTTYADSVKGRFTISRGNDKNTVYLQMNSLKPEDSGMYYCAAEVADPTWGSRDQRRYKYWGQGTQVTVSS |
| 275 | AS63932 | QVQLEESGGGSVQAGGSLRLSCVASGYTYGSTFMGWFRQNPGKEREGVAVIYTGGGSTWYASSVKGRFTISQDNAKNTVYLQMNSLKPEDTAMYYCAARYGSGNVNYWGQGTQVTVSS |
| 276 | AS63951 | QVHLMESGGGSVQAGGSLRLACETSRDIYGNNCMAWFRQAPGKEREGVASIYPAGGRPYYADSVKGRFTISQDNAKNTVYLQMDSLKPEDTAMYYCAARSFSIAVCATRSGITRSNFAYWGQGTQVTVSS |
| 277 | AS63984 | QVKLVESGGGSVQAGGSLRLSCAASGYTYSSNFMGWFRQAPGKEREGVATIVSGGGTTYYADSVRGRFTISQDNAKNTVYLQMNSLKPEDTAMYYCAAGGPVTNAPRWYPLRPPGYNYWGQGTQVTVSS |
| 278 | AS63987 | QVRLVESGGGSVQAGGSLRLSCEATGYRNCMAWFRQAPGKEREGVAVIYTPSGITDYASSVKGRFTISQNNARNTQYLQMNSLKPEDTAMYYCAADRPFVCNIANMRRSSNWGRGTQVTVSS |
| 279 | AS63997 | QVRLVESGGGSVQAGGSLRLSCAGSFSGYGVSTMAWFRQAPGKEREGVAAITVGSGNTYYADSVKGRFTISRDNAKRTVFLQMNSLKPEDTAMYYCAVGYLSGGSWDVPGRYNYWGQGTQVTVSS |
| 280 | AS64047 | QVHLVESGGGSVQAGGSLRLSCAASQYVYRWDLMGWFRQAPGKEREAVAAVYTGDGITYYADSVKGRFSISQDNAKNTVYLQMNSLKPEDTGMYFCAAGFVSGGRWNQSYRYKYWGQGTQVTVSS |
| 281 | AS64052 | QVHLMESGGGSVQAGGSLRLSCAASGYTYRSNFMGWFRQAPGKEREGIATIHSGVATTYYADSVKGRFTISQDNAKNTVYLQMNSLKPEDTAMYYCAAGGPPANADRWYPLRPPGYNYWGQGTQVTVSS |
| 282 | AS64062 | QVRLVESGGGSVQVGGSLRLSCAASRSPYSSSRCMGWFRQAPGKEREGVAALYTGGGSTSYADSVKGRFTISQDNAKNTVYLQMNSLKPEDTAMYYCAAVVPRGGSCRLDERGYYHWGQGTQVTVSS |
| 283 | AS64072 | QVQLVESGGGSVQAGGFLRLSCALSGYSYYINLMAWFRQAPGKEREAVAAHGPVSGTAYYTDSVKGRFTISRDPGKNTMYLQMFSLQPEDTALYYCAAETTMGWAHERGYRYWGQGTQVTVSS |

TABLE 3-continued

Anti-DLL3 camel sdAb amino acid sequences

| SEQ ID | Camel sdAb | Amino Acid Sequence |
|---|---|---|
| 284 | AS64097 | QVHLMESGGGSVQAGGSLRLSCEASGYTYSRNCMGWFRQAP GKEREGVAAINTGGGSTYYADSLEGRFTISQDNAKNTMYLQM NSLKPEDTAMYYCAAGPDLGGSWCRPVERAFTYWGQGTQVT VSS |
| 285 | AS64114 | QVQLQESGGGSVQAGGSLTLSCEASGNTYSTNYMGWFRQAPG KEREEVAVIYTRGGHTYYVDSVRGRFTISQDNAKNTVYLQMN SLKPEDTAMYYCAAASRHRLRLNNPRDYDYWGQGTQVTVSS |
| 286 | AS64123 | QVQLAESGGGSVQAGGSLRLSCAASGYTYTSNWLGWFRQAPG KEREEVAIIYTGSGSTHYRSSVKGRFTISQDNAKNTVYLQMNSL KPEDTAMYYCAARFSEYNYWGQGTQVTVSS |
| 287 | AS64130 | EVQLAESGGGSVQAGGSLRLSCAASGYTYRSNFMGWFRQAPA KEREGVATIDSRGTITYYADSVKGRFTISQDNEKNTVYLQMNSL KPEDTAMYYCAAGGPRTNDDRWYPLRPPGYNYWGQGTQVTV SS |
| 288 | AS64137 | QVRLVESGGGSVQAGGSLRLSCAASGSTYSTNFMGWFRQAPG KEREGVATLVTWVERTAYADSVKGRFTISQDRAKNTVYLQMNS LKPEDTAMYYCAAAASTDVRLLDPGDFAYWGQGTQVTVSS |
| 289 | AS64142 | QVHLMESGGGLVQTGGSLRLSCTASGFTFDRNAMRWYRQAPG KEREGVSCIDWTGANIAYADSVKGRFTISRDNAKNTLYLQMNS LKPEDTGMYYCAADTTSGYCSGFWSTSRYSWGQGTQVTVSS |
| 290 | AS64154 | QVQLKESGGGSVQAGGSLRLSCTASGYTYRYLYMGWFRQTPG KEREGVACIYTGSGSTGYADSVKGRFTISQDNAKNTVYLQMNN LKPEDTAMYYCAASSPRWGGTCRRWSQYNYWGQGTQVTVSS |
| 291 | AS64160 | EVQLVESGGGSVQAGGSLRLSCAASVYTSSSYCMGWFRQAPG KEREGVAAMCFGGLVTHYADSVKGRFTISQDNAKNTVYLQMN SLKPEDTAMYYCAADFGRDKNYLRPLLPHAYNYWGQGTQVT VSS |
| 292 | AS64228 | QVQLKESGGGSIQAGGSLRLSCAASGVSYNRCSMGWYRQAPG KGRELVSRIQPGGNTYYADSVKGRFTVSQDNAKNTVSLQMNS LKPEDTAMYYCNALCWRENVNYWGQGTQVTVSS |
| 293 | AS64300 | QVHLVESGGGSVQTGGSLRLSCAVSGDIYNLMSMAWFRRAPG KEREGVAYINTIIGNTYYTDSVKGRFTISRDNSKNTLYLQMNNL KPEDTAMYYCAAFNYGGAWYEERSYKYWGQGTQVTVSS |
| 294 | AS64380 | EVQLVESGGGSVQAGGSLTLSCEASGNTYSSNYMGWFRQAPG KEREEVAVIYTRGGHTYYVDSVRGRFTISQDNAKNTVYLQMN SLKPEDTAMYYCAASSRHRLGLNNPRDYDYWGQGTQVTVSS |
| 295 | AS64395 | QVRLVESGGGSVQAGGSLRLSCAASGSTYSTNFMGWFRQAPG KEREGVATLVTWAERTAYADSVKGRFTISQDRAKNTVYLQMN GLKPEDTAMYYCAAAASTAVRLLDPGDFAYWGQGTQVTVSS |
| 296 | AS64443 | QVHLVESGGGSVQAGGSLRLSCAASGYTDSSVYIGWFRQAPG KEREEVAIIYTGGESTHYRSSVKGRFTVSQDNAKNTLYLQMNS LKPEDTAMYYCAARFPAVTYWGQGTQVTVSS |
| 297 | AS64511 | QVQLVESGGGSVQAGGSLRLSCAASRATYSTNYISWFRQAPGK EREAVATITTGDGETAYADSVKGRFTISRDNAKNTVYLQMNSL KPEDTAMYYCAANLRIGGDWFDGRDFRAWGQGTQVTVSS |
| 298 | AS64536 | QVKLVESGGGSVQAGGSLRLSCAASRYTDNFVYMGWFRQAPG KEREGVALIYPGGGSTYYASSVKGRFTISQDNAKGTVHLQMNN LKPEDTAMYYCAAKWGLGGGGLKSDTYMYWGQGTQVTVSS |
| 299 | AS64597 | QVHLVESGGGSVQAGGSLRLSCAASGYTYRVNFMGWFRQTPG KEREGVATIDSGVGTTYYADSVKGRFTISHNNAKNTIYLQMNS LKPEDTAMYYCAAGGPPTDGDRWYPLRPPGYNYWGQGTQVT VSS |
| 300 | AS64617 | QVQLVESGGGSVQAGGSLRLSCAASGYTDRCSMAWYRQAPG KERELVSRISTSGFTNYAASVKGRFTISQDNAKNTVYLQMNSLN PGDTGMYYCAIIVGRTCSLNYWGNGILVTVSS |

TABLE 3-continued

Anti-DLL3 camel sdAb amino acid sequences

| SEQ ID | Camel sdAb | Amino Acid Sequence |
|---|---|---|
| 301 | AS64634 | QVRLVESGGGSVQAGGSLRLSCAASGYSFRGDFMCMGWFRQT<br>PGKGREGVAVFYPGGGSTNYADSAKGRFTISQDNAKNTMYLQ<br>MNTLKPEDTAMYYCAARRWVSGTCYWDSDFHYWGQGTQVT<br>VSS |
| 302 | AS69498 | QVQLQESGGGSVQAGGSLRLSCEASGNTYSSNYMAWFRQAPG<br>KEREEVAVIYTRGGHTYYIDSVRGRFTISQDNAKNTVYLQMNS<br>LKPEDTAMYYCAASSRHRLRLSDPRDYDYWGQGTQVTVSS |
| 303 | AS69500 | QVRLVESGGGSVQAGGSLRLSCAADRYTYSSACMGWFRQAPG<br>KEREGVASIFTGTGGSTYYADSVKGRFTISQDNAKNTVYLQMN<br>SLKPEDTAIYYCAARAFQVGYCYLRTDVYNYWGQGTQVTVSS |
| 304 | AS69527 | EVQLAESGGGSVQAGGSLRLSCVASRYTFSSTCMAWFRQAPG<br>KEREEVAAIYTDDGSTWYADSVKGRFTISRDNAKNTVYLQMN<br>SLKPEDTAMYYCAARRWACPRVGSWHEFAYWGQGTQVTVSS |
| 305 | AS68280 | QVQLVESGGGSVHPGGSLRLSCAASGSTYSSNYLGWFRQAPG<br>KGRDWVAAISTGDGATAYADSVKGRFTISQDNAKNTVYLQMN<br>SLKLEDSAMYYCAAARGRFIDWTKATQYDYWGQGTQVTVSS |
| 306 | AS68355 | QMQLVESGGDSVQAGGSLRLSCAASGYTYSGVCMGWFRQAP<br>GKEREGVAAIDSDGSTSYADSVKGRFTISKDNAKNTLYLQMNS<br>LKPEDTAMYYCAAAIVGGFNAYCSGGYVLDFGAWGQGTQVT<br>VSS |
| 307 | AS69443 | EVQLAESGGGSVQAGGSLRLSCSASGFTFDDSDMAWYRQAPG<br>DGCDLVSTISSDGSTYYADSVKGRFTISQDNAKNTVYLQMHSL<br>KPEDTAVYYCAADFLTGFYYSDSPHPAPCSASDFGYWGQGTQV<br>TVSS |
| 308 | AS75376 | QVQLKESGGGSVQAGGSLRLSCAASGYTYSSHSMGWFRQAPG<br>KEREGVAVIYTGDGSTYYADSVKGRFTISQDNAKNTVYLQMNS<br>LKPEDTAMYYCAADPNPDYMLPFRPSRRSWWGQGTQVTVSS |
| 309 | AS75387 | QVHLVESGGGSVQAGGSLRLSCAASGYPYSSPCMAWFRQAPG<br>KEREGVLVAYTGGDIQYLTDSVKGRFTISRDNAKNTVYLQMNS<br>LKPEDTAMYYCAADLRLPRAGGCAYSYWGQGTQVTVSS |
| 310 | AS75695 | QVRLVESGGGSVQAGGSLRLSCVASGYTVSAYCMGWFRQVLG<br>KGRERIAFIDAGGATIYADPVKGRFTISKDNAKNTLYLQMNSLK<br>PEDTAMYYCVADRRGRVRRCEYNAWGQGTQVTVSS |
| 311 | AS76169 | QVHLMESGGGSVQAGGSLRLSCAASGYIYSSFCMGWFRQAPG<br>KEREVVAYIRDNIMTSYTDSVKGRFTISKDNAKRTLYLQMNGL<br>KPEDTGMYYCAVDRGGYANSCAVAARYDYWGRGTQVTVSS |
| 312 | AS63931 | EVQLAESGGGSVQAGGSLRLSCAGSFSGYGVSTMAWFRQAPG<br>KEREGVAAITVGSGNTYYADSVTGRFTISRDNAKRTVYLQMNS<br>LKPEDTAMYYCAAGWLSGGSWHVPGRYNYWGQGTQVTVSS |
| 313 | AS63937 | QVKLVESGGGSVQAGGSLRLSCAASGSTISSRPMAWFRQAPGK<br>EREGVACIHTGLGRTYYADSVKGRFTISQDNAKNTVYLQVNSL<br>KPEDTAMYYCAADSRRPCMVAAGYTYWGQGTQVTVSS |
| 314 | AS63948 | QVQLVESGGGSVQAGGSLRLSCTASGYTYRYLYMGWFRQTPG<br>KEREGVACIYTGSGSTGYADSVKGRFTISQDNAENTVYLQMNS<br>LKPEDTAMYYCAAASPRWGGTCRRWSEYNYWGQGTQVTVSS |
| 315 | AS63956 | QVHLVESGGGLVQAGGSLRLSCAASGFTYSNCCMRWYRQAPG<br>KARELVSLINSSGGTYYADSVRGRFTISKDNAKNTLYLQMNSL<br>KPEDTAMYYCAAYQAKYCSGPCAPPTDWGQGTQVTVSS |
| 316 | AS63965 | QVQLVESGGGSVQAGGSLRLSCVASGYSSGSCRMGWYRQAPG<br>KERELVSKVISDGTTVYADSVKGRFTLSQGNAKNTVYLQMSSL<br>LPEDTAMYYCNAWCREYPGGILNNGWGQGTQVTVSS |
| 317 | AS63993 | QVKLVESGGGLVQAGGSLRLSCTVSGFTFDDLVMAWFRQAPG<br>KERQLVSLVATAGNSVYADSVKGRFTLSRDNAHSTAYLQMNGL<br>KPEDTAMYYCAARTDSEHAFKFWGQGTQVTVSS |
| 318 | AS63999 | EVQLVESGGGSVQAGGSLRLSCAASGYTYSSNWMGWFRQAP<br>GKEREEVAIIYTGGISTHYRSSVKGRFTISQDNAKNTVYLQMNS<br>LKPEDTAMYYCAARYTDYNYWGQGTQVTVSS |

TABLE 3-continued

Anti-DLL3 camel sdAb amino acid sequences

| SEQ ID | Camel sdAb | Amino Acid Sequence |
|---|---|---|
| 319 | AS64006 | QVHLVESGGGSVQAGGSLRLSCEVSGYTGDTTYIGWFRQAPG KEREGVALIYTSGTSEYYADSVKGRFIISRDNAKNTVYLQMNSL KPEDTAMYYCGARSRTMMYWGQGTQVTVSS |
| 320 | AS64057 | QVQLEESGGGLVQTGGSLRLSCTASGFTFDRNAMRWYRQAPG KEREGVSCISWTGANIAYADSVKGRFTISRDNAKNTLYLQMNS LKPEDTGMYYCAADTTSGSCSGFWSTSRYYWGQGTQVTVSS |
| 321 | AS64060 | QVKLVESGGGSVQAGGSLRLSCAASGSTYCTYRMSWFRQAPG KEREFVAVIDSGGSTSYADSVKGRFTISRDNAKNTVYLQMNSL KPEDTAMYYCKTDPTIGCPQTYRYNYWGQGTQVTVSS |
| 322 | AS64071 | QVHLMESGGGSVQAGGSLRLSCVASGNTYRLNSMGWFRQAP GKEREGVAFIVMIRGTTYYGASVKGRFTISQDNAQTTVYLQMS SLKPEDTAMYYCAASTKDQFYVFNPIGYDSWGQGTQVTVSS |
| 323 | AS64093 | QVHLVESGGGSVQAGGSLRLSCATSRYIYGNNCMAWFRQAPG KEREGVASIYPAGGRTYYADSVKGRFTISQDNAKNTVYLQIDSL KPEDTAMYYCAARSFSIGVCATQSGITWSNFAYWGQGTQVTVS S |
| 324 | AS64118 | QVQLAESGGGSVQAGGSLRLSCAASGYTYSACRMAWYRQAP GKERELVSFINSAGSTYYADSVKGRFAISRDNAKTTVYLQMNA LKAEDTAIYYCNTWDSSCRFQYWGQGTQVTVSS |
| 325 | AS64120 | QVRLVESGGGSVQAGGSLRLSCETSRYIYGNNCMAWFRQAPG KEREGVASIYPAGGRPYYADSVKGRFTISQDNAKNTVYLQMDS LKPEDTAMYYCAARSFSIADCATQSGITRSNFAYWGQGTQVTV SS |
| 326 | AS64124 | QVKLVESGGGSVQTGGSLRLSCAVSTYTPSNNYMGWFRQAPG KEREGVAAIATIGGTTRYADSVKGRFTISQDGAKNTIYLQMNGL KPEDTAMYYCAAGRPYSLPLPLPLESGAYRYWGQGTQVTVSS |
| 327 | AS64135 | QVKLVESGGGSVQAGGSLRLSCVASTSTYCRYYMRWYRQAPG KEREFVSAMQPDGTTSYSDSVKGRFTMSQDRANNMLYLQMNS LRPEDTAMYYCKRDPMGGSRTPCTSAWGQGTQVTVSS |
| 328 | AS64163 | QVRLVESGGGSVQAGGSLRLSCAVSGYRYRWNCMAWFRQAP GKEREGVAAISTGSGSTYYAGSVKGRFTISQDNAKNMYLQMNS LKPEDTAMYYCAADPSVCPGGMWYSKEYRYWGQGTQVTVSS |
| 329 | AS64182 | QVHLMESGGGSVQAGGSLRLSCTASGQTSRYLYMGWFRQTPG KEREGVACIYTGSGSTGYADSVKGRFTISQDNAKNTVYLQTNS LKPEDTAMYYCAASSPHWGGTCRRWSEYKYWGQGTQVTVSS |
| 330 | AS64183 | QVHLVESGGGSVQAGGSLRLSCAASGHTYSANCMAWFRRAPG KEREWVASVYTDDDSTMYTDSVKGRFTIFQDNAKNTVYLQM NSLKPEDTGMYICAADLSGGPAGCGYTHWGQGTQVTVSS |
| 331 | AS64207 | EVQLVESGGGSVQAGGSLRLSCAASGYTYSSNFMGWFRQAPG KEREGVATIVSGGGTTYYADSVRGRFTISQDNAKNTVYLQMNS LKPEDTAMYYCAAGGPPTNGAKWYPLRPPGYNYWGQGTQVT VSS |
| 332 | AS64276 | QVHLMESGGGSVQAGGSLSLSCVVSGYTGSSRCMAWFRQAPG KEREAVAQIFTGRGTTGYADSVKGRFTISQDNAKNTVYLRMNS LRPEDTAIYYCAASLGPGRGACGYNYWGQGTQVTVSS |
| 333 | AS64336 | QVQLVESGGGSVQAGGSLRLSCTTSGRTYSSCSMGWYRQAPG KERELVSHIFSDGSRYYADSVKGRFTISQDNAKNTVYLQMNSL KPEDTAMYYCNRRTGWAPRCAVPGYWGQGTQVTVSS |
| 334 | AS64346 | QVHLVESGGGSVQAGGSLRLSCAASGYTYFMGWFRQAPQKER EWVATIGTGDIFNGAAYYVDSVKGRFAISQDNAKNTVYLQMN SLKPEDTAVYVCAAVQSKSSNYVLRDASTYNYWGQGTQVTVS S |
| 335 | AS64420 | EVQLVESGGGSVQAEGSLRLSCAASGDTSRSVWMGWARQVPG KEREVVATISTAGGSTWYTDSVKGRFTISQDNAKNTVYLQMNS LKPEDTAIYYCAARSRYATYWGQGTQVTVSS |

TABLE 3-continued

Anti-DLL3 camel sdAb amino acid sequences

| SEQ ID | Camel sdAb | Amino Acid Sequence |
|---|---|---|
| 336 | AS64473 | QVRLVESGGGSVQAGGSLRLSCTASGYTYRYLYMAWFRQTPG KEREGVACIYTGSGTTGYADSVKGRFTISQDNAKNTVYLQMNS LNAEDTAMYYCAASSPQWGGTCRRWSEYNYWGQGTQVTVSS |
| 337 | AS64475 | QVQLQESGGGSVQAGGSLRLSCAASGYTWSRNWMGWFRQAP GKEREGFATITISGGSTWYADSVKGRFTISLDNAGNTVYLQMN SLKPEDTAMYYCAARDTARTYWGQGTQVTVSS |
| 338 | AS64513 | EVQLVESGGGSVQAGGSLRLSCVASDYPYIDNCMGWFRQGPG KEREGVAAACTGGGSTYYADSVKGRFTISRDNAKNTVYLQMN SLKPEDTDVYYCATGYYSGSGPGYLLPWRYNYWGQGTQVTVS S |
| 339 | AS64562 | EVQLVESGGGSVQAGGSLRLSCAASGYTARRDFMAWFRQVPG KEREGVAVIHTGDTTYYADSVKGRFTISRDNAQNIMNLQMNS LKPEDTAMYYCAAGFRPRGGGYTGDVLAQAAAYNYWGQGTQ VTVSS |
| 340 | AS64583 | EVQLAESGGGLVQAGGSLRLSCTASGFTIAVYTMGWFRQAPGK EREGISCTSWAGGRTYTADSVKGRFTISRDNAKNTLYLQMNSL KPEDTAMYYCAAKAHPDCSGDWSPSGYEYWGQGTQVTVSS |
| 341 | AS64594 | QVHLVESGGGSVQAGGSLRLSCAASGYTYNSNYMGWFRQAP GKEREGVALIYTGGGSTYYADSVKGRFTISRDNAKNTVYLQMN SLKPEDTAMYYCSVRTQTRNYWGQGTQVTVSS |
| 342 | AS64605 | QVKLVESGGGSVQAGGSLRLSCAVSRYPYSSICMGWFRQAPGK ESEGVARIYTGTGSTWYTDSVKGRFTIARDNAQNTVYLQMNSL KPEDTAMYYCAARSNSYSYSSCDYGPLTRGGYNFWGQGTQVT VSS |
| 343 | AS64606 | EVQLAESGGGSVQAGGSLRLSCAVSGYTSRSNYMGWFRQAPG KEREGVALIYTRGGSTYYASSVKGRFTISQDSAKKTYLQMNSV KPEDTAMYYCALRLDEKMYWGQGTQVTVSS |
| 344 | AS68121 | EVQLAESGGGSVQAGGSLRLSCDASGYTYSRNCMGWFRQAPG KEREGVAAFYTDYIRFGRTYYADSVKGRFTIFQDNAKNTVYLQ MNSLKPEDTAMYYCAADPGSRTDDSCGTSYNKGNFGYWGQG TQVTVSS |
| 345 | AS68170 | QVQLVESGGGSVQAGGSLRLSCTASGYTYRSNCMGWFRQAPG KEREGVATIYTGGGRNLYYADSVKGRFTISRDNAKNTLYLQMN SLKPEDSARYYCAAASDVAVGVNSCGGRTAGFDAWGQGTQVT VSS |
| 346 | AS63964 | QVRLVESGGGSVQAGGSLRLSCSASGYTYSYNNMGWFRQAPG NEREGVAAISGGRFTAYADSVKGRFTISRDNAENTLYLQMNNL KPEDTGMYYCAAEVVDPTWGSRDQRRYKYWGQGTQVTVSS |
| 347 | AS64116 | QVKLVESGGGSVQAGGSLRLSCAASGYIYSCVGWFRQAPGKE REGVAGISTGGGGTVYADSVKGQFTISRDNAKNTVYLQMDSLK PEDTAMYYCAADRWNSFANCGAWGRYTYWGQGTQVTVSS |
| 348 | AS68270 | QVQLAESGGGSVQAGGSLRLSCVASGYPSSTYYMLSMAWFRQ APGKEREGVAAITSGTGSTSYADSVKDRFTISKDYANNTLYLHI NNLKPEDTAMYYCAAASGWIVPSRSLTANLYRYWGQGTQVTV SS |
| 349 | AS68320 | QVHLVESGGDSVQAGGSLRLSCAASGYTYNTNYMGWFRQAP GKEREGVAAIYRHSGNTAYADSVKGRFTISQDYAKNTVYLQMN SLKPEDTAMYYCAAGRAGPWALMRPTEFGYWGQGTQVTVSS |
| 350 | AS68351 | QVQLEESGGGLVQPGGSLRLSCAASGDTFRAYYMNWVRQAPG KGFEWVSGISASGGRTSYADSVKGRFTISRDNAKNTLYLQLNSL STEDTGMYYCVKGAVRLSTSSVRDSSWGQGTQVTVSS |
| 351 | AS75378 | QVQLEESGGGSVQAGGSLRLSCVVSGNTRSTTYMGWFRQAPG KEREGVAIVYTGGRDTYYAASVKGRFTISQDNAKTTIYLQMNS LEPEDTAMYYCAARSYEYTYWGRGTQVTVSS |
| 352 | AS75383 | EVQLAESGGGSVQAGGSLRLSCVASGYTFSSYCLGWFRQAPGK QRQGVATFNNRGVANYHDSVKGRFTASVDNAKNTLLLQMNSL EPDDTAMYYCAADRRYGRQWYQPCEWNTWGQGTQVTVSS |

TABLE 3-continued

Anti-DLL3 camel sdAb amino acid sequences

| SEQ ID | Camel sdAb | Amino Acid Sequence |
| --- | --- | --- |
| 353 | AS75751 | QVRLVESGGGSVQAGGSLRLSCVASGYFYNTYYFMGWFRQAP<br>GKEREGVAAIDTDGRTSYADSVKGRFTISKDNAKNTLYLQMNS<br>LKPEDTAMYYCAAGFGYMNVIQALNGMRQNPDYWGQGTQV<br>TVSS |
| 354 | AS76422 | QVKLVESGGGSVQAGGSLRLSCAASGYTFAGNCLGWFRQAPG<br>KGREGVVTYNNFGVANYADSVKGRFTVSQDNAKNTLLLQMN<br>SLEPEDTAMYYCAADRRDGRRWSQPCEWNTWGQGTQVTVSS |

Amino acid sequences of VH and VL domains of anti-DLL3 human scFvs were listed in Table 4. Nucleic acid sequences encoding VH or VL domain of anti-DLL3 human scFvs were shown in SEQ ID NOs: 511-514.

TABLE 4

Anti-DLL3 human scFv amino acid sequences

| scFv | SEQ ID | Amino Acid Sequence |
| --- | --- | --- |
| A556704 | 507 | VL:<br>DIQMTQSPSSLSASVGDRVTITCRA<br>SQSVSSAVAWYQQKPGKAPKLLIYS<br>ASSLYSGVPSRFSGSRSGTDFTLTI<br>SSLQPEDFATYYCQQASWSPITFGQ<br>GTKVEIK |
|  | 508 | VH:<br>EVQLVESGGGLVQPGGSLRLSCAAS<br>GFNISSSYMHWVRQAPGKGLEWVAY<br>IYPSYGYTSYADSVKGRFTISADTS<br>KNTAYLQMNSLRAEDTAVYYCARGG<br>YYYHGMDYWGQGTLVTVSS |
| A556788 | 509 | VL:<br>DIQMTQSPSSLSASVGDRVTITCRA<br>SQSVSSAVAWYQQKPGKAPKLLIYS<br>ASSLYSGVPSRFSGSRSGTDFTLTI<br>SSLQPEDFATYYCQQHYAPSLITFG<br>QGTKVEIK |
|  | 510 | VH:<br>EVQLVESGGGLVQPGGSLRLSCAAS<br>GFNISSYSMHWVRQAPGKGLEWVAY<br>ISSYYGYTYYADSVKGRFTISADTS<br>KNTAYLQMNSLRAEDTAVYYCARYS<br>YYYGMDYWGQGTLVTVSS |

Example 3. Generation of Monospecific Camel CARs

The amino acid sequences of anti-DLL3 camel sdAb fragments were provided above in Table 3 and the nucleic acid sequences of anti-DLL3 camel sdAb fragments were provided in SEQ ID NOs: 368-448. sdAb fragments of Table 3 and additional sequences were used to generate CAR constructs (SEQ ID NOs: 476-484). CAR3 scFv (SEQ ID NO: 473), which is a human anti-DLL3 scFv, was also used to generate a CAR construct as a reference (CAR3). A full length CAR contains from the N-terminus to the C-terminus: a CD8α signal peptide (SEQ ID NO: 465), a DLL3 binding domain sdAb provided in Table 3, a CD8α hinge domain (SEQ ID NO: 466), a CD8α transmembrane domain (SEQ ID NO: 467), a CD137 intracellular domain (SEQ ID NO: 468) or a CD28 intracellular domain (SEQ ID NO: 469), and a CD3ζ intracellular domain (SEQ ID NO: 470). Schematic representation of a CAR construct is shown in FIG. 1. Nucleic acid encoding the CAR fragment was then cloned into a lentiviral vector to create full length CAR construct in a single coding frame, using human EF1 alpha promoter for expression. The resulting CAR backbone vector was named "PLLV-hEF1α-DLL3".

Example 4. Generation of Camel Anti-DLL3 CAR-T Cells

Preparation of Lentivirus

The lentivirus packaging plasmid mixture including pCMV-ΔR-8.47 and pMD2.G (Addgene, Cat #12259) was pre-mixed with PLLV-hEF1α-DLL3 vectors at a pre-optimized ratio (1:1:1:2) in the present of polyethylenimine before added to the HEK293 cells. The supernatants were collected after overnight incubation. The virus-containing supernatants were filtered through a 0.45 μm PES filter, and ultra-centrifuged to concentrate lentiviruses. The virus pellets were rinsed with pre-chilled DPBS. The viruses were aliquoted properly before stored at −80° C. immediately. Virus titer was determined by measurement of transduction efficiency to supT1 cell line via flow cytometric assay.

Collection and Transduction of T Lymphocytes

Leukocytes were collected from healthy donors by apheresis. Peripheral blood mononuclear cells (PBMCs) were isolated using Ficoll-Paque™ PLUS Media according to manufacturer's protocol. Human T cells were purified from PMBCs using Pan T cell isolation kit (Miltenyi, Cat #130-096-535), following manufacturer's protocol. The purified T cells were subsequently pre-activated for 48 hours with human T cell activation/expansion kit (Miltenyi, Cat #130-091-441) according to manufacturer's protocol, in which anti-CD3/CD28 MACSiBead particles were added at a bead-to-cell ratio of 1:2. The pre-activated T cells were transduced with lentivirus stock in the presence of 7 μg/mL polybrene. The transduced cells were then transferred to the cell culture incubator for transgene expression under suitable conditions.

Example 5. Evaluation of In Vitro Activity of Camel Anti-DLL3 CAR-T Cells

In Vitro Cytotoxicity Assay

On day 6 post transduction, transduced T cells were harvested and co-incubated with DLL3-expressing tumor cell line SHP-77 at an effector (CAR-T) to target cell ratio of 2:1 and 5:1 for 20 hours. CAR3 CAR-T cells were used as a reference in all assays to compare assay variation and/or act as a control. Un-transduced T cells (UnT) were used as a negative control.

Figure 2:
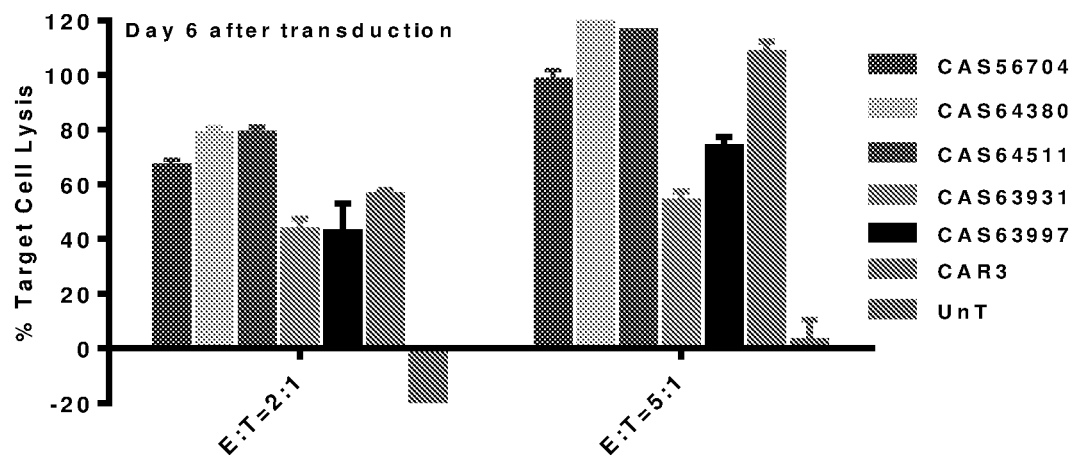
FIG. 2 shows the results of an in vitro cytotoxicity assay of T cells expressing exemplary monospecific CARs comprising various camel anti-DLL3 sdAbs against small cell lung cancer cell line SHP-77 with an E:T of 2:1 or 5:1. The results for the CARs are depicted in the order as in the legend shown on the right.

The cytotoxicity of the transduced T cells was determined by a lactate dehydrogenase (LDH) assay. Results show that CAR3 CAR-T and some anti-DLL3 CAR-Ts exhibit strong anti-tumor activities in vitro against SHP-77 cells, while UnT has no target cell killing effect (FIG. 2).

IFN-γ and TNF-α Release Detection

Figure 3A:
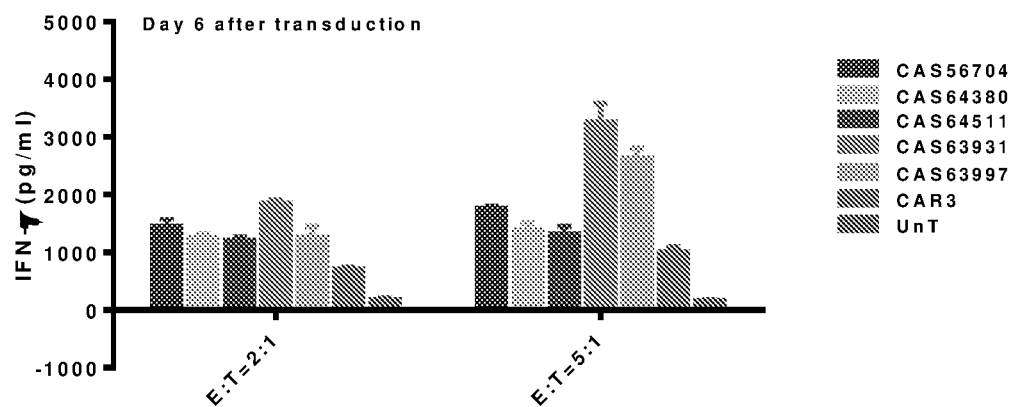
FIG. 3 shows the results of cytokine release levels of T cells expressing exemplary monospecific CARs comprising various camel anti-DLL3 sdAbs, after co-incubated with DLL3-expressing tumor cell line SHP-77. IFN-γ release levels and TNF-α release levels (with an E:T of 2:1 or 5:1) are showed in FIG. 3A and FIG. 3B, respectively. In each figure, the results for the CARs are depicted in the order as in the legend shown on the right.
Figure 3B:
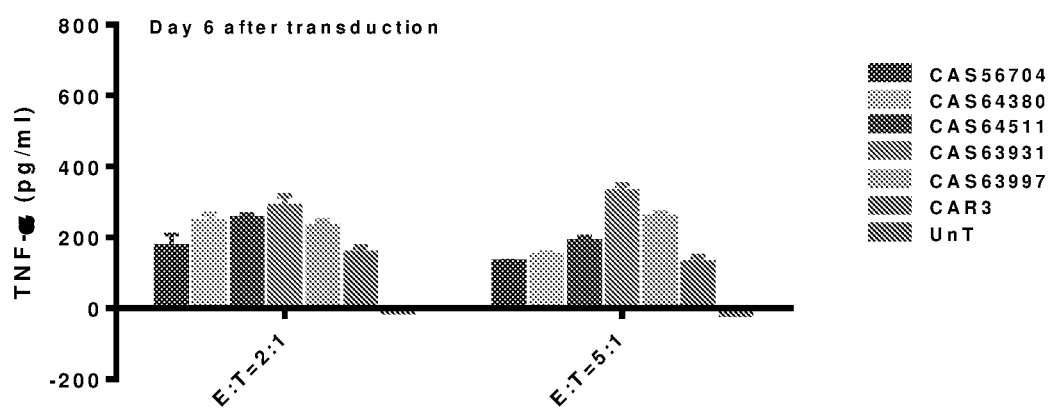
Figure 6A:
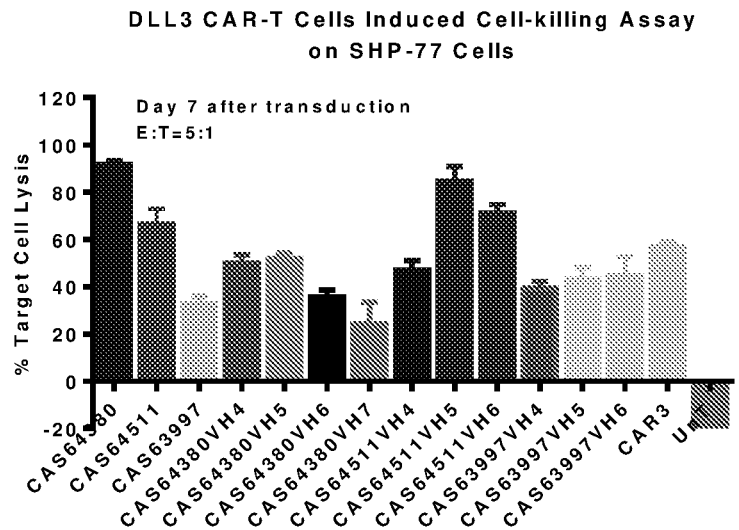
FIG. 6 shows the results of an in vitro cytotoxicity assay of T cells expressing exemplary monospecific CARs comprising various humanized camel anti-DLL3 sdAbs against small cell lung cancer cell line SHP-77 (FIG. 6A, 6B) and NCI-H82 (FIG. 6C, 6D).
Figure 6B:
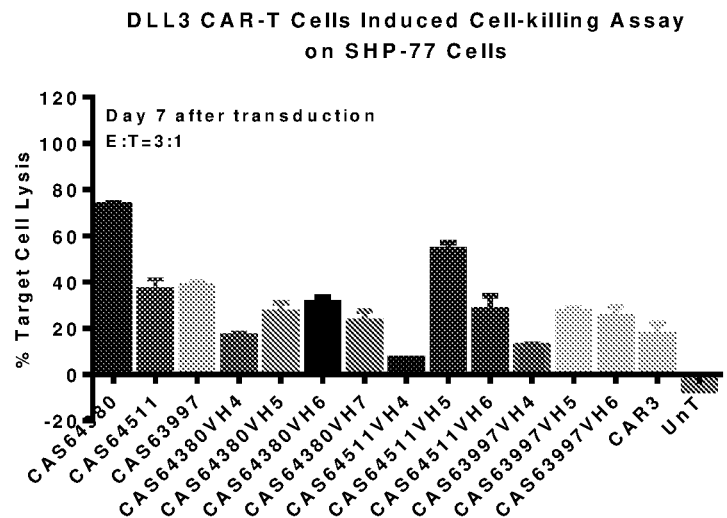
Figure 6C:
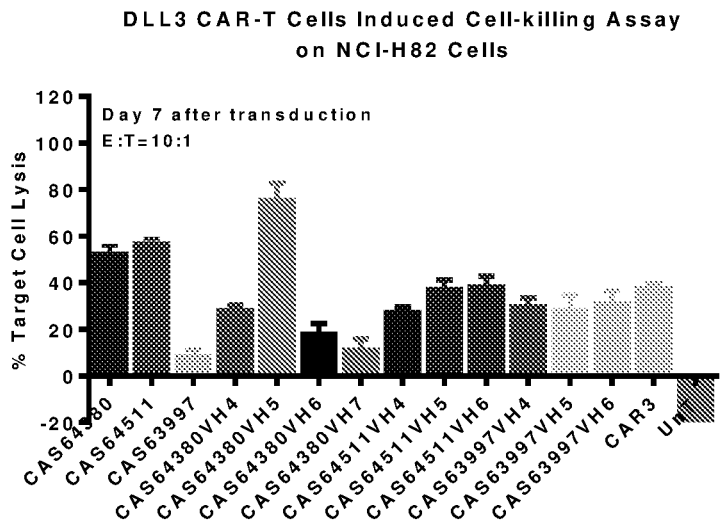
Figure 6D:
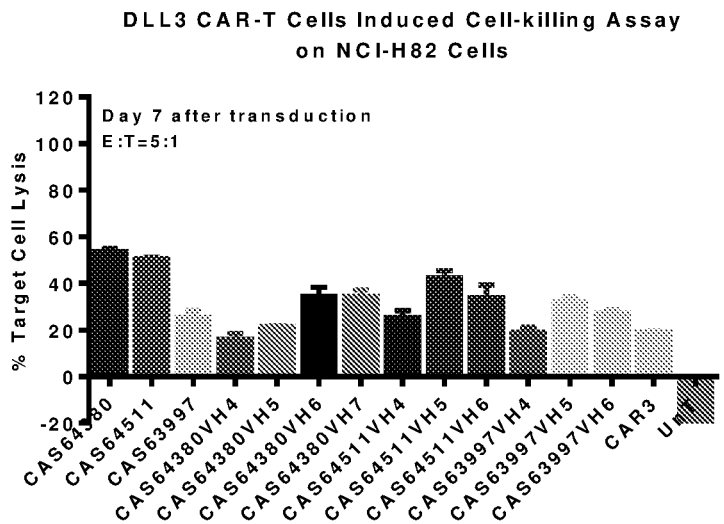

Additionally, supernatants from the in vitro cytotoxicity assay were collected to assess CAR-induced cytokine release, e.g., interferon gamma (IFN-γ) and TNF-α release. As shown in FIG. 3A and FIG. 3B, CAR3 CAR-T and some anti-DLL3 CAR-Ts were stimulated by SHP-77 to produce IFN-γ and TNF-α, whereas UnT produced little IFN-γ and TNF-α. Protocols of IFN-γ and TNF-α release detection can be referred to CISBIO's human TNF-α kits and IFN-γ kits.

CAR-T Expansion by Long-Term Stimulation Assay

On day 0, $1 \times 10^5$ SHP-77 cells were plated in 24 well plates to establish a monolayer. On day 1, transduced T cells were counted and $2 \times 10^5$ viable CAR$^+$ T cells were plated on top of the SHP-77 cells in fresh media in the absence of cytokines. On day 3, a new $1 \times 10^5$ SHP-77 cells monolayer were plated on top of the CAR-T cells. On day 4, viable CAR-T cells were counted for each well. One the same day, $2 \times 10^5$ CAR$^+$ T cells from wells that expanded (had at least this amount of cells) were re-plated to establish a new monolayer as on Day 1. The process was repeated to provide 3-4 rounds of stimulation. Fold expansion after each stimulation was calculated as [viable CAR$^+$ T cells on day 4]/$2 \times 10^5$, the amount of CAR T cells plated on day 1 of each stimulation. To normalize for cells discarded with each new stimulation, cumulative fold expansion was determined by [(fold expansion)×(fold expansion+1) . . . ].

After 3 rounds of stimulation, the fold expansions of different CAR-T constructs were calculated. As it was showed in FIG. 4, most CAR-T constructs expanded more than CAR3 CAR-T with 3 rounds of stimulation by SHP-77 tumor cells.

Example 6. In Vivo Efficacy Valuation of Camel CARs by CAR-T Cells Mediated Tumor Growth Inhibition The anti-tumor activity of the camel CARs was evaluated in a SHP-77 tumor model. SHP-77 cells were implanted subcutaneously in NOD/SCID mice and randomized into 7 groups (4 mice per group, day 0). Group 1: vehicle (PBS only); Group 2: UnT (negative control); Group 3: CAR3; Group 4: CAS64380; Group 5: CAS64511; Group 6: CAS63931; Group 7: CAS63997. Treatment with CAR-T cells, UnT cells or vehicle (PBS only) began when tumors were palpable (100 mm$^3$) and mice were euthanized when their tumor volumes reached about 3000 mm$^3$. Tumor volumes were measured 2 times per week. CAR-T cells were administered intravenously with $1 \times 10^6$ CAR positive T cells per mouse. Mice and tumors were monitored for about 21 days after tumor cell implantation.

As shown in FIG. 5, all selected camel CARs demonstrated anti-tumor activity in this animal tumor model.

Example 7. Humanization of Camel sdAbs

Selected camel sdAbs (SEQ ID NOs: 279, 294, 297, 312) were humanized using CDR grafting technology (see, e.g., U.S. Pat. No. 5,225,539). Briefly, the camel sdAb sequence was compared to those available in the Research Collaboratory for Structural Bioinformatics (RCSB) protein databank. A homology model of each camel sdAb was generated based on the nearest VH structures. From the model structure, residues that are in the proximity of CDRs or buried inside the molecule (i.e. with side chain solvent accessible surface area less than 15%) were identified.

Subsequently, each camel sdAb sequence was BLASTed against NCBI human germline V gene database to identify the human VH germline sequence (i.e. human acceptor) with highest identity to the sdAb (see, e.g., Foote and Winter, *J. Mol. Biol.* 224:487-499 (1992); Morea V. et al., *Methods* 20:267-279 (2000); Chothia C. et al., *J. Mol. Biol.* 186:651-663 (1985).) In the CDR grafting approach, CDRs of the human acceptor were replaced by those of the camel sdAbs, which produced the straight-graft sequence. Straight-graft antibody usually lost binding activity, which needed to be restored by replacing the framework residues that were critical for the activity of the antibody with non-human residues. Amino acid residues that were in the proximity of CDRs or buried inside the molecule were usually important for the activity and structure of the antibody, and therefore should be potential back-mutation sites. A series of humanized variants were designed using this method. CDR amino acid sequences of the humanized variants were shown in Table 5. Full length amino acid sequences of the humanized variants were shown in Table 6. CDRs were underlined.

TABLE 5

Anti-DLL3 humanized sdAb CDR sequences

| Ab | ID | CDR1 Sequence | ID | CDR2 Sequence | ID | CDR3 Sequence |
|---|---|---|---|---|---|---|
| AS64380VH4 | 244 | GNTYS SNYMG | 254 | VIYTR GGHTY YVDSV RG | 264 | SSRHR LGLNN PRDYD Y |
| AS64380VH5 | 245 | GNTYS SNYMG | 255 | VIYTR GGHTY YVDSV RG | 265 | SSRHR LGLNN PRDYD Y |
| AS64380VH6 | 246 | GNTYS SNYMG | 256 | VIYTR GGHTY YVDSV RG | 266 | SSRHR LGLNN PRDYD Y |
| AS64380VH7 | 247 | GNTYS SNYMG | 257 | VIYTR GGHTY YVDSV RG | 267 | SSRHR LGLNN PRDYD Y |
| AS64511VH4 | 248 | RATYS TNYIS | 258 | TITTG DGETA YADSV KG | 268 | NLRIG GDWFD GRDFR A |
| AS64511VH5 | 249 | RATYS TNYIS | 259 | TITTG DGETA YADSV KG | 269 | NLRIG GDWFD GRDFR A |
| AS64511VH6 | 250 | RATYS TNYIS | 260 | TITTG DGETA YADSV KG | 270 | NLRIG GDWFD GRDFR A |
| AS63997VH4 | 251 | FSGYG VSTMA | 261 | AITVG SGNTY YADSV KG | 271 | GYLSG GSWDV PGRYN Y |
| AS63997VH5 | 252 | FSGYG VSTMA | 262 | AITVG SGNTY YADSV KG | 272 | GYLSG GSWDV PGRYN Y |

TABLE 5-continued

Anti-DLL3 humanized sdAb CDR sequences

| Ab | ID | CDR1 Sequence | ID | CDR2 Sequence | ID | CDR3 Sequence |
|---|---|---|---|---|---|---|
| AS63997VH6 | 253 | FSGYG VSTMA | 263 | AITVG SGNTY YADSV KG | 273 | GYLSG GSWDV PGRYN Y |

TABLE 6

Anti-DLL3 humanized sdAb amino acid sequences

| SEQ ID | Humanized sdAb | Amino Acid Sequence |
|---|---|---|
| 355 | AS64380VH4 | EVQLVESGGGLVQPGGSLRLSCAASGNTYSSNYMGWFRQAPG KGLEEVAVIYTRGGHTYYVDSVRGRFTISRDNAKNSLYLQMN SLRAEDTAVYYCAASSRHRLGLNNPRDYDYWGQGTLVTVSS |
| 356 | AS64380VH5 | EVQLVESGGGLVQPGGSLRLSCAASGNTYSSNYMGWFRQAPG KGLEEVAVIYTRGGHTYYVDSVRGRFTISQDNAKNSLYLQMN SLRAEDTAVYYCAASSRHRLGLNNPRDYDYWGQGTLVTVSS |
| 357 | AS64380VH6 | EVQLVESGGGLVQPGGSLRLSCAASGNTYSSNYMGWFRQAPG KGLEEVAVIYTRGGHTYYVDSVRGRFTISQDNAKNSVYLQMN SLRAEDTAMYYCAASSRHRLGLNNPRDYDYWGQGTLVTVSS |
| 358 | AS64380VH7 | EVQLVESGGGLVQPGGSLRLSCAASGNTYSSNYMGWFRQAPG KGREEVAVIYTRGGHTYYVDSVRGRFTISQDNAKNSVYLQMN SLRAEDTAMYYCAASSRHRLGLNNPRDYDYWGQGTLVTVSS |
| 359 | AS64511VH4 | EVQLVESGGGLVQPGGSLRLSCAASRATYSTNYISWFRQAPG KGLEAVATITTGDGETAYADSVKGRFTISRDNAKNSLYLQMN SLRAEDTAVYYCAANLRIGGDWFDGRDFRAWGQGTLVTVSS |
| 360 | AS64511VH5 | EVQLVESGGGLVQPGGSLRLSCAASRATYSTNYISWFRQAPG KGLEAVATITTGDGETAYADSVKGRFTISRDNAKNSVYLQMN SLRAEDTAMYYCAANLRIGGDWFDGRDFRAWGQGTLVTVSS |
| 361 | AS64511VH6 | EVQLVESGGGLVQPGGSLRLSCAASRATYSTNYISWFRQAPG KGREAVATITTGDGETAYADSVKGRFTISRDNAKNSVYLQMN RSLAEDTAMYYCAANLRIGGDWFDGRDFRAWGQGTLVTVSS |
| 362 | AS63931VH4 | QVQLVESGGGVVQPGGSLRLSCAGSFSGYGVSTMAWFRQAPG KGLEGVAAITVGSGNTYYADSVTGRFTISRDNSKNTLYLQMN SLRAEDTAVYYCAAGWLSGGSWHVPGRYNYWGQGTLVTVSS |
| 363 | AS63931VH5 | QVQLVESGGGVVQPGGSLRLSCAGSFSGYGVSTMAWFRQAPG KGLEGVAAITVGSGNTYYADSVTGRFTISRDNSKNTVYLQMN SLRAEDTAMYYCAAGWLSGGSWHVPGRYNYWGQGTLVTVSS |
| 364 | AS63931VH6 | QVQLVESGGGVVQPGGSLRLSCAGSFSGYGVSTMAWFRQAPG KGREGVAAITVGSGNTYYADSVTGRFTISRDNSKNTVYLQMN SLRAEDTAMYYCAAGWLSGGSWHVPGRYNYWGQGTLVTVSS |
| 365 | AS63997VH4 | QVQLVESGGGVVQPGGSLRLSCAASFSGYGVSTMAWFRQAPG KGLEGVAAITVGSGNTYYADSVKGRFTISRDNSKNTLYLQMN SLRAEDTAVYYCAVGYLSGGSWDVPGRYNYWGQGTLVTVSS |
| 366 | AS63997VH5 | QVQLVESGGGVVQPGGSLRLSCAASFSGYGVSTMAWFRQAPG KGLEGVAAITVGSGNTYYADSVKGRFTISRDNSKNTVYLQMN SLRAEDTAMYYCAVGYLSGGSWDVPGRYNYWGQGTLVTVSS |
| 367 | AS63997VH6 | QVQLVESGGGVVQPGGSLRLSCAASFSGYGVSTMAWFRQAPG KGREGVAAITVGSGNTYYADSVKGRFTISRDNSKNTVYLQMN SLRAEDTAMYYCAVGYLSGGSWDVPGRYNYWGQGTLVTVSS |

The camel and humanized sdAb sequences were fused with human IgG1 hinge and Fc, resulting the chimeric and humanized HCAb sequences. The DNAs encoding these HCAbs were synthesized and inserted into pTT5 vector. HCAb expression plasmids were used to transfect HEK293 cells. Crude HCAb proteins secreted to the medium were subjected to SPR affinity measurement as follows: briefly, capturing antibody anti-human Fc pAb (GE healthcare) was immobilized on a Biacore™ CM5 chip to approximately 6,000 RU using EDC-activated amine coupling chemistry. HCAb of interest was captured for 300 seconds onto the sensorchip surface. Human DLL3 (AdipoGen, AG-40B-0151) was flowed over the sensorchip surface at a series of increasing concentrations. Association and dissociation phases were monitored. Captured antibody and antigen were removed between cycles using 10 mM Glycine-HCl, pH 2.0 buffer in order to ensure a fresh binding surface for the antigen. The resulting sensorgrams were fit globally using a 1:1 binding model in order to calculate on- and off-rates (ka and kd, respectively), as well as affinities ($K_D$).

The binding affinities of some humanized sdAbs were measured and compared those of the original camel sdAbs (Table 7). Most of the humanized antibodies retained the binding affinities of the camel sdAbs. This example demonstrated that the humanization of sdAbs using our standard protocol was successful. Most of the sdAbs retained their binding affinities after humanization.

The scFvs have comparable $K_D$ values (AS56788 and AS56704 in Table 7) when assayed with the same procedure as described above.

TABLE 7

Monovalent binding affinity of camel and humanized antibodies as well as scFvs.

| Ligand | ka (1/Ms) | kd (1/s) | $K_D$ (M) |
| --- | --- | --- | --- |
| AS64380 | 6.7E+05 | 5.6E−03 | 8.4E−09 |
| AS64380VH4 | 3.1E+05 | 4.4E−03 | 1.4E−08 |
| AS64380VH5 | 5.9E+04 | 1.5E−03 | 2.6E−08 |
| AS64380VH6 | 8.8E+04 | 1.5E−03 | 1.7E−08 |
| AS64380VH7 | 3.2E+04 | 1.5E−03 | 4.5E−08 |
| AS64511 | 1.3E+05 | 4.0E−04 | 3.0E−09 |
| AS64511VH4 | 1.6E+05 | 9.4E−04 | 6.0E−09 |
| AS64511VH5 | 1.6E+05 | 4.7E−04 | 2.9E−09 |
| AS64511VH6 | 1.4E+05 | 4.8E−04 | 3.4E−09 |
| AS63997 | 3.9E+05 | 6.4E−03 | 1.6E−08 |
| AS63997VH4 | 8.4E+05 | 1.8E−02 | 2.1E−08 |
| AS63997VH5 | 5.8E+05 | 2.1E−02 | 3.7E−08 |
| AS63997VH6 | 1.8E+06 | 6.0E−02 | 3.3E−08 |
| AS64617 | 1.9E+05 | 3.8E−03 | 2.0E−08 |
| AS69443 | 9.4E+04 | 9.0E−05 | 9.6E−10 |
| AS63931 | 3.6E+06 | 1.7E−01 | 4.7E−08 |
| AS64047 | 1.4E+05 | 9.6E−04 | 6.7E−09 |
| AS64052 | 1.0E+05 | 4.1E−04 | 4.0E−09 |
| AS64062 | 1.0E+05 | 7.1E−04 | 6.9E−09 |
| AS56788 | 1.3E+05 | 3.0E−03 | 2.3E−08 |
| AS56704 | 6.60E+04 | 5.59E−04 | 5.59E−09 |

Example 8. Generation of Monospecific Humanized CARs

The amino acid sequences of anti-DLL3 humanized sdAbs were provided above in Table 6 and the nucleic acid sequences of anti-DLL3 humanized sdAbs were listed in SEQ ID NOs: 449-461. Humanized sdAbs in Table 6 and additional sequences were used to generate full CAR constructs (SEQ ID NOs: 485-494). A full length CAR contains from the N-terminus to the C-terminus: a CD8α signal peptide (SEQ ID NO: 465), a DLL3 binding domain (humanized sdAbs) provided in Table 6, a CD8α hinge domain (SEQ ID NO: 466), a CD8α transmembrane domain (SEQ ID NO: 467), a CD137 intracellular domain (SEQ ID NO: 468) or a CD28 intracellular domain (SEQ ID NO: 469), and a CD3ζ cytoplasmic domain (SEQ ID NO: 470). Schematic representation of a CAR construct is shown in FIG. 1. Nucleic acid encoding the CAR fragment was then cloned into a lentiviral vector to create a full length CAR construct in a single coding frame, using human EF1 alpha promoter for expression. The resulting CAR backbone vector was named "PLLV-hEF1α-DLL3".

Example 9. Evaluation of In Vitro Activity of Humanized Anti-DLL3 CAR-T Cells

Similar to the procedure described in Example 4, potency of humanized CARs was evaluated via CAR-T cell mediated killing of tumor cells, cytokine releasing and long-term stimulation assay.

In Vitro Cytotoxicity Assay

The results were shown in FIG. 6A-6D. Our humanized CAR-Ts showed superior anti-tumor efficacy in vitro.

IFN-γ Release Assay

Figure 7A:
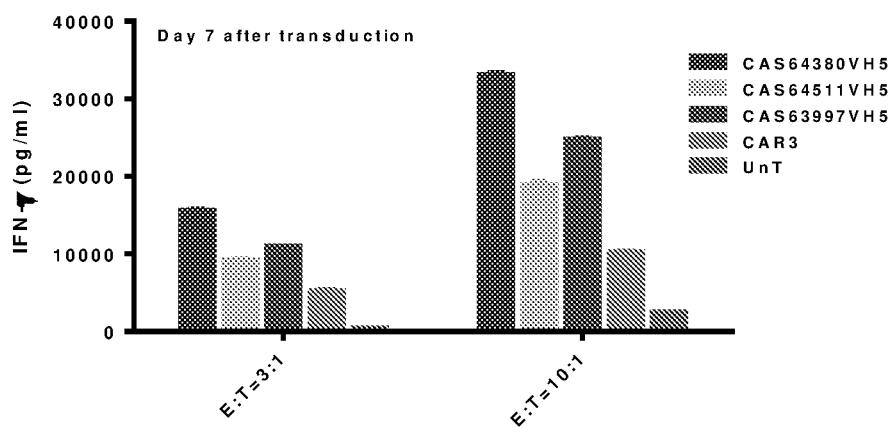
FIG. 7 shows the results of cytokine release levels of T cells expressing exemplary monospecific CARs comprising various humanized camel anti-DLL3 sdAbs after stimulated by SHP-77. IFN-γ release levels and TNF-α release levels (with an E:T of 3:1 or 10:1) are showed in FIG. 7A and FIG. 7B, respectively. In each figure, the results for the CARs are depicted in the order as in the legend shown on the right.
Figure 7B:
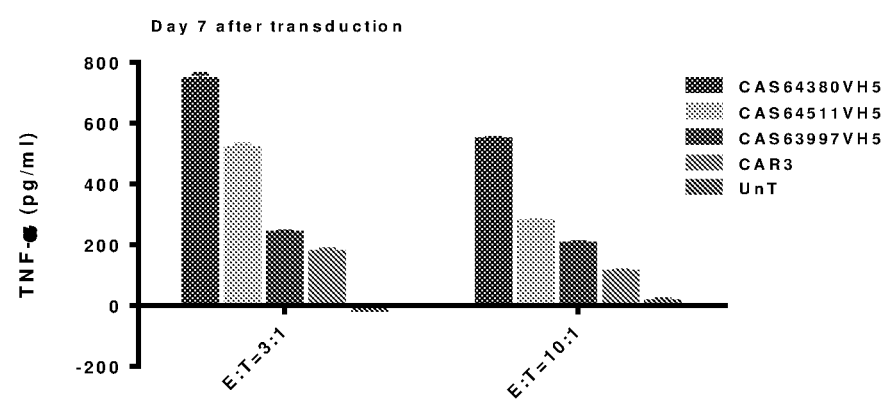

Additionally, supernatants from the in vitro cytotoxicity assay were collected to assess CAR-induced cytokine release, e.g., interferon gamma (IFN-γ) and tumor necrosis factor α (TNF-α) release. As shown in FIG. 7A and FIG. 7B, CAR3 CAR-T and some anti-DLL3 CAR-Ts were stimulated by SHP-77 to produce IFN-γ and TNF-α, whereas UnT produced little IFN-γ or TNF-α.

CART Expansion by Long-Term Stimulation Assay

On Day 0, $1 \times 10^5$ SHP-77 cells were plated in 24 well plates to establish a monolayer. On Day 1, CAR-T cells were counted and $2 \times 10^5$ viable CAR$^+$ T cells were plated on top of the SHP-77 cells in fresh media in the absence of cytokines. On day 3, a new $1 \times 10^5$ NCI-H82 cells monolayer were plated on top of the CAR-T cells. On day 4, viable CAR-T cells were counted for each well. On the same day, $2 \times 10^5$ CAR$^+$ T cells from wells that expanded (have at least this amount of cells) were re-plated to establish a new monolayer as on Day 1. The process was repeated for 3-4 rounds of stimulation. Fold expansion after each stimulation was calculated as [viable CAR$^+$ T cells on day 4]/$2 \times 10^5$, the amount of CAR-T cells plated on day 1 of each stimulation. To normalize for cells discarded with each new stimulation, cumulative fold expansion was determined by [(fold expansion)×(fold expansion+1) . . . ].

Figure 8:
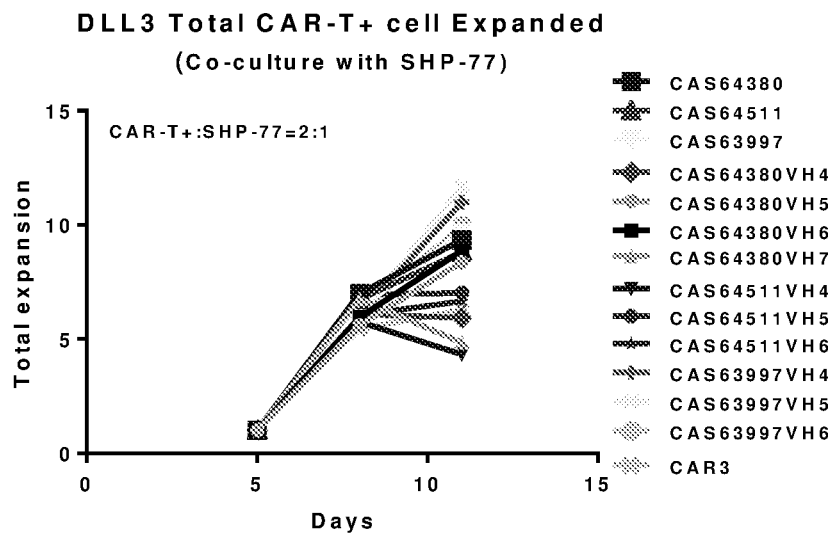
FIG. 8 shows fold expansions of T cells expressing exemplary monospecific CARs comprising various humanized camel anti-DLL3 sdAbs, after long-term stimulation of with small cell lung cancer cell line SHP-77.
Figure 9A:
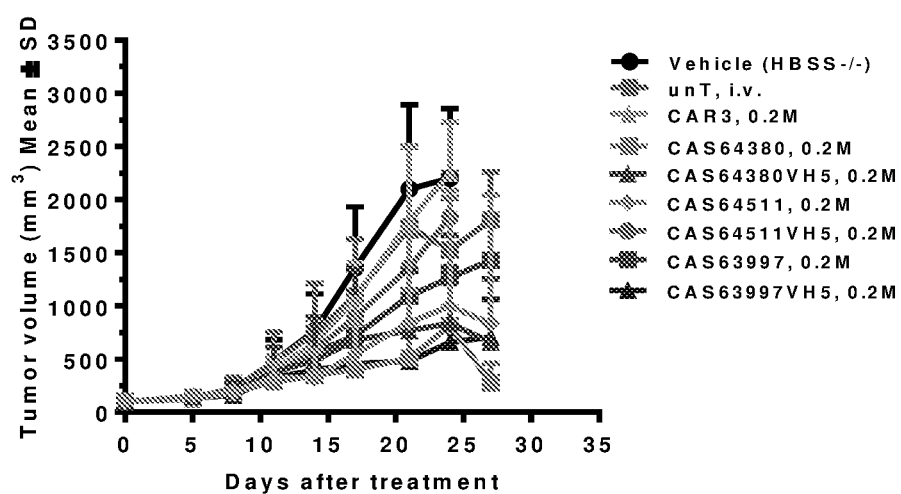
FIG. 9 shows the results of in vivo anti-tumor efficacy of the CAR-T cells expressing CARs with humanized camel anti-DLL3 sdAbs in a SHP-77 tumor model. In this model, each mouse was infused with a dose of 0.2 million CAR-T cells. The results of 9 groups are compared in FIG. 9A. The results of each mouse in each group are shown in FIG. 9B-9J, respectively.
Figure 9B:
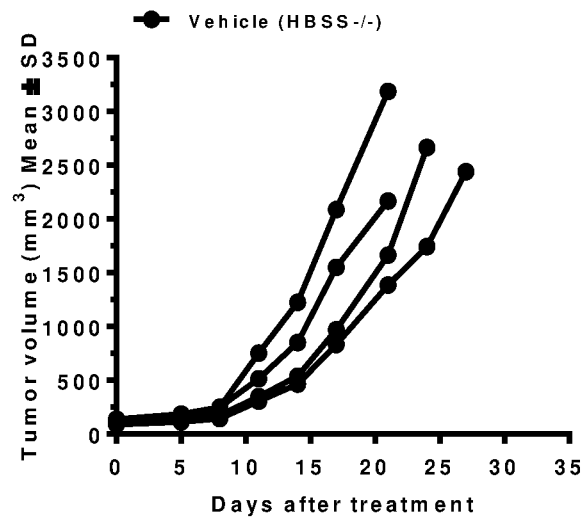
Figure 9C:
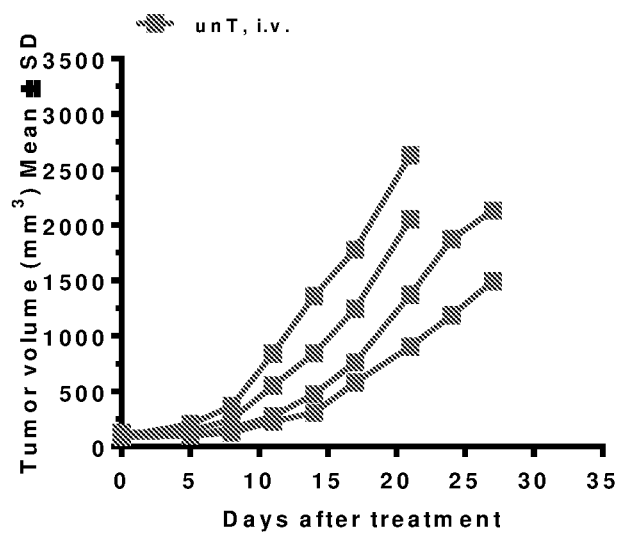
Figure 9D:
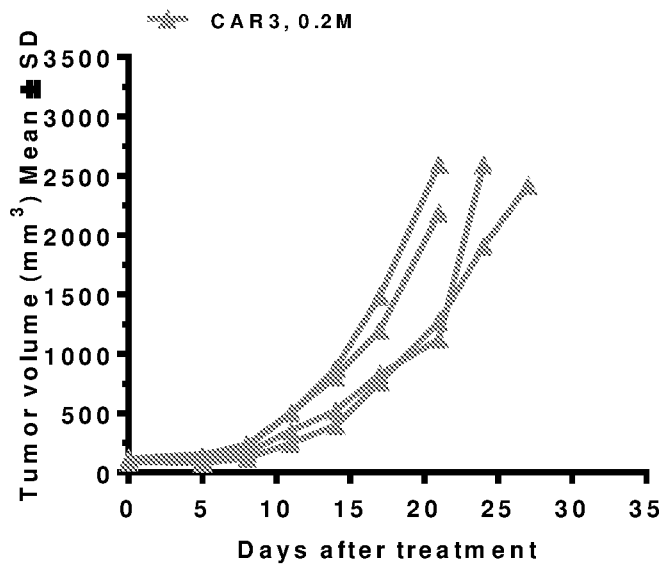
Figure 9E:
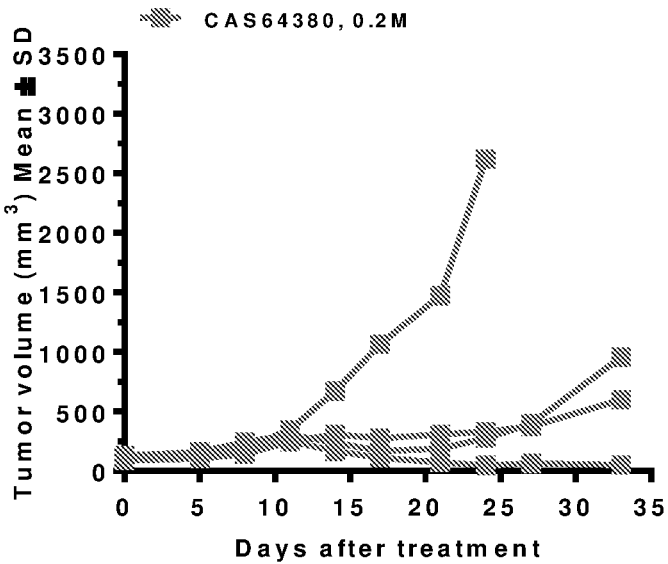
Figure 9F:
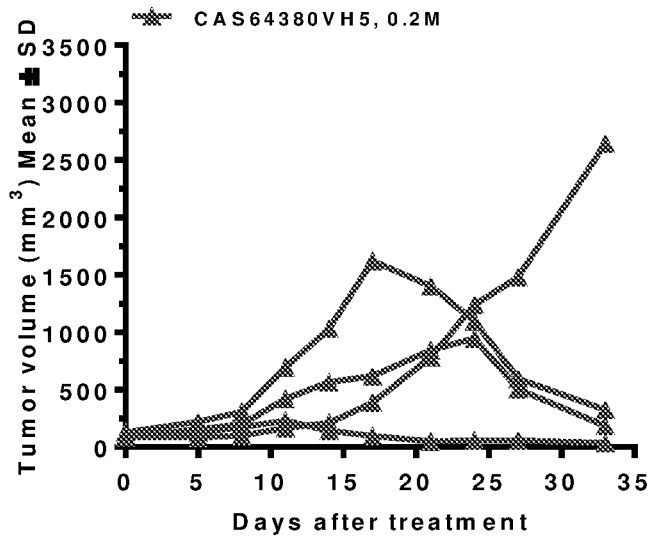
Figure 9G:
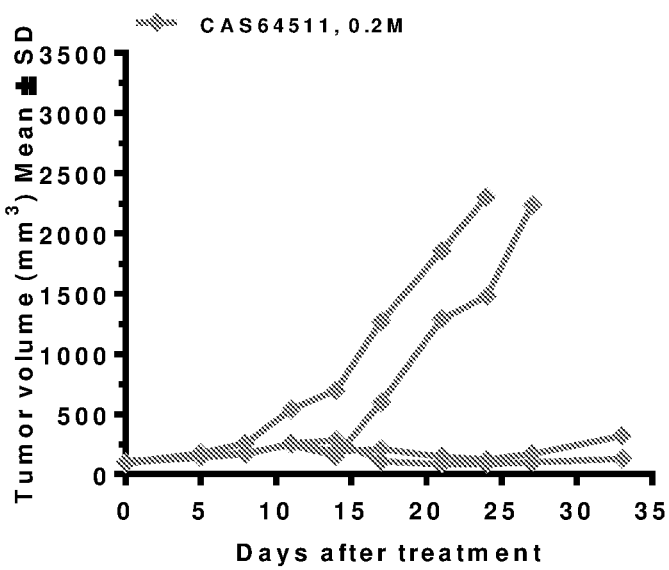
Figure 9H:
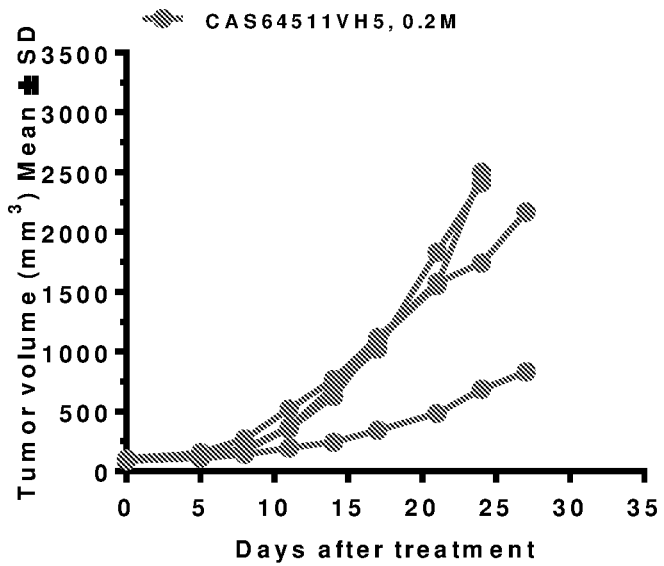
Figure 9I:
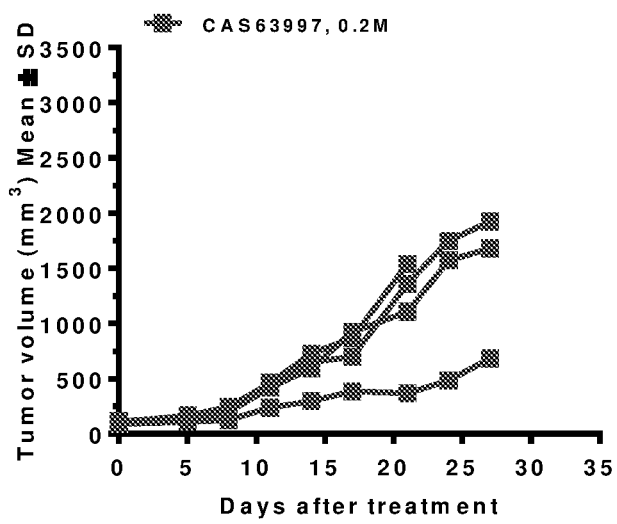
Figure 9J:
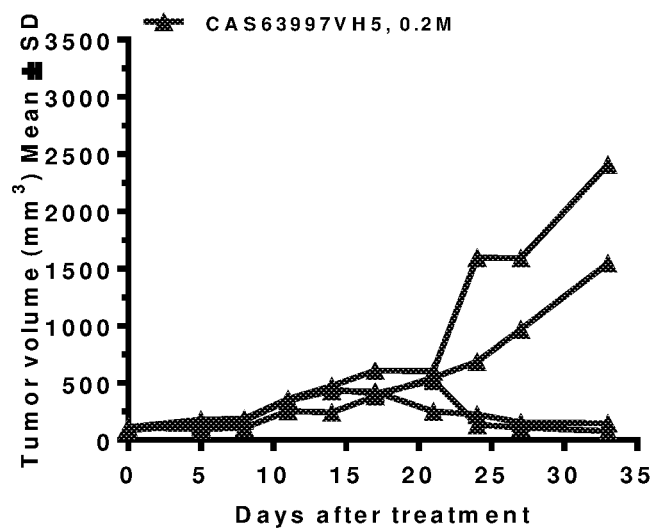

After 3 rounds of stimulation, the fold expansions of different CAR-T constructs were calculated. As it was showed in FIG. 8, most CAR-T constructs expanded more than CAR3 CAR-T with 3 rounds of stimulation by SHP-77 tumor cells.

Example 10. In Vivo Efficacy Valuation of Humanized CARs by CAR-T Cells Mediated Tumor Growth Inhibition The anti-tumor activity of the humanized CARs was evaluated in a SHP-77 tumor model. SHP-77 cells were implanted subcutaneously in NOD/SCID mice and randomized into 9 groups (4 mice per group, day 0): Vehicle (PBS only), UnT (negative control), CAR3, CAS64380, CAS64380VH5, CAS64511, CAS64511VH5, CAS63997, and CAS63997VH5. Treatment with CAR-T cells, UnT cells or vehicle (PBS only) began when tumors were palpable (100 mm$^3$) and mice were euthanized when their tumor volumes reached about 3000 mm$^3$. Tumor volumes were measured 2 times per week. CAR-T cells were administered intravenously with $0.2 \times 10^6$ CAR positive T cells per mouse. Mice and tumors were monitored for about 21 days after tumor cell implantation.

As shown in FIG. 9A-9J, compared to benchmark CAR3, CAS64380VH5 and CAS63997VH5 showed superior anti-tumor activity in this animal model.

Anti-tumor activities of these humanized CARs were not observed to correlate with their potency of in vitro cell killing.

Listed below are some amino acid sequences and nucleic acid sequences mentioned herein.

```
Camel sdAb Nucleic Acid Sequences
(Camel sdAb AS63930 Nucleic Acid Sequence)
                                    SEQ ID NO: 368
GAGGTGCAACTGGCGGAGTCTGGGGGAGGATCGGT

GCAGGCTGGAGGGTCTCTGAGACTCTCCTGTGCAG

CCTCTGGATACACCTACAGTGGCAACTATATGGCC

TGGTTCCGCCAGGCTCCAGGGAACGAGCGCGAGGG
```

-continued

GGTCGCAGTTGTTTATAATATTGACGGTGGCGGTC

GTTTCACTACCTATGCCGACTCCGTGAAGGGCCGA

TTCACCATCTCCCGAGGCAACGACAAGAACACGGT

GTATCTGCAAATGAACAGCCTGAAACCTGAGGATA

GTGGCATGTACTACTGTGCGGCAGAGGTAGCTGAT

CCGACCTGGGGTCGCGTGACCAAAGACGATATAA

GTACTGGGGCCAGGGGACCCAGGTCACCGTCTCCT

CA (Camel sdAb AS63932 Nucleic Acid Sequence)
SEQ ID NO: 369

CAGGTGCAATTGGAGGAGTCTGGGGGAGGCTCGGT

GCAGGCTGGAGGGTCTCTGAGACTCTCCTGTGTAG

CCTCTGGATACACCTACGGTAGCACCTTCATGGGC

TGGTTCCGCCAGAATCCAGGGAAGGAGCGCGAGGG

GGTCGCAGTTATTTATACTGGTGGTGGTAGTACAT

GGTATGCCAGCTCCGTGAAGGGCCGATTCACCATC

TCCCAGGACAACGCCAAGAACACGGTGTATCTGCA

AATGAACAGCCTGAAACCTGAGGACACTGCCATGT

ACTACTGTGCGGCGCGTTACGGGTCGGGAAACGTT

AACTACTGGGGCCAGGGGACCCAGGTCACCGTCTC

CTCA (Camel sdAb AS63951 Nucleic Acid Sequence)
SEQ ID NO: 370

CAGGTGCACCTGATGGAGTCTGGGGGAGGCTCGGT

GCAGGCTGGAGGGTCTCTGAGACTCGCCTGTGAAA

CCTCTAGAGACATCTACGGTAACAACTGCATGGCC

TGGTTCCGCCAGGCTCCAGGGAAGGAGCGCGAGGG

AGTCGCGTCTATTTATCCTGCTGGTGGTCGCCCGT

ACTATGCCGACTCCGTGAAGGGCCGATTCACCATC

TCCCAAGACAACGCCAAGAACACGGTGTATCTGCA

AATGGACAGCCTGAAACCTGAGGACACGGCCATGT

ACTACTGCGCGGCACGCTCTTTTTCGATAGCAGTT

TGCGCGACGCGCTCTGGTATTACCAGGTCTAATTT

TGCTTACTGGGGCCAGGGGACCCAGGTCACCGTCT

CCTCA (Camel sdAb AS63984 Nucleic Acid Sequence)
SEQ ID NO: 371

CAGGTGAAGTTGGTGGAGTCTGGGGGAGGCTCGGT

GCAGGCTGGAGGGTCTCTGAGACTCTCCTGTGCAG

CCTCTGGATACACCTACAGTAGCAACTTCATGGGC

TGGTTCCGCCAGGCTCCAGGGAAGGAGCGCGAGGG

GGTCGCAACTATTGTTTCTGGTGGTGGTACCACAT

ACTATGCCGACTCCGTGAGGGGCCGATTCACCATC

TCCCAAGACAACGCCAAGAACACGGTGTATCTGCA

AATGAACAGCCTGAAACCTGAGGACACTGCCATGT

ACTACTGTGCGGCAGGGGCCCCGTTACGAACGCA

CCTAGATGGTACCCCCTCCGACCTCCTGGTTATAA

CTACTGGGGCCAGGGGACCCAGGTCACCGTCTCCT

CA (Camel sdAb AS63987 Nucleic Acid Sequence)
SEQ ID NO: 372

CAGGTGAGGTTGGTGGAGTCTGGGGGAGGCTCGGT

GCAGGCTGGAGGGTCTCTGAGACTCTCCTGTGAAG

CCACTGGATATAGAAACTGCATGGCCTGGTTCCGC

CAAGCTCCAGGGAAGGAACGCGAGGGGGTCGCAGT

TATTTATACTCCTAGTGGTATCACGGACTATGCAA

GCTCCGTGAAGGGCCGATTCACCATCTCCCAAAAC

AACGCCAGGAACACGCAGTATCTGCAAATGAACAG

CCTGAAACCTGAGGACACTGCCATGTACTACTGTG

CGGCAGATCGACCCTTTGTTTGTAATATAGCGAAT

ATGAGAAGGTCCTCCAACTGGGGCCGGGGACCCA

GGTCACCGTCTCCTCA (Camel sdAb AS63997 Nucleic Acid Sequence)
SEQ ID NO: 373

CAGGTGAGGTTGGTGGAGTCTGGGGGAGGCTCGGT

GCAGGCTGGAGGGTCTCTGAGACTCTCCTGTGCAG

GCTCTTTCTCTGGATACGCGTCAGTACCATGGCC

TGGTTCCGCCAGGCTCCAGGGAAGGAGCGCGAGGG

GGTCGCAGCTATTACAGTTGGTAGTGGAAACACAT

ACTATGCCGACTCCGTGAAGGGCCGATTCACCATC

TCCCGAGACAACGCCAAGAGGACGGTGTTTTTGCA

AATGAACAGCCTGAAACCTGAGGACACTGCCATGT

ACTACTGTGCGGTCGGATACTTGTCGGGTGGTAGT

TGGGACGTTCCCGGAAGGTATAACTACTGGGGCCA

GGGGACCCAGGTCACCGTCTCCTCA (Camel sdAb AS64047 Nucleic Acid Sequence)
SEQ ID NO: 374

CAGGTGCACCTGGTGGAGTCTGGGGGAGGCTCGGT

GCAGGCTGGAGGGTCTCTGAGACTCTCCTGTGCAG

CCTCTCAGTACGTTTACAGGTGGGACCTCATGGGC

TGGTTCCGCCAGGCTCCAGGGAAGGAGCGCGAGGC

GGTCGCTGCTGTTTATACTGGTGATGGTATTACAT

ACTATGCCGACTCCGTGAAGGGCCGATTCAGCATT

TCCCAAGACAACGCCAAGAACACGGTGTATCTGCA

AATGAACAGCCTGAAACCTGAGGACACTGGCATGT

ACTTCTGTGCGGCAGGCTTCGTCTCTGGTGGTAGA

TGGAACCAGTCATATCGTTATAAATACTGGGGCCA

GGGGACCCAGGTCACCGTCTCCTCA (Camel sdAb AS64052 Nucleic Acid Sequence)
SEQ ID NO: 375
CAGGTGCACCTGATGGAGTCTGGGGGAGGCTCGGT

GCAGGCTGGAGGGTCTCTGAGACTCTCCTGTGCAG

CCTCTGGATACACCTACCGCAGCAACTTCATGGGC

TGGTTCCGCCAGGCTCCAGGGAAGGAGCGCGAGGG

GATCGCAACTATTCATTCTGGTGTGGCTACCACAT

ACTATGCCGACTCCGTGAAGGGCCGATTCACCATC

TCCCAAGACAACGCCAAGAACACGGTGTATCTGCA

AATGAACAGCCTGAAACCTGAGGACACTGCCATGT

ACTACTGTGCGGCAGGGGCCCCCCTGCGAACGCT

GATAGATGGTACCCCCTCCGACCTCCTGGTTATAA

CTACTGGGGCCAGGGGACCCAGGTCACCGTCTCCT

CA (Camel sdAb AS64062 Nucleic Acid Sequence)
SEQ ID NO: 376
CAGGTGAGGTTGGTGGAGTCTGGGGGAGGCTCGGT

GCAGGTTGGAGGGTCTCTGAGACTCTCCTGTGCAG

CCTCTAGATCTCCCTACAGTAGCAGTAGGTGCATG

GGGTGGTTCCGCCAGGCTCCAGGGAAGGAGCGCGA

GGGGGTCGCAGCTCTTTATACTGGTGGTGGTAGCA

CATCCTATGCCGACTCCGTGAAGGGCCGATTCACC

ATCTCCCAAGACAACGCCAAGAATACGGTGTATCT

GCAAATGAACAGCCTGAAACCTGAGGACACTGCCA

TGTACTACTGTGCGGCAGTTGTCCCTAGGGGTGGT

AGCTGCCGTCTTGATGAAAGAGGGTATTACCACTG

GGGCCAGGGGACCCAGGTCACCGTCTCCTCA (Camel sdAb AS64072 Nucleic Acid Sequence)
SEQ ID NO: 377
CAGGTGCAGCTGGTGGAGTCTGGGGGAGGCTCGGT

GCAGGCCGGAGGGTTTCTGAGACTCTCCTGTGCAC

TCTCTGGATACAGCTACTATATTAACTTGATGGCG

TGGTTCCGTCAGGCTCCAGGGAAGGAGCGCGAGGC

AGTCGCAGCTCATGGTCCTGTGAGTGGGACAGCAT

ACTATACCGACTCCGTGAAGGGCCGATTCACCATC

TCCCGAGACCCCGGCAAGAACACGATGTATCTTCA

AATGTTTAGCCTGCAACCGGAGGACACTGCCCTCT

ACTACTGTGCGGCGGAAACGACTATGGGTTGGGCC

CACGAACGCGGGTATAGGTACTGGGGCCAGGGGAC

CCAGGTCACCGTCTCCTCA (Camel sdAb AS64097 Nucleic Acid Sequence)
SEQ ID NO: 378
CAGGTGCACCTGATGGAGTCTGGGGGAGGCTCGGT

GCAGGCTGGAGGGTCTCTGAGACTCTCCTGTGAAG

CCTCTGGATACACCTACAGTCGCAACTGCATGGGC

TGGTTCCGCCAGGCTCCAGGGAAGGAGCGCGAGGG

GGTCGCAGCTATTAACACTGGTGGTGGTAGCACAT

ATTATGCCGACTCCCTTGAGGGCCGATTCACCATC

TCCCAAGACAACGCCAAGAATACTATGTATCTGCA

AATGAACAGCCTGAAACCTGAGGACACTGCCATGT

ACTACTGTGCGGCAGGTCCCGATCTCGGTGGTAGC

TGGTGTCGGCCCGTTGAGCGGGCTTTTACGTACTG

GGGCCAGGGGACCCAGGTCACCGTCTCCTCA (Camel sdAb AS64114 Nucleic Acid Sequence)
SEQ ID NO: 379
CAGGTGCAACTGCAGGAGTCTGGGGGGGCTCGGT

GCAGGCTGGAGGGTCTCTGACACTCTCCTGTGAAG

CCTCTGGAAACACCTACAGTACTAATTACATGGGC

TGGTTCCGCCAGGCTCCAGGGAAGGAGCGCGAAGA

GGTCGCGGTTATTTACACTCGTGGTGGTCACACAT

ACTATGTCGACTCCGTGAGGGGCCGATTCACCATC

TCCCAAGACAACGCCAAGAACACGGTGTATCTGCA

AATGAACAGCCTGAAACCTGAGGACACTGCCATGT

ACTACTGTGCGGCAGCTTCACGACATAGACTCCGT

TTAAATAACCCACGGGACTATGACTACTGGGGCCA

GGGGACCCAGGTCACCGTCTCCTCA (Camel sdAb AS64123 Nucleic Acid Sequence)
SEQ ID NO: 380
CAGGTGCAACTGGCGGAGTCTGGGGGAGGCTCGGT

GCAGGCTGGAGGGTCTCTGAGACTCTCCTGTGCAG

CCTCTGGATACACTTATACGAGCAACTGGCTGGGC

TGGTTCCGCCAGGCTCCAGGGAAGGAGCGCGAGGA

GGTCGCAATTATTTATACTGGTAGTGGTAGTACAC

ACTATCGCAGCTCCGTGAAGGGCCGATTCACCATC

TCCCAAGACAACGCCAAGAACACGGTGTATCTGCA

AATGAACAGCCTGAAACCTGAGGACACTGCCATGT

ACTACTGTGCGGCGCGTTTCTCAGAGTATAATTAC

TGGGGCCAGGGGACCCAGGTCACCGTCTCCTCA (Camel sdAb AS64130 Nucleic Acid Sequence)
SEQ ID NO: 381
GAGGTGCAACTGGCGGAGTCTGGGGGAGGCTCGGT

GCAGGCTGGAGGGTCTCTGAGACTCTCCTGTGCAG

CCTCTGGATACACCTACCGTAGCAACTTCATGGGC

TGGTTCCGCCAGGCTCCGGCGAAGGAGCGCGAGGG

GGTCGCAACTATTGATTCTCGTGGTACTATCACAT

ACTATGCCGACTCCGTGAAGGGCCGATTCACCATC

TCCCAAGACAACGAGAAGAACACGGTGTATCTGCA

AATGAACAGCCTGAAACCTGAGGACACTGCCATGT

ACTACTGTGCGGCAGGGGCCCCCGCACGAACGAT

GATAGATGGTACCCCCTCCGACCTCCTGGTTATAA

CTACTGGGGCCAGGGGACCCAGGTCACCGTCTCCT

CA (Camel sdAb AS64137 Nucleic Acid Sequence)
SEQ ID NO: 382
CAGGTGAGGTTAGTGGAGTCTGGGGGAGGCTCGGT

GCAGGCTGGAGGGTCTCTGAGACTCTCCTGTGCTG

CCTCTGGATCCACCTACAGTACAAACTTCATGGGC

TGGTTCCGCCAGGCTCCAGGGAAGGAGCGCGAGGG

GGTCGCAACGCTGGTTACTTGGGTTGAACGCACAG

CCTATGCCGACTCCGTGAAGGGCCGATTCACCATC

TCCCAAGACCGCGCCAAGAACACGGTGTATCTACA

AATGAACAGCCTGAAACCTGAGGACACTGCCATGT

ACTACTGTGCGGCAGCCGCCGCTTCCACTGATGTA

CGTCTCCTCGACCCGGGGACTTTGCTTACTGGGG

CCAGGGGACCCAGGTCACCGTCTCCTCA (Camel sdAb AS64142 Nucleic Acid Sequence)
SEQ ID NO: 383
CAGGTGCACCTGATGGAGTCTGGGGGAGGCTTGGT

GCAGACAGGGGGGTCTCTGAGACTCTCCTGTACAG

CCTCTGGATTCACTTTTGATCGTAATGCCATGCGC

TGGTACCGCCAGGCTCCAGGGAAGGAGCGCGAGGG

GGTCTCATGTATTGATTGGACGGGTGCAAATATTG

CCTATGCAGACTCCGTGAAGGGCCGATTCACCATC

TCCAGAGACAACGCCAAGAACACGCTGTATCTGCA

AATGAACAGCCTGAAACCTGAGGACACGGGCATGT

ATTACTGTGCGCAGATACGACGTCGGGGTATTGT

TCAGGCTTTTGGTCTACGAGCCGGTACTCATGGGG

CCAGGGGACCCAGGTCACCGTCTCCTCA (Camel sdAb AS64154 Nucleic Acid Sequence)
SEQ ID NO: 384
CAGGTGCAATTGAAGGAGTCTGGGGGAGGCTCGGT

GCAGGCTGGAGGGTCTCTGAGACTCTCCTGTACAG

CCTCTGGATACACCTACAGATACCTCTACATGGGC

TGGTTCCGCCAGACTCCAGGGAAGGAGCGCGAGGG

GGTCGCATGTATTTATACTGGTAGTGGTAGCACAG

GGTATGCCGACTCCGTGAAGGGCCGATTCACCATC

TCCCAAGACAACGCCAAGAACACGGTGTATCTGCA

AATGAACAACCTGAAACCTGAGGACACTGCCATGT

ACTACTGTGCGGCAAGTTCGCCCCGGTGGGGCGGT

ACCTGTCGACGCTGGTCTCAGTATAACTACTGGGG

CCAGGGGACCCAGGTCACCGTCTCCTCA (Camel sdAb AS64160 Nucleic Acid Sequence)
SEQ ID NO: 385
GAGGTGCAGCTGGTGGAGTCTGGGGGAGGCTCGGT

GCAGGCTGGAGGGTCTCTGAGACTCTCCTGTGCGG

CCTCTGTATACACCAGCAGTAGCTACTGCATGGGC

TGGTTCCGCCAGGCTCCAGGGAAGGAGCGCGAGGG

GGTCGCAGCTATGTGTTTTGGTGGTCTTGTCACAC

ACTATGCCGACTCCGTGAAGGGCCGATTCACCATC

TCCCAAGACAATGCCAAGAACACGGTGTATCTGCA

AATGAACAGCCTGAAACCTGAGGACACTGCCATGT

ACTACTGTGCGGCAGATTTCGGCAGGGATAAAAAC

TATTTACGACCGTTACTGCCCCATGCATATAACTA

CTGGGGCCAAGGGACCCAGGTCACCGTCTCCTCA (Camel sdAb AS64228 Nucleic Acid Sequence)
SEQ ID NO: 386
CAGGTGCAATTGAAGGAGTCTGGGGGAGGTTCGAT

CCAGGCTGGAGGGTCTCTGAGACTCTCCTGTGCAG

CCTCTGGAGTCTCCTACAATAGGTGCAGTATGGGC

TGGTACCGCCAGGCTCCAGGGAAGGGGCGCGAGTT

GGTCTCACGTATTCAGCCGGGTGGTAATACATACT

ATGCAGACTCCGTGAAGGGCCGATTCACCGTCTCC

CAAGACAACGCCAAGAACACAGTATCTCTACAAAT

GAACAGCCTGAAACCTGAGGACACGGCCATGTATT

ACTGTAACGCACTGTGCTGGCGGGAGAATGTTAAC

TACTGGGGCCAGGGGACCCAGGTCACCGTCTCCTC

A (Camel sdAb AS64300 Nucleic Acid Sequence)
SEQ ID NO: 387
CAGGTGCACCTGGTGGAGTCTGGGGGAGGCTCGGT

GCAGACTGGAGGATCTCTGAGACTCTCCTGTGCAG

TCTCTGGAGACATCTATAACCTCATGTCGATGGCC

TGGTTCCGCCGGGCTCCAGGGAAGGAGCGCGAGGG

GGTCGCATATATTAATACTATTATTGGTAACACAT

ACTATACTGACTCCGTGAAGGGCCGATTCACCATC

TCCCGCGATAACTCCAAGAACACTTTGTATCTGCA

AATGAACAACCTGAAACCTGAGGACACAGCCATGT

ACTACTGTGCGGCGTTCAATTACGGAGGTGCCTGG

TACGAGGAACGCAGCTATAAATACTGGGGCCAGGG

GACCCAGGTCACCGTCTCCTCA (Camel sdAb AS64380 Nucleic Acid Sequence)
SEQ ID NO: 388
GAGGTGCAGCTGGTGGAGTCTGGGGGGGGCTCGGT
GCAGGCTGGAGGGTCTCTGACACTCTCCTGTGAAG
CCTCTGGAAACACCTACAGTAGTAATTACATGGGC
TGGTTCCGCCAGGCTCCAGGGAAGGAGCGCGAGGA
GGTCGCGGTTATTTACACTCGTGGTGGTCACACAT
ACTATGTCGACTCCGTGAGGGCCGATTCACCATC
TCCCAAGACAACGCCAAGAACACGGTGTATCTGCA
AATGAACAGCCTGAAACCTGAGGACACTGCCATGT
ACTACTGTGCGCGTCTTCACGACATAGACTCGGT
TTAAATAACCCACGGGACTATGACTACTGGGGCCA
GGGGACCCAGGTCACCGTCTCCTCA (Camel sdAb AS64395 Nucleic Acid Sequence)
SEQ ID NO: 389
CAGGTGAGGTTGGTGGAGTCTGGGGGAGGCTCGGT
GCAGGCTGGAGGGTCTCTGAGACTCTCCTGTGCTG
CCTCTGGATCCACCTACAGTACAAACTTCATGGGC
TGGTTCCGCCAGGCTCCAGGGAAGGAGCGCGAGGG
GGTCGCAACGCTTGTTACTTGGGCTGAACGCACAG
CCTATGCCGACTCCGTGAAGGGCCGATTCACCATC
TCCCAAGACCGCGCCAAGAACACGGTGTATCTACA
AATGAACGGCCTGAAACCTGAGGACACTGCCATGT
ACTACTGTGCGGCAGCCGCTTCCACTGCTGTACGT
CTCCTCGACCCGGGGACTTTGCTTACTGGGGCCA
GGGGACCCAGGTCACCGTCTCCTCA (Camel sdAb AS64443 Nucleic Acid Sequence)
SEQ ID NO: 390
CAGGTGCACCTGGTGGAGTCTGGGGGAGGCTCGGT
GCAGGCTGGAGGGTCTCTGAGACTCTCCTGTGCAG
CCTCTGGATATACCGACAGTAGCGTCTACATAGGC
TGGTTCCGCCAGGCTCCAGGGAAGGAGCGCGAGGA
GGTCGCGATTATTTATACTGGTGGTGAAAGCACAC
ACTATCGCAGCTCCGTGAAGGGCCGATTCACCGTC
TCCAAGACAACGCCAAGAACACGCTGTATCTGCA
AATGAACAGCCTGAAACCTGAGGACACGGCCATGT
ATTACTGTGCAGCACGATTCCCAGCTGTTACCTAC
TGGGGCCAGGGGACCCAGGTCACCGTCTCCTCA (Camel sdAb AS64511 Nucleic Acid Sequence)
SEQ ID NO: 391
CAGGTGCAGCTGGTGGAGTCTGGGGGAGGCTCGGT
GCAGGCTGGAGGGTCTCTGAGACTCTCCTGTGCAG
CCTCTAGAGCCACCTACAGTACCAACTACATAAGC
TGGTTCCGCCAGGCTCCAGGGAAGGAGCGCGAGGC
GGTCGCAACAATTACTACTGGTGATGGTGAGACAG
CGTATGCCGACTCCGTGAAGGGCCGATTCACCATC
TCCCGAGACAACGCCAAGAACACGGTCTATCTGCA
AATGAACAGCCTGAAACCTGAGGACACTGCCATGT
ACTACTGTGCGGCGAACTTGCGAATCGGTGGCGAC
TGGTTCGACGGACGCGATTTTCGTGCCTGGGGCCA
GGGGACCCAGGTCACCGTCTCCTCA (Camel sdAb AS64536 Nucleic Acid Sequence)
SEQ ID NO: 392
CAGGTGAAGTTGGTGGAGTCTGGGGGAGGCTCGGT
GCAGGCTGGAGGGTCTCTGAGACTCTCCTGTGCAG
CCTCTAGATACACCGACAATTTCGTGTACATGGGC
TGGTTCCGCCAGGCTCCAGGGAAGGAGCGCGAGGG
GGTCGCACTGATTTATCCTGGTGGTGGTAGCACCT
ACTATGCCTCCTCCGTGAAGGGCCGATTCACCATC
TCCCAAGACAACGCCAAGGGCACGGTGCATCTGCA
AATGAACAACCTGAAACCTGAGGACACTGCCATGT
ACTACTGTGCGGCAAAATGGGGGCTGGGCGGGGGG
GGCCTGAAATCAGATACGTATATGTACTGGGGCCA
GGGGACCCAGGTCACCGTCTCCTCA (Camel sdAb AS64597 Nucleic Acid Sequence)
SEQ ID NO: 393
CAGGTGCACCTGGTGGAGTCTGGGGGAGGCTCGGT
GCAGGCTGGAGGGTCTCTGAGACTCTCCTGTGCAG
CCTCTGGATACACCTACCGTGTCAACTTCATGGGC
TGGTTCCGCCAGACTCCAGGGAAGGAGCGCGAGGG
GGTCGCAACTATTGATTCTGGTGTGGGTACCACAT
ACTATGCCGACTCCGTGAAGGGCCGATTCACCATC
TCCCATAACAACGCCAAGAACACGATTTATCTGCA
AATGAACAGCCTGAAACCTGAGGACACTGCCATGT
ACTACTGTGCGGCAGGGGCCCCCCTACGGACGGT
GATAGATGGTACCCCCTCCGACCTCCTGGTTATAA
CTATTGGGCCAGGGGACCCAGGTCACCGTCTCCT
CA (Camel sdAb AS64617 Nucleic Acid Sequence)
SEQ ID NO: 394
CAGGTGCAGCTGGTGGAGTCTGGGGGAGGCTCGGT
GCAGGCTGGAGGGTCTCTGAGACTCTCCTGTGCAG
CCTCTGGATACACTGATAGATGCAGCATGGCCTGG
TACCGCCAGGCTCCAGGGAAGGAGCGCGAGTTGGT
CTCGCGTATTAGCACGAGCGGTTTCACAAACTACG
CAGCCTCCGTGAAGGGCCGATTCACCATCTCCCAA
GACAACGCCAAGAACACGGTGTATCTGCAAATGAA
CAGCCTGAACCCCGGGGACACGGGCATGTATTACT

```
GTGCCATAATCGTAGGACGTACTTGTAGTTTGAAC

TACTGGGGCAACGGCATCCTGGTCACCGTCTCCTC

A (Camel sdAb AS64634 Nucleic Acid Sequence)
                                SEQ ID NO: 395
CAGGTGAGGTTGGTGGAGTCTGGGGGAGGCTCGGT

GCAGGCTGGAGGGTCTCTGAGACTCTCCTGTGCAG

CCTCCGGATACAGTTTTAGAGGCGACTTTATGTGT

ATGGGCTGGTTCCGCCAGACTCCAGGGAAGGGGCG

CGAGGGGGTCGCAGTTTTTTATCCTGGTGGCGGCA

GCACAAACTATGCCGACTCCGCGAAGGGCCGATTC

ACCATCTCCCAAGACAACGCCAAGAACACGATGTA

TCTGCAAATGAACACCCTGAAACCTGAGGACACTG

CCATGTACTACTGTGCGGCTCGACGGTGGGTCAGT

GGTACCTGCTACTGGGATAGTGACTTTCATTACTG

GGGCCAGGGGACCCAGGTCACCGTCTCCTCA (Camel sdAb AS69498 Nucleic Acid Sequence)
                                SEQ ID NO: 396
CAGATGCAGCTGGTGGAGTCTGGGGGAGGCTCGGT

GCAGGCTGGAGGGTCTCTGAGACTCTCCTGTGCAG

CCTCTGGAAACACCTACAGTACCAATTACATGGCG

TGGTTCCGCCAGGCTCCAGGGAAGGAGCGCGAGGA

GGTCGCGGTTATTTACACTCGTGGTGGTCACACCT

ACTATATCGACTCCGTGAGGGGCCGATTCACCATC

TCCCAAGACAACGCCAAGAACACGGTGTATCTGCA

AATAAACAGCCTGAAACCTGAGGACACTGCCATGT

ACTACTGTGCGGCGTCTTCACGAATTAGACTCCAT

TGAATCGACCCACGGGACTATACGACTGGGGCCA

GGGGACCCAGGTCACCGTCTCCTCA (Camel sdAb AS69500 Nucleic Acid Sequence)
                                SEQ ID NO: 397
CAGGTGAGGTTAGTGGAGTCTGGGGGAGGCTCGGT

GCAGGCTGGAGGGTCTCTGAGACTCTCCTGTGCAG

CCGACAGATACACCTACAGTAGCGCCTGCATGGGC

TGGTTCCGCCAGGCTCCAGGGAAGGAGCGCGAGGG

GGTCGCCTCTATTTTTACTGGTACTGGTGGTAGCA

CATACTATGCCGACTCCGTGAAGGGCCGATTCACC

ATCTCCCAAGACAACGCCAAGAACACGGTGTATCT

GCAAATGAACAGCCTGAAACCTGAGGACACTGCCA

TATACTACTGTGCGGCAAGGGCCTTCCAGGTCGGT

TACTGCTACCTGCGAACCGATGTGTATAACTACTG

GGGCCAGGGGACCCAGGTCACCGTCTCCTCA (Camel sdAb AS69527 Nucleic Acid Sequence)
                                SEQ ID NO: 398
GAGGTGCAGCTGGCGGAGTCTGGGGGAGGCTCGGTC

CAGGCTGGAGGGTCTCTGAGACTCTCCTGTGTAGC

CTCTAGATACACCTTCAGTAGCACCTGCATGGCCT

GGTTCCGCCAGGCTCCAGGGAAGGAGCGCGAGGAG

GTCGCAGCTATTTATACTGATGATGGTAGCACATG

GTATGCCGACTCCGTGAAGGGCCGATTCACCATCT

CCAGAGACAACGCCAAGAACACGGTGTATCTGCAA

ATGAACAGCCTGAAACCTGAGGACACTGCTATGTA

CTACTGTGCGGCACGTAGGTGGGCGTGCCCCAGGG

TTGGTAGCTGGCATGAGTTCGCCTACTGGGGCCAG

GGGACCCAGGTCACCGTCTCCTCA (Camel sdAb AS68280 Nucleic Acid Sequence)
                                SEQ ID NO: 399
CAGGTGCAACTGGTGGAGTCTGGGGGAGGCTCGGT

GCACCCTGGAGGGTCTCTGAGACTCTCCTGTGCAG

CCTCTGGATCCACCTACAGTTCCAACTACCTCGGC

TGGTTCCGCCAGGCTCCAGGAAAGGGGCGCGACTG

GGTTGCGGCTATTAGCACTGGTGACGGTGCCACAG

CCTATGCCGACTCCGTGAAGGGCCGATTCACCATC

TCCCAAGACAACGCCAAGAACACGGTGTATCTGCA

AATGAACAGCTTGAAACTTGAGGACAGTGCCATGT

ACTACTGTGCGGCGGCTCGCGGCAGATTTATCGAT

TGGACAAAGGCAACCCAGTATGACTACTGGGGCCA

GGGGACCCAGGTCACCGTCTCCTCA (Camel sdAb AS68355 Nucleic Acid Sequence)
                                SEQ ID NO: 400
CAGATGCAGCTGGTGGAGTCTGGGGGAGACTCGGT

GCAGGCTGGAGGGTCTCTGAGACTCTCCTGTGCAG

CCTCTGGATACACCTACAGCGGCGTCTGCATGGGC

TGGTTCCGCCAGGCTCCAGGGAAGGAGCGCGAGGG

GGTCGCAGCTATTGATAGTGATGGTAGCACAAGCT

ACGCAGACTCCGTGAAGGGCCGATTCACCATCTCC

AAAGACAACGCCAAGAACACTCTGTATCTGCAAAT

GAACAGCCTGAAACCTGAGGACACTGCCATGTACT

ACTGTGCGGCAGCCATTGTCGGGGTTTAATGCA

TATTGTAGTGGTGGTTATGTTCTGGACTTTGGTGC

CTGGGGCCAGGGGACCCAGGTCACCGTCTCCTCA (Camel sdAb AS69443 Nucleic Acid Sequence)
                                SEQ ID NO: 401
GAGGTGCAGCTGGCGGAGTCTGGGGGAGGCTCGGT

GCAGGCTGGAGGGTCTCTGAGACTCTCCTGTTCAG

CCTCTGGTTTCACTTTTGATGATTCTGACATGGCC
```

-continued
TGGTACCGCCAGGCTCCAGGGGATGGGTGCGACTT

GGTCTCAACTATTAGTAGTGATGGTAGCACATACT

ATGCAGACTCCGTGAAGGGCCGATTCACCATCTCC

CAAGACAACGCCAAGAACACGGTGTATCTGCAAAT

GCACAGCCTGAAACCTGAGGACACGGCCGTGTATT

ACTGTGCGGCAGATTTCCTCACCGGCTTTTACTAT

AGCGACTCCCCCCATCCGGCCCCTTGTTCTGCATC

CGACTTTGGTTACTGGGGCCAGGGGACCCAGGTCA

CCGTCTCCTCA (Camel sdAb AS75376 Nucleic Acid Sequence)
SEQ ID NO: 402
CAGGTGCAATTGAAGGAGTCTGGGGGAGGCTCGGT

GCAGGCTGGAGGGTCTCTGAGACTCTCCTGTGCAG

CCTCTGGATACACCTACAGTAGCCACTCCATGGGC

TGGTTCCGCCAGGCTCCAGGGAAGGAGCGCGAGGG

GGTCGCAGTTATTTATACTGGTGATGGTAGCACAT

ACTATGCCGACTCCGTGAAGGGCCGATTCACCATC

TCCCAAGACAACGCCAAGAACACGGTGTATCTGCA

AATGAACAGCCTGAAACCTGAGGACACTGCCATGT

ACTACTGTGCGCAGATCCGAACCCCGATTATATG

CTTCCGTTTCGGCCGTCCCGTAGGTCGTGGTGGGG

CCAGGGGACCCAGGTCACCGTCTCCTCA (Camel sdAb AS75387 Nucleic Acid Sequence)
SEQ ID NO: 403
CAGGTGCACCTGGTGGAGTCTGGGGGAGGCTCGGT

GCAGGCTGGAGGGTCTCTGAGACTCTCCTGTGCAG

CCTCTGGATACCCCTACAGTAGCCCCTGCATGGCC

TGGTTTCGCCAGGCTCCAGGGAAGGAGCGCGAGGG

GGTTTTAGTTGCTTATACTGGTGGGGACATTCAAT

ACCTTACCGACTCCGTGAAGGGCCGATTCACCATC

TCCCGAGACAACGCCAAGAACACGGTGTATCTGCA

AATGAACAGCCTGAAACCTGAGGACACTGCCATGT

ACTACTGTGCGGCGGATCTGCGATTACCTCGTGCC

GGCGGTTGTGCGTATAGCTACTGGGGCCAGGGGAC

CCAGGTCACCGTCTCCTCA (Camel sdAb AS75695 Nucleic Acid Sequence)
SEQ ID NO: 404
CAGGTGAGGTTGGTGGAGTCTGGGGGAGGCTCGGT

GCAGGCTGGAGGGTCTCTGAGACTCTCCTGTGTAG

CCTCTGGATACACCGTCAGTGCCTACTGTATGGGC

TGGTTCCGCCAGGTTCTAGGGAAGGGGCGCGAGAG

GATCGCATTATCGATGCCGGGGGTGCTACGATTT

ACGCAGACCCCGTGAAGGGCCGATTCACCATCTCC

AAAGACAACGCCAAGAACACTCTGTATCTGCAAAT

GAACAGCCTGAAACCTGAGGACACTGCCATGTACT

ACTGTGTTGCAGATCGCCGGGGGCGGGTACGTCGG

TGCGAGTATAACGCCTGGGGCCAGGGGACCCAGGT

CACCGTCTCCTCA (Camel sdAb AS76169 Nucleic Acid Sequence)
SEQ ID NO: 405
CAGGTGCACCTGATGGAGTCTGGGGGAGGCTCGGT

GCAGGCTGGAGGGTCTCTGAGACTCTCCTGTGCAG

CCTCTGGATACATTTACAGTAGCTTCTGCATGGGC

TGGTTCCGCCAGGCTCCAGGGAAGGAGCGCGAGGT

GGTCGCGTATATTCGCGATAATATTATGACAAGTT

ACACAGACTCCGTGAAGGGCCGATTCACCATCTCC

AAAGACAACGCCAAGAGAACTCTGTATCTACAAAT

GAACGGCCTGAAACCTGAAGATACTGGCATGTACT

ACTGTGCGGTAGACCGGGGGGATACGCTAATAGT

TGCGCGGTAGCGGCCCGGTATGATTACTGGGGCCG

GGGGACCCAGGTCACCGTCTCCTCA (Camel sdAb AS63931 Nucleic Acid Sequence)
SEQ ID NO: 406
GAGGTGCAGCTGGCGGAGTCTGGGGGAGGCTCGGT

GCAGGCTGGGGGGTCTCTGAGACTCTCCTGTGCAG

GCTCTTTCTCTGGATACGGCGTCAGTACCATGGCC

TGGTTCCGCCAGGCTCCAGGGAAGGAGCGCGAGGG

GGTCGCAGCTATTACTGTTGGTAGTGGAAACACAT

ACTATGCCGACTCCGTGACGGGCCGATTCACCATC

TCCCGAGACAACGCCAAGAGGACGGTGTATTTGCA

AATGAACAGCCTGAAACCTGAGGACACTGCCATGT

ACTACTGTGCGGCCGGATGGTTGTCGGGTGGTAGT

TGGCACGTTCCCGGCAGGTATAACTACTGGGGCCA

GGGGACCCAGGTCACCGTCTCCTCA (Camel sdAb AS63937 Nucleic Acid Sequence)
SEQ ID NO: 407
CAGGTGAAGTTAGTGGAGTCTGGGGGAGGCTCGGT

GCAGGCTGGAGGGTCTCTGAGACTCTCCTGTGCAG

CCTCTGGATCCACCATCAGTAGTCGCCCGATGGCC

TGGTTCCGCCAGGCTCCAGGGAAGGAGCGCGAGGG

GGTCGCGTGTATACATACTGGTCTTGGTAGAACAT

ACTATGCCGACTCCGTGAAGGGCCGATTCACCATC

TCCCAAGACAACGCCAAGAACACGGTGTATCTGCA

AGTGAACAGCCTGAAACCTGAGGACACTGCCATGT

ACTACTGTGCGGCAGACTCGCGGCGGCCGTGTATG

GTAGCCGCAGGGTATACCTACTGGGGCCAGGGGAC

CCAGGTCACCGTCTCCTCA (Camel sdAb AS63948 Nucleic Acid Sequence)
SEQ ID NO: 408
CAGGTGCAGCTGGTGGAGTCTGGGGGAGGCTCGGT
GCAGGCTGGAGGGTCTCTGAGACTCTCCTGTACAG
CCTCTGGATACACCTATAGATACCTCTACATGGGC
TGGTTCCGCCAGACTCCAGGGAAGGAGCGCGAGGG
GGTCGCATGTATTTATACTGGTAGTGGTAGCACAG
GGTATGCCGACTCCGTGAAGGGCCGATTCACCATC
TCCCAAGACAACGCCGAGAACACGGTGTATCTGCA
AATGAACAGCCTGAAACCTGAGGACACTGCCATGT
ACTACTGTGCGGCAGCTTCGCCCCGGTGGGGTGGT
ACCTGTCGACGGTGGTCCGAGTATAACTACTGGGG
CCAGGGGACCCAGGTCACCGTCTCCTCA (Camel sdAb AS63956 Nucleic Acid Sequence)
SEQ ID NO: 409
CAGGTGCACCTGGTGGAGTCTGGGGGAGGCTTGGT
GCAGGCTGGAGGGTCTCTGAGACTCTCCTGTGCAG
CCTCCGGATTCACCTACAGTAACTGCTGCATGAGG
TGGTACCGCCAGGCTCCAGGGAAGGCGCGCGAGTT
GGTCTCATTAATTAATAGTAGTGGTGGCACATACT
ATGCAGACTCTGTGAGGGGCCGATTCACCATCTCC
AAAGACAACGCCAAGAACACGCTGTATCTGCAAAT
GAACAGCCTGAAACCTGAGGACACGGCCATGTATT
ACTGTGCGGCTTACCAAGCCAAGTACTGTTCAGGC
CCTTGCGCCCCCCCAACTGACTGGGGCCAGGGGAC
CCAGGTCACCGTCTCCTCA (Camel sdAb AS63965 Nucleic Acid Sequence)
SEQ ID NO: 410
CAGGTGCAGCTGGTGGAGTCTGGGGGAGGCTCGGT
GCAGGCTGGAGGGTCTCTGAGACTCTCCTGTGTAG
CCTCTGGATACAGCAGCGGTAGTTGTCGCATGGGC
TGGTACCGCCAGGCTCCAGGGAAGGAGCGCGAGTT
GGTTTCAAAGGTTATTAGTGATGGTACTACAGTCT
ATGCAGACTCCGTGAAGGGCCGATTCACCCTCTCC
CAAGGAAACGCCAAGAACACGGTGTATCTGCAAAT
GAGTAGCCTGTTACCTGAGGACACGGCCATGTATT
ACTGTAATGCATGGTGTAGGGAGTATCCCGGGGGG
ATCCTGAATAACGGCTGGGGCCAGGGGACCCAGGT
CACCGTCTCCTCA (Camel sdAb AS63993 Nucleic Acid Sequence)
SEQ ID NO: 411
CAGGTGAAGTTGGTGGAGTCTGGGGGGGGCTTGGT
GCAGGCAGGGGGTCTCTGAGACTCTCCTGTACAG
TTTCTGGATTCACTTTCGATGACCTCGTCATGGCC
TGGTTCCGCCAGGCTCCAGGGAAGGAGCGCCAACT
TGTCTCGTTGGTTGCGACTGCTGGTAATAGCGTCT
ATGCAGACTCCGTGAAGGGCCGATTCACACTCTCC
AGAGACAACGCCCACAGCACGGCGTATCTGCAAAT
GAACGGCCTGAAACCTGAGGACACGCCATGTATT
ACTGTGCGGCACGTACCGATTCTGAGCATGCGTTT
AAGTTCTGGGGTCAGGGGACCCAGGTCACCGTCTC
CTCA (Camel sdAb AS63999 Nucleic Acid Sequence)
SEQ ID NO: 412
GAGGTGCAACTGGTGGAGTCTGGGGGAGGCTCGGT
GCAGGCTGGAGGGTCTCTGAGACTCTCCTGTGCAG
CCTCTGGATACACTTACAGTAGCAACTGGATGGGC
TGGTTCCGCCAGGCTCCAGGGAAGGAGCGCGAGGA
GGTCGCAATTATTTATACTGGTGGTATTAGTACAC
ACTATCGCAGCTCCGTGAAGGGCCGATTCACCATC
TCCCAAGACAACGCCAAGAACACGGTGTATCTGCA
AATGAACAGCCTGAAACCTGAGGACACTGCCATGT
ACTACTGTGCGGCGCGTTATACAGACTATAACTAC
TGGGGCCAGGGGACCCAGGTCACCGTCTCCTCA (Camel sdAb AS64006 Nucleic Acid Sequence)
SEQ ID NO: 413
CAGGTGCACCTGGTGGAGTCTGGGGGAGGCTCGGT
GCAGGCTGGAGGGTCTCTGAGACTCTCCTGTGAAG
TCTCTGGATACACCGGCGATACGACTTACATAGGC
TGGTTCCGCCAGGCTCCAGGGAAGGAGCGCGAGGG
GGTCGCACTTATTTATACTAGTGGTACTAGCGAGT
ACTACGCCGACTCCGTGAAGGGCCGATTCATCATC
TCCCGAGACAACGCCAAGAACACGGTGTATTTACA
AATGAACAGCCTGAAACCTGAGGACACTGCCATGT
ACTACTGTGGCGCACGGAGCCGCACGATGATGTAC
TGGGGCCAGGGGACCCAGGTCACCGTCTCCTCA (Camel sdAb AS64057 Nucleic Acid Sequence)
SEQ ID NO: 414
CAGGTGCAATTGGAGGAGTCTGGGGGAGGCTTGGT
GCAGACAGGGGGTCTCTGAGACTCTCCTGTACAG
CCTCTGGATTCACTTTTGATCGTAATGCCATGCGC
TGGTACCGCCAGGCTCCAGGGAAGGAGCGCGAGGG
GGTCTCATGTATTAGTGGACGGGTGCAAATATTG
CCTATGCAGACTCCGTGAAGGGCCGATTCACCATC
TCCAGAGACAACGCCAAGAACACGCTGTATCTGCA
AATGAACAGCCTGAAACCTGAGGACACGGGCATGT
ATTACTGTGCGGCAGATACGACGTCGGGGTCTTGT
TCAGGCTTTTGGTCTACGAGCCGGTACTACTGGGG (Camel sdAb AS64060 Nucleic Acid Sequence)
SEQ ID NO: 415
CAGGTGAAGTTAGTGGAGTCTGGGGGAGGCTCGGT
GCAGGCTGGAGGGTCTCTGAGACTCTCCTGTGCAG
CCTCTGGATCCACCTACTGTACCTACCGTATGAGC
TGGTTCCGCCAGGCTCCAGGGAAGGAGCGCGAGTT
CGTCGCAGTTATTGATAGTGGCGGTAGCACAAGCT
ACGCAGACTCCGTGAAGGGCCGATTCACCATCTCC
CGAGACAACGCCAAGAACACGGTGTATCTGCAAAT
GAACAGCCTGAAACCTGAGGACACGGCCATGTATT
ACTGTAAAACAGATCCAACCATCGGCTGCCCCCAG
ACATATAGGTATAACTACTGGGGCCAGGGGACCCA
GGTCACCGTCTCCTCA (Camel sdAb AS64071 Nucleic Acid Sequence)
SEQ ID NO: 416
CAGGTGCACCTGATGGAGTCTGGGGGAGGCTCGGT
GCAGGCTGGAGGGTCTCTGAGACTCTCCTGTGTAG
CCTCTGGAAACACTTACAGGCTCAACTCTATGGGC
TGGTTCCGCCAGGCTCCAGGGAAGGAGCGCGAGGG
GGTCGCATTTATTGTTATGATTAGAGGTACCACAT
ACTATGGCGCCTCCGTAAAGGGCCGATTCACCATC
TCCCAAGACAACGCCCAGACCACGGTGTATCTGCA
AATGAGCAGCCTGAAACCGGAGGACACTGCCATGT
ACTACTGTGCGGCATCCACTAAGGACCAGTTTTAT
GTATTTAATCCTATTGGGTATGACTCTTGGGGCCA
GGGGACCCAGGTCACCGTCTCCTCA (Camel sdAb AS64093 Nucleic Acid Sequence)
SEQ ID NO: 417
CAGGTGCACCTGGTGGAGTCTGGGGGAGGCTCGGT
GCAGGCTGGAGGGTCTCTGAGACTCTCCTGTGCAA
CCTCTAGATACATCTACGGTAACAACTGCATGGCC
TGGTTCCGCCAGGCTCCAGGGAAGGAGCGCGAGGG
AGTCGCGTCTATTTATCCTGCTGGTGGTCGCACGT
ACTATGCCGACTCCGTGAAGGGCCGATTCACCATC
TCCCAAGACAACGCCAAGAACACGGTGTATCTGCA
AATTGACAGCCTGAAACCTGAGGACACGGCCATGT
ACTACTGCGCGGCACGCTCTTTTTCGATAGGAGTT
TGCGCGACGCAGTCTGGTATTACCTGGTCTAATTT
TGCTTACTGGGGCCAGGGGACCCAGGTCACCGTCT
CCTCA (Camel sdAb AS64118 Nucleic Acid Sequence)
SEQ ID NO: 418
CAGGTGCAACTGGCGGAGTCTGGGGGAGGCTCGGT
GCAGGCTGGAGGGTCTCTGAGACTCTCCTGTGCAG
CCTCTGGATACACCTACAGTGCCTGTAGAATGGCC
TGGTACCGCCAGGCTCCCGGGAAGGAGCGCGAGTT
GGTTTCATTTATTAATAGTGCTGGTAGCACATACT
ATGCCGACTCCGTGAAGGGCCGATTCGCCATCTCC
CGAGACAACGCCAAGACAACGGTGTATCTACAAAT
GAACGCCCTGAAAGCTGAGGACACGCCATATATT
ACTGTAACACATGGGATAGTAGCTGCCGCTTTCAG
TACTGGGGCCAGGGGACCCAGGTCACCGTCTCCTC
A (Camel sdAb AS64120 Nucleic Acid Sequence)
SEQ ID NO: 419
CAGGTGAGGTTGGTGGAGTCTGGGGGAGGCTCGGT
GCAGGCTGGAGGGTCTCTGAGACTCTCCTGTGAAA
CCTCTAGATACATCTACGGTAACAACTGCATGGCC
TGGTTCCGCCAGGCTCCAGGGAAGGAGCGCGAGGG
AGTCGCGTCTATTTATCCTGCTGGTGGTCGCCCGT
ACTATGCCGACTCCGTGAAGGGCCGATTCACCATC
TCCCAAAGACAACGCCAAGAACACGGTGTATCTGC
AAAATGGACAGCCCTGAAAACCTGAGGACACGGCC
CATGTACTACTGCGCGGGCACGCTTCTTTTTTCGA
TAGCAAATTGCGCCAACGCAATCCTGGTATTAACC
AGGGGCCAAATTTTGGCTTACGGGGGCCAGGGGACC
CAGGTCACCCTTCTCCTCA (Camel sdAb AS64124 Nucleic Acid Sequence)
SEQ ID NO: 420
CAGGTGAAGTTGGTGGAGTCTGGGGGAGGCTCGGT
GCAGACTGGAGGGTCTCTGAGACTCTCCTGTGCAG
TCTCTACGTACACCCCCAGTAACAACTACATGGGC
TGGTTCCGCCAGGCTCCAGGGAAGGAGCGCGAGGG
CGTCGCGGCTATCGCTACTATTGGTGGTACCACAC
GTTATGCCGACTCCGTGAAGGGCCGATTCACCATC
TCCCAAGACGGCGCCAAGAACACGATATATCTGCA
AATGAACGCCCTGAAACCGGAGGACACTGCCATGT
ACTACTGTGCGGCCGGGCGGCCATACTCATTACCC
TTACCCTTACCCTTGGAAAGCGGTGCGTATCGCTA
CTGGGGCCAGGGGACCCAGGTCACCGTCTCCTCA (Camel sdAb AS64135 Nucleic Acid Sequence)
SEQ ID NO: 421
CAGGTGAAGTTGGTGGAGTCTGGGGGAGGCTCGGT
GCAGGCTGGAGGGTCTCTGAGACTCTCCTGTGTAG
CCTCTACATCAACCTACTGTAGGTACTACATGCGC
TGGTACCGGCAGGCTCCAGGGAAAGAGCGCGAGTT
CGTCTCAGCGATGCAACCCGATGGTACGACAAGCT -continued
ACTCAGACTCCGTGAAGGGCCGATTCACCATGTCC

CAAGACAGAGCCAACAATATGTTGTATCTGCAAAT

GAACAGCCTGAGGCCTGAGGACACGGCCATGTATT

ACTGTAAAAGAGATCCAATGGGGGGTTCAAGGACC

CCGTGCACCTCCGCCTGGGGCCAGGGGACCCAGGT

CACCGTCTCCTCA (Camel sdAb AS64163 Nucleic Acid Sequence)
SEQ ID NO: 422
CAGGTGAGGTTGGTGGAGTCTGGGGGAGGCTCGGT

GCAGGCTGGAGGGTCTCTGAGACTCTCCTGTGCAG

TCTCTGGATACAGATATAGATGGAACTGCATGGCC

TGGTTCCGCCAGGCTCCAGGGAAGGAGCGCGAGGG

GGTCGCAGCTATTTCTACTGGAAGCGGAAGCACAT

ACTATGCCGGCTCCGTGAAGGGCCGATTCACCATC

TCCCAAGACAACGCCAAGAACATGTATCTGCAAAT

GAACAGCCTGAAACCTGAGGACACTGCCATGTACT

ACTGTGCGGCAGATCCTTCGGTTTGCCCCGGTGGT

ATGTGGTACTCCAAAGAGTATAGGTACTGGGGCCA

GGGGACCCAGGTCACCGTCTCCTCA (Camel sdAb AS64182 Nucleic Acid Sequence)
SEQ ID NO: 423
CAGGTGCACCTGATGGAGTCTGGGGGAGGCTCGGT

GCAGGCTGGAGGGTCTCTGAGACTCTCCTGCACAG

CCTCTGGACAGACCTCCAGATACCTCTACATGGGC

TGGTTTCGCCAGACTCCAGGGAAGGAGCGCGAGGG

GGTCGCATGTATTTATACTGGTAGTGGTAGCACAG

GGTATGCCGACTCCGTGAAGGGCCGATTCACCATC

TCCCAAGACAACGCCAAGAACACGGTGTATCTGCA

AACGAATAGCCTGAAACCTGAGGACACTGCCATGT

ACTACTGTGCGGCAAGTTCGCCCCATTGGGGCGGT

ACCTGTCGACGCTGGTCCGAGTATAAGTACTGGGG

CCAGGGGACCCAGGTCACCGTCTCCTCA (Camel sdAb AS64183 Nucleic Acid Sequence)
SEQ ID NO: 424
CAGGTGCACCTGGTGGAGTCTGGGGGAGGCTCGGT

GCAGGCTGGAGGGTCTCTGAGACTCTCCTGTGCAG

CCTCTGGACACACCTACAGTGCCAACTGCATGGCC

TGGTTCCGCCGGGCCCCAGGGAAGGAGCGCGAGTG

GGTCGCGTCGGTTTATACTGATGATGATAGCACAA

TGTATACCGACTCCGTGAAGGGCCGATTCACCATC

TTCCAAGACAACGCCAAGAACACGGTGTATCTGCA

AATGAACAGCCTGAAACCTGAGGACACTGGCATGT

-continued
ACATCTGTGCGGCAGATTTAAGCGGAGGACCGGCC

GGTTGTGGGTATACCCACTGGGGCCAGGGGACCCA

GGTCACCGTCTCCTCA (Camel sdAb AS64207 Nucleic Acid Sequence)
SEQ ID NO: 425
GAGGTGCAGCTGGTGGAGTCTGGGGGAGGCTCGGT

GCAGGCTGGAGGGTCTCTGAGACTCTCCTGTGCAG

CCTCTGGATACACCTACAGTAGCAACTTCATGGGC

TGGTTCCGCCAGGCTCCAGGGAAGGAGCGCGAGGG

GGTCGCAACTATTGTTTCTGGTGGTGGTACCACAT

ACTATGCCGACTCCGTGAGGGCCGATTCACCATC

TCCCAAGACAACGCCAAGAACACGGTGTATCTGCA

AATGAACAGCCTGAAACCTGAGGACACTGCCATGT

ACTACTGTGCGGCAGGGGCCCCCCTACGAACGGT

GCTAAGTGGTACCCCCTCCGACCTCCTGGTTATAA

CTACTGGGGCCAGGGGACCCAGGTCACCGTCTCCT

CA (Camel sdAb AS64276 Nucleic Acid Sequence)
SEQ ID NO: 426
CAGGTGCACCTGATGGAGTCTGGGGGAGGCTCGGT

GCAGGCTGGAGGGTCTCTGAGCCTCTCCTGTGTAG

TCTCTGGATACACCGGCAGTAGCCGCTGTATGGCC

TGGTTCCGCCAGGCTCCAGGGAAGGAGCGCGAGGC

GGTCGCACAAATTTTTACTGGTCGTGGTACCACAG

GCTATGCCGACTCCGTGAAGGGCCGATTCACTATT

TCCCAAGACAACGCCAAGAACACGGTGTATCTGCG

AATGAACAGTCTGAGACCTGAGGACACTGCCATTT

ACTACTGTGCGGCGAGTCTCGGCCCGGGACGCGGA

GCCTGTGGGTATAACTACTGGGGCCAGGGGACCCA

GGTCACCGTCTCCTCA (Camel sdAb AS64336 Nucleic Acid Sequence)
SEQ ID NO: 427
CAGGTGCAGCTGGTGGAGTCTGGGGGAGGCTCGGT

GCAGGCTGGAGGGTCTCTAAGACTCTCCTGTACAA

CCTCTGGACGCACCTACAGTAGCTGCAGCATGGGC

TGGTACCGCCAGGCTCCAGGGAAGGAGCGCGAGTT

GGTCTCACATATTTTTAGTGATGGTAGCAGATACT

ATGCAGACTCCGTGAAGGGCCGATTCACCATCTCC

CAAGACAACGCCAAGAACACGGTGTATCTGCAAAT

GAACAGCCTGAAACCTGAGGACACGGCCATGTATT

ACTGTAACCGCCGTACGGGTTGGGCACCAAGGTGC

GCTGTTCCCGGTTACTGGGGCCAGGGGACCCAGGT

CACCGTCTCCTCA

-continued (Camel sdAb AS64346 Nucleic Acid Sequence)
SEQ ID NO: 428
CAGGTGCACCTGGTGGAGTCTGGGGGAGGCTCGGT

GCAGGCTGGAGGGTCTCTGAGACTCTCCTGTGCAG

CCTCTGGATACACCTATTTCATGGGCTGGTTCCGC

CAGGCTCCACAGAAGGAGCGCGAATGGGTCGCGAC

TATTGGTACTGGTGATATTTTCAATGGCGCTGCTT

ACTATGTCGACTCCGTGAAGGGCCGATTCGCCATC

TCCCAAGACAACGCCAAGAACACGGTGTATCTGCA

AATGAACAGCCTGAAACCTGAAGACACTGCCGTGT

ACGTCTGTGCGGCAGTTCAATCGAAATCCTCAAAC

TACGTGTTGAGAGACGCATCTACCTACAACTACTG

GGGCCAGGGGACCCAGGTCACCGTCTCCTCA (Camel sdAb AS64420 Nucleic Acid Sequence)
SEQ ID NO: 429
GAGGTGCAGCTGGTGGAGTCTGGGGGAGGCTCGGT

GCAGGCTGAAGGGTCTCTGAGACTCTCCTGTGCAG

CCTCTGGAGACACCAGTAGAAGCGTCTGGATGGGC

TGGGCCCGCCAGGTTCCAGGGAAAGAGCGCGAGGT

GGTCGCAACCATTAGTACTGCCGGTGGTAGTACAT

GGTATACCGACTCCGTGAAGGGCCGATTCACCATC

TCCCAAGACAACGCCAAGAACACGGTGTACCTGCA

AATGAACAGCCTGAAACCTGAGGACACTGCCATAT

ACTATTGTGCGGCCAGAAGCAGATATGCTACCTAC

TGGGGCCAGGGGACCCAGGTCACCGTCTCCTCA (Camel sdAb AS64473 Nucleic Acid Sequence)
SEQ ID NO: 430
CAGGTGAGGTTGGTGGAGTCTGGGGGAGGCTCGGT

GCAGGCTGGAGGGTCTCTGAGACTCTCCTGTACAG

CCTCTGGATACACCTACAGATACCTCTACATGGCC

TGGTTCCGCCAGACTCCAGGGAAGGAGCGCGAGGG

GGTCGCATGTATTTATACTGGTAGTGGTACCACAG

GGTATGCCGACTCCGTGAAGGGCCGATTCACCATC

TCCCAAGACAACGCCAAGAATACGGTGTATCTGCA

AATGAACAGCCTGAACGCTGAGGACACTGCCATGT

ACTACTGTGCGGCAAGTTCGCCCCAGTGGGGCGGT

ACCTGTCGACGCTGGTCCGAGTATAACTACTGGGG

CCAGGGGACCCAGGTCACCGTCTCCTCA (Camel sdAb AS64475 Nucleic Acid Sequence)
SEQ ID NO: 431
CAGGTGCAACTGCAGGAGTCTGGGGGAGGCTCGGT

GCAGGCTGGAGGGTCTCTGAGACTCTCCTGTGCAG

CCTCTGGATACACCTGGAGTCGCAACTGGATGGGC

TGGTTCCGCCAGGCTCCAGGGAAGGAGCGCGAGGG

GTTCGCAACTATTACAATTAGTGGTGGTAGCACAT

GGTATGCCGACTCCGTGAAGGGCCGATTCACCATC

TCCCTAGACAACGCCGGGAACACGGTGTATCTGCA

AATGAACAGCCTGAAACCTGAGGACACTGCCATGT

ACTACTGTGCGGCGCGGGATACCGCGCGGACCTAC

TGGGGCCAGGGTACCCAGGTCACCGTCTCCTCA (Camel sdAb AS64513 Nucleic Acid Sequence)
SEQ ID NO: 432
GAGGTGCAGCTGGTGGAATCTGGGGGAGGCTCGGT

GCAGGCTGGAGGGTCTCTGAGACTCTCCTGTGTAG

CCTCTGACTACCCCTACATAGACAACTGCATGGGC

TGGTTCCGCCAGGGTCCAGGGAAGGAGCGCGAGGG

GGTCGCAGCTGCGTGTACTGGTGGTGGTAGCACAT

ATTATGCCGACTCCGTGAAGGGCCGATTCACCATC

TCCCGAGACAACGCCAAGAACACGGTGTATCTGCA

AATGAACAGCCTGAAACCTGAGGACACTGACGTGT

ACTACTGTGCGACAGGCTACTATAGCGGCTCTGGT

CCGGGGTATTTACTCCCATGGAGGTATAACTACTG

GGGCCAGGGGACCCAGGTCACCGTCTCCTCA (Camel sdAb AS64562 Nucleic Acid Sequence)
SEQ ID NO: 433
GAGGTGCAACTGGTGGAATCTGGGGGAGGCTCGGT

GCAGGCTGGAGGGTCTCTGAGACTCTCCTGTGCAG

CCTCTGGATACACCGCTAGGCGCGACTTCATGGCC

TGGTTCCGCCAGGTTCCAGGGAAGGAGCGCGAGGG

GGTCGCAGTCATTCATACTGGTGGTGACACCACAT

ACTATGCCGACTCCGTGAAGGGCCGATTCACCATC

TCCCGCGACAACGCCCAGAACATAATGAATCTGCA

AATGAACAGCCTTAAACCTGAGGACACTGCCATGT

ACTACTGTGCGGCAGGTTTCCGTCCGCGTGGTGGA

GGATACACGGGTGACGTCTTGGCCCAGGCTGCGGC

ATACAACTACTGGGGCCAGGGGACCCAGGTCACCG

TCTCCTCA (Camel sdAb AS64583 Nucleic Acid Sequence)
SEQ ID NO: 434
GAGGTGCAGCTGGCGGAGTCTGGGGGAGGCTTGGT

GCAGGCAGGGGGTCTCTGAGACTCTCCTGTACAG

CCTCTGGATTCACTATTGCTGTTTATACCATGGGC

TGGTTCCGCCAGGCTCCAGGGAAGGAGCGCGAGGG

AATCTCATGTACTAGCTGGGCTGGTGGTCGCACAT

ACACTGAGACTCCGTGAAGGGCCGATTCACCATC

TCCAGAGACAACGCCAAGAACACGCTGTATCTGCA

AATGAACAGCCTGAAACCTGAGGACACGGCCATGT

ATTACTGTGCGGCAAAGGCACATCCCGACTGTTCA

-continued

GGGGATTGGTCCCCATCTGGGTATGAATACTGGGG

CCAGGGGACCCAGGTCACCGTCTCCTCA (Camel sdAb AS64594 Nucleic Acid Sequence)
SEQ ID NO: 435
CAGGTGCACCTGGTGGAGTCTGGGGGAGGCTCGGT

GCAGGCTGGAGGGTCTCTGAGACTCTCCTGTGCAG

CCTCTGGATACACCTACAATAGCAACTACATGGGC

TGGTTCCGCCAGGCTCCAGGGAAGGAGCGCGAGGG

GGTCGCACTTATTTATACTGGTGGTGGTAGCACAT

ATTATGCCGACTCCGTGAAGGGCCGATTCACCATC

TCCCGAGACAACGCCAAAAACACGGTGTATCTGCA

AATGAACAGCCTGAAACCTGAGGACACTGCCATGT

ACTACTGTTCGGTAAGAACGCAGACGCGTAACTAC

TGGGGCCAGGGGACCCAGGTCACCGTCTCCTCA (Camel sdAb AS64605 Nucleic Acid Sequence)
SEQ ID NO: 436
CAGGTGAAGTTGGTGGAGTCTGGGGGAGGCTCGGT

GCAGGCTGGAGGGTCTCTGAGACTCTCCTGTGCAG

TTTCTAGATATCCCTACAGCAGCATCTGCATGGGC

TGGTTCCGCCAGGCTCCAGGGAAGGAGAGCGAGGG

TGTCGCACGTATTTATACTGGTACTGGTAGTACAT

GGTATACCGACTCCGTGAAGGGCCGATTCACCATC

GCCCGAGACAACGCCCAGAACACGGTGTATCTGCA

AATGAACAGCCTGAAACCTGAGGACACTGCCATGT

ACTACTGTGCGGCGCGTAGCAATTCATATTCATAT

TCAAGTTGTGATTACGGCCCCCTCACGAGGGGGGG

GTATAACTTCTGGGGCCAGGGGACCCAGGTCACCG

TCTCCTCA (Camel sdAb AS64606 Nucleic Acid Sequence)
SEQ ID NO: 437
GAGGTGCAGCTGGCGGAGTCTGGGGGAGGATCGGT

GCAGGCTGGAGGGTCTCTGAGACTCTCCTGTGCAG

TCTCTGGATACACCAGCCGTAGCAATTACATGGGC

TGGTTCCGCCAGGCTCCAGGGAAGGAGCGCGAGGG

GGTCGCGCTAATTTATACTCGTGGTGGTAGCACAT

ACTATGCCTCCTCCGTGAAGGGCCGGTTCACCATC

TCCCAAGACAGTGCCAAGAAAACGTATCTGCAAAT

GAACAGTGTGAAACGGAGGACACTGCCATGTACT

ACTGTGCTTTGCGCCTTGATGAGAAGATGTACTGG

GGCCAGGGGACCCAGGTCACCGTCTCCTCA (Camel sdAb AS68121 Nucleic Acid Sequence)
SEQ ID NO: 438
GAGGTGCAGCTGGCGGAGTCTGGGGGAGGCTCGGT

GCAGGCTGGAGGGTCTCTGAGACTCTCCTGTGATG

CCTCTGGATACACCTACAGCCGCAACTGCATGGGC

-continued

TGGTTCCGCCAGGCTCCAGGGAAGGAGCGCGAGGG

GGTCGCAGCGTTCTATACTGATTATATTCGTTTTG

GGCGCACATATTATGCCGACTCCGTGAAGGGCCGA

TTCACCATCTTCCAAGACAACGCCAAGAACACGGT

GTATCTGCAAATGAACAGCCTGAAACCTGAGGACA

CTGCCATGTACTACTGTGCGGCAGATCCTGGGAGT

CGTACAGACGATAGTTGTGGTACCTCATACAACAA

AGGGAATTTTGGTTACTGGGGCCAGGGGACCCAGG

TCACCGTCTCCTCA (Camel sdAb AS68170 Nucleic Acid Sequence)
SEQ ID NO: 439
CAGGTGCAGCTGGTGGAGTCTGGGGGAGGCTCGGT

GCAGGCTGGAGGGTCGCTGAGACTCTCCTGTACAG

CCTCTGGATACACCTACAGAAGCAACTGTATGGGC

TGGTTCCGCCAGGCTCCAGGGAAGGAGCGCGAGGG

GGTCGCAACAATCTATACTGGTGGTGGTCGTAATC

TATACTATGCCGACTCCGTGAAGGGCCGATTCACC

ATCTCCCGAGACAACGCCAAGAACACCCTGTACCT

GCAAATGAACAGCCTGAAGCCTGAGGACTCTGCCA

GGTACTACTGTGCGGCCGCGAGTGACGTGGCAGTT

GGTGTTAATTCCTGCGGGGAAGGACTGCGGGGTT

TGACGCCTGGGGCCAGGGGACCCAGGTCACCGTCT

CCTCA (Camel sdAb AS63964 Nucleic Acid Sequence)
SEQ ID NO: 440
CAGGTGAGGTTAGTGGAGTCTGGGGGAGGATCGGT

ACAGGCTGGAGGGTCTCTGAGACTCTCCTGCTCAG

CCTCTGGATACACCTACAGTTACAACAATATGGGC

TGGTTCCGCCAGGCTCCAGGGAACGAGCGCGAGGG

GGTCGCAGCTATTAGTGGTGGTCGTTTCACCGCCT

ATGCCGACTCCGTGAAGGGCCGATTCACCATCTCC

CGAGACAACGCCGAGAACACGCTGTATCTGCAAAT

GAACAACCTGAAACCTGAGGACACTGGGATGTACT

ACTGTGCGGCAGAGGTAGTTGATCCGACCTGGGGG

TCGCGTGACCAAAGACGATATAAGTACTGGGGCCA

GGGGACCCAGGTCACCGTCTCCTCA (Camel sdAb AS64116 Nucleic Acid Sequence)
SEQ ID NO: 441
CAGGTGAAGTTGGTGGAGTCTGGGGGAGGCTCGGT

GCAGGCTGGAGGGTCTCTGAGACTCTCGTGTGCAG

CCTCTGGATACATCTACAGTTGCGTGGCTGGTTC

CGCCAGGCTCCAGGGAAGGAGCGCGAGGGGGTCGC

AGGTATTAGTACTGGTGGTGGTGGCACAGTCTATG

CCGACTCCGTGAAGGGCCAATTCACCATCTCCCGA

GACAACGCCAAGAACACGGTGTACCTGCAAATGGA

CAGCCTGAAACCTGAGGACACTGCCATGTACTACT

GTGCGGCAGATCGATGGAATTCATTCGCTAATTGC

GGTGCCTGGGGAAGGTATACCTACTGGGGCCAGGG

GACCCAGGTCACCGTCTCCTCA (Camel sdAb AS68270 Nucleic Acid Sequence)
SEQ ID NO: 442
CAGGTGCAACTGGCGGAGTCTGGGGGAGGCTCGGT

GCAGGCTGGAGGGTCTCTGAGACTCTCCTGTGTAG

CCTCTGGATACCCCTCTTCCACCTACTACATGCTC

AGCATGGCGTGGTTCCGCCAGGCTCCAGGGAAGGA

GCGCGAGGGGGTCGCCGCTATTACTAGCGGTACTG

GGAGCACAAGCTACGCAGACTCCGTGAAGGACCGA

TTCACCATCTCCAAAGACTACGCCAACAACACTCT

GTATCTGCACATAAACAACCTGAAACCTGAGGACA

CTGCCATGTACTACTGTGCGGCAGCCTCAGGTTGG

ATCGTTCCTAGTAGGTCCCTGACCGCCAACCTATA

TAGGTATTGGGGCCAGGGGACCCAGGTCACCGTCT

CCTCA (Camel sdAb AS68320 Nucleic Acid Sequence)
SEQ ID NO: 443
CAGGTGCACCTGGTGGAGTCTGGGGGAGACTCGGT

GCAGGCTGGAGGGTCCCTGAGACTCTCCTGTGCAG

CCTCTGGATACACCTACAATACCAACTACATGGGC

TGGTTCCGCCAGGCTCCAGGGAAGGAGCGCGAGGG

GGTCGCAGCTATTTATAGACATAGTGGTAACACAG

CCTATGCCGACTCCGTGAAGGGCCGATTCACCATC

TCCCAAGACTACGCCAAGAACACCGTGTATCTGCA

AATGAACAGCCTGAAACCTGAGGACACTGCCATGT

ACTACTGTGCGGCAGGGCGCGCTGGTCCCTGGGCC

CTGATGCGCCCGACTGAGTTTGGTTACTGGGGCCA

GGGGACCCAGGTCACCGTCTCCTCA (Camel sdAb AS68351 Nucleic Acid Sequence)
SEQ ID NO: 444
CAGGTGCAATTGGAGGAGTCTGGGGGAGGCTTGGT

GCAGCCTGGGGGGTCTCTGAGACTCTCCTGTGCGG

CCTCTGGAGACACATTTCGTGCCTATTACATGAAC

TGGGTCCGCCAGGCTCCAGGGAAGGGATTCGAGTG

GGTCTCAGGTATTAGCGCCAGTGGCGGCCGTACGT

CATACGCAGACTCCGTGAAGGGCCGATTCACCATC

TCCAGAGACAACGCCAAAAACACGCTGTATCTGCA

ATTGAACAGCCTGAGCACTGAGGACACGGGCATGT

ATTATTGTGTAAAGGGAGCTGTCCGTCTCTCGACA

TCGTCAGTACGGGATTCGTCCTGGGGCCAGGGGAC

CCAGGTCACCGTCTCCTCA (Camel sdAb AS75378 Nucleic Acid Sequence)
SEQ ID NO: 445
CAGGTGCAATTGGAGGAGTCTGGGGGAGGCTCGGT

GCAGGCTGGAGGGTCTCTGAGACTCTCCTGTGTAG

TCTCTGGAAACACCCGCAGTACCACGTACATGGGC

TGGTTCCGCCAGGCTCCAGGGAAGGAGCGCGAGGG

GGTCGCAATAGTTTATACTGGTGGTCGTGACACAT

ACTATGCCGCCTCCGTGAAGGGCCGATTCACCATC

TCCCAAGACAACGCCAAGACAACGATCTATCTGCA

AATGAACAGTCTGGAACCTGAGGACACTGCCATGT

ACTACTGTGCGGCACGCTCATATGAGTATACCTAC

TGGGGTCGGGGGACCCAGGTCACCGTCTCCTCA (Camel sdAb AS75383 Nucleic Acid Sequence)
SEQ ID NO: 446
GAGGTGCAACTGGCGGAGTCTGGGGGAGGCTCGGT

GCAGGCTGGAGGGTCTCTGAGACTCTCCTGTGTAG

CCTCTGGATACACCTTCAGTAGCTACTGCTTGGGC

TGGTTCCGCCAGGCTCCAGGGAAGCAGCGCCAGGG

GGTCGCAACGTTTAATAATAGAGGTGTCGCAAACT

ACCACGATTCCGTGAAGGGCCGATTCACCGCCTCC

GTAGACAACGCCAAGAACACTCTGCTTCTGCAAAT

GAACAGCCTGGAACCTGACGACACGGCCATGTACT

ACTGTGCGGCGGATCGCCGGTACGGTCGTCAGTGG

TATCAGCCTTGCGAGTGGAACACCTGGGGCCAGGG

GACCCAGGTCACCGTCTCCTCA (Camel sdAb AS75751 Nucleic Acid Sequence)
SEQ ID NO: 447
CAGGTGAGGTTGGTGGAGTCTGGGGGAGGCTCGGT

GCAGGCTGGAGGGTCTCTGAGACTCTCCTGTGTAG

CCTCTGGATACTTCTACAATACCTACTACTTTATG

GGCTGGTTCCGCCAGGCTCCAGGGAAGGAGCGCGA

GGGGGTCGCAGCTATTGATACTGATGGTAGAACAA

GTTACGCAGACTCCGTGAAGGGCCGATTCACCATC

TCCAAAGACAACGCCAAGAACACTCTGTATCTGCA

AATGAACAGCCTGAAACCTGAGGACACTGCCATGT

ACTACTGTGCGGCAGGTTTTGGCTATATGAATGTT

ATTCAGGCTCTTAATGGCATGAGACAGAATCCCGA

CTACTGGGGCCAGGGGACCCAGGTCACCGTCTCCT

CA (Camel sdAb AS76422 Nucleic Acid Sequence)
SEQ ID NO: 448
CAGGTGAAGTTGGTGGAGTCTGGGGGAGGCTCGGT

GCAGGCTGGAGGGTCTCTGAGACTCTCCTGTGCAG

CCTCTGGATACACCTTCGCTGGCAACTGCTTGGGC

TGGTTTCGCCAGGCTCCAGGGAAGGGGCGCGAGGG

GGTCGTAACGTACAATAACTTCGGTGTCGCCAACT

ACGCCGATTCCGTGAAGGGCCGATTCACCGTCTCC

CAAGACAACGCCAAGAACACTCTGCTTCTGCAAAT

GAACAGCCTGGAACCTGAGGACACTGCCATGTACT

ACTGTGCGGCGGACCGCCGGGACGGTCGTCGCTGG

TCTCAGCCTTGCGAGTGGAATACCTGGGGCCAGGG

GACCCAGGTCACCGTCTCCTCA

Humanized Camel sdAb Nucleic Acid Sequences (Humanized sdAb AS64380VH4 Nucleic Acid Sequence)
SEQ ID NO: 449
GAGGTGCAGCTGGTGGAGAGCGGAGGAGGACTGGT

GCAGCCAGGAGGCAGCCTGAGGCTGTCCTGCGCAG

CATCTGGAAACACCTACAGCTCCAATTATATGGGA

TGGTTCAGGCAGGCACCTGGCAAGGGACTGGAGGA

GGTGGCCGTGATCTACACCAGGGGAGGACACACAT

ACTATGTGGACTCCGTGCGGGGACGGTTCACCATC

AGCAGGGATAACGCCAAGAACAGCCTGTATCTGCA

GATGAACTCTCTGAGAGCCGAGGACACAGCCGTGT

ACTATTGTGCAGCATCTAGCAGGCACAGGCTGGGC

CTGAACAATCCAAGGGACTACGATTATTGGGGCCA

GGGCACCCTGGTGACAGTGTCCTCT (Humanized sdAb AS64380VH5 Nucleic Acid Sequence)
SEQ ID NO: 450
GAGGTGCAGCTGGTGGAGAGCGGAGGAGGACTGGT

GCAGCCAGGAGGCAGCCTGAGGCTGTCCTGCGCAG

CATCTGGAAACACCTACAGCTCCAATTATATGGGA

TGGTTCAGGCAGGCACCTGGCAAGGGCCTGGAGGA

GGTGGCCGTGATCTACACCAGAGGCGGCCACACAT

ACTATGTGGACTCCGTGCGGGGACGGTTCACCATC

AGCCAGGATAACGCCAAGAACAGCCTGTATCTGCA

GATGAACTCTCTGAGGGCCGAGGACACAGCCGTGT

ACTATTGTGCAGCATCTAGCAGGCACAGGCTGGGC

CTGAACAATCCAAGGGACTACGATTATTGGGGCCA

GGGCACCCTGGTGACAGTGTCCTCT (Humanized sdAb AS64380VH6 Nucleic Acid Sequence)
SEQ ID NO: 451
GAGGTGCAGCTGGTGGAGAGCGGAGGAGGACTGGT

GCAGCCAGGAGGCAGCCTGAGGCTGTCCTGCGCAG

CATCTGGAAACACCTACAGCTCCAATTATATGGGA

TGGTTCAGGCAGGCACCTGGCAAGGGCCTGGAGGA

GGTGGCCGTGATCTACACCAGAGGCGGCCACACAT

ACTATGTGGACTCCGTGCGGGGACGGTTCACCATC

AGCCAGGATAACGCCAAGAACAGCGTGTATCTGCA

GATGAACTCTCTGAGGGCCGAGGACACAGCCATGT

ACTATTGTGCAGCATCTAGCAGGCACAGGCTGGGC

CTGAACAATCCAAGGGACTACGATTATTGGGCCA

GGGCACCCTGGTGACAGTGTCCTCT (Humanized sdAb AS64380VH7 Nucleic Acid Sequence)
SEQ ID NO: 452
GAGGTGCAGCTGGTGGAGAGCGGAGGAGGACTGGT

GCAGCCAGGAGGCAGCCTGAGGCTGTCCTGCGCAG

CATCTGGAAACACCTACAGCTCCAATTATATGGGA

TGGTTCAGGCAGGCACCTGGCAAGGGAAGAGAGGA

GGTGGCCGTGATCTACACCAGGGGAGGACACACAT

ACTATGTGGACTCCGTGCGGGGACGGTTCACCATC

AGCCAGGATAACGCCAAGAACAGCGTGTATCTGCA

GATGAACTCTCTGAGGGCCGAGGACACAGCCATGT

ACTATTGTGCAGCATCTAGCAGGCACAGGCTGGGC

CTGAACAATCCAAGGGACTACGATTATTGGGGCCA

GGGCACCCTGGTGACAGTGTCCTCT (Humanized sdAb AS64511VH4 Nucleic Acid Sequence)
SEQ ID NO: 453
GAGGTGCAGCTGGTGGAGTCCGGAGGAGGACTGGT

GCAGCCAGGAGGCTCTCTGAGGCTGAGCTGCGCAG

CATCCAGAGCAACCTACTCTACAAACTATATCAGC

TGGTTCAGGCAGGCACCTGGCAAGGGACTGGAGGC

AGTGGCAACCATCACCACAGGCGATGGCGAGACAG

CCTACGCCGACTCTGTGAAGGGCAGGTTTACCATC

TCCCGCGATAACGCCAAGAACAGCCTGTATCTGCA

GATGAACAGCCTGAGGGCCGAGGACACAGCCGTGT

ACTATTGTGCAGCAAATCTGAGGATCGGAGGCGAC

TGGTTCGATGGAAGGGACTTTAGAGCATGGGACA

GGGAACCCTGGTGACAGTGAGCTCC (Humanized sdAb AS64511VH5 Nucleic
Acid Sequence)
SEQ ID NO: 454
GAGGTGCAGCTGGTGGAGTCCGGAGGAGGACTGGT
GCAGCCAGGAGGCTCTCTGAGGCTGAGCTGCGCAG
CATCCAGAGCAACCTACTCTACAAACTATATCAGC
TGGTTCAGGCAGGCACCTGGCAAGGGACTGGAGGC
AGTGGCAACCATCACCACAGGCGATGGCGAGACAG
CCTACGCCGACTCTGTGAAGGGCAGGTTTACCATC
TCCCGCGATAACGCCAAGAACAGCGTGTATCTGCA
GATGAACAGCCTGAGGGCCGAGGACACAGCCATGT
ACTATTGTGCAGCAAATCTGAGGATCGGAGGCGAC
TGGTTCGATGGAAGGGACTTTAGAGCATGGGACA
GGGAACCCTGGTGACAGTGAGCTCC (Humanized sdAb AS64511VH6 Nucleic
Acid Sequence)
SEQ ID NO: 455
GAGGTGCAGCTGGTGGAGTCCGGAGGAGGACTGGT
GCAGCCAGGAGGCTCTCTGAGGCTGAGCTGCGCAG
CATCCAGAGCAACCTACTCTACAAACTATATCAGC
TGGTTCAGGCAGGCACCTGGCAAGGGAAGGGAGGC
AGTGGCACCATCACCACAGGCGATGGCGAGACAG
CCTACGCCGACTCTGTGAAGGGCAGGTTTACCATC
TCCCGCGATAACGCCAAGAACAGCGTGTATCTGCA
GATGAACAGCCTGCGGGCCGAGGACACAGCCATGT
ACTATTGTGCAGCAAATCTGAGGATCGGAGGCGAC
TGGTTCGATGGAAGGGACTTTAGAGCATGGGACA
GGGAACCCTGGTGACAGTGAGCTCC (Humanized sdAb AS63931VH4 Nucleic
Acid Sequence)
SEQ ID NO: 456
CAGGTGCAGCTGGTGGAGAGCGGAGGAGGAGTGGT
GCAGCCAGGAGGCAGCCTGAGGCTGTCCTGCGCAG
GCTCTTTCAGCGGATACGGCGTGTCCACCATGGCA
TGGTTTAGGCAGGCACCTGGCAAGGGACTGGAGGG
AGTGGCAGCAATCACCGTGGGATCCGGAAACACAT
ACTATGCCGACTCTGTGACCGGCCGGTTCACAATC
TCTAGAGATAACAGCAAGAATACCCTGTATCTGCA
GATGAACAGCCTGCGGGCCGAGGACACAGCCGTGT
ACTATTGTGCAGCAGGATGGCTGTCCGGAGGATCT
TGGCACGTGCCCGGCAGGTACAACTATTGGGGCCA
GGGCACCCTGGTGACAGTGAGCTCC (Humanized sdAb AS63931VH5 Nucleic
Acid Sequence)
SEQ ID NO: 457
CAGGTGCAGCTGGTGGAGAGCGGAGGAGGAGTGGT
GCAGCCAGGAGGCAGCCTGAGGCTGTCCTGCGCAG
GCTCTTTCAGCGGATACGGCGTGTCCACCATGGCA
TGGTTTAGGCAGGCACCTGGCAAGGGACTGGAGGG
AGTGGCAGCAATCACCGTGGGATCCGGAAACACAT
ACTATGCCGACTCTGTGACCGGCCGGTTCACAATC
TCTAGAGATAACAGCAAGAATACCGTGTATCTGCA
GATGAACAGCCTGCGGGCCGAGGACACAGCCATGT
ACTATTGTGCAGCAGGATGGCTGTCCGGAGGATCT
TGGCACGTGCCCGGCAGGTACAACTATTGGGGCCA
GGGCACCCTGGTGACAGTGAGCTCC (Humanized sdAb AS63931VH6 Nucleic
Acid Sequence)
SEQ ID NO: 458
CAGGTGCAGCTGGTGGAGAGCGGAGGAGGAGTGGT
GCAGCCAGGAGGCAGCCTGAGGCTGTCCTGCGCAG
GCTCTTTCAGCGGATACGGCGTGTCCACCATGGCC
TGGTTTAGGCAGGCACCTGGCAAGGGAAGGGAGGG
AGTGGCAGCAATCACCGTGGGATCCGGAAACACAT
ACTATGCCGACTCTGTGACCGGCCGGTTCACAATC
TCTAGAGATAACAGCAAGAATACCGTGTATCTGCA
GATGAACAGCCTGCGGGCCGAGGACACAGCCATGT
ACTATTGTGCAGCAGGATGGCTGTCCGGAGGATCT
TGGCACGTGCCCGGCAGGTACAACTATTGGGGCCA
GGGCACCCTGGTGACAGTGAGCTCC (Humanized sdAb AS63997VH4 Nucleic
Acid Sequence)
SEQ ID NO: 459
CAGGTGCAGCTGGTGGAGAGCGGAGGAGGAGTGGT
GCAGCCAGGAGGCAGCCTGAGGCTGTCCTGCGCAG
CCTCTTTCAGCGGATACGGCGTGTCCACCATGGCA
TGGTTTAGGCAGGCACCTGGCAAGGGACTGGAGGG
AGTGGCAGCAATCACCGTGGGATCCGGAAACACAT
ACTATGCCGACTCTGTGAAGGGCCGGTTCACCATC
TCTAGAGATAACAGCAAGAATACACTGTACCTGCA
GATGAACAGCCTGCGGGCCGAGGACACAGCCGTGT
ACTATTGTGCCGTGGGCTATCTGTCCGGAGGATCT
TGGGATGTGCCAGGAAGGTACAACTATTGGGGCCA
GGGCACCCTGGTGACAGTGAGCTCC (Humanized sdAb AS63997VH5 Nucleic
Acid Sequence)
SEQ ID NO: 460
CAGGTGCAGCTGGTGGAGAGCGGAGGAGGAGTGGT
GCAGCCAGGAGGCAGCCTGAGGCTGTCCTGCGCAG
CCTCTTTCAGCGGATACGGCGTGTCCACCATGGCA
TGGTTTAGGCAGGCACCTGGCAAGGGACTGGAGGG
AGTGGCAGCAATCACCGTGGGATCCGGAAACACAT

ACTATGCCGACTCTGTGAAGGGCCGGTTCACCATC

TCTAGAGATAACAGCAAGAATACAGTGTACCTGCA

GATGAACAGCCTGCGGGCCGAGGACACAGCCATGT

ACTATTGTGCCGTGGGCTATCTGTCCGGAGGATCT

TGGGATGTGCCAGGAAGGTACAACTATTGGGCCA

GGGCACCCTGGTGACAGTGAGCTCC (Humanized sdAb AS63997VH6 Nucleic
Acid Sequence)
SEQ ID NO: 461
CAGGTGCAGCTGGTGGAGAGCGGAGGAGGAGTGGT

GCAGCCAGGAGGCAGCCTGAGGCTGTCCTGCGCAG

CCTCTTTCAGCGGATACGGCGTGTCCACCATGGCC

TGGTTTAGGCAGGCACCTGGCAAGGGAAGGGAGGG

AGTGGCAGCAATCACCGTGGGATCCGGAAACACAT

ACTATGCCGACTCTGTGAAGGGCCGGTTCACCATC

TCTAGAGATAACAGCAAGAATACAGTGTACCTGCA

GATGAACAGCCTGCGGGCCGAGGACACAGCCATGT

ACTATTGTGCCGTGGGCTATCTGTCCGGAGGATCT

TGGGATGTGCCAGGAAGGTACAACTATTGGGCCA

GGGCACCCTGGTGACAGTGAGCTCC (Linker amino acid sequence)
SEQ ID NO: 462
GGGGSGGGGSGGGGS (Linker amino acid sequence)
SEQ ID NO: 463
GGGGSGGGGS (Linker amino acid sequence)
SEQ ID NO: 464
GGGGS (CD8α signal peptide amino acid
sequence)
SEQ ID NO: 465
MALPVTALLLPLALLLHAARP (CD8α hinge amino acid sequence)
SEQ ID NO: 466
TTTPAPRPPTPAPTIASQPLSRPEACRPAAGGAV

HTRGLDFACDIYIWAPLAGTCGVLLLSLVITLYC (CD8α transmembrane domain amino
acid sequence)
SEQ ID NO: 467
IYIWAPLAGTCGVLLLSLVITLYC (4-1BB intracellular domain amino
acid sequence)
SEQ ID NO: 468
KRGRKKLLYIFKQPFMRPVQTTQEEDGCSCRFPEE

EEGGCEL (CD28 intracellular domain amino
acid sequence)
SEQ ID NO: 469
RSKRSRLLHSDYMNMTPRRPGPTRKHYQPYAPPRDFAAYRS (CD3ζ intracellular domain
amino acid sequence)
SEQ ID NO: 470
RVKFSRSADAPAYKQGQNQLYNELNLGRREEYDVL

DKRRGRDPEMGGKPRRKNPQEGLYNELQKDKMAEA

YSEIGMKGERRRGKGHDGLYQGLSTATKDTYDALH

MQALPPR (F2A element amino acid sequence)
SEQ ID NO: 471
GSGVKQTLNFDLLKLAGDVESNPGP (P2A element amino acid sequence)
SEQ ID NO: 472
GSGATNFSLLKQAGDVEENPGP (CAR3 anti-DLL3 scFv amino acid sequence)
SEQ ID NO: 473
MALPVTALLLPLALLLHAARPAIQLTQSPSSLSAS

VGDRVTITCRASENIYYNLAWYQQKPGKAPKWYTA

NSLEDVPSRFSGSGSGTDFTLTISSLQPEDFATYF

CKQAYDVPPTFGGGTKLEIKGGGGSGGGGSGGGGS

QVQLVQSGAEVKKPGASVKVSCKASGYTFTRYWIF

IWIRQAPGQGLEWMGYINPTVYTEFNQNFKDRVTM

TRDTSTSTVYMELSSLRSEDTAVYYCARGGSNFFD

YWQGTTVTVSS (CD28 transmembrane domain amino acid
sequence)
SEQ ID NO: 474
FWVLVVVGGVLACYSLLVTVAFIIFWV (CD28 hinge)
SEQ ID NO: 475
IEVMYPPPYLDNEKSNGTIIHVKGKHLCPSPLFPG

PSKP

Camel anti-DLL3 CAR sequences
(CAS63997)
SEQ ID NO: 476
MALPVTALLLPLALLLHAARPQVRLVESGGGSVQA

GGSLRLSCAGSFSGYGVSTMAWFRQAPGKEREGVA

AITVGSGNTYYADSVKGRFTISRDNAKRTVFLQMN

SLKPEDTAMYYCAVGYLSGGSWDVPGRYNYWGQGT

QVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPR (CAS64380)
SEQ ID NO: 477
MALPVTALLLPLALLLHAARPEVQLVESGGGSVQA

GGSLTLSCEASGNTYSSNYMGWFRQAPGKEREEVA

VIYTRGGHTYYVDSVRGRFTISQDNAKNTVYLQMN

```
SLKPEDTAMYYCAASSRHRLGLNNPRDYDYWGQGT
QVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKHDGLYQGL
STATKDTYDALHMQALPPR (CAS64511)
                                  SEQ ID NO: 478
MALPVTALLLPLALLLHAARPQVQLVESGGGSVQA
GGSLRLSCAASRATYSTNYISWFRQAPGKEREAVA
TITTGDGETAYADSVKGRFTISRDNAKNTVYLQMN
SLKPEDTAMYYCAANLRIGGDWFDGRDFRAWGQGT
QVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKHDGLYQGL
STATKDTYDALHMQALPPR (CAS64617)
                                  SEQ ID NO: 479
MALPVTALLLPLALLLHAARPQVQLVESGGGSVQA
GGSLRLSCAASGYTDRCSMAWYRQAPGKERELVSR
ISTSGFTNYAASVKGRFTISQDNAKNTVYLQMNSL
NPGDTGMYYCAIIVGRTCSLNYWGNGILVTVSSTT
TPAPRPPTPAPTIASQPLSLRPEACRPAAGGAVHT
RGLDFACDIYIWAPLAGTCGVLLLSLVITLYCKRG
RKKLLYIFKQPFMRPVQTTQEEDGCSCRFPEEEEG
GCELRVKFSRSADAPAYKQGQNQLYNELNLGRREE
YDVLDKRRGRDPEMGGKPRRKNPQEGLYNELQKDK
MAEAYSEIGMKGERRRGKHDGLYQGLSTATKDTY
DALHMQALPPR (CAS69443)
                                  SEQ ID NO: 480
MALPVTALLLPLALLLHAARPEVQLAESGGGSVQA
GGSLRLSCSASGFTFDDSDMAWYRQAPGDGCDLVS
TISSDGSTYYADSVKGRFTISQDNAKNTVYLQMHS
LKPEDTAVYYCAADFLTGFYYSDSPHPAPCSASDF
GYWGQGTQVTVSSTTTPAPRPPTPAPTIASQPLSL
RPEACRPAAGGAVHTRGLDFACDIYIWAPLAGTCG
VLLLSLVITLYCKRGRKKLLYIFKQPFMRPVQTTQ
EEDGCSCRFPEEEEGGCELRVKFSRSADAPAYKQG

QNQLYNELNLGRREEYDVLDKRRGRDPEMGGKPRR
KNPQEGLYNELQKDKMAEAYSEIGMKGERRRGKGH
DGLYQGLSTATKDTYDALHMQALPPR (CAS63931)
                                  SEQ ID NO: 481
MALPVTALLLPLALLLHAARPEVQLAESGGGSVQA
GGSLRLSCAGSFSGYGVSTMAWFRQAPGKEREGVA
AITVGSGNTYYADSVTGRFTISRDNAKRTVYLQMN
SLKPEDTAMYYCAAGWLSGGSWHVPGRYNYWGQGT
QVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKHDGLYQGL
STATKDTYDALHMQALPPR (CAS64047)
                                  SEQ ID NO: 482
MALPVTALLLPLALLLHAARPQVHLVESGGGSVQA
GGSLRLSCAASQYVYRWDLMGWFRQAPGKEREAVA
AVYTGDGITYYADSVKGRFSISQDNAKNTVYLQMN
SLKPEDTGMYFCAAGFVSGGRWNQSYRYKYWGQGT
QVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKHDGLYQGL
STATKDTYDALHMQALPPR (CAS64052)
                                  SEQ ID NO: 483
MALPVTALLLPLALLLHAARPQVHLMESGGGSVQAG
GSLRLSCAASGYTYRSNFMGWFRQAPGKEREGIAT
IHSGVATTYYADSVKGRFTISQDNAKNTVYLQMNS
LKPEDTAMYYCAAGGPPANADRWYPLRPPGYNYWG
QGTQVTVSSTTTPAPRPPTPAPTIASQPLSLRPEA
CRPAAGGAVHTRGLDFACDIYIWAPLAGTCGVLLL
SLVITLYCKRGRKKLLYIFKQPFMRPVQTTQEEDG
CSCRFPEEEEGGCELRVKFSRSADAPAYKQGQNQL
YNELNLGRREEYDVLDKRRGRDPEMGGKPRRKNPQ
EGLYNELQKDKMAEAYSEIGMKGERRRGKHDGLY
QGLSTATKDTYDALHMQALPPR
```

(CAS64062)

SEQ ID NO: 484

MALPVTALLLPLALLLHAARPQVRLVESGGGSVQVGGSLRLSCAASRSPYSSSRCMGWFRQAPGKEREGVAALYTGGGSTSYADSVKGRFTISQDNAKNTVYLQMNSLKPEDTAMYYCAAVVPRGGSCRLDERGYYHWGQGTQVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR

Humanized anti-DLL3 CAR sequences (CAS64380VH4)

SEQ ID NO: 485

MALPVTALLLPLALLLHAARPEVQLVESGGGLVQPGGSLRLSCAASGNTYSSNYMGWFRQAPGKGLEEVAVIYTRGGHTYYVDSVRGRFTISRDNAKNSLYLQMNSLRAEDTAVYYCAASSRHRLGLNNPRDYDYWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (CAS64380VH5)

SEQ ID NO: 486

MALPVTALLLPLALLLHAARPEVQLVESGGGLVQPGGSLRLSCAASGNTYSSNYMGWFRQAPGKGLEEVAVIYTRGGHTYYVDSVRGRFTISQDNAKNSLYLQMNSLRAEDTAVYYCAASSRHRLGLNNPRDYDYWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (CAS64380VH6)

SEQ ID NO: 487

MALPVTALLLPLALLLHAARPEVQLVESGGGLVQPGGSLRLSCAASGNTYSSNYMGWFRQAPGKGLEEVAVIYTRGGHTYYVDSVRGRFTISQDNAKNSVYLQMNSLRAEDTAMYYCAASSRHRLGLNNPRDYDYWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (CAS64380VH7)

SEQ ID NO: 488

MALPVTALLLPLALLLHAARPEVQLVESGGGLVQPGGSLRLSCAASGNTYSSNYMGWFRQAPGKGREEVAVIYTRGGHTYYVDSVRGRFTISQDNAKNSVYLQMNSLRAEDTAMYYCAASSRHRLGLNNPRDYDYWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (CAS64511VH4)

SEQ ID NO: 489

MALPVTALLLPLALLLHAARPEVQLVESGGGLVQPGGSLRLSCAASRATYSTNYISWFRQAPGKOLEAVATITTGDGETAYADSVKGRETISRDNAKNSLYLQMNSLRAEDTAVYYCAANLRIGGDWFDGRDFRAWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR (CAS64511VH5)

SEQ ID NO: 490

MALPVTALLLPLALLLHAARPEVQLVESGGGLVQPGGSLRLSCAASRATYSTNYISWFRQAPGKOLEAVATITTGDGETAYADSVKGRETISRDNAKNSVYLQMNSLRAEDTAMYYCAANLRIGGDWFDGRDFRAWGQGTLVTVSSTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSC

-continued
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKGHDGLYQGL
STATKDTYDALHMQALPPR (CAS64511VH6)
SEQ ID NO: 491
MALPVTALLLPLALLLHAARPEVQLVESGGGLVQP
GGSLRLSCAASRATYSTNYISWFRQAPGKGREAVA
TITTGDGETAYADSVKGRFTISRDNAKNSVYLQMN
SLRAEDTAMYYCAANLRIGGDWFDGRDFRAWGQGT
LVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKGHDGLYQGL
STATKDTYDALHMQALPPR (CAS63997VH4)
SEQ ID NO: 492
MALPVTALLLPLALLLHAARPQVQLVESGGGVVQP
GGSLRLSCAASFSGYGVSTMAWFRQAPGKQLEGVA
AITVGSGNTYYADSVKGRETISRDNSKNTLYLQMN
SLRAEDTAVYYCAVGYLSGGSWDVPGRYNYWGQGT
LVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKGHDGLYQGL
STATKDTYDALHMQALPPR (CAS63997VH5)
SEQ ID NO: 493
MALPVTALLLPLALLLHAARPQVQLVESGGGVVQP
GGSLRLSCAASFSGYGVSTMAWFRQAPGKQLEGVA
AITVGSGNTYYADSVKGRETISRDNSKNTVYLQMN
SLRAEDTAMYYCAVGYLSGGSWDVPGRYNYWGQGT
LVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKGHDGLYQGL
STATKDTYDALHMQALPPR -continued
(CAS63997VH6)
SEQ ID NO: 494
MALPVTALLLPLALLLHAARPQVQLVESGGGVVQP
GGSLRLSCAASFSGYGVSTMAWFRQAPGKGREGVA
AITVGSGNTYYADSVKGRFTISRDNSKNTVYLQMN
SLRAEDTAMYYCAVGYLSGGSWDVPGRYNYWGQGT
LVTVSSTTTPAPRPPTPAPTIASQPLSLRPEACRP
AAGGAVHTRGLDFACDIYIWAPLAGTCGVLLLSLV
ITLYCKRGRKKLLYIFKQPFMRPVQTTQEEDGCSC
RFPEEEEGGCELRVKFSRSADAPAYKQGQNQLYNE
LNLGRREEYDVLDKRRGRDPEMGGKPRRKNPQEGL
YNELQKDKMAEAYSEIGMKGERRRGKGHDGLYQGL
STATKDTYDALHMQALPPR Anti-DLL3 Human scFv VL and VH Domain
Nucleic Acid Sequences
(Nucleic Acid Sequence for VL domain
of anti-DLL3 human scFv A556704)
SEQ ID NO: 511
GACATCCAGATGACCCAGAGCCCGAGCAGCCTGAG
CGCGAGCGTTGGTGACCGTGTTACCATTACCTGCC
GTGCGAGCCAGAGCGTTAGCAGCGCGGTGGCGTGG
TACCAGCAAAAGCCGGGTAAAGCGCCGAAGCTGCT
GATCTATAGCGCGAGCAGCCTGTATAGCGGCGTTC
CGAGCCGTTTCAGCGGTAGCCGTAGCGGCACCGAC
TTTACCCTGACCATTAGCAGCCTGCAGCCGGAAGA
TTTCGCAACTTATTACTGTCAGCAAGCTTCTTGGT
CTCCGATCACGTTCGGACAGGGCACCAAAGTTGAG
ATTAAA (Nucleic Acid Sequence for VH domain
of anti-DLL3 human scFv A556704)
SEQ ID NO: 512
GAGGTTCAACTGGTGGAGAGCGGTGGTGGTCTGGT
TCAGCCGGGTGGTAGCCTGCGTCTGAGCTGCGCAG
CTTCTGGCTTCAACATCTCTTCTTCTTATATGCAC
TGGGTGCGTCAGGCGCCGGGTAAAGGCCTGGAATG
GGTTGCATATATTTATCCTTCTTATGGCTATACTT
CTTATGCCGATAGCGTCAAGGGCCGTTTCACCATC
AGCGCGGATACCAGCAAAAACACCGCATACCTGCA
AATGAACAGCCTGCGTGCGGAAGATACCGCCGTCT
ATTATTGTGCTCGCGGTGGTTACTACTACCATGGT
ATGGACTACTGGGGTCAAGGCACCCTGGTTACCGT
GAGCAGC (Nucleic Acid Sequence for VL domain
of anti-DLL3 human scFv A556788)
SEQ ID NO: 513
GACATCCAGATGACCCAGAGCCCGAGCAGCCTGAG
CGCGAGCGTTGGTGACCGTGTTACCATTACCTGCC

```
GTGCGAGCCAGAGCGTTAGCAGCGCGGTGGCGTGG

TACCAGCAAAAGCCGGGTAAAGCGCCGAAGCTGCT

GATCTATAGCGCGAGCAGCCTGTATAGCGGCGTTC

CGAGCCGTTTCAGCGGTAGCCGTAGCGGCACCGAC

TTTACCCTGACCATTAGCAGCCTGCAGCCGGAAGA

TTTCGCAACTTATTACTGTCAGCAACATTACGCTC

CGTCTCTGATCACGTTCGGACAGGGCACCAAAGTT

GAGATTAAA (Nucleic Acid Sequence for VH domain
of anti-DLL3 human scFv A556788)
                             SEQ ID NO: 514
GAGGTTCAACTGGTGGAGAGCGGTGGTGGTCTGGT

TCAGCCGGGTGGTAGCCTGCGTCTGAGCTGCGCAG

CTTCTGGCTTCAACATCTCTTCTTATTCTATGCAC

TGGGTGCGTCAGGCGCCGGGTAAAGGCCTGGAATG

GGTTGCATATATTTCTTCTTATTATGGCTATACTT

ATTATGCCGATAGCGTCAAGGGCCGTTTCACCATC

AGCGCGGATACCAGCAAAAACACCGCATACCTGCA

AATGAACAGCCTGCGTGCGGAAGATACCGCCGTCT

ATTATTGTGCTCGCTACTCTTACTACTACGGTATG

GACTACTGGGGTCAAGGCACCCTGGTTACCGTGAG

CAGC
Human anti-DLL3 scFv CAR sequences
(CA556704)
                             SEQ ID NO: 515
MALPVTALLLPLALLLHAARPDIQMTQSPSSLSAS

VGDRVTITCRASQSVSSAVAWYQQKPGKAPKLLIY

SASSLYSGVPSRFSGSRSGTDFTLTISSLQPEDFA

TYYCQQASWSPITFGQGTKVEIKGGGGSGGGGSGG

GGSEVQLVESGGGLVQPGGSLRLSCAASGFNISSS

YMHWVRQAPGKGLEWVAYIYPSYGYTSYADSVKGR

FTISADTSKNTAYLQMNSLRAEDTAVYYCARGGYY

YHGMDYWGQGTLVTVSSTTTPAPRPPTPAPTIASQ

PLSLRPEACRPAAGGAVHTRGLDFACDIYIWAPLA

GTCGVLLLSLVITLYCKRGRKKLLYIFKQPFMRPV

QTTQEEDGCSCRFPEEEEGGCELRVKFSRSADAPA

YKQGQNQLYNELNLGRREEYDVLDKRRGRDPEMGG

KPRRKNPQEGLYNELQKDKMAEAYSEIGMKGERRR

GKGHDGLYQGLSTATKDTYDALHMQALPPR (CA556788)
                             SEQ ID NO: 516
MALPVTALLLPLALLLHAARPDIQMTQSPSSLSAS

VGDRVTITCRASQSVSSAVAWYQQKPGKAPKLLIY

SASSLYSGVPSRFSGSRSGTDFTLTISSLQPEDFA

TYYCQQHYAPSLITFGQGTKVEIKGGGGSGGGGSG

GGGSEVQLVESGGGLVQPGGSLRLSCAASGFNISS

YSMHWVRQAPGKGLEWVAYISSYYGYTYYADSVKG

RFTISADTSKNTAYLQMNSLRAEDTAVYYCARYSY

YYGMDYWGQGTLVTVSSTTTPAPRPPTPAPTIASQ

PLSLRPEACRPAAGGAVHTRGLDFACDIYIWAPLA

GTCGVLLLSLVITLYCKRGRKKLLYIFKQPFMRPV

QTTQEEDGCSCRFPEEEEGGCELRVKFSRSADAPA

YKQGQNQLYNELNLGRREEYDVLDKRRGRDPEMGG

KPRRKNPQEGLYNELQKDKMAEAYSEIGMKGERRR

GKGHDGLYQGLSTATKDTYDALHMQALPPR

Anti-DLL3 benchmark CAR
(1H2.1 amino acid sequence)
                             SEQ ID NO: 517
MALPVTALLLPLALLLHAARPQVQLQESGPGLVKP

SETLSLTCTVSGDSISSYYWTWIRQPPGKGLEWIG

YIYYSGTTNYNPSLKSRVTISVDTSKSQFSLKLSS

VTAADTAVYYCASIAVRGFFFDYWGQGTLVTVSSG

GGGSGGGGSGGGGSEIVLTQSPGTLSLSPGERATL

SCRASQSVSSSYLAWYQQKPGQAPRLLIYGASTRA

TGIPDRFSGSGSGTDFTLTISRLEPEDFAVYYCQQ

YGTSPLTFGGGTKVEIKRAAALDNEKSNGTIIHVK

GKHLCPSPLFPGPSKPFWVLVVVGGVLACYSLLVT

VAFIIFWVRSKRSRLLHSDYMNMTPRRPGPTRKHY

QPYAPPRDFAAYRSRVKFSRSADAPAYQQGQNQLY

NELNLGRREEYDVLDKRRGRDPEMGGKPRRKNPQE

GLYNELQKDKMAEAYSEIGMKGERRRGKGHDGLYQ

GLSTATKDTYDALHMQALPPR
```

Figure 10A:
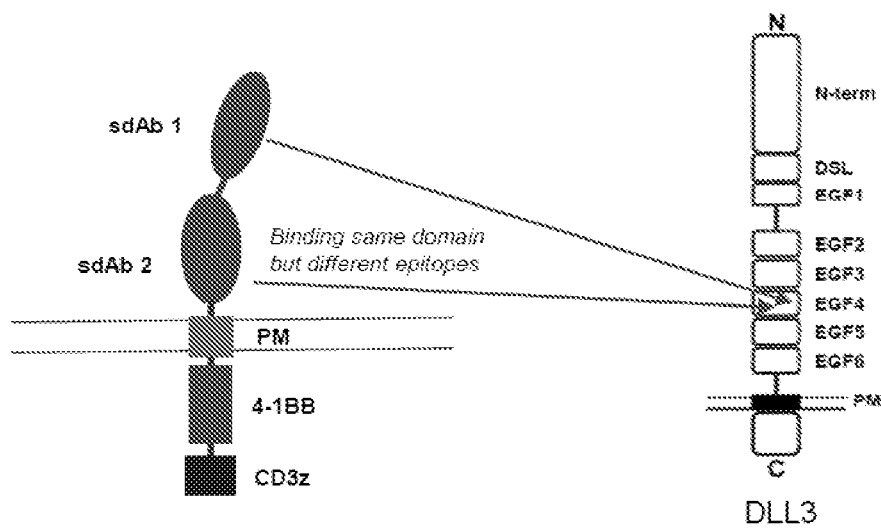
FIG. 10 shows schematic representation of tandem CAR (FIG. 10A) and armored CAR constructs (FIG. 10B, C)

Example 11. Evaluation of In Vitro Activity of Humanized Anti-DLL3 Tandem CAR-T Cells To improve anti-tumor efficacy of CAR-Ts, we constructed three tandem CARs (T1, T2 and T3). The amino acid sequences of the tandem CARs were provided in SEQ ID: 518-520. The amino acid sequences of anti-DLL3 humanized sdAb fragments were provided in SEQ ID NO:356 (AS64380VH5) and SEQ ID NO: 366 (AS63997VH5). 1H2.1 (SEQ ID NO: 517, e.g, see, WO2019200007), which is an anti-DLL3 CAR, was also used to generate a CAR construct as a reference. A full length CAR contains from the N-terminus to the C-terminus: a CD8α signal peptide (SEQ ID NO: 465), DLL3 binding domain sdAbs provided in SEQ ID NO: 356 (AS64380VH5) and SEQ ID NO: 366 (AS63997VH5), a CD8α hinge domain (SEQ ID NO: 466), a CD8α transmembrane domain (SEQ ID NO: 467), a CD137 intracellular domain (SEQ ID NO: 468) or a CD28 intracellular domain (SEQ ID NO: 469), and a CD3ζ intracellular domain (SEQ ID NO: 470). Schematic representation of a CAR construct is shown in FIG. 10A. For T1, both of sdAb 1 and sdAb 2 were AS64380VH5. For T2, both of sdAb 1 and sdAb 2 were AS63997VH5. For T3, sdAb 1 and sdAb 2 were AS63997VH5 and AS64380VH5, respectively. Nucleic acid encoding the CAR fragment was then cloned into a lentiviral vector to create full length CAR construct in a single coding frame, using human EF1 alpha promoter for expression.

```
(T1 amino acid sequence)
                          SEQ ID NO: 518
MALPVTALLLPLALLLHAARPEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPR (T2 amino acid sequence)
                          SEQ ID NO: 519
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPR (T3 amino acid sequence)
                          SEQ ID NO: 520
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPR
```

In Vitro Cytotoxicity Assay

On day 9 post transduction, transduced T cells were harvested and co-incubated with DLL3-expressing tumor cell lines (SHP-77 with DLL3 high expression, NCI-H82 with DLL3 medium expression and NCI-H2171 with DLL3 low expression) and DLL3 negative expressing cell lines (NCI-H460 and HEK293) at an effector (CAR-T) to target cell ratio of 0.5:1 and 2:1 for 22 hours. CAR3 CAR-T cells were used as a reference in all assays to compare assay variation and/or act as a control. Un-transduced T cells (UnT) were used as a negative control.

Figure 11A:
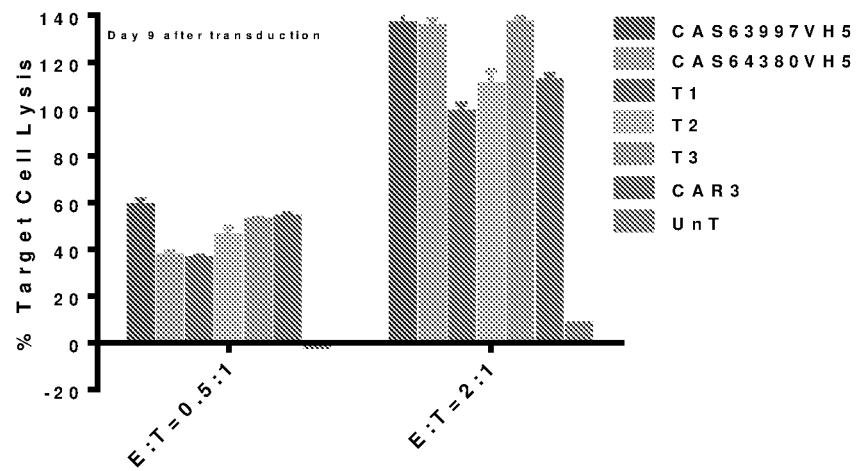
FIG. 11 shows comparison results of tandem CAR-T cells and monospecific CAR-T cells in vitro functional activities by measuring short-term cytotoxicity (FIG. 11A-E,V) and cytokine release (FIG. 11F-K, W-X), and by long-term stimulation assays (FIG. 11L-U, Y-Z).
Figure 11B:
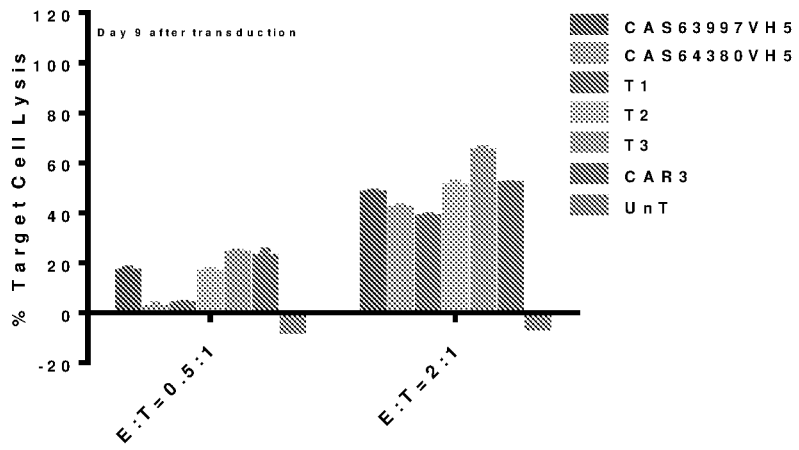
Figure 11C:
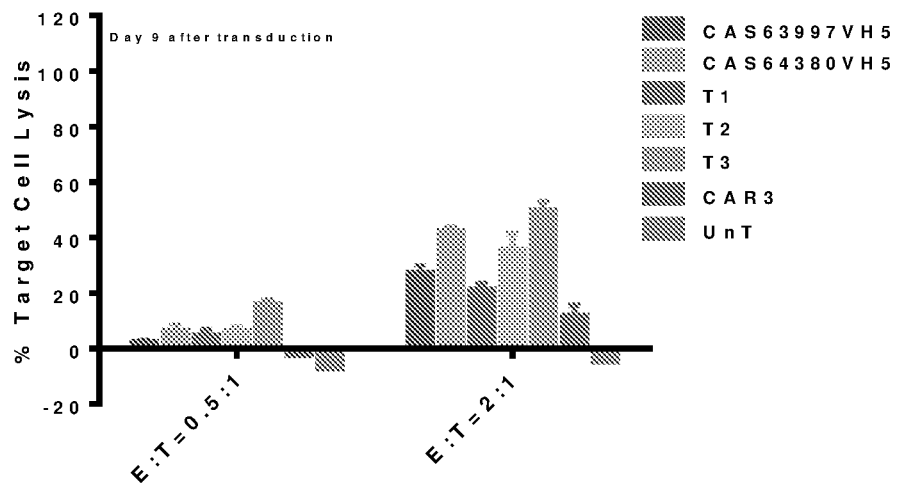
Figure 11D:
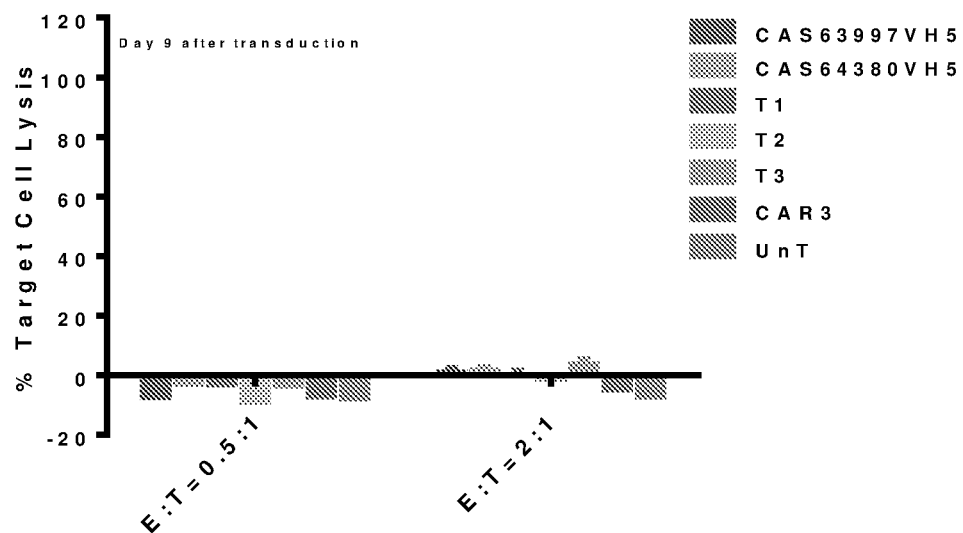
Figure 11E:
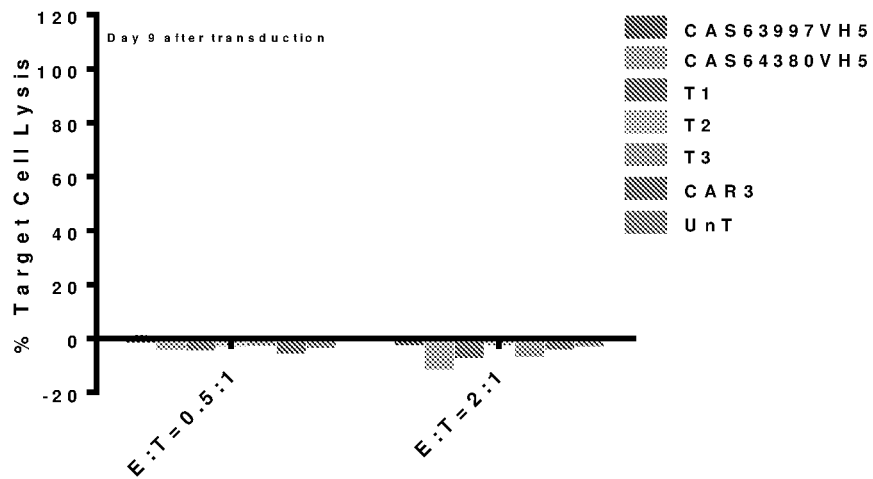
Figure 11F:
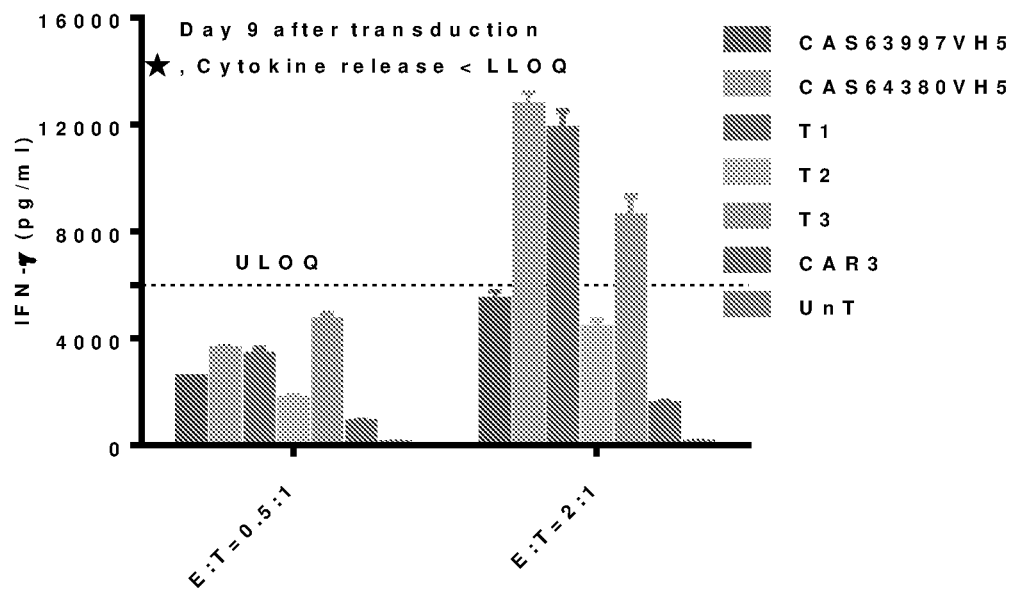
Figure 11G:
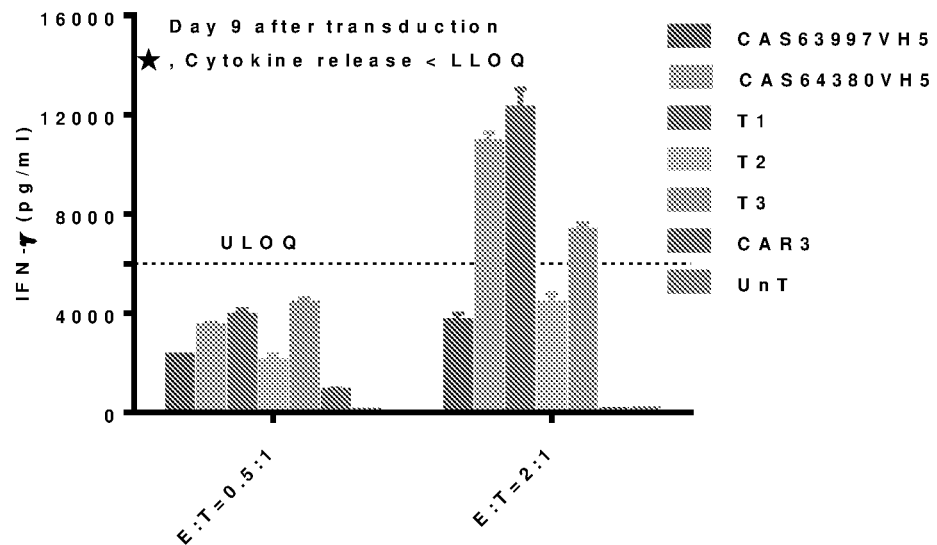
Figure 11H:
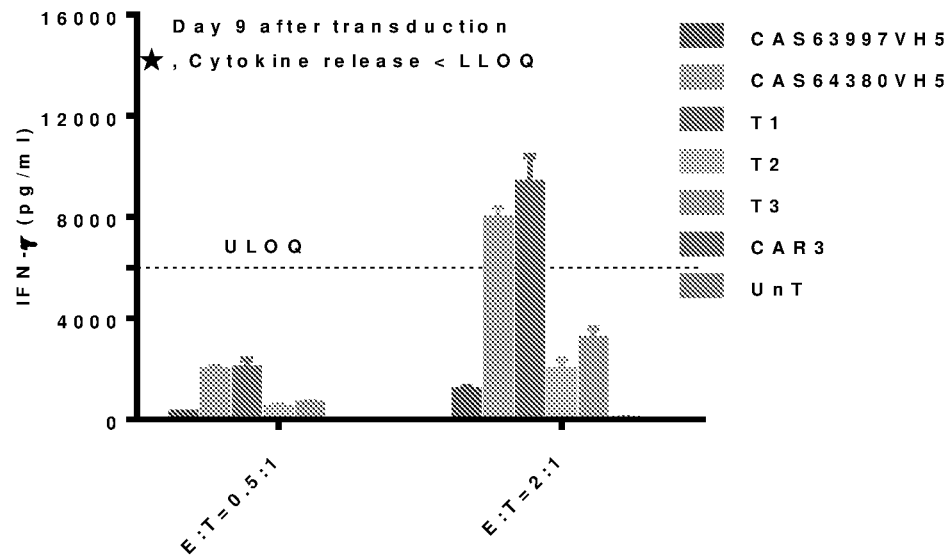
Figure 11I:
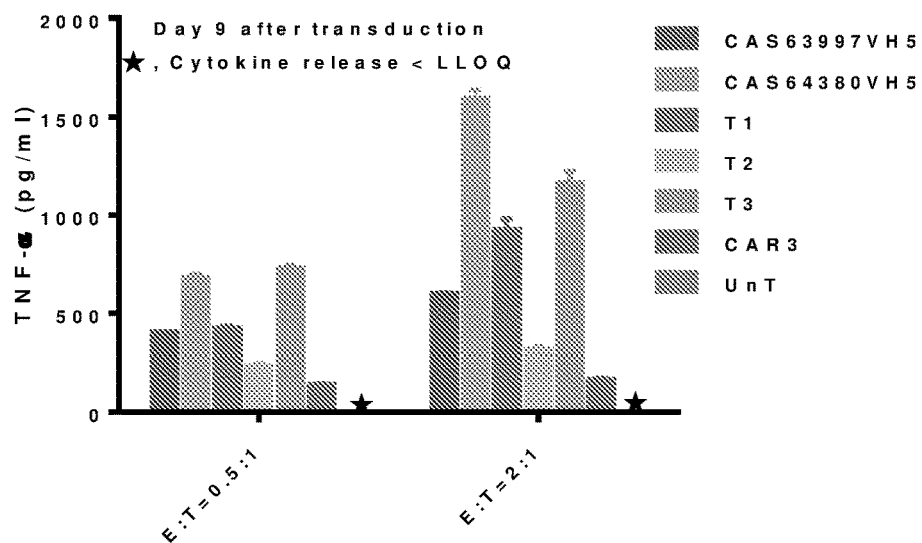
Figure 11J:
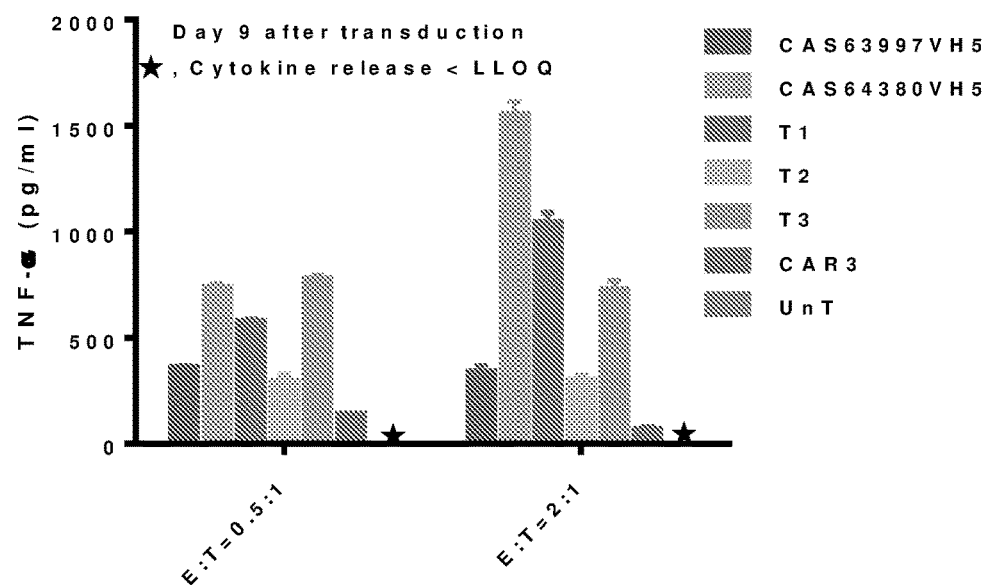
Figure 11K:
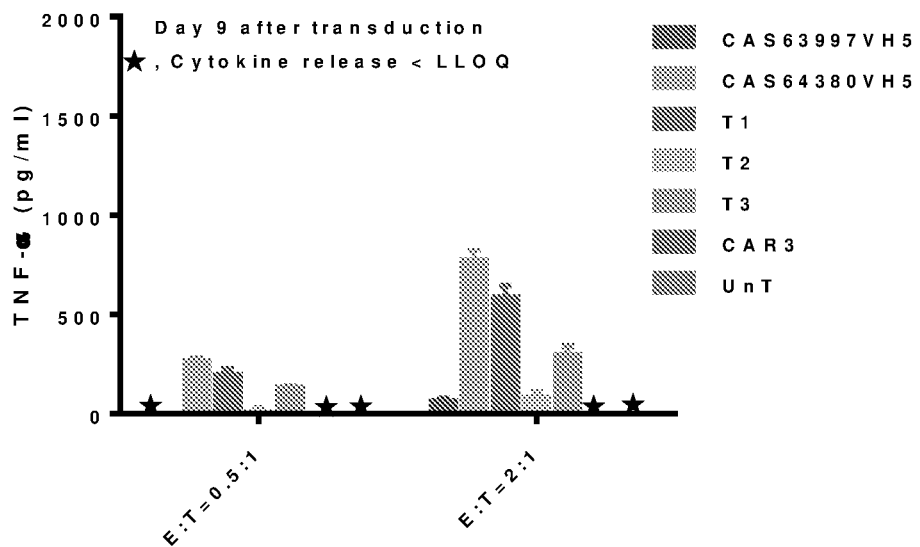
Figure 11L:
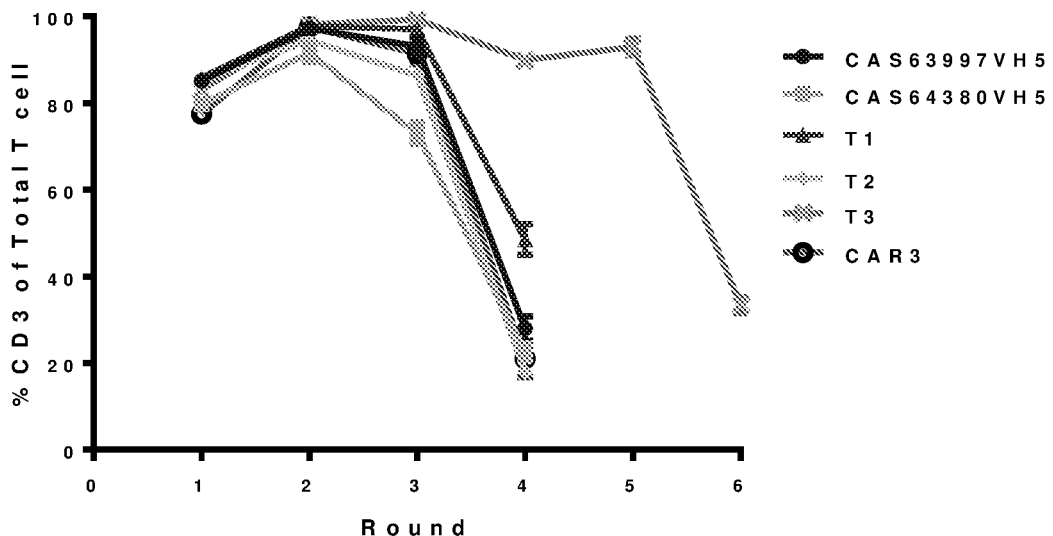
Figure 11M:
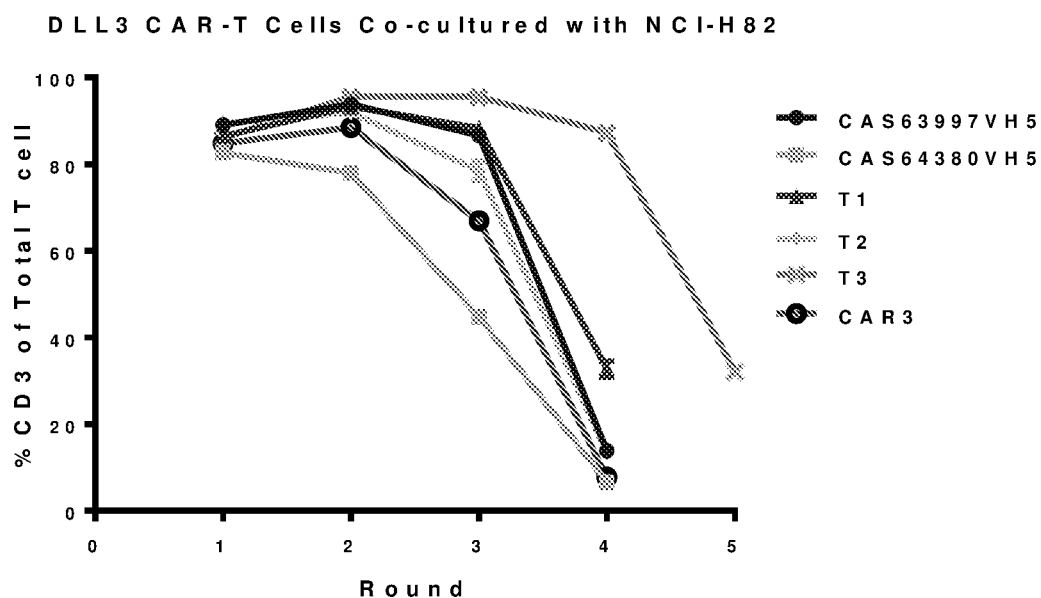
Figure 11N:
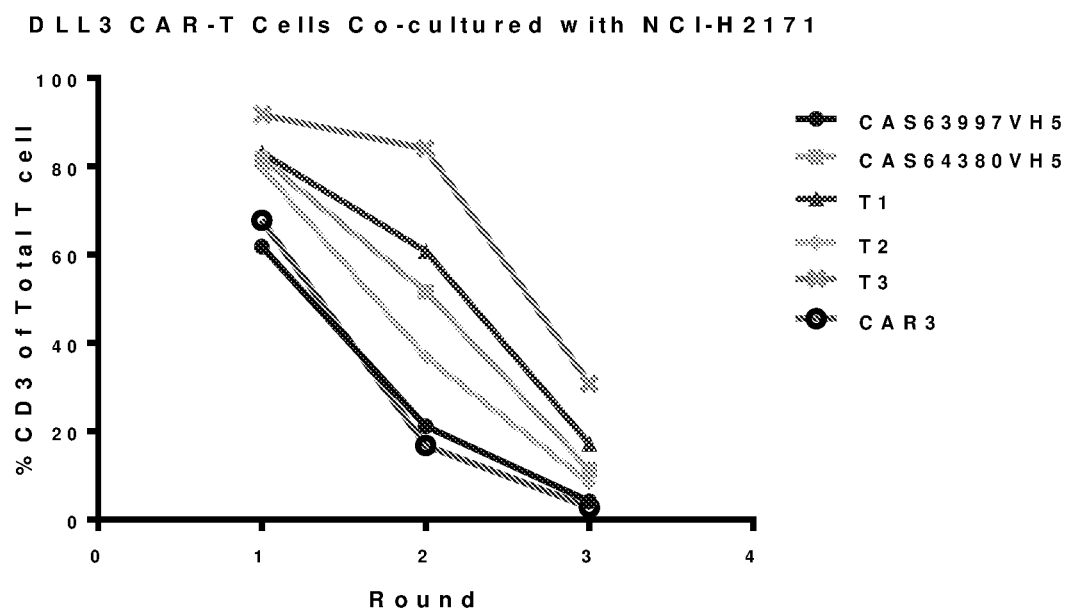
Figure 11O:
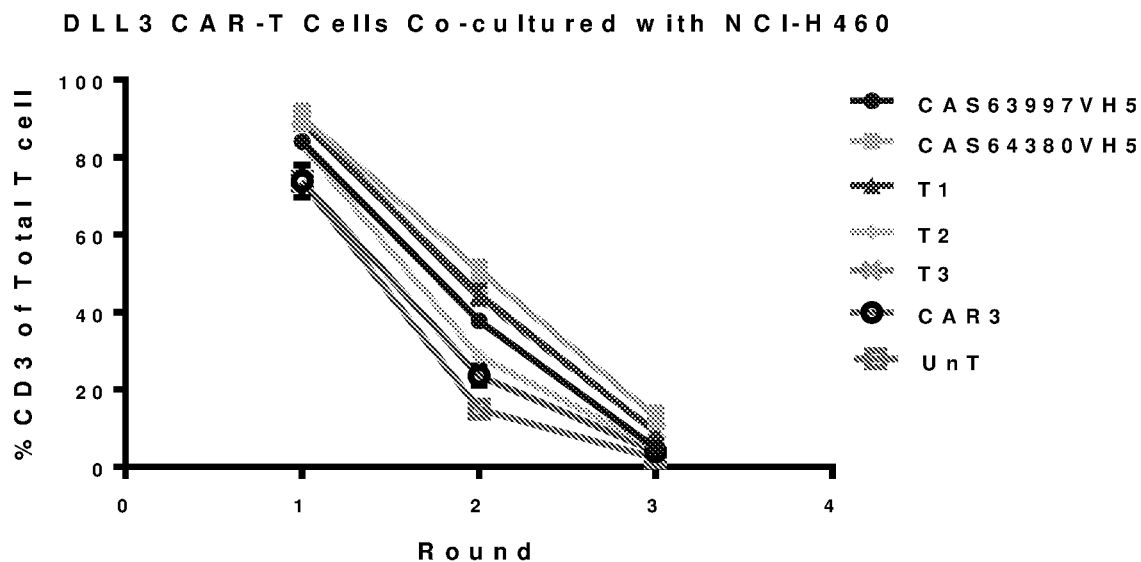
Figure 11P:
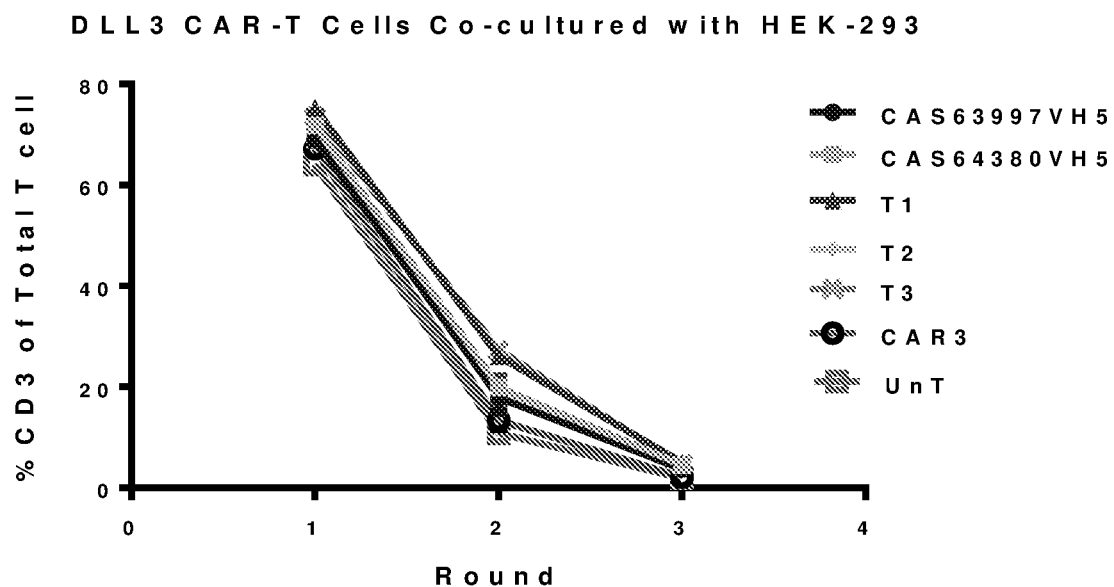
Figure 11Q:
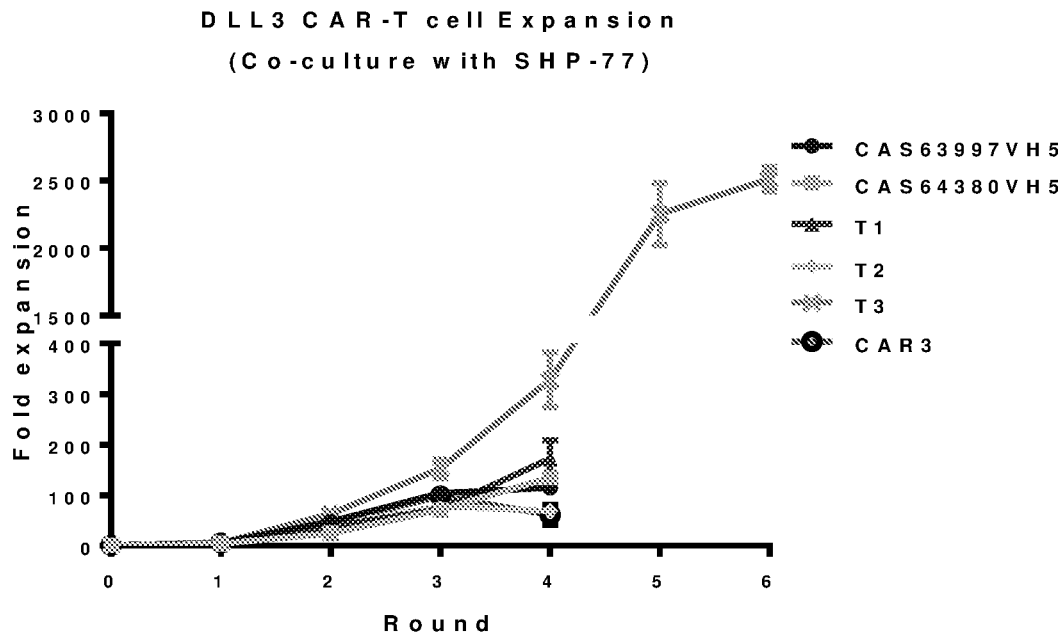
Figure 11R:
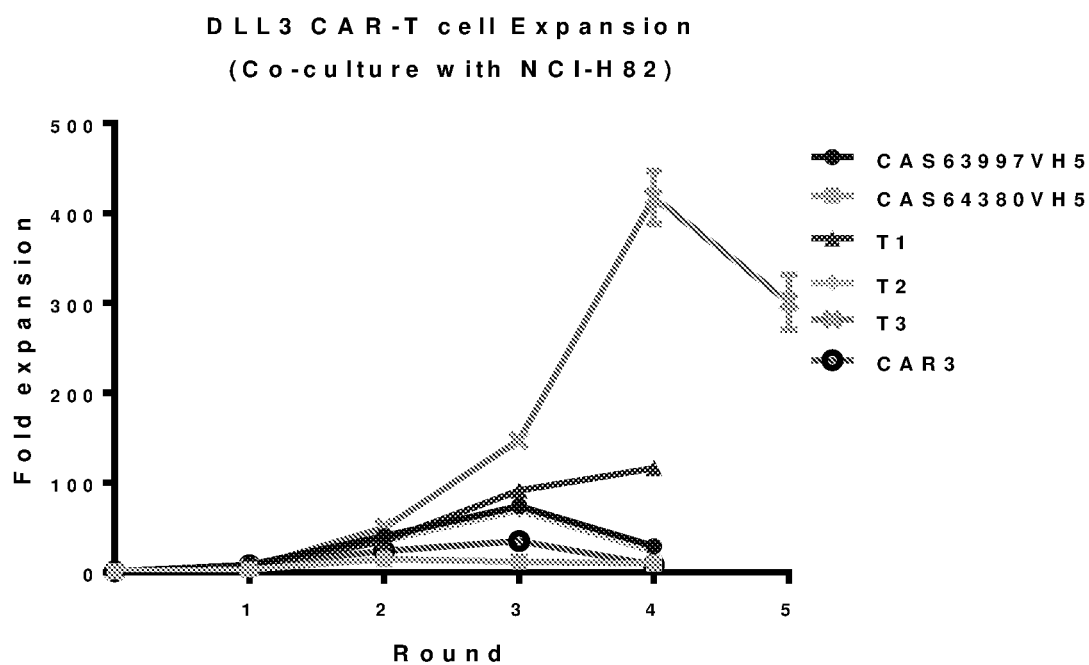
Figure 11S:
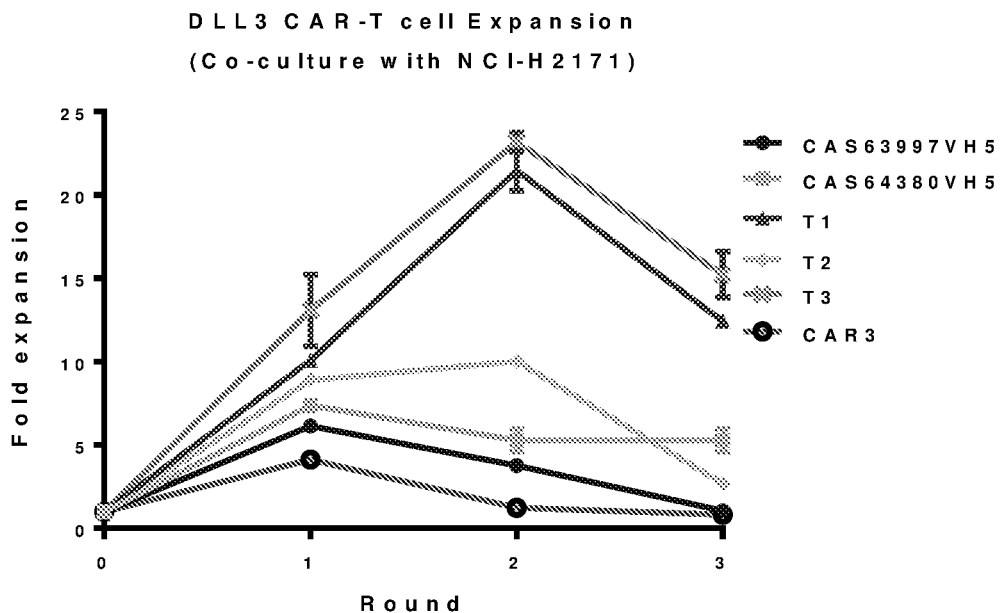
Figure 11T:
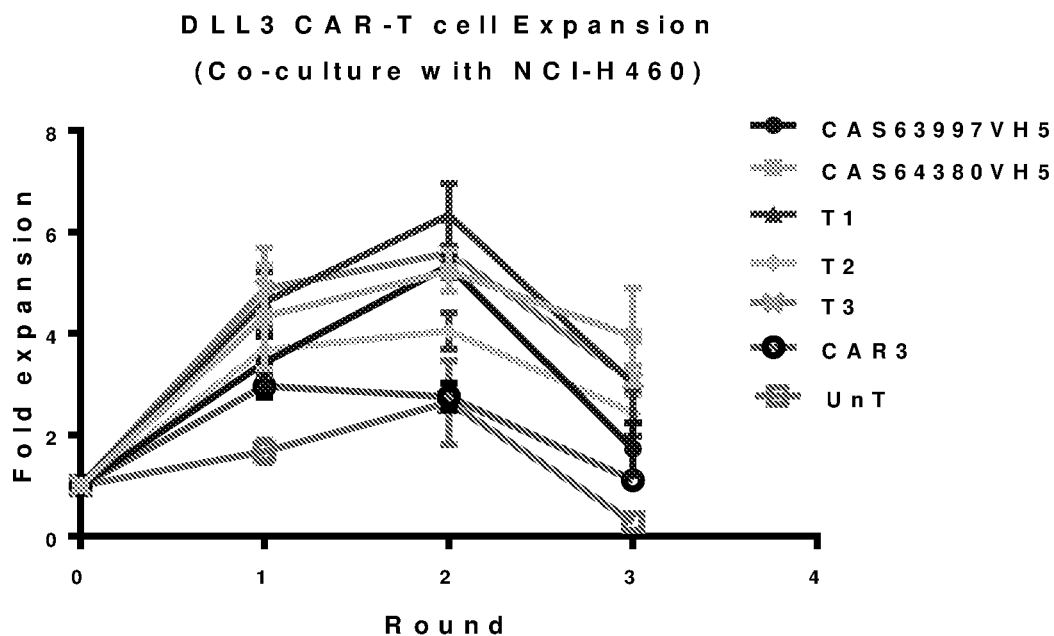
Figure 11U:
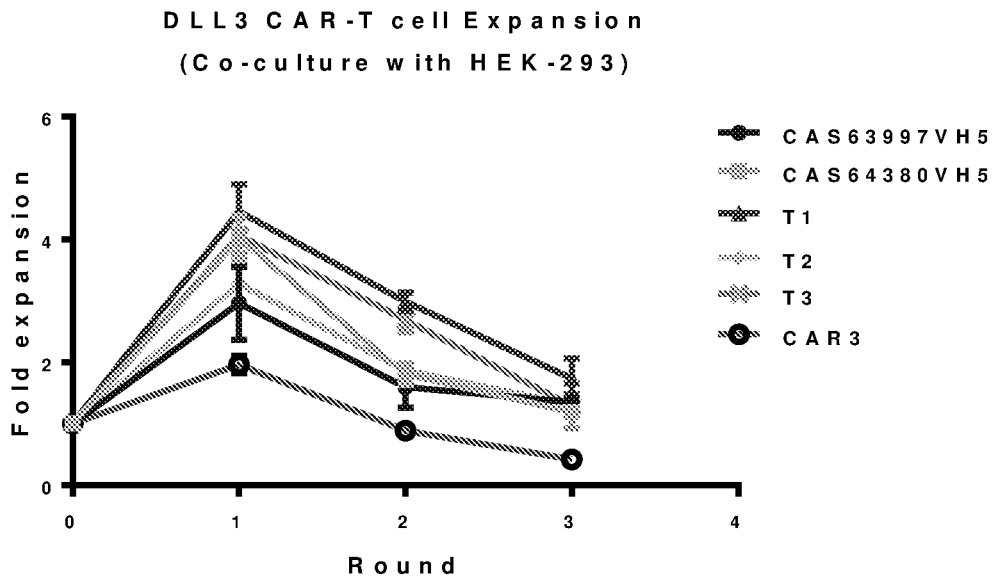
Figure 11V:
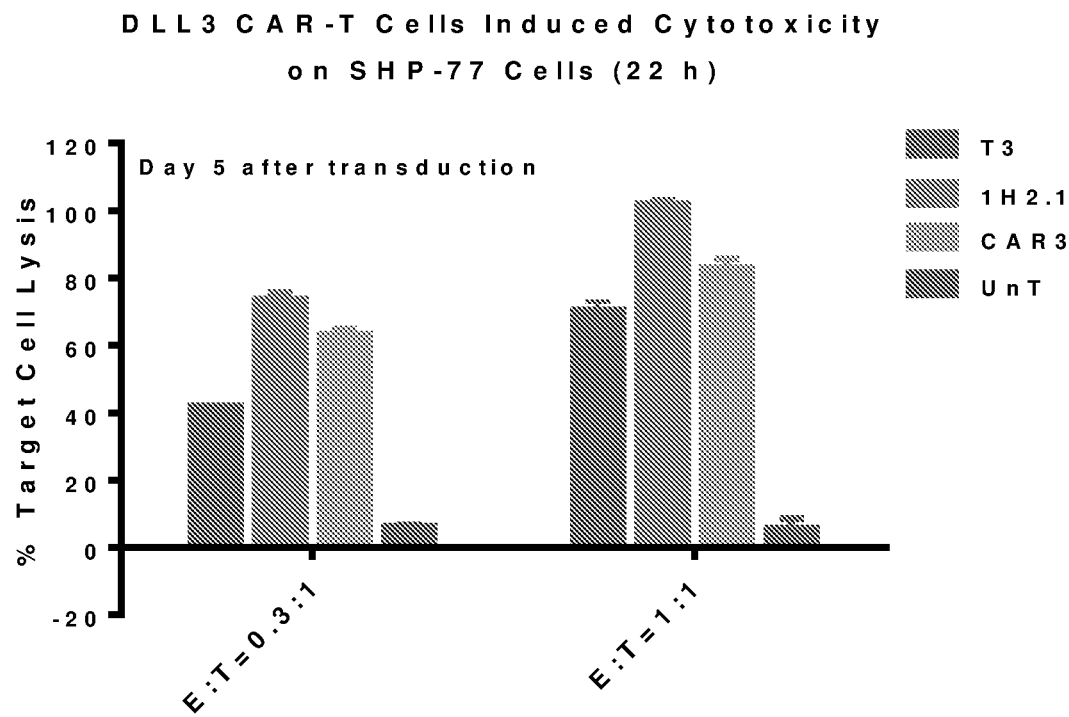

The cytotoxicity of the transduced T cells was determined by a lactate dehydrogenase (LDH) assay. Results show that CAR3 CAR-T and some anti-DLL3 tandem CAR-Ts exhibit strong anti-tumor activities in vitro against SHP-77 cells, while UnT has no target cell killing effect (FIG. 11A-C) and DLL3 negative expression cells (NCI-H460 and HEK293) did not induce cytotoxicity (FIG. 11D-E). Besides CAR3, We also compared in vitro cytotoxicity of SHP-77 cells of T3 and 1H2.1. Result shows that T3 had a comparable or less potent cell killing activity in short-term stimulation (FIG. 11V).

IFN-γ and TNF-α Release Detection

Additionally, supernatants from the in vitro cytotoxicity assay were collected to assess CAR-induced cytokine release, e.g., interferon gamma (IFN-γ) and TNF-α release. As shown in FIG. 11F-K, CAR3 CAR-T and some anti-DLL3 tandem CAR-Ts were stimulated by DLL3 expressing cell lines to produce IFN-γ and TNF-α, whereas UnT produced little IFN-γ and TNF-α. DLL3 negative expressing cell lines did not reduce specific release of IFN-γ and TNF-α (data not shown). Protocols of IFN-γ and TNF-α release detection can be referred to CISBIO's human TNF-α kits and IFN-γ kits.

Figure 11W:
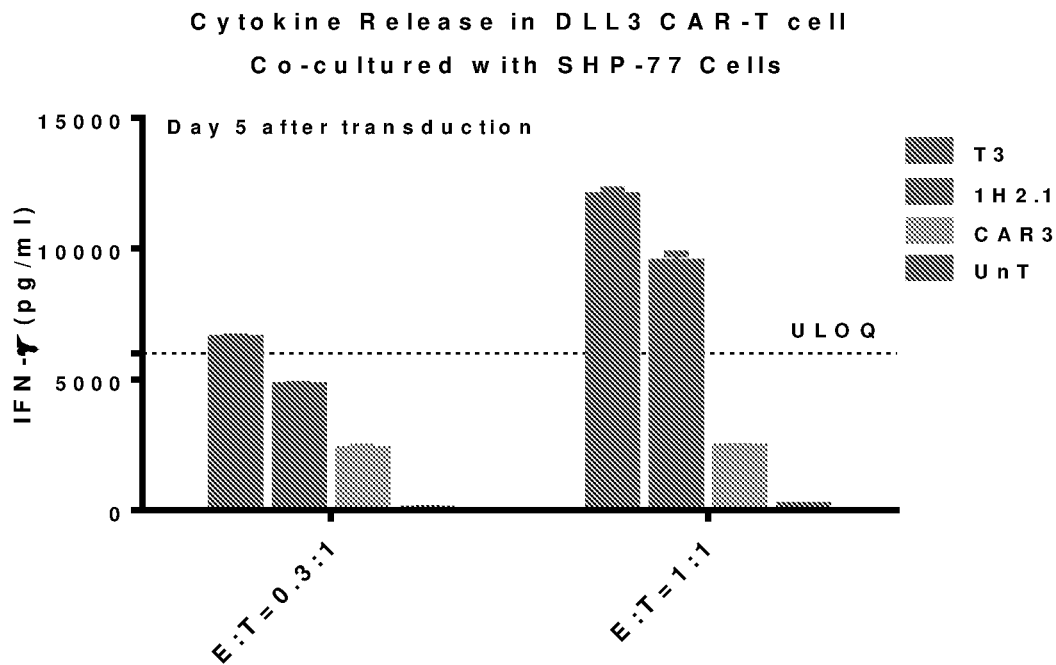
Figure 11X:
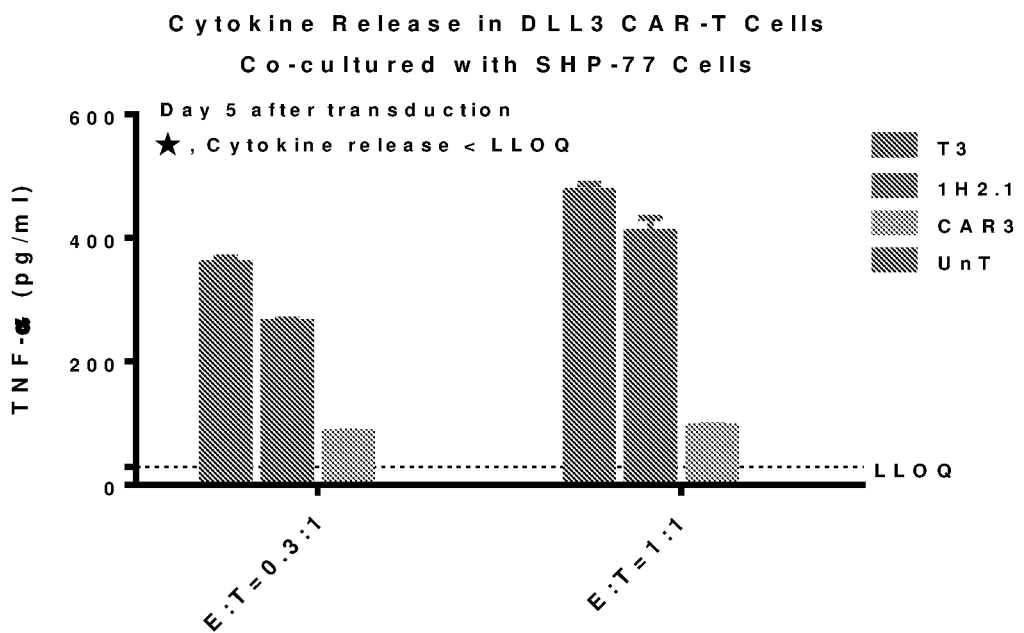

Compared with 1H2.1, T3 released more IFN-γ and TNF-α (after co-incubation for 22 hours)(FIG. 11W-X).

Tandem CAR-T Cytotoxicity and Expansion by Long-Term Stimulation Assay

The DLL3 CAR-T cells were evaluated by repetitive antigen stimulation assay. Upon repetitive stimulation by the SCLC cell lines and control cell lines, the tandem CAR-T cell T3 showed more potent cytotoxicity to SCLC cells, especially to SHP-77 and NCI-H82 cells (FIG. 11L-P). In addition to cytotoxicity activity, tandem CAR-T cell T3 also showed higher proliferation capacity than other CARTs, especially when stimulated by SHP-77 and NCI-H82 cells (FIG. 11Q-U).

Figure 11Y:
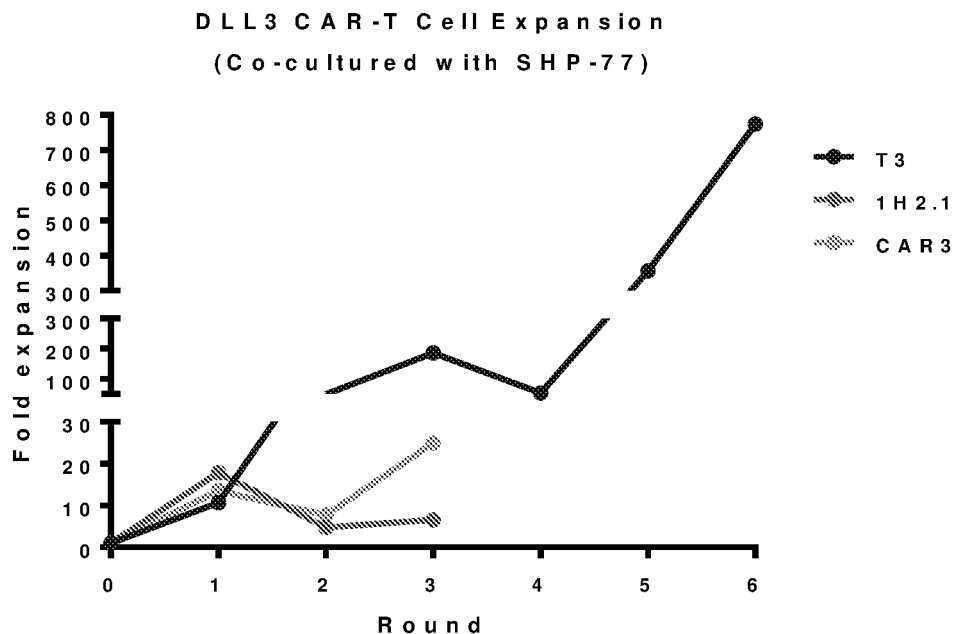
Figure 11Z:
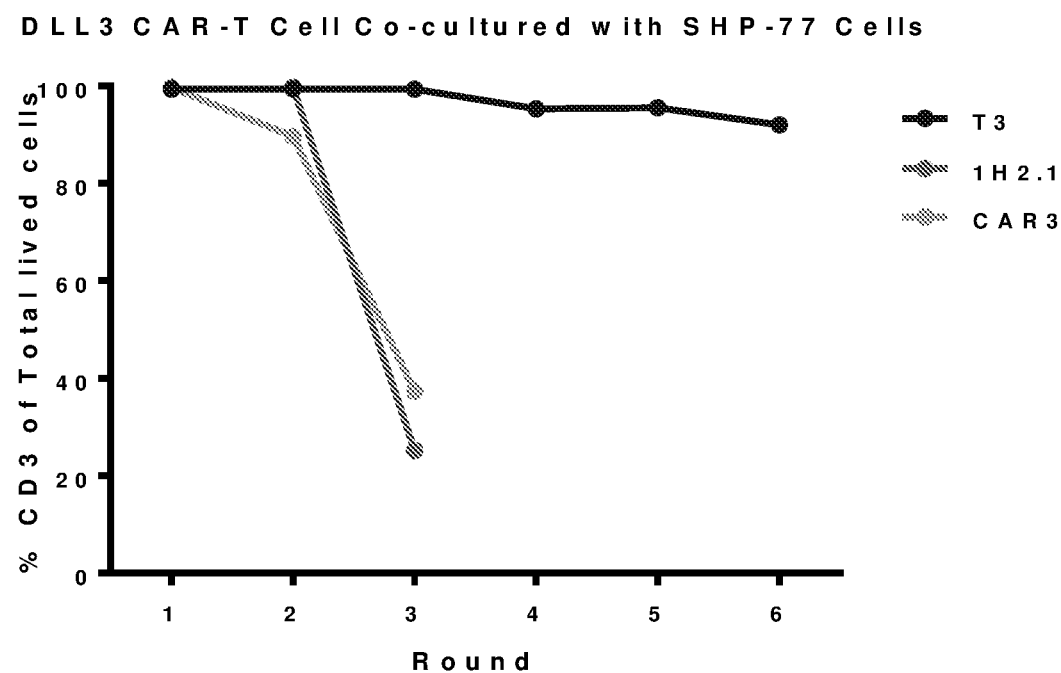

Besides CAR3, We also compared in vitro cytotoxicity of SHP-77 cells of T3 and 1H2.1. Result shows that T3 had a superior cytotoxicity and expansion in long-term stimulation (FIG. 11Y-Z).

The repetitive stimulation were carried out as follows.

Round 1: CAR-T cells and $3 \times 10^5$ target cells (e.g, SHP-77) were added to a 24-well plate at an effector to target cell ratio of 1:5, and co-incubated in a carbon dioxide incubator in 37° C., 5% $CO_2$ for 3 days. 200 μL of the cell culture supernatant was pipetted for cytokine detection, and the co-incubated cells were harvested to assess % CD3 and CAR positive rate by flow cytometry;

Round 2: Based on the CAR-T positive rate of the harvested cells in Round 1, the harvested cells were continued to co-incubate with the same volume of fresh target cells (SHP-77) at an effector to target cell ratio of 1:2 for another 3 days. 200 μL of the cell culture supernatant was pipetted for cytokine detection, and the co-incubated cells were harvested to assess % CD3 and CAR positive rate by flow cytometry; Based on the CAR-T positive rate of each previous Round, Round 3 and next Rounds were performed in a similar manner to that of Round 2.

Figure 10B:
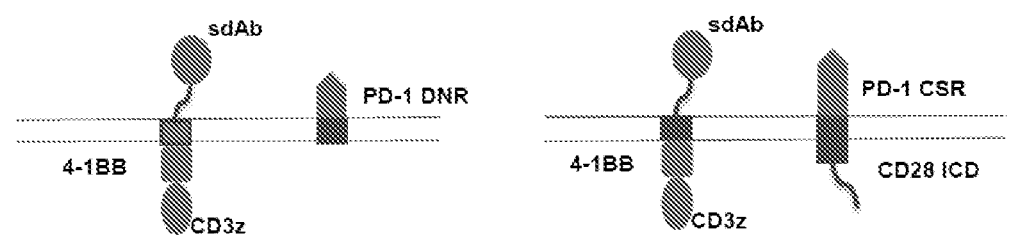
Figure 10C:
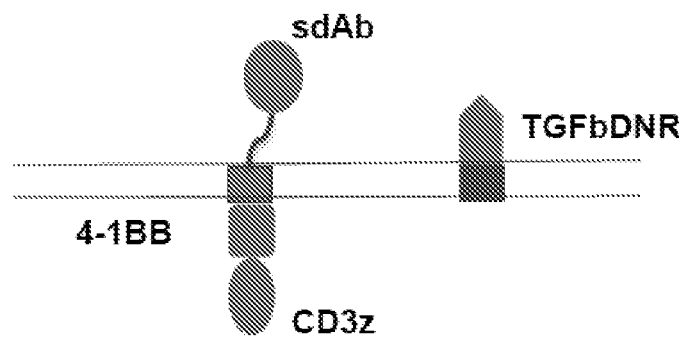

Example 12. Evaluation of In Vitro Activity of Humanized Anti-DLL3 PD-1 DNR or CSR Armed CAR-T Cells To improve persistence of CAR-Ts, we constructed PD-1 Dominant Negative Receptor (PD-1DNR) or PD-1 Chimeric Switch Receptor (PD-1CSR) armored DLL3 CARs. The amino acid sequences of the two CARs were provided in SEQ ID: 521-522. PD-1DNR and PD-1CSR sequences were linked to T3 C terminal via P2A. The amino acid sequences of PD-1DNR and PD-1CRS were provided in SEQ ID: 523-524. Schematic representation of the CAR construct were shown in FIG. 10B.

```
(T3-PD-1DNR amino acid sequence)
                        SEQ ID NO: 521
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPRGSGATNFSLLKQAGDV

EENPGPMQIPQAPWPVVWAVLQLGWRPGWFLDSPD

RPWNPPTFSPALLVVTEGDNATFTCSFSNTSESFV

LNWYRMSPSNQTDKLAAFPEDRSQPGQDCRFRVTQ

LPNGRDFHMSVVRARRNDSGTYLCGAISLAPKAQI

KESLRAELRVTERRAEVPTAHPSPSPRPAGQAAAP

TTTPAPRPPTPAPTIASQPLSLRPEACRPAAGGAV

HTRGLDFACDIYIWAPLAGTCGVLLLSLVITLYCN

HRRIQ (T3-PD-1CSR amino acid sequence)
                        SEQ ID NO: 522
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPRGSGATNFSLLKQAGDV

EENPGPMQIPQAPWPVVWAVLQLGWRPGWFLDSPD

RPWNPPTFSPALLVVTEGDNATFTCSFSNTSESFV

LNWYRMSPSNQTDKLAAFPEDRSQPGQDCRFRVTQ

LPNGRDFHMSVVRARRNDSGTYLCGAISLAPKAQI

KESLRAELRVTERRAEVPTAHCPSPLFPGPSKPFW

VLVVVGGVLACYSLLVTVAFIIFWVRSKRSRLLHS

DYMNMTPRRPGPTRKHYQPYAPPRDFAAYRS (PD-1DNR amino acid sequence)
                        SEQ ID NO: 523
MQIPQAPWPVVWAVLQLGWRPGWFLDSPDRPWNPP

TFSPALLVVTEGDNATFTCSFSNTSESFVLNWYRM

SPSNQTDKLAAFPEDRSQPGQDCRFRVTQLPNGRD

FHMSVVRARRNDSGTYLCGAISLAPKAQIKESLRA

ELRVTERRAEVPTAHPSPSPRPAGQAAAPTTTPAP

RPPTPAPTIASQPLSLRPEACRPAAGGAVHTRGLD

FACDIYIWAPLAGTCGVLLLSLVITLYCNHRRIQ (PD-1CSR amino acid sequence)
                        SEQ ID NO: 524
MQIPQAPWPVVWAVLQLGWRPGWFLDSPDRPWNPP

TFSPALLVVTEGDNATFTCSFSNTSESFVLNWYRM
```

```
SPSNQTDKLAAFPEDRSQPGQDCRFRVTQLPNGRD

FHMSVVRARRNDSGTYLCGAISLAPKAQIKESLRA

ELRVTERRAEVPTAHCPSPLFPGPSKPFWVLVVVG

GVLACYSLLVTVAHIFWVRSKRSRLLHSDYMNMTP

RRPGPTRKHYQPYAPPRDFAAYRS
```

Figure 12A:
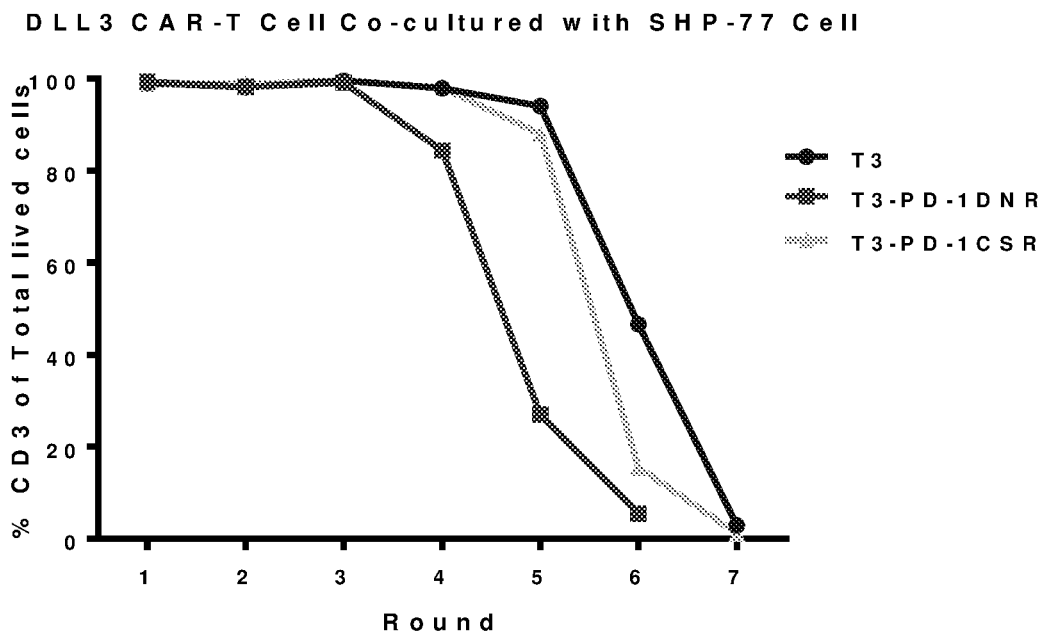
FIG. 12 shows in vitro functional comparison results of PD-1 DNR or PD-1 CSR armored CAR-T cells and T3 targeting SHP-77 cells (FIG. 12A, B) and SHP-77/PD-L1, respectively (FIG. 12C, D).
Figure 12B:
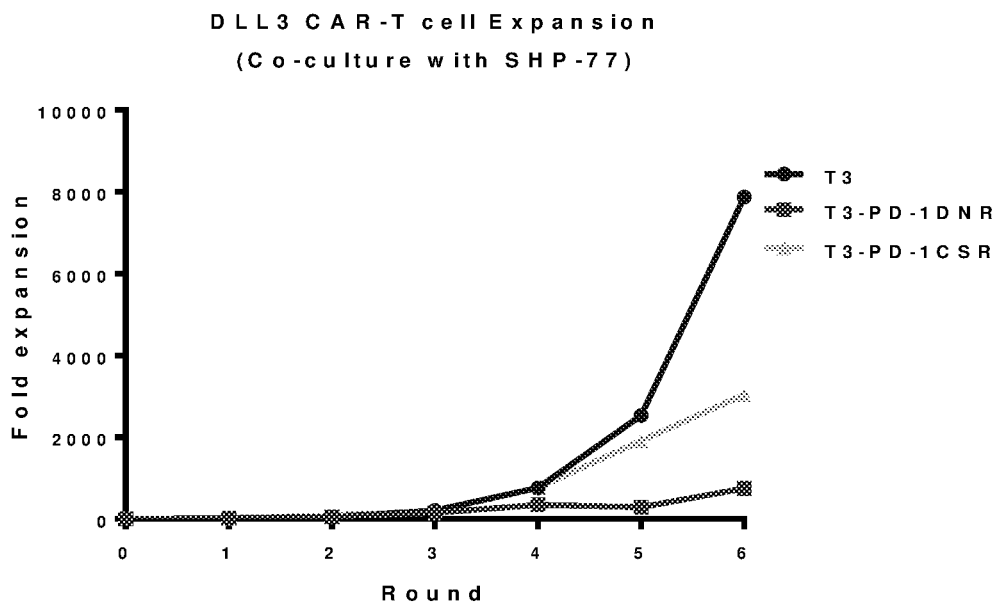
Figure 12C:
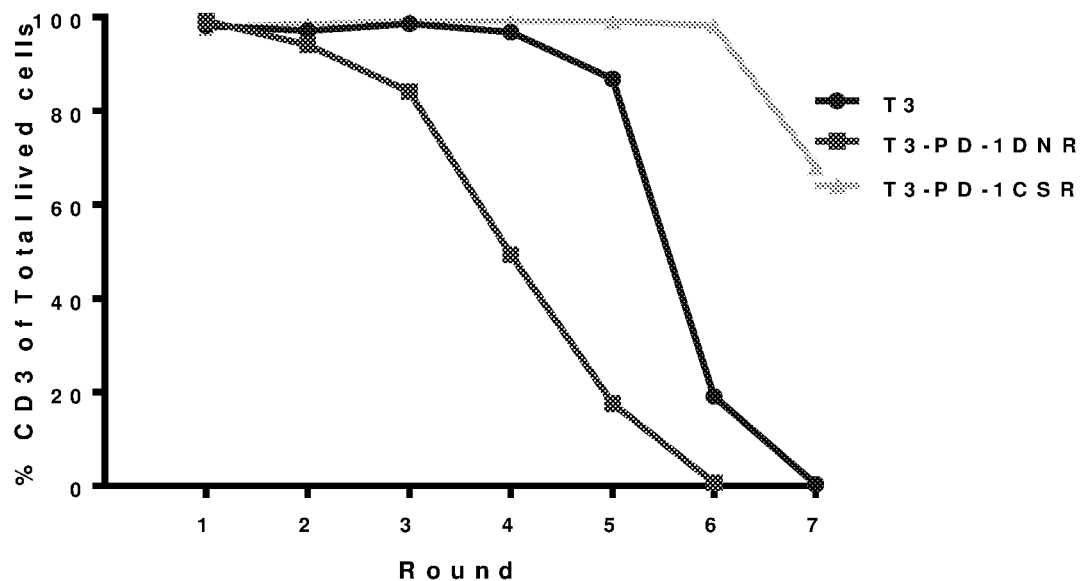
Figure 12D:
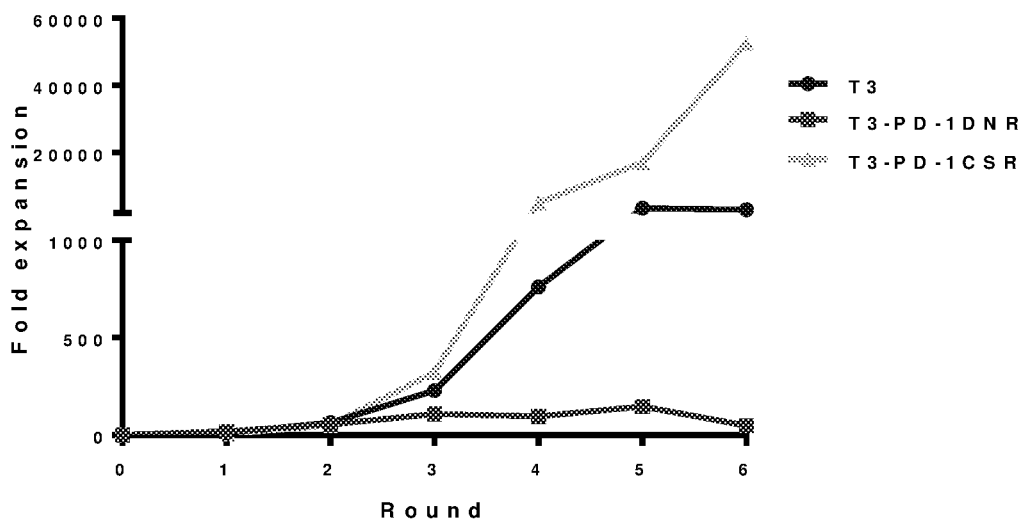

The PD-1DNR or PD-1CSR armored DLL3 CAR-T cells were evaluated by repetitive antigen stimulation assay. Upon repetitive stimulation by the SHP-77 cells, the armored CAR-T cells did not increase cytotoxicity potency and did not improve expansion capability compared with conventional CARTs (FIG. 12A-B). Upon repetitive stimulation by the SHP-77/PD-L1 cells (overexpressing human PD-L1 in SHP-77 cells), the PD-1 CSR armored CAR-T cells showed a superior cytotoxicity potency and expansion capability (FIG. 12C-D).

Figure 13A:
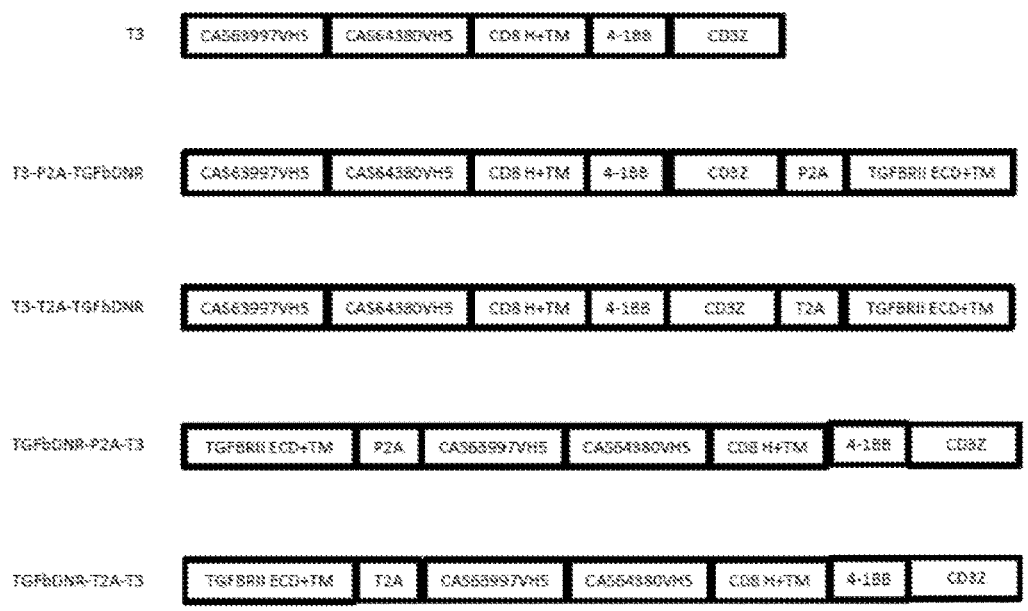
FIG. 13A shows schematic representation of the TGF-β-DNR armored CARs.

Example 13. TGF-β-DNR Enhances the Anti-Tumor Efficacy of DLL3 CAR-T Cells Construction of TGF-β-DNR Armored DLL3 CAR-T Cells To improve the antitumor performance of the DLL3 CAR-T cells in tumor microenvironment, a TGF-β-DNR sequence was incorporated into the DLL3 CAR as shown in FIG. 13A. The TGF-β-DNR is a truncated version of TGFBRII, which consist of the extracellular and transmembrane domain of the TGFBRII. The constructs T3-P2A-TGF-β-DNR, T3-T2A-TGF-β-DNR comprise a T3-BBZ sequence in the N terminal, a P2A or T2A peptide as indicated, a TGF-β-DNR in the C terminal; the constructs TGF-β-DNR-P2A-T3 and TGF-β-DNR-T2A-T3 comprise a TGF-β-DNR sequence in the N terminal, a P2A or T2A peptide as indicated, and a T3-BBZ sequence in the C terminal. The detailed sequences of the TGF-β-DNR and armored DLL3 CARs were provided in SEQ ID: 525-529.

```
(T3-P2A-TGF-β-DNR amino acid sequence)
                                     SEQ ID NO: 525
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC

RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPRGSGATNFSLLKQAGDV

EENPGPMGRGLLRGLWPLHIVLWTRIASTIPPHVQ

KSVNNDMIVTDNNGAVKFPQLCKFCDVRFSTCDNQ

KSCMSNCSITSICEKPQEVCVAVWRKNDENITLET

VCHDPKLPYHDFILEDAASPKCIMKEKKKPGETFF

MCSCSSDECNDNIIFSEEYNTSNPDLLLVIFQVTG

ISLLPPLGVAISVIIIFYCYRVNRQQKLSS (TGF-β-DNR-P2A-T3 amino acid sequence)
                                     SEQ ID NO: 526
MGRGLLRGLWPLHIVLWTRIASTIPPHVQKSVNND

MIVTDNNGAVKFPQLCKFCDVRFSTCDNQKSCMSN

CSITSICEKPQEVCVAVWRKNDENITLETVCHDPK

LPYHDFILEDAASPKCIMKEKKKPGETFFMCSCSS

DECNDNIIFSEEYNTSNPDLLLVIFQVTGISLLPP

LGVAISVIIIFYCYRVNRQQKLSSGSGATNFSLLK

QAGDVEENPGPMALPVTALLLPLALLLHAARPQVQ

LVESGGGVVQPGGSLRLSCAASFSGYGVSTMAWFR

QAPGKGLEGVAAITVGSGNTYYADSVKGRFTISRD

NSKNTVYLQMNSLRAEDTAMYYCAVGYLSGGSWDV

PGRYNYWGQGTLVTVSSGGGGSGGGGSGGGGSEVQ

LVESGGGLVQPGGSLRLSCAASGNTYSSNYMGWFR

QAPGKGLEEVAVIYTRGGHTYYVDSVRGRFTISQD

NAKNSLYLQMNSLRAEDTAVYYCAASSRHRLGLNN

PRDYDYWGQGTLVTVSSTTTPAPRPPTPAPTIASQ

PLSLRPEACRPAAGGAVHTRGLDFACDIYIWAPLA

GTCGVLLLSLVITLYCKRGRKKLLYIFKQPFMRPV

QTTQEEDGCSCRFPEEEEGGCELRVKFSRSADAPA

YKQGQNQLYNELNLGRREEYDVLDKRRGRDPEMGG

KPRRKNPQEGLYNELQKDKMAEAYSEIGMKGERRR

GKGHDGLYQGLSTATKDTYDALHMQALPPR (T3-T2A-TGF-β-DNR amino acid sequence)
                                     SEQ ID NO: 527
MALPVTALLLPLALLLHAARPQVQLVESGGGVVQP

GGSLRLSCAASFSGYGVSTMAWFRQAPGKGLEGVA

AITVGSGNTYYADSVKGRFTISRDNSKNTVYLQMN

SLRAEDTAMYYCAVGYLSGGSWDVPGRYNYWGQGT

LVTVSSGGGGSGGGGSGGGGSEVQLVESGGGLVQP

GGSLRLSCAASGNTYSSNYMGWFRQAPGKGLEEVA

VIYTRGGHTYYVDSVRGRFTISQDNAKNSLYLQMN

SLRAEDTAVYYCAASSRHRLGLNNPRDYDYWGQGT

LVTVSSTTTPAPRPPTPAPTIASQPLSLRPEACRP

AAGGAVHTRGLDFACDIYIWAPLAGTCGVLLLSLV

ITLYCKRGRKKLLYIFKQPFMRPVQTTQEEDGCSC
```

-continued
RFPEEEEGGCELRVKFSRSADAPAYKQGQNQLYNE

LNLGRREEYDVLDKRRGRDPEMGGKPRRKNPQEGL

YNELQKDKMAEAYSEIGMKGERRRGKGHDGLYQGL

STATKDTYDALHMQALPPRGSGEGRGSLLTCGDVE

ENPGPMGRGLLRGLWPLHIVLWTRIASTIPPHVQK

SVNNDMIVTDNNGAVKFPQLCKFCDVRFSTCDNQK

SCMSNCSITSICEKPQEVCVAVWRKNDENITLETV

CHDPKLPYHDFILEDAASPKCIMKEKKKPGETFFM

CSCSSDECNDNIIFSEEYNTSNPDLLLVIFQVTGI

SLLPPLGVAISVIIIFYCYRVNRQQKLSS (TGF-β-DNR-T2A-T3 amino acid sequence)
                              SEQ ID NO: 528
MGRGLLRGLWPLHIVLWTRIASTIPPHVQKSVNND

MIVTDNNGAVKFPQLCKFCDVRFSTCDNQKSCMSN

CSITSICEKPQEVCVAVWRKNDENITLETVCHDPK

LPYHDFILEDAASPKCIMKEKKKPGETFFMCSCSS

DECNDNIIFSEEYNTSNPDLLLVIFQVTGISLLPP

LGVAISVIIIFYCYRVNRQQKLSSGSGEGRGSLLT

CGDVEENPGPMALPVTALLLPLALLLHAARPQVQL

VESGGGVVQPGGSLRLSCAASFSGYGVSTMAWFRQ

APGKGLEGVAAITVGSGNTYYADSVKGRFTISRDN

SKNTVYLQMNSLRAEDTAMYYCAVGYLSGGSWDVP

GRYNYWGQGTLVTVSSGGGGSGGGGSGGGGSEVQL

VESGGGLVQPGGSLRLSCAASGNTYSSNYMGWFRQ

APGKGLEEVAVIYTRGGHTYYVDSVRGRFTISQDN

AKNSLYLQMNSLRAEDTAVYYCAASSRHRLGLNNP

RDYDYWGQGTLVTVSSTTTPAPRPPTPAPTIASQP

LSLRPEACRPAAGGAVHTRGLDFACDIYIWAPLAG

TCGVLLLSLVITLYCKRGRKKLLYIFKQPFMRPVQ

TTQEEDGCSCRFPEEEGGCELRVKFSRSADAPAY

KQGQNQLYNELNLGRREEYDVLDKRRGRDPEMGGK

PRRKNPQEGLYNELQKDKMAEAYSEIGMKGERRRG

KGHDGLYQGLSTATKDTYDALHMQALPPR (TGF-β-DNR amino acid sequence)
                              SEQ ID NO: 529
MGRGLLRGLWPLHIVLWTRIASTIPPHVQKSVNND

MIVTDNNGAVKFPQLCKFCDVRFSTCDNQKSCMSN

CSITSICEKPQEVCVAVWRKNDENITLETVCHDPK

LPYHDFILEDAASPKCIMKEKKKPGETFFMCSCSS

DECNDNIIFSEEYNTSNPDLLLVIFQVTGISLLPP

LGVAISVIIIFYCYRVNRQQKLSS

Figure 13B:
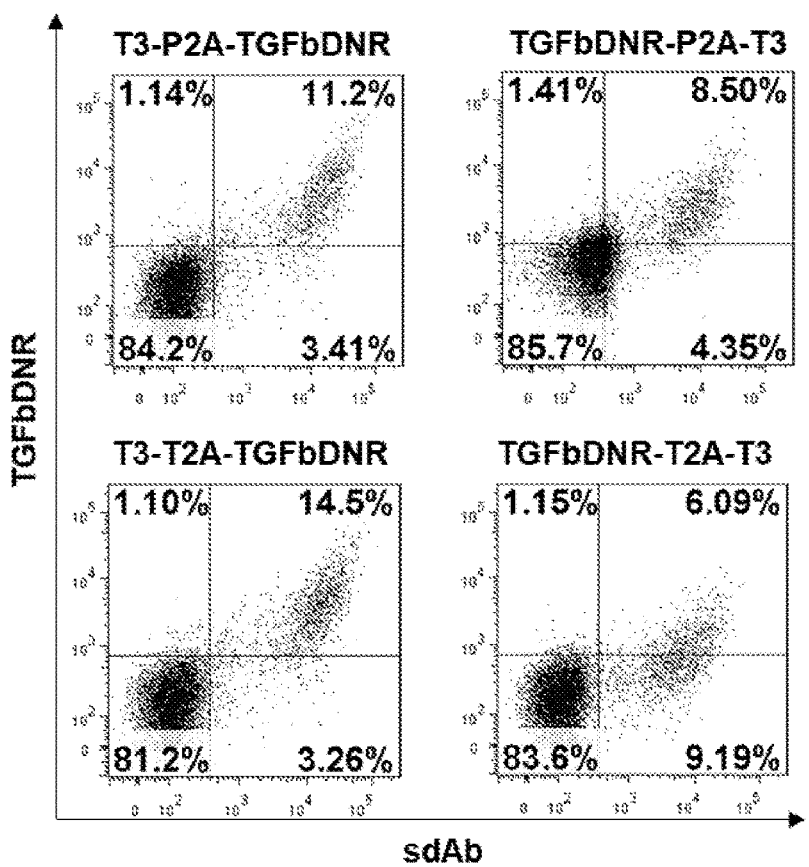
FIG. 13B shows the positive ratio of CAR and TGF-β-DNR on respective CAR-T cells. In vitro anti-tumor efficacy was evaluated in short-term (FIG. 13C, D) and long-term stimulation assays (FIG. 13E-G).

All the constructs were packaged into lentiviruses based on the second generation lentiviral system. Then primary T cells isolated from the PBMC of healthy donors were transduced with the lentiviruses. 4 days after transduction, the positive ratios of sdAb and TGF-β-DNR were detected by FACS (FIG. 13B). Results showed that the sdAb positive ratios of T3-P2A-TGF-β-DNR, T3-T2A-TGF-β-DNR, TGF-β-DNR-P2A-T3 and TGF-β-DNR-T2A-T3 CAR-T cells were comparable. However, the positive ratio of TGF-β-DNR were higher in constructs T3-P2A-TGF-β-DNR and T3-T2A-TGF-β-DNR than in TGF-β-DNR-P2A-T3 and TGF-β-DNR-T2A-T3. These results indicated the expression of TGF-β-DNR was higher when it conjugates to the C terminal of CAR.

In Vitro Cytotoxicity Assays

Figure 13C:
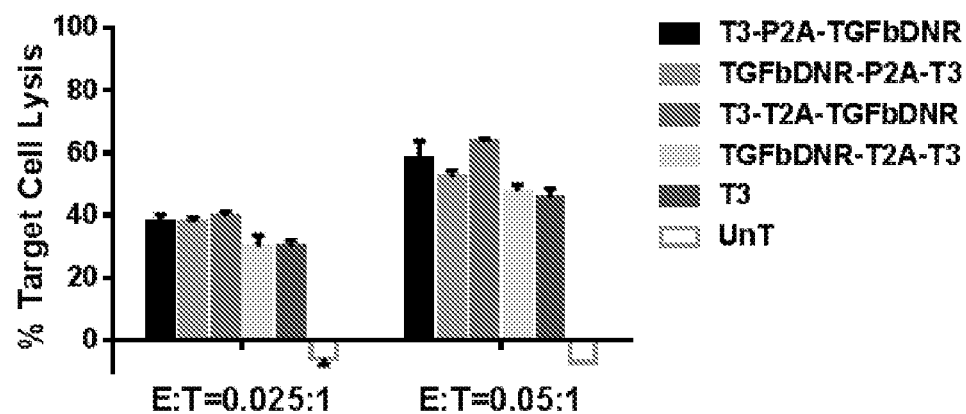
FIG. 13 shows that TGF-β-DNR enhances the in vitro and in vivo anti-tumor efficacy of DLL3 CAR-T cells.
FIG. 13H shows in vivo anti-tumor efficacy.
FIG. 13I shows the pharmacokinetics of CAR-T cells in the peripheral blood of SHP77 xenograft model after treatment.
Figure 13D:
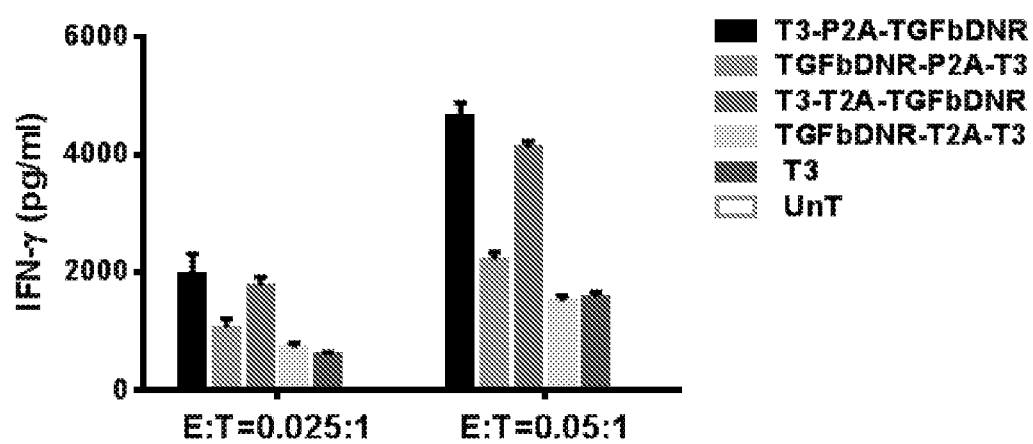

Then the cytotoxicity of these CAR-T cells was evaluated by LDH or IFN-γ releasing assays. 5 days after transduction, the CAR-T cells were adjusted to same sdAb positive ratios by untransduced T cells (UnT). Then the CAR-T cells or UnT cells were co-incubated with SHP77 for 48 h in the presence of 5 ng/mL TGF-β, and the LDH and IFN-γ releasing were measured (FIG. 13C-D). The results showed that the TGF-β-DNR armored CAR-T cells induced more specific lysis of target cell than the unarmored CAR-T cells. Accordingly, the TGF-β-DNR armored CAR-T cells showed a higher capacity of IFN-γ release upon antigen activation. In consistent with the TGF-β-DNR expression levels of the different CAR-T cells, the T3-P2A-TGF-β-DNR, T3-T2A-TGF-β-DNR showed higher levels of IFN-γ secretion than TGF-β-DNR-P2A-T3 and TGF-β-DNR-T2A-T3 CAR-T cells. Collectively these results demonstrated that the TGF-β-DNR was able to enhance the cytotoxicity of DLL3 CAR-T cells against the DLL3 positive SCLC cells.

Long-Term Stimulation Assay

Figure 13E:
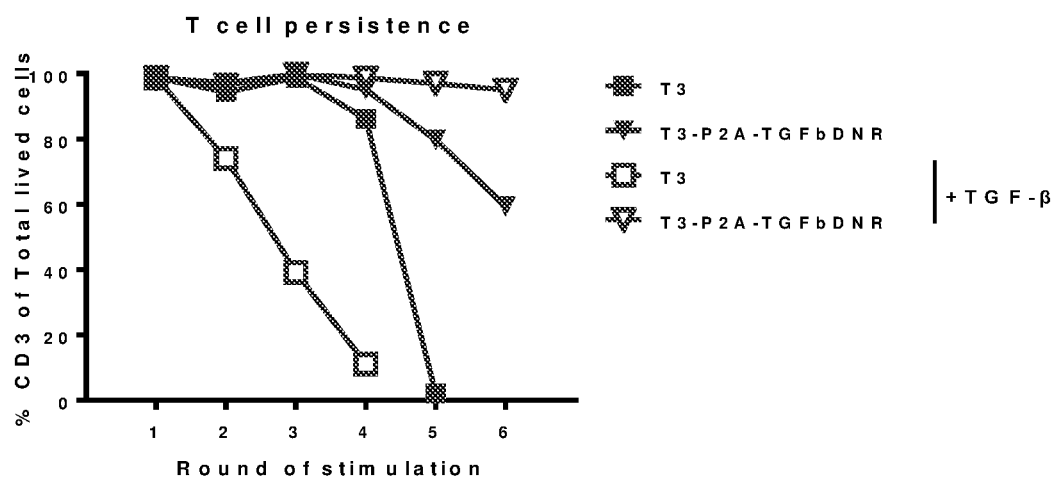
Figure 13F:
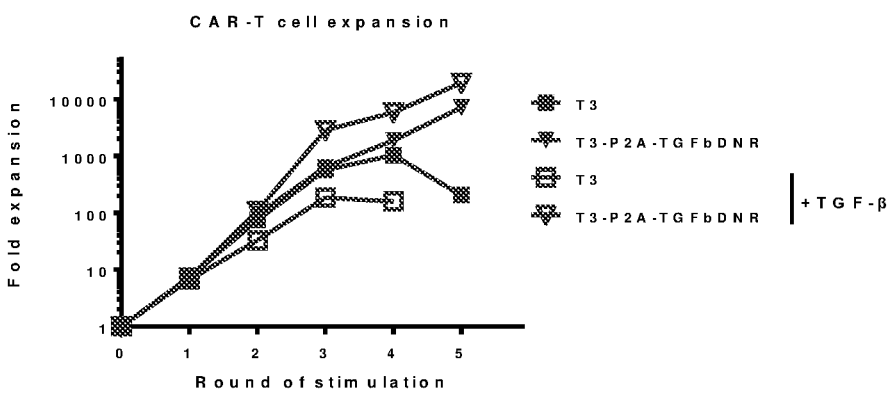
Figure 13G:
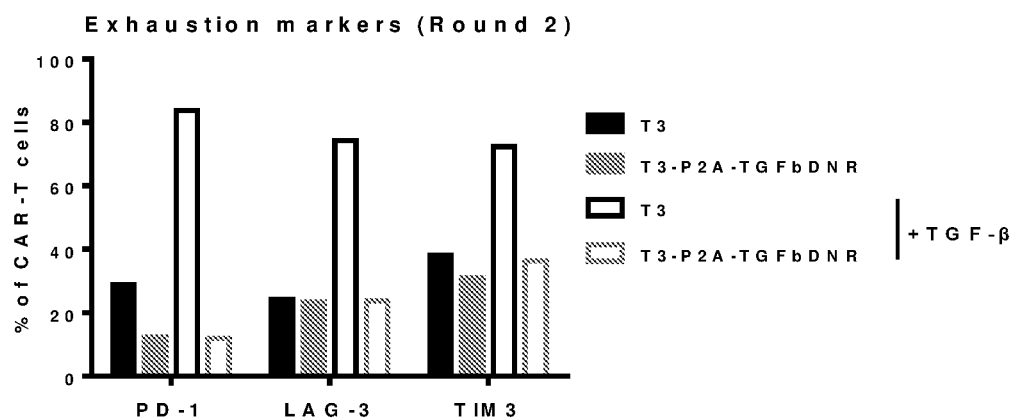

To determine whether the TGF-β-DNR could resist the inhibitory effects of TGF-β on CAR-T cells, a long-term stimulation assay was performed. Briefly, the T3-P2A-TGF-β-DNR and T3 CAR-T cells were repetitively challenged with SHP77 cells every 3 days in the presence or absence of 5 ng/mL of TGF-β. At the end of each round stimulation, the percentages of T cells in total viable cells were analyzed by FACS, and the expansion of CAR-T cells were calculated. As shown in FIG. 13E and FIG. 13F, the persistence and expansion of T3 CAR-T cells was inhibited by TGF-β. In contrast, the persistence and expansion of T3-P2A-TGF-β-DNR was well maintained even in the presence of TGF-β. T cell exhaustion markers were analyzed by FACS after 2 rounds stimulation with SHP77 cells. As shown in FIG. 13G, treatment with TGF-β upregulated the expression of exhaustion markers in T3 cells, but not in T3-P2A-TGF-β-DNR CAR-T cells. Collectively, these results demonstrated that TGF-β-DNR protects DLL3 CAR-T cells from the inhibition by TGF-β. Because the expression level of TGF-β is usually elevated in the microenvironment of solid tumors, our results indicate that the addition of TGF-β-DNR improves the anti-tumor efficacy of DLL3 CAR-T cells in solid tumors.

In Vivo Anti-Tumor Efficacy Study

Figure 13H:
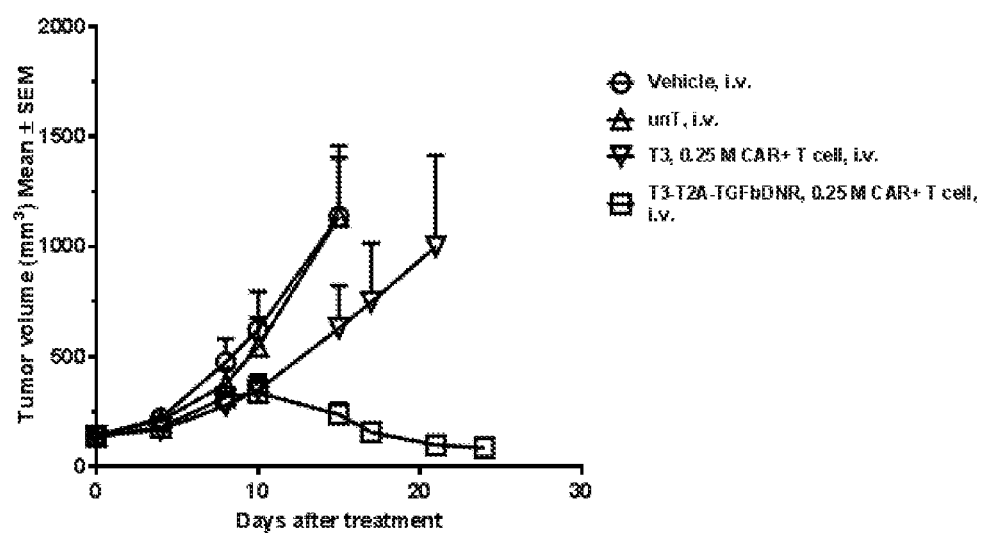
Figure 13I:
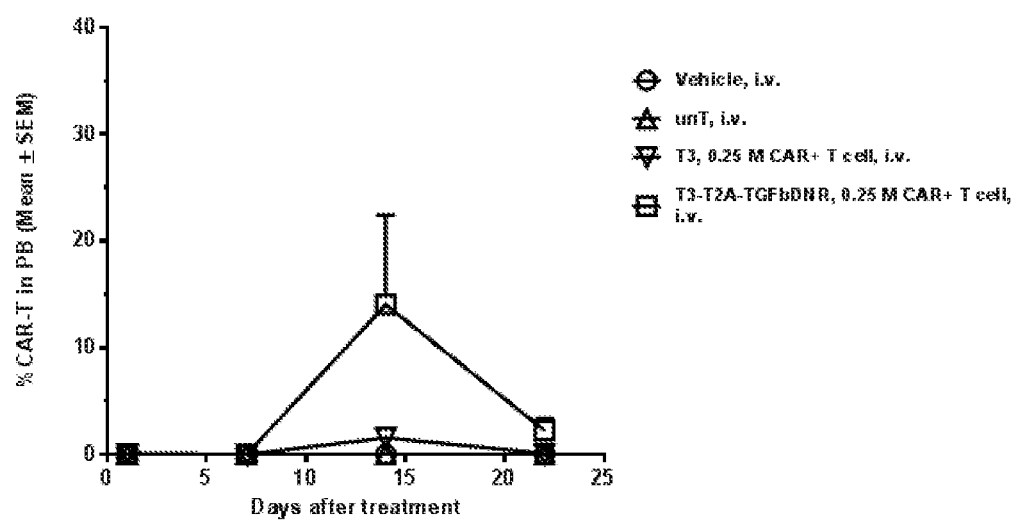

To further investigate whether the TGF-β-DNR could enhance the anti-tumor efficacy of DLL3 CAR-T cells in vivo, the T3-T2A-TGF-β-DNR CAR-T cells or the parental CAR-T cells were evaluated in xenograft model. Briefly, $1 \times 10^7$ SHP77 cells were subcutaneously implanted into NCG mice. After 7~10 days, when tumor volume reached 100-200 mm$^3$, $2.5 \times 10^5$ CAR-T cells were injected intravenously into the mice. Then tumor volume was measured twice a week, and percentage of CAR-T in peripheral blood was measured once a week. As shown in FIG. 13H, at a suboptimal dose, the T3-T2A-TGF-β-DNR CAR-T cells could potently suppress tumor growth, while the parental T3 CAR-T could not. As shown in FIG. 13I, the percentage of T3-T2A-TGF-β-DNR CAR-T in peripheral blood leukocytes was higher than T3. Collectively, these results demonstrate that the TGF-β-DNR could enhance the anti-tumor efficacy of DLL3 CAR-T cells in vivo.

What is claimed is:

1. A chimeric antigen receptor (CAR) that specifically binds to DLL3, wherein the CAR comprises a first single domain antibody (sdAb) moiety and a second sdAb moiety, wherein:
   (a) the first sdAb moiety comprises a CDR1 comprising the amino acid sequence of SEQ ID NO: 6; a CDR2 comprising the amino acid sequence of SEQ ID NO: 87; and a CDR3 comprising the amino acid sequence of SEQ ID NO: 168; and
   (b) the second sdAb moiety comprises a CDR1 comprising the amino acid sequence of SEQ ID NO: 21; a CDR2 comprising the amino acid sequence of SEQ ID NO: 102; and a CDR3 comprising the amino acid sequence of SEQ ID NO: 183.

2. A nucleic acid molecule encoding the CAR of claim 1.

3. An expression vector comprising the nucleic acid molecule of claim 2.

4. An engineered immune cell comprising the nucleic acid molecule of claim 2.

5. A pharmaceutical composition comprising the engineered immune cell of claim 4 and a physiologically acceptable excipient.

6. A method for treating a DLL3 associated disorder in a subject, the method comprising administering to the subject in need thereof a therapeutically effective amount of the pharmaceutical composition of claim 5.

* * * * *